(12) United States Patent
Ward et al.

(10) Patent No.: US 7,709,453 B2
(45) Date of Patent: May 4, 2010

(54) MODULATION OF THE RNA INTERFERENCE PATHWAY

(75) Inventors: Donna T. Ward, Carlsbad, CA (US); Andrew T. Watt, Oceanside, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 237 days.

(21) Appl. No.: 10/852,630

(22) Filed: May 24, 2004

(65) Prior Publication Data

US 2005/0037387 A1 Feb. 17, 2005

Related U.S. Application Data

(60) Provisional application No. 60/472,723, filed on May 22, 2003, provisional application No. 60/562,693, filed on Apr. 14, 2004.

(51) Int. Cl.
*A61K 31/70* (2006.01)
*C07H 21/04* (2006.01)
(52) U.S. Cl. ................ 514/44; 536/23.1; 536/24.5
(58) Field of Classification Search ............. None
See application file for complete search history.

(56) References Cited

U.S. PATENT DOCUMENTS

| | | | | |
|---|---|---|---|---|
| 5,801,154 | A | * 9/1998 | Baracchini et al. ............ | 514/44 |
| 5,998,148 | A | * 12/1999 | Bennett et al. ............ | 435/6 |
| 6,001,991 | A | * 12/1999 | Dean et al. ............ | 536/24.5 |
| 2002/0068709 | A1* | 6/2002 | Orum et al. ............ | 514/44 |
| 2003/0155026 | A1* | 8/2003 | Michlin et al. ............ | 138/26 |
| 2004/0029275 | A1 | 2/2004 | Brown et al. | |

FOREIGN PATENT DOCUMENTS

WO 0129058 A 4/2001

OTHER PUBLICATIONS

Opalinska et al. Nature Reviews Drug Discovery, 2002, vol. 1, p. 503-514.*
Taylor et al. Drug Discovery Today 1999 vol. 4, pp. 562-567.*
Thonberg et al., "Characterization of RNA Interference in Rat PC12 Cells: Requirement of GERp95," *Biochemical and Biophysical Research Communications*, 2004, vol. 318, pp. 927-934.
Hammond et al., "Argonaute2, a link between genetic and biochemical analyses of RNAik" *Science*, 2001, vol. 293 pp. 1146-1150.
Martinez et al., "Single-stranded antisense siRNAs guide target RNA cleavage in RNAi," *Cell*, 2002, vol. 16, pp. 2733-2742.
Carmell et al., "The Argonaute family: tentacles that reach into RNAi, developmental control, stem cell maintenance, and tumorigenesis," *Genes Dev.*, 2002, vol. 110, pp. 563-574.
Koesters et al., "Human eukaryotic initiation factor EIF2C1 gene: cDNA sequence, genomic organization, localization to chromosomal bands 1p34-p35, and expression," *Genomics*, 1999, vol. 61, pp. 210-218.
Caudy et al., "Fragile X-related protein and VIG associate with the RNA interference machinery," *Genes Dev.* 2002 vol. 16, pp. 2491-2496.
Ishizuka et al., "A *Drosophila* fragile X protein interacts with components of RNAi and ribosomal proteins," *Genes Dev.*, 2002, vol. 16, pp. 2497-2508.
Mourelatos et al., "miRNPs: a novel class of ribonucleoproteins containing numerous microRNAs," *Genes Dev.* 2002, vol. 16, pp. 720-728.
Findley et al., Maelstrom, a *Drosophila* spindle-class gene, encodes a protein that colocalizes with Vasa and RDE1/AGO1 homolog, Aubergine, in nuage, *Development*, 2003, vol. 130, pp. 859-871.
Guo et al., "par-1, a gene required for establishing polarity in *C. elegans* embryos, encodes a putative Ser/Thr kinase that is asymmetrically distributed," *Cell*, 1995, vol. 81, pp. 611-620.
Montgomery et al., "RNA as a target of double-stranded RNA-mediated genetic interference in *Caenorhabditis elegans*," *Proc. Natl. Acad. Sci.*, 1998, vol. 95, pp. 15502-15507.
Fire et al., *Nature*, 1998, vol. 391, pp. 806-811.
Tijsterman et al., "RNA helicase MUT-14-dependent gene silencing triggered in *C. elegans* by short antisense RNAs," 2002, vol. 295. pp. 694-697.
Timmons et al., "Specific interference by ingested dsRNA," *Nature*, 1998, vol. 395, p. 854.
Timmons et al., "Ingestion of bacterially expressed dsRNAs can produce specific and potent genetic interference in *Caenorhabditis elegans*," 2001, vol. 263, pp. 103-112.
Tabara et al., "RNAi in *C. elegans*: soaking in the genome sequence," *Science*, 1998, vol. 282, pp. 430-431.
Tuschl et al., "Targeted mRNA degradation by double-stranded RNA in vitro," *Genes Div.*, 1999, vol. 13, pp. 3191-3197.
Elbashir et al., "Duplexes of 21-nucleotide RNAs mediate RNA interference in cultured mammalian cells," *Nature*, 2001, vol. 411, pp. 494-498.
Elbashir et al., "RNA interference is mediated by 21- and 22-nucleotide RNAs," *Genes Dev.*, vol. 15. pp. 188-200.
Hutvagner, G., et al., "A microRNA in a multiple-turnover RNAi enzyme complex," Science, 2002, 297(5589), 2056-2060.
Caplen et al., "RNAi as a gene therapy approach" *Expert Opin. Biol. Ther.* (2003) 3:575-586.
European Search Report for EP 04753155.3 dated Jan. 16, 2008.
International Search Report for PCT/US2004/016279 dated Jun. 29, 2006.

\* cited by examiner

*Primary Examiner*—Tracy Vivlemore
(74) *Attorney, Agent, or Firm*—Isis Pharmaceuticals, Inc. Patent Department

(57) ABSTRACT

Compounds, compositions and methods are provided for modulating the RNAi pathway. The compositions comprise oligonucleotides, targeted to nucleic acid molecules encoding EIF2C2. Methods of using these compounds for modulation of RNA interference as well as EIF2C2 expression and for diagnosis and treatment of disease associated with expression of EIF2C2 are provided. Also provided are compounds, compositions and methods for modulating the expression of DDX36. The compositions comprise oligonucleotides, targeted to nucleic acid encoding DDX36. Methods of using these compounds for modulation of DDX36 expression and for diagnosis and treatment of diseases and conditions associated with expression of DDX36 are provided.

51 Claims, No Drawings

SEQUENCE LISTING

```
<160> NUMBER OF SEQ ID NOS: 392

<210> SEQ ID NO 1
<211> LENGTH: 20
<212> TYPE: DNA
<213> ORGANISM: Artificial Sequence
<220> FEATURE:
<223> OTHER INFORMATION: Antisense Compound

<400> SEQUENCE: 1
tccgtcatcg ctcctcaggg                                               20

<210> SEQ ID NO 2
<211> LENGTH: 20
<212> TYPE: DNA
<213> ORGANISM: Artificial Sequence
<220> FEATURE:
<223> OTHER INFORMATION: Antisense Compound

<400> SEQUENCE: 2
gtgcgcgcga gcccgaaatc                                               20

<210> SEQ ID NO 3
<211> LENGTH: 20
<212> TYPE: DNA
<213> ORGANISM: Artificial Sequence
<220> FEATURE:
<223> OTHER INFORMATION: Antisense Compound

<400> SEQUENCE: 3
atgcattctg cccccaagga                                               20

<210> SEQ ID NO 4
```

<211> LENGTH: 3307
<212> TYPE: DNA
<213> ORGANISM: H. sapiens
<220> FEATURE:
<221> NAME/KEY: CDS
<222> LOCATION: (42)...(2618)
<220> FEATURE:
<221> NAME/KEY: misc_feature
<222> LOCATION: 3161
<223> OTHER INFORMATION: n = A,T,C or G

<400> SEQUENCE: 4

```
gcggccgccc ctcggccccg gagctcctcg gcggcgccac c atg tac tcg gga gcc          56
                                              Met Tyr Ser Gly Ala
                                              1               5 ggc ccc gca ctt gca cct cct gcg ccg ccg ccc ccc atc caa gga tat           104
Gly Pro Ala Leu Ala Pro Pro Ala Pro Pro Pro Pro Ile Gln Gly Tyr
             10                  15                  20 gcc ttc aag cct cca cct aga ccc gac ttt ggg acc tcc ggg aga aca           152
Ala Phe Lys Pro Pro Pro Arg Pro Asp Phe Gly Thr Ser Gly Arg Thr
         25                  30                  35 atc aaa tta cag gcc aat ttc ttc gaa atg gac atc ccc aaa att gac           200
Ile Lys Leu Gln Ala Asn Phe Phe Glu Met Asp Ile Pro Lys Ile Asp
     40                  45                  50 atc tat cat tat gaa ttg gat atc aag cca gag aag tgc ccg agg aga           248
Ile Tyr His Tyr Glu Leu Asp Ile Lys Pro Glu Lys Cys Pro Arg Arg
 55                  60                  65 gtt aac agg gaa atc gtg gaa cac atg gtc cag cac ttt aaa aca cag           296
Val Asn Arg Glu Ile Val Glu His Met Val Gln His Phe Lys Thr Gln
 70                  75                  80                  85 atc ttt ggg gat cgg aag ccc gtg ttt gac ggc agg aag aat cta tac           344
Ile Phe Gly Asp Arg Lys Pro Val Phe Asp Gly Arg Lys Asn Leu Tyr
             90                  95                 100 aca gcc atg ccc ctt ccg att ggg agg gac aag gtg gag ctg gag gtc           392
Thr Ala Met Pro Leu Pro Ile Gly Arg Asp Lys Val Glu Leu Glu Val
         105                 110                 115 acg ctg cca gga gaa ggc aag gat cgc atc ttc aag gtg tcc atc aag           440
Thr Leu Pro Gly Glu Gly Lys Asp Arg Ile Phe Lys Val Ser Ile Lys
     120                 125                 130 tgg gtg tcc tgc gtg agc ttg cag gcg tta cac gat gca ctt tca ggg           488
Trp Val Ser Cys Val Ser Leu Gln Ala Leu His Asp Ala Leu Ser Gly
 135                 140                 145 cgg ctg ccc agc gtc cct ttt gag acg atc cag gcc ctg gac gtg gtc           536
Arg Leu Pro Ser Val Pro Phe Glu Thr Ile Gln Ala Leu Asp Val Val
150                 155                 160                 165 atg agg cac ttg cca tcc atg agg tac acc ccc gtg ggc cgc tcc ttc           584
Met Arg His Leu Pro Ser Met Arg Tyr Thr Pro Val Gly Arg Ser Phe
             170                 175                 180 ttc acc gcg tcc gaa ggc tgc tct aac cct ctt ggc ggg ggc cga gaa           632
Phe Thr Ala Ser Glu Gly Cys Ser Asn Pro Leu Gly Gly Gly Arg Glu
         185                 190                 195 gtg tgg ttt ggc ttc cat cag tcc gtc cgg cct tct ctc tgg aaa atg           680
Val Trp Phe Gly Phe His Gln Ser Val Arg Pro Ser Leu Trp Lys Met
     200                 205                 210 atg ctg aat att gat gtg tca gca aca gcg ttt tac aag gca cag cca           728
Met Leu Asn Ile Asp Val Ser Ala Thr Ala Phe Tyr Lys Ala Gln Pro
 215                 220                 225 gta atc gag ttt tgt tgt gaa gtt ttg gat ttt aaa agt atg aaa gaa           776
Val Ile Glu Phe Cys Cys Glu Val Leu Asp Phe Lys Ser Met Lys Glu
230                 235                 240                 245 caa caa aaa cct ctg aca gat tcc caa agg gta aag ttt acc aaa gaa           824
Gln Gln Lys Pro Leu Thr Asp Ser Gln Arg Val Lys Phe Thr Lys Glu
```

-continued

```
                       250                 255                 260
att aaa ggt cta aag gtg gag ata acg cac tgt ggg cag atg aag agg    872
Ile Lys Gly Leu Lys Val Glu Ile Thr His Cys Gly Gln Met Lys Arg
        265                 270                 275 aag tac cgc gtc tgc aat gtg acc cgg cgg ccc gcc agt cac caa aca    920
Lys Tyr Arg Val Cys Asn Val Thr Arg Arg Pro Ala Ser His Gln Thr
    280                 285                 290 ttc ccg ctg cag cag gag agc ggg cag acg gtg gag tgc acg gtg gcc    968
Phe Pro Leu Gln Gln Glu Ser Gly Gln Thr Val Glu Cys Thr Val Ala
295                 300                 305 cag tat ttc aag gac agg cac aag tgg gtt ctg cgc tac ccc cac ctc   1016
Gln Tyr Phe Lys Asp Arg His Lys Trp Val Leu Arg Tyr Pro His Leu
310                 315                 320                 325 cca tgt tta caa gtc gga cag gag cag aaa cac acc tac ctt ccc ctg   1064
Pro Cys Leu Gln Val Gly Gln Glu Gln Lys His Thr Tyr Leu Pro Leu
                330                 335                 340 gag gtc tgt aac att gtg gca gga caa aga tgt att aaa aaa tta acg   1112
Glu Val Cys Asn Ile Val Ala Gly Gln Arg Cys Ile Lys Lys Leu Thr
            345                 350                 355 gac aat cag acc tca acc atg atc aga gca act gct agg tcg gcg ccc   1160
Asp Asn Gln Thr Ser Thr Met Ile Arg Ala Thr Ala Arg Ser Ala Pro
        360                 365                 370 gat cgg caa gaa gag att agc aaa ttg atg cga agt gca agt ttc aac   1208
Asp Arg Gln Glu Glu Ile Ser Lys Leu Met Arg Ser Ala Ser Phe Asn
    375                 380                 385 aca gat cca tac gtc cgt gaa ttt gga atc atg gtc aaa gat gag atg   1256
Thr Asp Pro Tyr Val Arg Glu Phe Gly Ile Met Val Lys Asp Glu Met
390                 395                 400                 405 aca gac gtg act ggg cgg gtg ctg ccc gcc tcc atc ctc tac ggg ggc   1304
Thr Asp Val Thr Gly Arg Val Leu Pro Ala Ser Ile Leu Tyr Gly Gly
                410                 415                 420 agg aat aaa gct att gcg acc cct gtc cag ggc gtc tgg gac atg cgg   1352
Arg Asn Lys Ala Ile Ala Thr Pro Val Gln Gly Val Trp Asp Met Arg
            425                 430                 435 aac aag cag ttc cac acg ggc atc gag atc aag gtg tgg gcc att gcg   1400
Asn Lys Gln Phe His Thr Gly Ile Glu Ile Lys Val Trp Ala Ile Ala
        440                 445                 450 tgc ttc gcc ccc cag cgc cag tgc acg gaa gtc cat ctg aag tcc ttc   1448
Cys Phe Ala Pro Gln Arg Gln Cys Thr Glu Val His Leu Lys Ser Phe
455                 460                 465 aca gag cag ctc aga aag atc tcg aga gac gct ggc atg ccc atc cag   1496
Thr Glu Gln Leu Arg Lys Ile Ser Arg Asp Ala Gly Met Pro Ile Gln
470                 475                 480                 485 ggc cag ccg tgc ttc tgc aaa tac gcg cag ggg gcg gac agc gtg gag   1544
Gly Gln Pro Cys Phe Cys Lys Tyr Ala Gln Gly Ala Asp Ser Val Glu
                490                 495                 500 ccc atg ttc cgg cac ctg aag aac acg tat gcg ggc ctg cag ctg gtg   1592
Pro Met Phe Arg His Leu Lys Asn Thr Tyr Ala Gly Leu Gln Leu Val
            505                 510                 515 gtg gtc atc ctg ccc ggc aag acg ccc gtg tac gcc gag gtc aag cgc   1640
Val Val Ile Leu Pro Gly Lys Thr Pro Val Tyr Ala Glu Val Lys Arg
        520                 525                 530 gtg gga gac acg gtg ctg ggg atg gcc acg cag tgc gtg cag atg aag   1688
Val Gly Asp Thr Val Leu Gly Met Ala Thr Gln Cys Val Gln Met Lys
535                 540                 545 aac gtg cag agg acc acg cca cag acc ctg tcc aac ctc tgg ctg aag   1736
Asn Val Gln Arg Thr Thr Pro Gln Thr Leu Ser Asn Leu Trp Leu Lys
550                 555                 560                 565 atc aac gtc aag ctg gga ggc gtg aac aac atc ctg ctg ccc cag gga   1784
```

```
              Ile Asn Val Lys Leu Gly Gly Val Asn Asn Ile Leu Pro Gln Gly
                              570                 575                 580 agg ccg ccg gtg ttc cag gag ccc gtc atc ttt ctg gga gca gac gtc        1832
Arg Pro Pro Val Phe Gln Glu Pro Val Ile Phe Leu Gly Ala Asp Val
                585                 590                 595 act cac ccc ccc gcc ggg gat ggg aag aag ccc tcc att gcc gcc gtg        1880
Thr His Pro Pro Ala Gly Asp Gly Lys Lys Pro Ser Ile Ala Ala Val
                600                 605                 610 gtg ggg aga atg gac gcc cac ccc aat cgt tac tgc gcc acc gtg cgc        1928
Val Gly Arg Met Asp Ala His Pro Asn Arg Tyr Cys Ala Thr Val Arg
                615                 620                 625 gtg cag cag cac cgg cag gag atc ata caa gac ctg gcc gcc atg gtc        1976
Val Gln Gln His Arg Gln Glu Ile Ile Gln Asp Leu Ala Ala Met Val
630                 635                 640                 645 cgc gag ctc ctc atc cag ttc tac aag tcc acg cgc ttc aag ccc acc        2024
Arg Glu Leu Leu Ile Gln Phe Tyr Lys Ser Thr Arg Phe Lys Pro Thr
                650                 655                 660 cgc atc atc ttc tac cgc gac ggt gtc tct gaa ggc cag ttc cag cag        2072
Arg Ile Ile Phe Tyr Arg Asp Gly Val Ser Glu Gly Gln Phe Gln Gln
                665                 670                 675 gtt ctc cac cac gag ttg ctg gcc atc cgt gag gcc tgt atc aag cta        2120
Val Leu His His Glu Leu Leu Ala Ile Arg Glu Ala Cys Ile Lys Leu
                680                 685                 690 gaa aaa gac tac cag ccc ggg atc acc ttc atc gtg gtg cag aag agg        2168
Glu Lys Asp Tyr Gln Pro Gly Ile Thr Phe Ile Val Val Gln Lys Arg
                695                 700                 705 cac cac acc cgg ctc ttc tgc act gac aag aac gag cgg gtt ggg aaa        2216
His His Thr Arg Leu Phe Cys Thr Asp Lys Asn Glu Arg Val Gly Lys
710                 715                 720                 725 agt gga aac att cca gca ggc acg act gtg gac acg aaa atc acc cac        2264
Ser Gly Asn Ile Pro Ala Gly Thr Thr Val Asp Thr Lys Ile Thr His
                730                 735                 740 ccc acc gag ttc gac ttc tac ctg tgt agt cac gct ggc atc cag ggg        2312
Pro Thr Glu Phe Asp Phe Tyr Leu Cys Ser His Ala Gly Ile Gln Gly
                745                 750                 755 aca agc agg cct tcg cac tat cac gtc ctc tgg gac gac aat cgt ttc        2360
Thr Ser Arg Pro Ser His Tyr His Val Leu Trp Asp Asp Asn Arg Phe
                760                 765                 770 tcc tct gat gag ctg cag atc cta acc tac cag ctg tgt cac acc tac        2408
Ser Ser Asp Glu Leu Gln Ile Leu Thr Tyr Gln Leu Cys His Thr Tyr
775                 780                 785 gtg cgc tgc aca cgc tcc gtg tcc atc cca gcg cca gca tac tac gct        2456
Val Arg Cys Thr Arg Ser Val Ser Ile Pro Ala Pro Ala Tyr Tyr Ala
790                 795                 800                 805 cac ctg gtg gcc ttc cgg gcc agg tac cac ctg gtg gat aag gaa cat        2504
His Leu Val Ala Phe Arg Ala Arg Tyr His Leu Val Asp Lys Glu His
                810                 815                 820 gac agt gct gaa gga agc cat acc tct ggg cag agt aac ggg cga gac        2552
Asp Ser Ala Glu Gly Ser His Thr Ser Gly Gln Ser Asn Gly Arg Asp
                825                 830                 835 cac caa gca ctg gcc aag gcg gtc cag gtt cac caa gac act ctg cgc        2600
His Gln Ala Leu Ala Lys Ala Val Gln Val His Gln Asp Thr Leu Arg
                840                 845                 850 acc atg tac ttt gct tga catgttttag tgtttagcga ttgtgtaccg              2648
Thr Met Tyr Phe Ala
        855 agtgggattc acgagaccag ctacactcag accaacagat ggccagccct tccgtgacag     2708 ccagcatcga acatgagacg tcattgattt tattagattc tccgttttcc agaatgcctt     2768
```

```
ccgtcccaga tttcaacttg gattttgact gcagactgta tgagaaccca atgtcatagg    2828
aaatatggtt tgctaaaatc tataagctgc ttattaaaac agagtcccgt gtgtcctaaa    2888
aatctcctaa aaccagtcta tgaactcagg gctttaaaac atttttaatt tatttggtca    2948
ttcaatttac ttgtttttaa tacatgattc tctatgaaat tgatgggctc aaactagctg    3008
tgaatcttct gagagtgaaa gcaacacaaa acacaagtgt ggttttaaag ccttgaacat    3068
tctgatgttg tcactaaagt tgatttccag gcgatgctcg tgtgccsctg gcgtggctca    3128
cccaagttcc tcgactgagg gccggtggcc atncagaggc gtccgcaggt gccgtgttct    3188
gccagcaccg cccttcaccc ggcctgaact aaggagcagt gccagaaggt gggccccgtg    3248
tgtttacagc atttccaggt ccagagaggt tggcagacaa gtgccatttt aataaaaaa    3307
```

```
<210> SEQ ID NO 5
<211> LENGTH: 20
<212> TYPE: DNA
<213> ORGANISM: Artificial Sequence
<220> FEATURE:
<223> OTHER INFORMATION: PCR Primer

<400> SEQUENCE: 5
gatggagctg aacgctttgg                                                 20

<210> SEQ ID NO 6
<211> LENGTH: 22
<212> TYPE: DNA
<213> ORGANISM: Artificial Sequence
<220> FEATURE:
<223> OTHER INFORMATION: PCR Primer

<400> SEQUENCE: 6
caatatgtgg ctcaacgggt aa                                              22

<210> SEQ ID NO 7
<211> LENGTH: 29
<212> TYPE: DNA
<213> ORGANISM: Artificial Sequence
<220> FEATURE:
<223> OTHER INFORMATION: PCR Probe

<400> SEQUENCE: 7
aattgacacc tcttggagtc cacttggca                                       29

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gaaggtgaag gtcggagtc                                                  19

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gaagatggtg atgggatttc                                                 20
```

```
<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10
caagcttccc gttctcagcc                                              20

<210> SEQ ID NO 11
<211> LENGTH: 20
<212> TYPE: DNA
<213> ORGANISM: Artificial Sequence
<220> FEATURE:
<223> OTHER INFORMATION: Antisense Compound

<400> SEQUENCE: 11
gcatacgtgt tcttcaggtg                                              20

<210> SEQ ID NO 12
<211> LENGTH: 20
<212> TYPE: DNA
<213> ORGANISM: Artificial Sequence
<220> FEATURE:
<223> OTHER INFORMATION: Antisense Compound

<400> SEQUENCE: 12
ggcccgcata cgtgttcttc                                              20

<210> SEQ ID NO 13
<211> LENGTH: 20
<212> TYPE: DNA
<213> ORGANISM: Artificial Sequence
<220> FEATURE:
<223> OTHER INFORMATION: Antisense Compound

<400> SEQUENCE: 13
gctgcaggcc cgcatacgtg                                              20

<210> SEQ ID NO 14
<211> LENGTH: 20
<212> TYPE: DNA
<213> ORGANISM: Artificial Sequence
<220> FEATURE:
<223> OTHER INFORMATION: Antisense Compound

<400> SEQUENCE: 14
tgtctcccac gcgcttgacc                                              20

<210> SEQ ID NO 15
<211> LENGTH: 20
<212> TYPE: DNA
<213> ORGANISM: Artificial Sequence
<220> FEATURE:
<223> OTHER INFORMATION: Antisense Compound

<400> SEQUENCE: 15
tgcgtggcca tccccagcac                                              20

<210> SEQ ID NO 16
<211> LENGTH: 20
<212> TYPE: DNA
<213> ORGANISM: Artificial Sequence
<220> FEATURE:
<223> OTHER INFORMATION: Antisense Compound
```

```
<400> SEQUENCE: 16
ctctgcacgt tcttcatctg                                          20

<210> SEQ ID NO 17
<211> LENGTH: 20
<212> TYPE: DNA
<213> ORGANISM: Artificial Sequence
<220> FEATURE:
<223> OTHER INFORMATION: Antisense Compound

<400> SEQUENCE: 17
gtggtcctct gcacgttctt                                          20

<210> SEQ ID NO 18
<211> LENGTH: 20
<212> TYPE: DNA
<213> ORGANISM: Artificial Sequence
<220> FEATURE:
<223> OTHER INFORMATION: Antisense Compound

<400> SEQUENCE: 18
tgtggcgtgg tcctctgcac                                          20

<210> SEQ ID NO 19
<211> LENGTH: 20
<212> TYPE: DNA
<213> ORGANISM: Artificial Sequence
<220> FEATURE:
<223> OTHER INFORMATION: Antisense Compound

<400> SEQUENCE: 19
agggtctgtg gcgtggtcct                                          20

<210> SEQ ID NO 20
<211> LENGTH: 20
<212> TYPE: DNA
<213> ORGANISM: Artificial Sequence
<220> FEATURE:
<223> OTHER INFORMATION: Antisense Compound

<400> SEQUENCE: 20
gatgttgttc acgcctccca                                          20

<210> SEQ ID NO 21
<211> LENGTH: 20
<212> TYPE: DNA
<213> ORGANISM: Artificial Sequence
<220> FEATURE:
<223> OTHER INFORMATION: Antisense Compound

<400> SEQUENCE: 21
agcaggatgt tgttcacgcc                                          20

<210> SEQ ID NO 22
<211> LENGTH: 20
<212> TYPE: DNA
<213> ORGANISM: Artificial Sequence
<220> FEATURE:
<223> OTHER INFORMATION: Antisense Compound

<400> SEQUENCE: 22
tggaacaccg gcggccttcc                                          20

<210> SEQ ID NO 23
<211> LENGTH: 20
```

```
<212> TYPE: DNA
<213> ORGANISM: Artificial Sequence
<220> FEATURE:
<223> OTHER INFORMATION: Antisense Compound

<400> SEQUENCE: 23
tgtatgatct cctgccggtg                                                  20

<210> SEQ ID NO 24
<211> LENGTH: 20
<212> TYPE: DNA
<213> ORGANISM: Artificial Sequence
<220> FEATURE:
<223> OTHER INFORMATION: Antisense Compound

<400> SEQUENCE: 24
ggccttcaga gacaccgtcg                                                  20

<210> SEQ ID NO 25
<211> LENGTH: 20
<212> TYPE: DNA
<213> ORGANISM: Artificial Sequence
<220> FEATURE:
<223> OTHER INFORMATION: Antisense Compound

<400> SEQUENCE: 25
ctggaactgg ccttcagaga                                                  20

<210> SEQ ID NO 26
<211> LENGTH: 20
<212> TYPE: DNA
<213> ORGANISM: Artificial Sequence
<220> FEATURE:
<223> OTHER INFORMATION: Antisense Compound

<400> SEQUENCE: 26
ctgctggaac tggccttcag                                                  20

<210> SEQ ID NO 27
<211> LENGTH: 20
<212> TYPE: DNA
<213> ORGANISM: Artificial Sequence
<220> FEATURE:
<223> OTHER INFORMATION: Antisense Compound

<400> SEQUENCE: 27
agaacctgct ggaactggcc                                                  20

<210> SEQ ID NO 28
<211> LENGTH: 20
<212> TYPE: DNA
<213> ORGANISM: Artificial Sequence
<220> FEATURE:
<223> OTHER INFORMATION: Antisense Compound

<400> SEQUENCE: 28
tggagaacct gctggaactg                                                  20

<210> SEQ ID NO 29
<211> LENGTH: 20
<212> TYPE: DNA
<213> ORGANISM: Artificial Sequence
<220> FEATURE:
<223> OTHER INFORMATION: Antisense Compound

<400> SEQUENCE: 29
```
caactcgtgg tggagaacct            20

<210> SEQ ID NO 30
<211> LENGTH: 20
<212> TYPE: DNA
<213> ORGANISM: Artificial Sequence
<220> FEATURE:
<223> OTHER INFORMATION: Antisense Compound

<400> SEQUENCE: 30
agccgggtgt ggtgcctctt            20

<210> SEQ ID NO 31
<211> LENGTH: 20
<212> TYPE: DNA
<213> ORGANISM: Artificial Sequence
<220> FEATURE:
<223> OTHER INFORMATION: Antisense Compound

<400> SEQUENCE: 31
aagagccggg tgtggtgcct            20

<210> SEQ ID NO 32
<211> LENGTH: 20
<212> TYPE: DNA
<213> ORGANISM: Artificial Sequence
<220> FEATURE:
<223> OTHER INFORMATION: Antisense Compound

<400> SEQUENCE: 32
acttttccca acccgctcgt            20

<210> SEQ ID NO 33
<211> LENGTH: 20
<212> TYPE: DNA
<213> ORGANISM: Artificial Sequence
<220> FEATURE:
<223> OTHER INFORMATION: Antisense Compound

<400> SEQUENCE: 33
ctgctggaat gtttccactt            20

<210> SEQ ID NO 34
<211> LENGTH: 20
<212> TYPE: DNA
<213> ORGANISM: Artificial Sequence
<220> FEATURE:
<223> OTHER INFORMATION: Antisense Compound

<400> SEQUENCE: 34
gtcgtgcctg ctggaatgtt            20

<210> SEQ ID NO 35
<211> LENGTH: 20
<212> TYPE: DNA
<213> ORGANISM: Artificial Sequence
<220> FEATURE:
<223> OTHER INFORMATION: Antisense Compound

<400> SEQUENCE: 35
tagaagtcga actcggtggg            20

<210> SEQ ID NO 36
<211> LENGTH: 20
<212> TYPE: DNA
<213> ORGANISM: Artificial Sequence

```
<220> FEATURE:
<223> OTHER INFORMATION: Antisense Compound

<400> SEQUENCE: 36
gccagcgtga ctacacaggt                                               20

<210> SEQ ID NO 37
<211> LENGTH: 20
<212> TYPE: DNA
<213> ORGANISM: Artificial Sequence
<220> FEATURE:
<223> OTHER INFORMATION: Antisense Compound

<400> SEQUENCE: 37
tgcttgtccc ctggatgcca                                               20

<210> SEQ ID NO 38
<211> LENGTH: 20
<212> TYPE: DNA
<213> ORGANISM: Artificial Sequence
<220> FEATURE:
<223> OTHER INFORMATION: Antisense Compound

<400> SEQUENCE: 38
ccagaggacg tgatagtgcg                                               20

<210> SEQ ID NO 39
<211> LENGTH: 20
<212> TYPE: DNA
<213> ORGANISM: Artificial Sequence
<220> FEATURE:
<223> OTHER INFORMATION: Antisense Compound

<400> SEQUENCE: 39
tcatcagagg agaaacgatt                                               20

<210> SEQ ID NO 40
<211> LENGTH: 20
<212> TYPE: DNA
<213> ORGANISM: Artificial Sequence
<220> FEATURE:
<223> OTHER INFORMATION: Antisense Compound

<400> SEQUENCE: 40
caggtgagcg tagtatgctg                                               20

<210> SEQ ID NO 41
<211> LENGTH: 20
<212> TYPE: DNA
<213> ORGANISM: Artificial Sequence
<220> FEATURE:
<223> OTHER INFORMATION: Antisense Compound

<400> SEQUENCE: 41
cctggcccgg aaggccacca                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Compound

<400> SEQUENCE: 42
gaggtatggc ttccttcagc                                               20
```

```
<210> SEQ ID NO 43
<211> LENGTH: 20
<212> TYPE: DNA
<213> ORGANISM: Artificial Sequence
<220> FEATURE:
<223> OTHER INFORMATION: Antisense Compound

<400> SEQUENCE: 43
tgcccagagg tatggcttcc                                              20

<210> SEQ ID NO 44
<211> LENGTH: 20
<212> TYPE: DNA
<213> ORGANISM: Artificial Sequence
<220> FEATURE:
<223> OTHER INFORMATION: Antisense Compound

<400> SEQUENCE: 44
tggtggtctc gcccgttact                                              20

<210> SEQ ID NO 45
<211> LENGTH: 20
<212> TYPE: DNA
<213> ORGANISM: Artificial Sequence
<220> FEATURE:
<223> OTHER INFORMATION: Antisense Compound

<400> SEQUENCE: 45
tggccagtgc ttggtggtct                                              20

<210> SEQ ID NO 46
<211> LENGTH: 20
<212> TYPE: DNA
<213> ORGANISM: Artificial Sequence
<220> FEATURE:
<223> OTHER INFORMATION: Antisense Compound

<400> SEQUENCE: 46
gccttggcca gtgcttggtg                                              20

<210> SEQ ID NO 47
<211> LENGTH: 20
<212> TYPE: DNA
<213> ORGANISM: Artificial Sequence
<220> FEATURE:
<223> OTHER INFORMATION: Antisense Compound

<400> SEQUENCE: 47
catgtcaagc aaagtacatg                                              20

<210> SEQ ID NO 48
<211> LENGTH: 20
<212> TYPE: DNA
<213> ORGANISM: Artificial Sequence
<220> FEATURE:
<223> OTHER INFORMATION: Antisense Compound

<400> SEQUENCE: 48
acatgtcaag caaagtacat                                              20

<210> SEQ ID NO 49
<211> LENGTH: 20
<212> TYPE: DNA
<213> ORGANISM: Artificial Sequence
<220> FEATURE:
<223> OTHER INFORMATION: Antisense Compound
```

<400> SEQUENCE: 49
cggtacacaa tcgctaaaca                                        20

<210> SEQ ID NO 50
<211> LENGTH: 20
<212> TYPE: DNA
<213> ORGANISM: Artificial Sequence
<220> FEATURE:
<223> OTHER INFORMATION: Antisense Compound

<400> SEQUENCE: 50
tcccactcgg tacacaatcg                                        20

<210> SEQ ID NO 51
<211> LENGTH: 20
<212> TYPE: DNA
<213> ORGANISM: Artificial Sequence
<220> FEATURE:
<223> OTHER INFORMATION: Antisense Compound

<400> SEQUENCE: 51
tagctggtct cgtgaatccc                                        20

<210> SEQ ID NO 52
<211> LENGTH: 20
<212> TYPE: DNA
<213> ORGANISM: Artificial Sequence
<220> FEATURE:
<223> OTHER INFORMATION: Antisense Compound

<400> SEQUENCE: 52
gagtgtagct ggtctcgtga                                        20

<210> SEQ ID NO 53
<211> LENGTH: 20
<212> TYPE: DNA
<213> ORGANISM: Artificial Sequence
<220> FEATURE:
<223> OTHER INFORMATION: Antisense Compound

<400> SEQUENCE: 53
tctgttggtc tgagtgtagc                                        20

<210> SEQ ID NO 54
<211> LENGTH: 20
<212> TYPE: DNA
<213> ORGANISM: Artificial Sequence
<220> FEATURE:
<223> OTHER INFORMATION: Antisense Compound

<400> SEQUENCE: 54
gctggccatc tgttggtctg                                        20

<210> SEQ ID NO 55
<211> LENGTH: 20
<212> TYPE: DNA
<213> ORGANISM: Artificial Sequence
<220> FEATURE:
<223> OTHER INFORMATION: Antisense Compound

<400> SEQUENCE: 55
tctcatgttc gatgctggct                                        20

<210> SEQ ID NO 56

```
<211> LENGTH: 20
<212> TYPE: DNA
<213> ORGANISM: Artificial Sequence
<220> FEATURE:
<223> OTHER INFORMATION: Antisense Compound

<400> SEQUENCE: 56
tctaataaaa tcaatgacgt                                                 20

<210> SEQ ID NO 57
<211> LENGTH: 20
<212> TYPE: DNA
<213> ORGANISM: Artificial Sequence
<220> FEATURE:
<223> OTHER INFORMATION: Antisense Compound

<400> SEQUENCE: 57
tgggacggaa ggcattctgg                                                 20

<210> SEQ ID NO 58
<211> LENGTH: 20
<212> TYPE: DNA
<213> ORGANISM: Artificial Sequence
<220> FEATURE:
<223> OTHER INFORMATION: Antisense Compound

<400> SEQUENCE: 58
ctcatacagt ctgcagtcaa                                                 20

<210> SEQ ID NO 59
<211> LENGTH: 20
<212> TYPE: DNA
<213> ORGANISM: Artificial Sequence
<220> FEATURE:
<223> OTHER INFORMATION: Antisense Compound

<400> SEQUENCE: 59
ttgggttctc atacagtctg                                                 20

<210> SEQ ID NO 60
<211> LENGTH: 20
<212> TYPE: DNA
<213> ORGANISM: Artificial Sequence
<220> FEATURE:
<223> OTHER INFORMATION: Antisense Compound

<400> SEQUENCE: 60
tgacattggg ttctcataca                                                 20

<210> SEQ ID NO 61
<211> LENGTH: 20
<212> TYPE: DNA
<213> ORGANISM: Artificial Sequence
<220> FEATURE:
<223> OTHER INFORMATION: Antisense Compound

<400> SEQUENCE: 61
caaaccatat ttcctatgac                                                 20

<210> SEQ ID NO 62
<211> LENGTH: 20
<212> TYPE: DNA
<213> ORGANISM: Artificial Sequence
<220> FEATURE:
<223> OTHER INFORMATION: Antisense Compound

<400> SEQUENCE: 62
```

-continued tagattttag caaaccatat                                          20

<210> SEQ ID NO 63
<211> LENGTH: 20
<212> TYPE: DNA
<213> ORGANISM: Artificial Sequence
<220> FEATURE:
<223> OTHER INFORMATION: Antisense Compound

<400> SEQUENCE: 63
agcagcttat agattttagc                                          20

<210> SEQ ID NO 64
<211> LENGTH: 20
<212> TYPE: DNA
<213> ORGANISM: Artificial Sequence
<220> FEATURE:
<223> OTHER INFORMATION: Antisense Compound

<400> SEQUENCE: 64
ataagcagct tatagatttt                                          20

<210> SEQ ID NO 65
<211> LENGTH: 20
<212> TYPE: DNA
<213> ORGANISM: Artificial Sequence
<220> FEATURE:
<223> OTHER INFORMATION: Antisense Compound

<400> SEQUENCE: 65
actctgtttt aataagcagc                                          20

<210> SEQ ID NO 66
<211> LENGTH: 20
<212> TYPE: DNA
<213> ORGANISM: Artificial Sequence
<220> FEATURE:
<223> OTHER INFORMATION: Antisense Compound

<400> SEQUENCE: 66
cacgggactc tgttttaata                                          20

<210> SEQ ID NO 67
<211> LENGTH: 20
<212> TYPE: DNA
<213> ORGANISM: Artificial Sequence
<220> FEATURE:
<223> OTHER INFORMATION: Antisense Compound

<400> SEQUENCE: 67
ggagattttt aggacacacg                                          20

<210> SEQ ID NO 68
<211> LENGTH: 20
<212> TYPE: DNA
<213> ORGANISM: Artificial Sequence
<220> FEATURE:
<223> OTHER INFORMATION: Antisense Compound

<400> SEQUENCE: 68
tgagttcata gactggtttt                                          20

<210> SEQ ID NO 69
<211> LENGTH: 20
<212> TYPE: DNA

```
<213> ORGANISM: Artificial Sequence
<220> FEATURE:
<223> OTHER INFORMATION: Antisense Compound

<400> SEQUENCE: 69
aagccctgag ttcatagact                                               20

<210> SEQ ID NO 70
<211> LENGTH: 20
<212> TYPE: DNA
<213> ORGANISM: Artificial Sequence
<220> FEATURE:
<223> OTHER INFORMATION: Antisense Compound

<400> SEQUENCE: 70
tgttttaaag ccctgagttc                                               20

<210> SEQ ID NO 71
<211> LENGTH: 20
<212> TYPE: DNA
<213> ORGANISM: Artificial Sequence
<220> FEATURE:
<223> OTHER INFORMATION: Antisense Compound

<400> SEQUENCE: 71
aaaatgtttt aaagccctga                                               20

<210> SEQ ID NO 72
<211> LENGTH: 20
<212> TYPE: DNA
<213> ORGANISM: Artificial Sequence
<220> FEATURE:
<223> OTHER INFORMATION: Antisense Compound

<400> SEQUENCE: 72
tgagcccatc aatttcatag                                               20

<210> SEQ ID NO 73
<211> LENGTH: 20
<212> TYPE: DNA
<213> ORGANISM: Artificial Sequence
<220> FEATURE:
<223> OTHER INFORMATION: Antisense Compound

<400> SEQUENCE: 73
cagctagttt gagcccatca                                               20

<210> SEQ ID NO 74
<211> LENGTH: 20
<212> TYPE: DNA
<213> ORGANISM: Artificial Sequence
<220> FEATURE:
<223> OTHER INFORMATION: Antisense Compound

<400> SEQUENCE: 74
cagaagattc acagctagtt                                               20

<210> SEQ ID NO 75
<211> LENGTH: 20
<212> TYPE: DNA
<213> ORGANISM: Artificial Sequence
<220> FEATURE:
<223> OTHER INFORMATION: Antisense Compound

<400> SEQUENCE: 75
tgttcaaggc tttaaaacca                                               20
```

<210> SEQ ID NO 76
<211> LENGTH: 20
<212> TYPE: DNA
<213> ORGANISM: Artificial Sequence
<220> FEATURE:
<223> OTHER INFORMATION: Antisense Compound

<400> SEQUENCE: 76
acatcagaat gttcaaggct                                           20

<210> SEQ ID NO 77
<211> LENGTH: 20
<212> TYPE: DNA
<213> ORGANISM: Artificial Sequence
<220> FEATURE:
<223> OTHER INFORMATION: Antisense Compound

<400> SEQUENCE: 77
atcaacttta gtgacaacat                                           20

<210> SEQ ID NO 78
<211> LENGTH: 20
<212> TYPE: DNA
<213> ORGANISM: Artificial Sequence
<220> FEATURE:
<223> OTHER INFORMATION: Antisense Compound

<400> SEQUENCE: 78
aaatcaactt tagtgacaac                                           20

<210> SEQ ID NO 79
<211> LENGTH: 20
<212> TYPE: DNA
<213> ORGANISM: Artificial Sequence
<220> FEATURE:
<223> OTHER INFORMATION: Antisense Compound

<400> SEQUENCE: 79
acgagcatcg cctggaaatc                                           20

<210> SEQ ID NO 80
<211> LENGTH: 20
<212> TYPE: DNA
<213> ORGANISM: Artificial Sequence
<220> FEATURE:
<223> OTHER INFORMATION: Antisense Compound

<400> SEQUENCE: 80
aacttgggtg agccacgcca                                           20

<210> SEQ ID NO 81
<211> LENGTH: 20
<212> TYPE: DNA
<213> ORGANISM: Artificial Sequence
<220> FEATURE:
<223> OTHER INFORMATION: Antisense Compound

<400> SEQUENCE: 81
ccaccggccc tcagtcgagg                                           20

<210> SEQ ID NO 82
<211> LENGTH: 20
<212> TYPE: DNA
<213> ORGANISM: Artificial Sequence
<220> FEATURE:

<223> OTHER INFORMATION: Antisense Compound

<400> SEQUENCE: 82
ggcggtgctg gcagaacacg                                               20

<210> SEQ ID NO 83
<211> LENGTH: 20
<212> TYPE: DNA
<213> ORGANISM: Artificial Sequence
<220> FEATURE:
<223> OTHER INFORMATION: Antisense Compound

<400> SEQUENCE: 83
tgctccttag ttcaggccgg                                               20

<210> SEQ ID NO 84
<211> LENGTH: 20
<212> TYPE: DNA
<213> ORGANISM: Artificial Sequence
<220> FEATURE:
<223> OTHER INFORMATION: Antisense Compound

<400> SEQUENCE: 84
caccttctgg cactgctcct                                               20

<210> SEQ ID NO 85
<211> LENGTH: 20
<212> TYPE: DNA
<213> ORGANISM: Artificial Sequence
<220> FEATURE:
<223> OTHER INFORMATION: Antisense Compound

<400> SEQUENCE: 85
ctctctggac ctggaaatgc                                               20

<210> SEQ ID NO 86
<211> LENGTH: 20
<212> TYPE: DNA
<213> ORGANISM: Artificial Sequence
<220> FEATURE:
<223> OTHER INFORMATION: Antisense Compound

<400> SEQUENCE: 86
aacctctctg gacctggaaa                                               20

<210> SEQ ID NO 87
<211> LENGTH: 20
<212> TYPE: DNA
<213> ORGANISM: Artificial Sequence
<220> FEATURE:
<223> OTHER INFORMATION: Antisense Compound

<400> SEQUENCE: 87
aaatggcact tgtctgccaa                                               20

<210> SEQ ID NO 88
<211> LENGTH: 20
<212> TYPE: DNA
<213> ORGANISM: Artificial Sequence
<220> FEATURE:
<223> OTHER INFORMATION: Antisense Compound

<400> SEQUENCE: 88
ttattaaaat ggcacttgtc                                               20

```
<210> SEQ ID NO 89
<211> LENGTH: 20
<212> TYPE: DNA
<213> ORGANISM: H. sapiens

<400> SEQUENCE: 89
cacctgaaga acacgtatgc                                               20

<210> SEQ ID NO 90
<211> LENGTH: 20
<212> TYPE: DNA
<213> ORGANISM: H. sapiens

<400> SEQUENCE: 90
gaagaacacg tatgcgggcc                                               20

<210> SEQ ID NO 91
<211> LENGTH: 20
<212> TYPE: DNA
<213> ORGANISM: H. sapiens

<400> SEQUENCE: 91
cacgtatgcg ggcctgcagc                                               20

<210> SEQ ID NO 92
<211> LENGTH: 20
<212> TYPE: DNA
<213> ORGANISM: H. sapiens

<400> SEQUENCE: 92
ggtcaagcgc gtgggagaca                                               20

<210> SEQ ID NO 93
<211> LENGTH: 20
<212> TYPE: DNA
<213> ORGANISM: H. sapiens

<400> SEQUENCE: 93
gtgctgggga tggccacgca                                               20

<210> SEQ ID NO 94
<211> LENGTH: 20
<212> TYPE: DNA
<213> ORGANISM: H. sapiens

<400> SEQUENCE: 94
cagatgaaga acgtgcagag                                               20

<210> SEQ ID NO 95
<211> LENGTH: 20
<212> TYPE: DNA
<213> ORGANISM: H. sapiens

<400> SEQUENCE: 95
aagaacgtgc agaggaccac                                               20

<210> SEQ ID NO 96
<211> LENGTH: 20
<212> TYPE: DNA
<213> ORGANISM: H. sapiens

<400> SEQUENCE: 96
gtgcagagga ccacgccaca                                               20
```

```
<210> SEQ ID NO 97
<211> LENGTH: 20
<212> TYPE: DNA
<213> ORGANISM: H. sapiens

<400> SEQUENCE: 97
aggaccacgc cacagaccct                                               20

<210> SEQ ID NO 98
<211> LENGTH: 20
<212> TYPE: DNA
<213> ORGANISM: H. sapiens

<400> SEQUENCE: 98
tgggaggcgt gaacaacatc                                               20

<210> SEQ ID NO 99
<211> LENGTH: 20
<212> TYPE: DNA
<213> ORGANISM: H. sapiens

<400> SEQUENCE: 99
ggcgtgaaca acatcctgct                                               20

<210> SEQ ID NO 100
<211> LENGTH: 20
<212> TYPE: DNA
<213> ORGANISM: H. sapiens

<400> SEQUENCE: 100
ggaaggccgc cggtgttcca                                               20

<210> SEQ ID NO 101
<211> LENGTH: 20
<212> TYPE: DNA
<213> ORGANISM: H. sapiens

<400> SEQUENCE: 101
caccggcagg agatcataca                                               20

<210> SEQ ID NO 102
<211> LENGTH: 20
<212> TYPE: DNA
<213> ORGANISM: H. sapiens

<400> SEQUENCE: 102
cgacggtgtc tctgaaggcc                                               20

<210> SEQ ID NO 103
<211> LENGTH: 20
<212> TYPE: DNA
<213> ORGANISM: H. sapiens

<400> SEQUENCE: 103
tctctgaagg ccagttccag                                               20

<210> SEQ ID NO 104
<211> LENGTH: 20
<212> TYPE: DNA
<213> ORGANISM: H. sapiens

<400> SEQUENCE: 104
ctgaaggcca gttccagcag                                               20
```

```
<210> SEQ ID NO 105
<211> LENGTH: 20
<212> TYPE: DNA
<213> ORGANISM: H. sapiens

<400> SEQUENCE: 105
ggccagttcc agcaggttct                                               20

<210> SEQ ID NO 106
<211> LENGTH: 20
<212> TYPE: DNA
<213> ORGANISM: H. sapiens

<400> SEQUENCE: 106
cagttccagc aggttctcca                                               20

<210> SEQ ID NO 107
<211> LENGTH: 20
<212> TYPE: DNA
<213> ORGANISM: H. sapiens

<400> SEQUENCE: 107
aggttctcca ccacgagttg                                               20

<210> SEQ ID NO 108
<211> LENGTH: 20
<212> TYPE: DNA
<213> ORGANISM: H. sapiens

<400> SEQUENCE: 108
aagaggcacc acacccggct                                               20

<210> SEQ ID NO 109
<211> LENGTH: 20
<212> TYPE: DNA
<213> ORGANISM: H. sapiens

<400> SEQUENCE: 109
aggcaccaca cccggctctt                                               20

<210> SEQ ID NO 110
<211> LENGTH: 20
<212> TYPE: DNA
<213> ORGANISM: H. sapiens

<400> SEQUENCE: 110
aagtggaaac attccagcag                                               20

<210> SEQ ID NO 111
<211> LENGTH: 20
<212> TYPE: DNA
<213> ORGANISM: H. sapiens

<400> SEQUENCE: 111
aacattccag caggcacgac                                               20

<210> SEQ ID NO 112
<211> LENGTH: 20
<212> TYPE: DNA
<213> ORGANISM: H. sapiens

<400> SEQUENCE: 112
```
acctgtgtag tcacgctggc                                               20

<210> SEQ ID NO 113
<211> LENGTH: 20
<212> TYPE: DNA
<213> ORGANISM: H. sapiens

<400> SEQUENCE: 113
tggcatccag gggacaagca                                               20

<210> SEQ ID NO 114
<211> LENGTH: 20
<212> TYPE: DNA
<213> ORGANISM: H. sapiens

<400> SEQUENCE: 114
cgcactatca cgtcctctgg                                               20

<210> SEQ ID NO 115
<211> LENGTH: 20
<212> TYPE: DNA
<213> ORGANISM: H. sapiens

<400> SEQUENCE: 115
aatcgtttct cctctgatga                                               20

<210> SEQ ID NO 116
<211> LENGTH: 20
<212> TYPE: DNA
<213> ORGANISM: H. sapiens

<400> SEQUENCE: 116
cagcatacta cgctcacctg                                               20

<210> SEQ ID NO 117
<211> LENGTH: 20
<212> TYPE: DNA
<213> ORGANISM: H. sapiens

<400> SEQUENCE: 117
tggtggcctt ccgggccagg                                               20

<210> SEQ ID NO 118
<211> LENGTH: 20
<212> TYPE: DNA
<213> ORGANISM: H. sapiens

<400> SEQUENCE: 118
gctgaaggaa gccatacctc                                               20

<210> SEQ ID NO 119
<211> LENGTH: 20
<212> TYPE: DNA
<213> ORGANISM: H. sapiens

<400> SEQUENCE: 119
ggaagccata cctctgggca                                               20

<210> SEQ ID NO 120
<211> LENGTH: 20
<212> TYPE: DNA
<213> ORGANISM: H. sapiens

<400> SEQUENCE: 120
agtaacgggc gagaccacca 20

<210> SEQ ID NO 121
<211> LENGTH: 20
<212> TYPE: DNA
<213> ORGANISM: H. sapiens

<400> SEQUENCE: 121
agaccaccaa gcactggcca 20

<210> SEQ ID NO 122
<211> LENGTH: 20
<212> TYPE: DNA
<213> ORGANISM: H. sapiens

<400> SEQUENCE: 122
catgtacttt gcttgacatg 20

<210> SEQ ID NO 123
<211> LENGTH: 20
<212> TYPE: DNA
<213> ORGANISM: H. sapiens

<400> SEQUENCE: 123
atgtactttg cttgacatgt 20

<210> SEQ ID NO 124
<211> LENGTH: 20
<212> TYPE: DNA
<213> ORGANISM: H. sapiens

<400> SEQUENCE: 124
tgtttagcga ttgtgtaccg 20

<210> SEQ ID NO 125
<211> LENGTH: 20
<212> TYPE: DNA
<213> ORGANISM: H. sapiens

<400> SEQUENCE: 125
cgattgtgta ccgagtggga 20

<210> SEQ ID NO 126
<211> LENGTH: 20
<212> TYPE: DNA
<213> ORGANISM: H. sapiens

<400> SEQUENCE: 126
gggattcacg agaccagcta 20

<210> SEQ ID NO 127
<211> LENGTH: 20
<212> TYPE: DNA
<213> ORGANISM: H. sapiens

<400> SEQUENCE: 127
tcacgagacc agctacactc 20

<210> SEQ ID NO 128
<211> LENGTH: 20
<212> TYPE: DNA
<213> ORGANISM: H. sapiens

<400> SEQUENCE: 128
gctacactca gaccaacaga                      20

<210> SEQ ID NO 129
<211> LENGTH: 20
<212> TYPE: DNA
<213> ORGANISM: H. sapiens

<400> SEQUENCE: 129
cagaccaaca gatggccagc                      20

<210> SEQ ID NO 130
<211> LENGTH: 20
<212> TYPE: DNA
<213> ORGANISM: H. sapiens

<400> SEQUENCE: 130
agccagcatc gaacatgaga                      20

<210> SEQ ID NO 131
<211> LENGTH: 20
<212> TYPE: DNA
<213> ORGANISM: H. sapiens

<400> SEQUENCE: 131
acgtcattga ttttattaga                      20

<210> SEQ ID NO 132
<211> LENGTH: 20
<212> TYPE: DNA
<213> ORGANISM: H. sapiens

<400> SEQUENCE: 132
ccagaatgcc ttccgtccca                      20

<210> SEQ ID NO 133
<211> LENGTH: 20
<212> TYPE: DNA
<213> ORGANISM: H. sapiens

<400> SEQUENCE: 133
ttgactgcag actgtatgag                      20

<210> SEQ ID NO 134
<211> LENGTH: 20
<212> TYPE: DNA
<213> ORGANISM: H. sapiens

<400> SEQUENCE: 134
cagactgtat gagaacccaa                      20

<210> SEQ ID NO 135
<211> LENGTH: 20
<212> TYPE: DNA
<213> ORGANISM: H. sapiens

<400> SEQUENCE: 135
tgtatgagaa cccaatgtca                      20

<210> SEQ ID NO 136
<211> LENGTH: 20
<212> TYPE: DNA
<213> ORGANISM: H. sapiens

```
<400> SEQUENCE: 136
gtcataggaa atatggtttg                                        20

<210> SEQ ID NO 137
<211> LENGTH: 20
<212> TYPE: DNA
<213> ORGANISM: H. sapiens

<400> SEQUENCE: 137
atatggtttg ctaaaatcta                                        20

<210> SEQ ID NO 138
<211> LENGTH: 20
<212> TYPE: DNA
<213> ORGANISM: H. sapiens

<400> SEQUENCE: 138
gctaaaatct ataagctgct                                        20

<210> SEQ ID NO 139
<211> LENGTH: 20
<212> TYPE: DNA
<213> ORGANISM: H. sapiens

<400> SEQUENCE: 139
aaaatctata agctgcttat                                        20

<210> SEQ ID NO 140
<211> LENGTH: 20
<212> TYPE: DNA
<213> ORGANISM: H. sapiens

<400> SEQUENCE: 140
gctgcttatt aaaacagagt                                        20

<210> SEQ ID NO 141
<211> LENGTH: 20
<212> TYPE: DNA
<213> ORGANISM: H. sapiens

<400> SEQUENCE: 141
tattaaaaca gagtcccgtg                                        20

<210> SEQ ID NO 142
<211> LENGTH: 20
<212> TYPE: DNA
<213> ORGANISM: H. sapiens

<400> SEQUENCE: 142
cgtgtgtcct aaaaatctcc                                        20

<210> SEQ ID NO 143
<211> LENGTH: 20
<212> TYPE: DNA
<213> ORGANISM: H. sapiens

<400> SEQUENCE: 143
aaaaccagtc tatgaactca                                        20

<210> SEQ ID NO 144
<211> LENGTH: 20
<212> TYPE: DNA
```

<213> ORGANISM: H. sapiens

<400> SEQUENCE: 144
agtctatgaa ctcagggctt                                        20

<210> SEQ ID NO 145
<211> LENGTH: 20
<212> TYPE: DNA
<213> ORGANISM: H. sapiens

<400> SEQUENCE: 145
tcagggcttt aaaacatttt                                        20

<210> SEQ ID NO 146
<211> LENGTH: 20
<212> TYPE: DNA
<213> ORGANISM: H. sapiens

<400> SEQUENCE: 146
ctatgaaatt gatgggctca                                        20

<210> SEQ ID NO 147
<211> LENGTH: 20
<212> TYPE: DNA
<213> ORGANISM: H. sapiens

<400> SEQUENCE: 147
tgatgggctc aaactagctg                                        20

<210> SEQ ID NO 148
<211> LENGTH: 20
<212> TYPE: DNA
<213> ORGANISM: H. sapiens

<400> SEQUENCE: 148
aactagctgt gaatcttctg                                        20

<210> SEQ ID NO 149
<211> LENGTH: 20
<212> TYPE: DNA
<213> ORGANISM: H. sapiens

<400> SEQUENCE: 149
tggttttaaa gccttgaaca                                        20

<210> SEQ ID NO 150
<211> LENGTH: 20
<212> TYPE: DNA
<213> ORGANISM: H. sapiens

<400> SEQUENCE: 150
agccttgaac attctgatgt                                        20

<210> SEQ ID NO 151
<211> LENGTH: 20
<212> TYPE: DNA
<213> ORGANISM: H. sapiens

<400> SEQUENCE: 151
atgttgtcac taaagttgat                                        20

<210> SEQ ID NO 152
<211> LENGTH: 20

```
<212> TYPE: DNA
<213> ORGANISM: H. sapiens

<400> SEQUENCE: 152
gttgtcacta aagttgattt                                               20

<210> SEQ ID NO 153
<211> LENGTH: 20
<212> TYPE: DNA
<213> ORGANISM: H. sapiens

<400> SEQUENCE: 153
gatttccagg cgatgctcgt                                               20

<210> SEQ ID NO 154
<211> LENGTH: 20
<212> TYPE: DNA
<213> ORGANISM: H. sapiens

<400> SEQUENCE: 154
tggcgtggct cacccaagtt                                               20

<210> SEQ ID NO 155
<211> LENGTH: 20
<212> TYPE: DNA
<213> ORGANISM: H. sapiens

<400> SEQUENCE: 155
cctcgactga gggccggtgg                                               20

<210> SEQ ID NO 156
<211> LENGTH: 20
<212> TYPE: DNA
<213> ORGANISM: H. sapiens

<400> SEQUENCE: 156
cgtgttctgc cagcaccgcc                                               20

<210> SEQ ID NO 157
<211> LENGTH: 20
<212> TYPE: DNA
<213> ORGANISM: H. sapiens

<400> SEQUENCE: 157
ccggcctgaa ctaaggagca                                               20

<210> SEQ ID NO 158
<211> LENGTH: 20
<212> TYPE: DNA
<213> ORGANISM: H. sapiens

<400> SEQUENCE: 158
gcatttccag gtccagagag                                               20

<210> SEQ ID NO 159
<211> LENGTH: 20
<212> TYPE: DNA
<213> ORGANISM: H. sapiens

<400> SEQUENCE: 159
tttccaggtc cagagaggtt                                               20

<210> SEQ ID NO 160
```

```
<211> LENGTH: 20
<212> TYPE: DNA
<213> ORGANISM: H. sapiens

<400> SEQUENCE: 160
ttggcagaca agtgccattt                                              20

<210> SEQ ID NO 161
<211> LENGTH: 20
<212> TYPE: DNA
<213> ORGANISM: H. sapiens

<400> SEQUENCE: 161
gacaagtgcc attttaataa                                              20

<210> SEQ ID NO 162
<211> LENGTH: 20
<212> TYPE: DNA
<213> ORGANISM: Artificial Sequence
<220> FEATURE:
<223> OTHER INFORMATION: Antisense Compound

<400> SEQUENCE: 162
cttctggcat ccggtttaga                                              20

<210> SEQ ID NO 163
<211> LENGTH: 20
<212> TYPE: RNA
<213> ORGANISM: Artificial Sequence
<220> FEATURE:
<223> OTHER INFORMATION: Antisense Compound

<400> SEQUENCE: 163
ucaccucagc auacaccggc                                              20

<210> SEQ ID NO 164
<211> LENGTH: 18
<212> TYPE: RNA
<213> ORGANISM: Artificial Sequence
<220> FEATURE:
<223> OTHER INFORMATION: Antisense Compound

<400> SEQUENCE: 164
auuacaccag uucguccc                                                18

<210> SEQ ID NO 165
<211> LENGTH: 18
<212> TYPE: RNA
<213> ORGANISM: Artificial Sequence
<220> FEATURE:
<223> OTHER INFORMATION: Sense Compound

<400> SEQUENCE: 165
uaaugugguc aagcaggg                                                18

<210> SEQ ID NO 166
<211> LENGTH: 21
<212> TYPE: DNA
<213> ORGANISM: Artificial Sequence
<220> FEATURE:
<223> OTHER INFORMATION: Antisense Compound
<220> FEATURE:
<221> NAME/KEY: misc_feature
<222> LOCATION: (1)...(19)
<223> OTHER INFORMATION: bases at these positions are RNA

<400> SEQUENCE: 166
```

```
ctggccttca gagacaccgt t                                              21
```

<210> SEQ ID NO 167
<211> LENGTH: 21
<212> TYPE: DNA
<213> ORGANISM: Artificial Sequence
<220> FEATURE:
<223> OTHER INFORMATION: Sense Compound
<220> FEATURE:
<221> NAME/KEY: misc_feature
<222> LOCATION: (1)...(19)
<223> OTHER INFORMATION: bases at these positions are RNA

<400> SEQUENCE: 167

```
cggtguctct gaaggccagt t                                              21
```

<210> SEQ ID NO 168
<211> LENGTH: 21
<212> TYPE: RNA
<213> ORGANISM: Artificial Sequence
<220> FEATURE:
<223> OTHER INFORMATION: Antisense Compound

<400> SEQUENCE: 168

```
ucucauguuc gaugcuggcu g                                              21
```

<210> SEQ ID NO 169
<211> LENGTH: 21
<212> TYPE: RNA
<213> ORGANISM: Artificial Sequence
<220> FEATURE:
<223> OTHER INFORMATION: Sense Compound

<400> SEQUENCE: 169

```
gccagcaucg aacaugagac g                                              21
```

<210> SEQ ID NO 170
<211> LENGTH: 21
<212> TYPE: RNA
<213> ORGANISM: Artificial Sequence
<220> FEATURE:
<223> OTHER INFORMATION: Antisense Compound

<400> SEQUENCE: 170

```
ugggacggaa ggcauucugg a                                              21
```

<210> SEQ ID NO 171
<211> LENGTH: 22
<212> TYPE: RNA
<213> ORGANISM: Artificial Sequence
<220> FEATURE:
<223> OTHER INFORMATION: Sense Compound

<400> SEQUENCE: 171

```
ccagaaugcc uuccguccca uu                                             22
```

<210> SEQ ID NO 172
<211> LENGTH: 21
<212> TYPE: DNA
<213> ORGANISM: Artificial Sequence
<220> FEATURE:
<223> OTHER INFORMATION: Antisense Compound
<220> FEATURE:
<221> NAME/KEY: misc_feature
<222> LOCATION: (1)...(19)
<223> OTHER INFORMATION: bases at these positions are RNA

```
<400> SEQUENCE: 172
caaatccaga ggctagcagt t                                              21

<210> SEQ ID NO 173
<211> LENGTH: 21
<212> TYPE: DNA
<213> ORGANISM: Artificial Sequence
<220> FEATURE:
<223> OTHER INFORMATION: Sense Compound
<220> FEATURE:
<221> NAME/KEY: misc_feature
<222> LOCATION: (1)...(19)
<223> OTHER INFORMATION: bases at these positions are RNA

<400> SEQUENCE: 173
ctgctagcct ctggatttgt t                                              21

<210> SEQ ID NO 174
<211> LENGTH: 19
<212> TYPE: DNA
<213> ORGANISM: Artificial Sequence
<220> FEATURE:
<223> OTHER INFORMATION: Antisense Compound

<400> SEQUENCE: 174
ctgctagcct ctggatttg                                                 19

<210> SEQ ID NO 175
<211> LENGTH: 20
<212> TYPE: DNA
<213> ORGANISM: Artificial Sequence
<220> FEATURE:
<223> OTHER INFORMATION: Antisense Compound

<400> SEQUENCE: 175
tccgtcatcg ctcctcaggg                                                20

<210> SEQ ID NO 176
<211> LENGTH: 21
<212> TYPE: DNA
<213> ORGANISM: Artificial Sequence
<220> FEATURE:
<223> OTHER INFORMATION: Antisense Compound

<400> SEQUENCE: 176
gcccacaccg acggcgccca c                                              21

<210> SEQ ID NO 177
<211> LENGTH: 17
<212> TYPE: DNA
<213> ORGANISM: Artificial Sequence
<220> FEATURE:
<223> OTHER INFORMATION: Antisense Compound

<400> SEQUENCE: 177
ccacaccgac ggcgccc                                                   17

<210> SEQ ID NO 178
<211> LENGTH: 21
<212> TYPE: DNA
<213> ORGANISM: Artificial Sequence
<220> FEATURE:
<223> OTHER INFORMATION: Antisense Compound
<220> FEATURE:
<221> NAME/KEY: misc_feature
<222> LOCATION: (1)...(19)
<223> OTHER INFORMATION: bases at these positions are RNA
```

<400> SEQUENCE: 178
gcccacaccg acggcgccct t                                              21

<210> SEQ ID NO 179
<211> LENGTH: 21
<212> TYPE: DNA
<213> ORGANISM: Artificial Sequence
<220> FEATURE:
<223> OTHER INFORMATION: Antisense Compound
<220> FEATURE:
<221> NAME/KEY: misc_feature
<222> LOCATION: (1)...(19)
<223> OTHER INFORMATION: bases at these positions are RNA

<400> SEQUENCE: 179
gggcgccgtc ggtgtgggct t                                              21

<210> SEQ ID NO 180
<211> LENGTH: 20
<212> TYPE: RNA
<213> ORGANISM: Artificial Sequence
<220> FEATURE:
<223> OTHER INFORMATION: Antisense Compound

<400> SEQUENCE: 180
uuugucucug guccuuacuu                                                20

<210> SEQ ID NO 181
<211> LENGTH: 20
<212> TYPE: DNA
<213> ORGANISM: Artificial Sequence
<220> FEATURE:
<223> OTHER INFORMATION: Antisense Compound

<400> SEQUENCE: 181
atccctttct tccgcatgtg                                                20

<210> SEQ ID NO 182
<211> LENGTH: 20
<212> TYPE: DNA
<213> ORGANISM: Artificial Sequence
<220> FEATURE:
<223> OTHER INFORMATION: Antisense Compound

<400> SEQUENCE: 182
tgtgcctgat tccgtgtgaa                                                20

<210> SEQ ID NO 183
<211> LENGTH: 20
<212> TYPE: DNA
<213> ORGANISM: Artificial Sequence
<220> FEATURE:
<223> OTHER INFORMATION: Antisense Compound

<400> SEQUENCE: 183
ttggaccttc aaattcccag                                                20

<210> SEQ ID NO 184
<211> LENGTH: 20
<212> TYPE: DNA
<213> ORGANISM: Artificial Sequence
<220> FEATURE:
<223> OTHER INFORMATION: Antisense Compound

<400> SEQUENCE: 184

-continued agctgctaat aaacaggctt                                          20

<210> SEQ ID NO 185
<211> LENGTH: 20
<212> TYPE: DNA
<213> ORGANISM: Artificial Sequence
<220> FEATURE:
<223> OTHER INFORMATION: Antisense Compound

<400> SEQUENCE: 185
acacaggcag ggagctggta                                          20

<210> SEQ ID NO 186
<211> LENGTH: 20
<212> TYPE: DNA
<213> ORGANISM: Artificial Sequence
<220> FEATURE:
<223> OTHER INFORMATION: Antisense Compound

<400> SEQUENCE: 186
ggtcatgccc gagtgtatgc                                          20

<210> SEQ ID NO 187
<211> LENGTH: 20
<212> TYPE: DNA
<213> ORGANISM: Artificial Sequence
<220> FEATURE:
<223> OTHER INFORMATION: Antisense Compound

<400> SEQUENCE: 187
aagaccttct tcagcgtact                                          20

<210> SEQ ID NO 188
<211> LENGTH: 20
<212> TYPE: DNA
<213> ORGANISM: Artificial Sequence
<220> FEATURE:
<223> OTHER INFORMATION: Antisense Compound

<400> SEQUENCE: 188
tgtgatttgc caaggactct                                          20

<210> SEQ ID NO 189
<211> LENGTH: 20
<212> TYPE: DNA
<213> ORGANISM: Artificial Sequence
<220> FEATURE:
<223> OTHER INFORMATION: Antisense Compound

<400> SEQUENCE: 189
ttgctttgaa aacttggcca                                          20

<210> SEQ ID NO 190
<211> LENGTH: 20
<212> TYPE: DNA
<213> ORGANISM: Artificial Sequence
<220> FEATURE:
<223> OTHER INFORMATION: Antisense Compound

<400> SEQUENCE: 190
gctgaccttt ttgcttctca                                          20

<210> SEQ ID NO 191
<211> LENGTH: 20
<212> TYPE: DNA
<213> ORGANISM: Artificial Sequence

```
<220> FEATURE:
<223> OTHER INFORMATION: Antisense Compound

<400> SEQUENCE: 191
cttgaaaaca gttagccagc                                               20

<210> SEQ ID NO 192
<211> LENGTH: 20
<212> TYPE: DNA
<213> ORGANISM: Artificial Sequence
<220> FEATURE:
<223> OTHER INFORMATION: Antisense Compound

<400> SEQUENCE: 192
cagcataaaa tgggcacttt                                               20

<210> SEQ ID NO 193
<211> LENGTH: 20
<212> TYPE: DNA
<213> ORGANISM: Artificial Sequence
<220> FEATURE:
<223> OTHER INFORMATION: Antisense Compound

<400> SEQUENCE: 193
ttgtgaaatc atgtgcagtt                                               20

<210> SEQ ID NO 194
<211> LENGTH: 20
<212> TYPE: DNA
<213> ORGANISM: Artificial Sequence
<220> FEATURE:
<223> OTHER INFORMATION: Antisense Compound

<400> SEQUENCE: 194
cagaatttga tacccagca                                                20

<210> SEQ ID NO 195
<211> LENGTH: 20
<212> TYPE: DNA
<213> ORGANISM: Artificial Sequence
<220> FEATURE:
<223> OTHER INFORMATION: Antisense Compound

<400> SEQUENCE: 195
caatgctttc tttagtgcca                                               20

<210> SEQ ID NO 196
<211> LENGTH: 20
<212> TYPE: DNA
<213> ORGANISM: Artificial Sequence
<220> FEATURE:
<223> OTHER INFORMATION: Antisense Compound

<400> SEQUENCE: 196
gcacctcgac gggcagtccc                                               20

<210> SEQ ID NO 197
<211> LENGTH: 20
<212> TYPE: DNA
<213> ORGANISM: Artificial Sequence
<220> FEATURE:
<223> OTHER INFORMATION: Antisense Compound

<400> SEQUENCE: 197
aagaagagtt acccattcca                                               20
```

<210> SEQ ID NO 198
<211> LENGTH: 20
<212> TYPE: DNA
<213> ORGANISM: Artificial Sequence
<220> FEATURE:
<223> OTHER INFORMATION: Antisense Compound

<400> SEQUENCE: 198
agtgaatgag cctcaggtaa                                                    20

<210> SEQ ID NO 199
<211> LENGTH: 20
<212> TYPE: DNA
<213> ORGANISM: Artificial Sequence
<220> FEATURE:
<223> OTHER INFORMATION: Antisense Compound

<400> SEQUENCE: 199
aatttctatg caagctgctt                                                    20

<210> SEQ ID NO 200
<211> LENGTH: 20
<212> TYPE: DNA
<213> ORGANISM: Artificial Sequence
<220> FEATURE:
<223> OTHER INFORMATION: Antisense Compound

<400> SEQUENCE: 200
tgctgagtct tttcctcaaa                                                    20

<210> SEQ ID NO 201
<211> LENGTH: 20
<212> TYPE: DNA
<213> ORGANISM: Artificial Sequence
<220> FEATURE:
<223> OTHER INFORMATION: Antisense Compound

<400> SEQUENCE: 201
agtttagcca tagcatcaag                                                    20

<210> SEQ ID NO 202
<211> LENGTH: 20
<212> TYPE: DNA
<213> ORGANISM: Artificial Sequence
<220> FEATURE:
<223> OTHER INFORMATION: Antisense Compound

<400> SEQUENCE: 202
ccatgacttt ttgtggacag                                                    20

<210> SEQ ID NO 203
<211> LENGTH: 20
<212> TYPE: DNA
<213> ORGANISM: Artificial Sequence
<220> FEATURE:
<223> OTHER INFORMATION: Antisense Compound

<400> SEQUENCE: 203
aagcagcctt gacatactga                                                    20

<210> SEQ ID NO 204
<211> LENGTH: 20
<212> TYPE: DNA
<213> ORGANISM: Artificial Sequence
<220> FEATURE:
<223> OTHER INFORMATION: Antisense Compound

```
<400> SEQUENCE: 204
cgcgacagaa taatctcatt                                                20

<210> SEQ ID NO 205
<211> LENGTH: 20
<212> TYPE: DNA
<213> ORGANISM: Artificial Sequence
<220> FEATURE:
<223> OTHER INFORMATION: Antisense Compound

<400> SEQUENCE: 205
tctgcagctg tgacacgtag                                                20

<210> SEQ ID NO 206
<211> LENGTH: 20
<212> TYPE: DNA
<213> ORGANISM: Artificial Sequence
<220> FEATURE:
<223> OTHER INFORMATION: Antisense Compound

<400> SEQUENCE: 206
gtcatcgtca tcctcatcat                                                20

<210> SEQ ID NO 207
<211> LENGTH: 20
<212> TYPE: DNA
<213> ORGANISM: Artificial Sequence
<220> FEATURE:
<223> OTHER INFORMATION: Antisense Compound

<400> SEQUENCE: 207
ttcctccaat ggtgacagtg                                                20

<210> SEQ ID NO 208
<211> LENGTH: 20
<212> TYPE: DNA
<213> ORGANISM: Artificial Sequence
<220> FEATURE:
<223> OTHER INFORMATION: Antisense Compound

<400> SEQUENCE: 208
atccctttct tggctgcctt                                                20

<210> SEQ ID NO 209

<400> SEQUENCE: 209

000

<210> SEQ ID NO 210

<400> SEQUENCE: 210

000

<210> SEQ ID NO 211
<211> LENGTH: 20
<212> TYPE: DNA
<213> ORGANISM: Artificial Sequence
<220> FEATURE:
<223> OTHER INFORMATION: Antisense Compound

<400> SEQUENCE: 211
cctacgtgtg gttctcctta                                                20
```

```
<210> SEQ ID NO 212
<211> LENGTH: 20
<212> TYPE: DNA
<213> ORGANISM: Artificial Sequence
<220> FEATURE:
<223> OTHER INFORMATION: Antisense Compound

<400> SEQUENCE: 212
gccaaggcgt gacatgatat                                                   20

<210> SEQ ID NO 213
<211> LENGTH: 20
<212> TYPE: DNA
<213> ORGANISM: Artificial Sequence
<220> FEATURE:
<223> OTHER INFORMATION: Antisense Compound

<400> SEQUENCE: 213
gaattcattt attaacccat                                                   20

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000
```

```
<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225
<211> LENGTH: 50
<212> TYPE: DNA
<213> ORGANISM: H. sapiens

<400> SEQUENCE: 225
gatttctatg gggaagtaag gaccagagac aaaaagggag taactattcc            50

<210> SEQ ID NO 226
<211> LENGTH: 21
<212> TYPE: DNA
<213> ORGANISM: Artificial Sequence
<220> FEATURE:
<223> OTHER INFORMATION: Antisense Compound
<220> FEATURE:
<221> NAME/KEY: misc_feature
<222> LOCATION: (1)...(19)
<223> OTHER INFORMATION: bases at these positions are RNA

<400> SEQUENCE: 226
agtaaggacc agagacaaat t                                           21

<210> SEQ ID NO 227
<211> LENGTH: 21
<212> TYPE: DNA
<213> ORGANISM: Artificial Sequence
<220> FEATURE:
<223> OTHER INFORMATION: Sense Compound
<220> FEATURE:
<221> NAME/KEY: misc_feature
<222> LOCATION: (1)...(19)
<223> OTHER INFORMATION: bases at these positions are RNA

<400> SEQUENCE: 227
tttgtctctg gtccttactt t                                           21

<210> SEQ ID NO 228
<211> LENGTH: 20
<212> TYPE: RNA
<213> ORGANISM: Artificial Sequence
<220> FEATURE:
<223> OTHER INFORMATION: Antisense Compound

<400> SEQUENCE: 228
uuugucucug guccuuacuu                                             20

<210> SEQ ID NO 229
<211> LENGTH: 20
```

-continued

```
<212> TYPE: RNA
<213> ORGANISM: Artificial Sequence
<220> FEATURE:
<223> OTHER INFORMATION: Sense Compound

<400> SEQUENCE: 229
aaguaaggac cagagacaaa                                               20

<210> SEQ ID NO 230
<211> LENGTH: 21
<212> TYPE: DNA
<213> ORGANISM: Artificial Sequence
<220> FEATURE:
<223> OTHER INFORMATION: Antisense Compound
<220> FEATURE:
<221> NAME/KEY: misc_feature
<222> LOCATION: (1)...(9)
<223> OTHER INFORMATION: bases at these positions are RNA

<400> SEQUENCE: 230
tcccgcctgt gacatgcatt t                                             21

<210> SEQ ID NO 231
<211> LENGTH: 21
<212> TYPE: DNA
<213> ORGANISM: Artificial Sequence
<220> FEATURE:
<223> OTHER INFORMATION: Sense Compound
<220> FEATURE:
<221> NAME/KEY: misc_feature
<222> LOCATION: (1)...(19)
<223> OTHER INFORMATION: bases at these positions are RNA

<400> SEQUENCE: 231
atgcatgtca caggcgggat t                                             21

<210> SEQ ID NO 232
<211> LENGTH: 3600
<212> TYPE: DNA
<213> ORGANISM: H. sapiens
<220> FEATURE:
<221> NAME/KEY: CDS
<222> LOCATION: (74)...(3100)

<400> SEQUENCE: 232 cacgagggc ttccgggccc ggacgccatt tccagcggtt gctggttctg acgggttgta      60
gtctgccagg aca atg agt tat gac tac cat cag aac tgg ggc cgt gat      109
            Met Ser Tyr Asp Tyr His Gln Asn Trp Gly Arg Asp
              1               5                  10 ggg ggt ccc cgc agc tcc ggt ggg ggc tat gga ggg ggg cca gca ggg      157
Gly Gly Pro Arg Ser Ser Gly Gly Gly Tyr Gly Gly Gly Pro Ala Gly
             15                  20                  25 ggt cat gga ggt aac cga ggc tcc gga gga ggc ggc ggc gga ggg          205
Gly His Gly Gly Asn Arg Gly Ser Gly Gly Gly Gly Gly Gly Gly
         30                  35                  40 ggt ggt cga ggc ggc agg ggc cgg cat ccc ggg cac ctg aaa ggc cgc      253
Gly Gly Arg Gly Gly Arg Gly Arg His Pro Gly His Leu Lys Gly Arg
 45                  50                  55                  60 gaa atc ggc atg tgg tac gcg aaa aaa cag ggg cag aag aac aag gaa      301
Glu Ile Gly Met Trp Tyr Ala Lys Lys Gln Gly Gln Lys Asn Lys Glu
                 65                  70                  75 gcg gag agg caa gag aga gct gta gta cac atg gat gaa cga cga gaa      349
Ala Glu Arg Gln Glu Arg Ala Val Val His Met Asp Glu Arg Arg Glu
             80                  85                  90 gaa caa att gta cag tta ctg aat tct gtt caa gcg aag aat gat aaa      397
```

```
                Glu Gln Ile Val Gln Leu Leu Asn Ser Val Gln Ala Lys Asn Asp Lys
                             95                 100                 105 gag tca gaa gca cag ata tcc tgg ttt gct cct gag gat cat gga tac          445
Glu Ser Glu Ala Gln Ile Ser Trp Phe Ala Pro Glu Asp His Gly Tyr
    110                 115                 120 ggt act gaa gtt tct act aag aac aca cca tgc tca gag aac aaa ctt          493
Gly Thr Glu Val Ser Thr Lys Asn Thr Pro Cys Ser Glu Asn Lys Leu
125                 130                 135                 140 gac atc cag gaa aag aag ttg ata aat caa gaa aaa aaa atg ttt aga          541
Asp Ile Gln Glu Lys Lys Leu Ile Asn Gln Glu Lys Lys Met Phe Arg
                145                 150                 155 atc agg aac aga tca tat att gac cga gat tct gag tat ctc ttg caa          589
Ile Arg Asn Arg Ser Tyr Ile Asp Arg Asp Ser Glu Tyr Leu Leu Gln
                160                 165                 170 gaa aat gaa cca gat gga act tta gac caa aaa tta ttg gaa gat tta          637
Glu Asn Glu Pro Asp Gly Thr Leu Asp Gln Lys Leu Leu Glu Asp Leu
            175                 180                 185 caa aag aaa aaa aat gac ctt cgg tat att gaa atg cag cat ttc aga          685
Gln Lys Lys Lys Asn Asp Leu Arg Tyr Ile Glu Met Gln His Phe Arg
        190                 195                 200 gaa aag ctg cct tcg tat gga atg caa aag gaa ttg gta aat tta att          733
Glu Lys Leu Pro Ser Tyr Gly Met Gln Lys Glu Leu Val Asn Leu Ile
205                 210                 215                 220 gat aac cat cag gta aca gta ata agt ggt gaa act ggt tgt ggc aaa          781
Asp Asn His Gln Val Thr Val Ile Ser Gly Glu Thr Gly Cys Gly Lys
                225                 230                 235 acc act caa gtt act cag ttc att ttg gat aac tac att gaa aga gga          829
Thr Thr Gln Val Thr Gln Phe Ile Leu Asp Asn Tyr Ile Glu Arg Gly
                240                 245                 250 aaa gga tct gct tgc aga ata gtt tgt act cag cca aga aga att agt          877
Lys Gly Ser Ala Cys Arg Ile Val Cys Thr Gln Pro Arg Arg Ile Ser
            255                 260                 265 gcc att tca gtt gcg gaa aga gta gct gca gaa agg gca gaa tct tgt          925
Ala Ile Ser Val Ala Glu Arg Val Ala Ala Glu Arg Ala Glu Ser Cys
        270                 275                 280 ggc agt ggt aat agt act gga tat caa att cgt ctc cag agt cgg ttg          973
Gly Ser Gly Asn Ser Thr Gly Tyr Gln Ile Arg Leu Gln Ser Arg Leu
285                 290                 295                 300 cca agg aaa cag ggt tct atc tta tac tgt aca aca gga atc atc ctt         1021
Pro Arg Lys Gln Gly Ser Ile Leu Tyr Cys Thr Thr Gly Ile Ile Leu
                305                 310                 315 cag tgg ctc cag tca gac ccg tat ttg tcc agt gtt agt cat atc gta         1069
Gln Trp Leu Gln Ser Asp Pro Tyr Leu Ser Ser Val Ser His Ile Val
                320                 325                 330 ctt gat gaa atc cat gaa aga aat ctg cag tca gat gtt tta atg act         1117
Leu Asp Glu Ile His Glu Arg Asn Leu Gln Ser Asp Val Leu Met Thr
            335                 340                 345 gtt gtt aaa gac ctt ctc aat ttt cga tct gac ttg aaa gta ata ttg         1165
Val Val Lys Asp Leu Leu Asn Phe Arg Ser Asp Leu Lys Val Ile Leu
        350                 355                 360 atg agt gca aca ttg aat gca gaa aag ttt tca gaa tat ttt ggt aac         1213
Met Ser Ala Thr Leu Asn Ala Glu Lys Phe Ser Glu Tyr Phe Gly Asn
365                 370                 375                 380 tgt cca atg ata cat ata cct ggt ttt acc ttt ccg gtt gtg gaa tat         1261
Cys Pro Met Ile His Ile Pro Gly Phe Thr Phe Pro Val Val Glu Tyr
                385                 390                 395 ctt ttg gaa gat gta att gaa aaa ata agg tat gtt cca gaa caa aaa         1309
Leu Leu Glu Asp Val Ile Glu Lys Ile Arg Tyr Val Pro Glu Gln Lys
                400                 405                 410
```

```
                                                        -continued gaa cac aga tgc cag ttt aag agg ggt ttc atg caa ggg cat gta aat       1357
Glu His Arg Cys Gln Phe Lys Arg Gly Phe Met Gln Gly His Val Asn
        415                 420                 425 aga caa gaa aaa gaa gaa aaa gaa gca ata tat aaa gaa cgt tgg cca       1405
Arg Gln Glu Lys Glu Glu Lys Glu Ala Ile Tyr Lys Glu Arg Trp Pro
    430                 435                 440 gat tat gta agg gaa ctg cga aga agg tat tct gca agt act gta gat       1453
Asp Tyr Val Arg Glu Leu Arg Arg Arg Tyr Ser Ala Ser Thr Val Asp
445                 450                 455                 460 gtt ata gaa atg atg gag gat gat aaa gtt gat ctg aat ttg att gtt       1501
Val Ile Glu Met Met Glu Asp Asp Lys Val Asp Leu Asn Leu Ile Val
            465                 470                 475 gcc ctc atc cga tac att gtt ttg gaa gaa gag gat ggt gcg ata ctg       1549
Ala Leu Ile Arg Tyr Ile Val Leu Glu Glu Glu Asp Gly Ala Ile Leu
        480                 485                 490 gtc ttt ctg cca ggc tgg gac aat atc agc act tta cat gat ctc ttg       1597
Val Phe Leu Pro Gly Trp Asp Asn Ile Ser Thr Leu His Asp Leu Leu
    495                 500                 505 atg tca caa gta atg ttt aaa tca gat aaa ttt tta att ata cct tta       1645
Met Ser Gln Val Met Phe Lys Ser Asp Lys Phe Leu Ile Ile Pro Leu
510                 515                 520 cat tca ctg atg cct aca gtt aac cag aca cag gtg ttt aaa aga acc       1693
His Ser Leu Met Pro Thr Val Asn Gln Thr Gln Val Phe Lys Arg Thr
525                 530                 535                 540 cct cct ggt gtt cgg aaa ata gta att gct acc aac att gcg gag act       1741
Pro Pro Gly Val Arg Lys Ile Val Ile Ala Thr Asn Ile Ala Glu Thr
            545                 550                 555 agc att acc ata gat gat gtc gtt tat gtg ata gat gga gga aaa ata       1789
Ser Ile Thr Ile Asp Asp Val Val Tyr Val Ile Asp Gly Gly Lys Ile
        560                 565                 570 aaa gag acg cat ttt gat act cag aac aat atc agt aca atg tcc gct       1837
Lys Glu Thr His Phe Asp Thr Gln Asn Asn Ile Ser Thr Met Ser Ala
    575                 580                 585 gag tgg gtt agt aaa gct aat gcc aaa cag aga aaa ggt cga gct gga       1885
Glu Trp Val Ser Lys Ala Asn Ala Lys Gln Arg Lys Gly Arg Ala Gly
590                 595                 600 aga gtt caa cct ggt cat tgc tat cat ctg tat aat ggt ctt aga gca       1933
Arg Val Gln Pro Gly His Cys Tyr His Leu Tyr Asn Gly Leu Arg Ala
605                 610                 615                 620 agt ctt cta gat gac tat caa ctg cca gaa att ttg aga act cct ttg       1981
Ser Leu Leu Asp Asp Tyr Gln Leu Pro Glu Ile Leu Arg Thr Pro Leu
            625                 630                 635 gaa gaa ctt tgt tta caa ata aag att tta agg cta gga gga att gct       2029
Glu Glu Leu Cys Leu Gln Ile Lys Ile Leu Arg Leu Gly Gly Ile Ala
        640                 645                 650 tat ttt ctg agt aga tta atg gac cca cca tca aat gag gca gtg tta       2077
Tyr Phe Leu Ser Arg Leu Met Asp Pro Pro Ser Asn Glu Ala Val Leu
    655                 660                 665 ctc tcc ata aga cac ctg atg gag ctg aac gct ttg gat aaa caa gaa       2125
Leu Ser Ile Arg His Leu Met Glu Leu Asn Ala Leu Asp Lys Gln Glu
670                 675                 680 gaa ttg aca cct ctt gga gtc cac ttg gca cga tta ccc gtt gag cca       2173
Glu Leu Thr Pro Leu Gly Val His Leu Ala Arg Leu Pro Val Glu Pro
685                 690                 695                 700 cat att gga aaa atg att ctt ttt gga gca ctg ttc tgc tgc tta gac       2221
His Ile Gly Lys Met Ile Leu Phe Gly Ala Leu Phe Cys Cys Leu Asp
            705                 710                 715 cca gta ctc act att gct gct agt ctc agt ttc aaa gat cca ttt gtc       2269
Pro Val Leu Thr Ile Ala Ala Ser Leu Ser Phe Lys Asp Pro Phe Val
        720                 725                 730
```

```
att cca ctg gga aaa gaa aag att gca gat gca aga aga aag gaa ttg      2317
Ile Pro Leu Gly Lys Glu Lys Ile Ala Asp Ala Arg Arg Lys Glu Leu
        735                 740                 745 gca aag gat act aga agt gat cac tta aca gtt gtg aat gcg ttt gag      2365
Ala Lys Asp Thr Arg Ser Asp His Leu Thr Val Val Asn Ala Phe Glu
750                 755                 760 ggc tgg gaa gag gct agg cga cgt ggt ttc aga tac gaa aag gac tat      2413
Gly Trp Glu Glu Ala Arg Arg Arg Gly Phe Arg Tyr Glu Lys Asp Tyr
765                 770                 775                 780 tgc tgg gaa tat ttt ctg tct tca aac aca ctg cag atg ctg cat aac      2461
Cys Trp Glu Tyr Phe Leu Ser Ser Asn Thr Leu Gln Met Leu His Asn
                785                 790                 795 atg aaa gga cag ttt gct gag cat ctt ctt gga gct gga ttt gta agc      2509
Met Lys Gly Gln Phe Ala Glu His Leu Leu Gly Ala Gly Phe Val Ser
            800                 805                 810 agt aga aat cct aaa gat cca gaa tct aat ata aat tca gat aat gag      2557
Ser Arg Asn Pro Lys Asp Pro Glu Ser Asn Ile Asn Ser Asp Asn Glu
        815                 820                 825 aag ata att aaa gct gtc atc tgt gct ggt tta tat ccc aaa gtt gct      2605
Lys Ile Ile Lys Ala Val Ile Cys Ala Gly Leu Tyr Pro Lys Val Ala
830                 835                 840 aaa att cga cta aat ttg ggt aaa aaa aga aaa atg gta aaa gtt tac      2653
Lys Ile Arg Leu Asn Leu Gly Lys Lys Arg Lys Met Val Lys Val Tyr
845                 850                 855                 860 aca aaa acc gat ggc ctg gtt gct gtt cat cct aaa tct gtt aat gtg      2701
Thr Lys Thr Asp Gly Leu Val Ala Val His Pro Lys Ser Val Asn Val
                865                 870                 875 gag caa aca gac ttt cac tac aac tgg ctt atc tat cac cta aag atg      2749
Glu Gln Thr Asp Phe His Tyr Asn Trp Leu Ile Tyr His Leu Lys Met
            880                 885                 890 aga aca agc agt ata tac ttg tat gac tgc aca gag gtt tcc cca tac      2797
Arg Thr Ser Ser Ile Tyr Leu Tyr Asp Cys Thr Glu Val Ser Pro Tyr
        895                 900                 905 tgt ctc ttg ttt ttt gga ggt gac att tcc atc cag aag gat aac gat      2845
Cys Leu Leu Phe Phe Gly Gly Asp Ile Ser Ile Gln Lys Asp Asn Asp
910                 915                 920 cag gaa act att gct gta gat gag tgg att gta ttt cag tct cca gca      2893
Gln Glu Thr Ile Ala Val Asp Glu Trp Ile Val Phe Gln Ser Pro Ala
925                 930                 935                 940 aga att gcc cat ctt gtt aag gaa tta aga aag gaa cta gat att ctt      2941
Arg Ile Ala His Leu Val Lys Glu Leu Arg Lys Glu Leu Asp Ile Leu
                945                 950                 955 ctg caa gag aag att gaa agt cct cat cct gta gac tgg aat gac act      2989
Leu Gln Glu Lys Ile Glu Ser Pro His Pro Val Asp Trp Asn Asp Thr
            960                 965                 970 aaa tcc aga gac tgt gca gta ctg tca gct att ata gac ttg atc aaa      3037
Lys Ser Arg Asp Cys Ala Val Leu Ser Ala Ile Ile Asp Leu Ile Lys
        975                 980                 985 aca cag gaa aag gca act ccc agg aac ttt ccg cca cga ttc cag gat      3085
Thr Gln Glu Lys Ala Thr Pro Arg Asn Phe Pro Pro Arg Phe Gln Asp
    990                 995                 1000 gga tat tac agc tga cagcttttca ggggtggtct gaaaagccag tttgacagcc      3140
Gly Tyr Tyr Ser *
1005 attcttcatc attgtttaaa ttttggctgg atgccaaacc ctgggacatg aacaattttc    3200 atgtgtaagg tagaagcctt cagtaggtag taaagactta atgtgcatga cttgatgtta    3260 tatgtagaga tatatatata tatatatata ccataaaagc aatatgttct ctgatcatat    3320
```

```
actctgctgt ggtcatgccc actctttggg agtatattcc ctttatatat attgagtatt    3380
gtaccacttg agaaattcct tgttctgtt atacaaaatt aatctttctg ctcataatga    3440
ttgatgatac caccagtaaa ataggatgt ttaccccaaa acaagtgtca attaagaatt    3500
tgaacacaac cacattttt aaaatgaaac ttctatcgga agtaaattaa tttgttgtaa    3560
taaagtccag tatttaataa aatgtacaat gttaaatctc                        3600
```

<210> SEQ ID NO 233
<211> LENGTH: 49620
<212> TYPE: DNA
<213> ORGANISM: H. sapiens

<400> SEQUENCE: 233

```
tagttgtcag gctgttttca agactagaag aactcatttt ttagagactt ttctttagaa     60
gacggcgaat tgatccaagg gttcttttgt ttcaatcaac gtttactacc ctaggaccta    120
agtgcaaaaa aactgcggat ttaccaggaa taagaaagta aaaccaaaa gctattggct    180 cacttgctgg gcctagggaa agaaaatcta cgagcctttg gctggctgtt gctccagagg    240
tacaaagata aacaactcgg gggctcagac agaacctgat ccctgccacc ctccagacca    300
ccggggtcgt cctcccgtga cgtcaccaga aaccactgct tgtgacgcta atggcccgc    360 cctcttgtgc ggtgctacgg aagcaaaacg gaagtgggcg cacagtgct tccgggcccg    420 gacgccattt ccagcggttg ctggttctga cgggttgtag tctgccagga caatgagtta    480
tgactaccat cagaactggg gccgtgatgg ggtccccgc agctccggtg ggggctatgg    540
aggggggcca gcaggggtc atggaggtaa ccgaggctcc ggaggaggcg gcggcggcgg    600 aggggtggt cgaggcggca ggggccggca tcccgggcac ctgaaaggcc gcgaaatcgg    660
catgtggtac gcgaaaaaac aggggcagaa gaacaaggaa gcggagaggc aagaggtaat    720
ctcggattca gtagtggaga ggatgaggca gcacaggttt tcttctctct cccgctgccc    780 ccttttttctt ggttttgttt cttaagtgat gcacgtgttt tgtgaaatgt aaatgaggcg    840
caaatatatt atgctggcgc tccccgtagc gggtgtactg cgtaacatta gccatgctca    900
tctgaccaaa aacaggcagg atttatgcag gctgaatata tactttgctt aaaggacttg    960
agaactgtga caaagcaaat gttaagttca cgttccaacc gaaattaact ttattaggag   1020
tgtcgttgtc gtatctctgg ccgtcctttc ccttagaata ataattgtca ctttaaggtc   1080
tttgcctggt gaagaagcac atagcgacct ttctacattt gagataggtt tgcgcggaac   1140
aaaagcaggc agacactgtt ttggatgtgg atcattcaga aaaatagtcc agctttttatt  1200 attagtgtta aaattatctg caaacctagg ttttgtttt ttatgttggg gtggagaaat    1260
ttctattgat gagcagattc tctttgaaaa ggaaaatgaa aggaatctcc agagatgatt   1320
tggcttactc tcctctcttc aggtgattgt caggttgatt tgtgtcttaa agatctgtag   1380
taagggaaac aaagttctcc gagtgactag taaataaaat tctaataaaa aataatttt   1440 atcattaagc aggaactttc ttagtatagg cctttggtga cttttttaaaa gcaccttata  1500 aaatgtatta tagagtgtaa ttagatcatc atttaggcaa ctttttttt ttttaagaca   1560 gggtctcact ctgtcgccca ggctggagtg cagtggcacg atcttagctc actgcaacct   1620
ccgcctccca agttcaagcg attctcctgc ttcagcctcc cgagtagctg ggattacagg   1680
cgtccgccac cacctccggc taattttgt atttttagta gagacggggt ttcaccatgt    1740
tggccaggtt ggtctcgaac tcctgacctc aggtgatcca cccaactcgg cctcccaaag   1800
tgctgggatt acaggcgtga gccaccacgc caggcctaga ctactatttt taaaccgttc   1860
```

```
catttctttt tatttctttt aaccatgtca tgttcattca ggtgttttgg gggccttatc   1920
catttatctt cataatttaa acttttcttt aaaaaacaaa tccatttctt ttacagcccc   1980
aaattaactt tttcgttggg catactggct tgaaaatcag gatacggacg tctaagtaac   2040
tttacaactt ttatttatta aggctctgtt tgaaacaagg ttttatgcat attgctccag   2100
ggacttgaag aaatgtggta ttcaaagagc ttacagtcta gctgagaaaa taatacctaa   2160
acagatgaaa agttaaataa gtcaggaaaa aatgttcatt attgtttcca catgaagggt   2220
atagccagtg tgcagtggga tgttatgaat ggaacttttc atttctactt gcgttcccat   2280
cctccttta gtggtgacac gaccatttat tcacttggca aggccaaatg agatttatct   2340
ttgcttcttc cccttcattt cagcaaatct ctgccttgtt aatatatccc aatctaacca   2400
cttacctcca gaatagttac catagatcaa gccactgttt gttttctgtt cttgccttct   2460
aactagtcat ctagcttcca ttcttgctct gcattgtctg tgctttacag agccgcctat   2520
ggtgatcttt taaaaggaaa aattagatca ttttattacc taattcacaa cttcagattg   2580
gaagtcatgt cacttctgtc tcagtctgat atatttcagt tgcatcttga catgttctct   2640
ggaaatcttg gtaatacggc ttcaacgtaa caggtttacc gctgtgcaca tttctctgag   2700
cccatgtctc cagtctgata taattatagt tttttaggc atactttatt tttacttttc   2760
attacagtgt catactgttc tcctgtccaa aatgtacctt tctttcttgt ttaaatagga   2820
gtatttttca atgggctcgt cccagctctt ctttgaccac ctttagcttg atatcattgt   2880
ttcccagtca gaatttcggt agctttcact tttaaagtca tgtcatgtgt tttcaaaatg   2940
aagactttt tttttttttt ttgagttgga gtctcactct gttgcccagt ctggagtgca   3000
gtggtgtgat ctcggctcac tgcaccctct gcttcctgag tagctgagat tacgggtgtg   3060
caccaccaca cttggctaat ttttgtattt ttagaagaga cagggttttg ccatgttggc   3120
caggctggtc ttgagctcct gacctcaggt gatccaccag ccctggcctc ccaaagtgct   3180
gggattacag gcgtgagcca tggcgcctgg ctgaaaatga atgcattcta atgatgcatt   3240
cttgaacaaa tgttctttca acaaatattt attgaggaca ttattttgt gacagtatct   3300
taagcactgt attaattaat aaaatagata taggctctac agagattgtg gtgtgtttgg   3360
agcgataaat agaatacagt attaaggtat tagagaatat gggctatcac ctaactcagg   3420
gcaaggtatt ttagaagatt tttcagggac agtaacccctt aagttgaaac ttgaaagata   3480
acaaagtgaa tgtacgtgtg tgtgtttgaa gtttggggtt tggaaaagat tccaggcaaa   3540
ggcagtagca tgtgccataa catagagatc aaggaagcac attttcagtt cgagaaactg   3600
taaaagataa gaacatggat gtggagtgta ttgagatgag gttagggcag tcaatttcaa   3660
acttgttggc cactttgccc aaaaaggaat gtatttgaat ttacaaccca gtacacacat   3720
atgtataact agatgaaaag ttttgtaaaa taatatttaa ttatctgcac attgctttga   3780
ggttttttg cttttgaact tctctgttct cttttttatta atgctggtca tgatcccttta   3840
atataatttc agaaacagca atttgaaaat ctctgggcta gaaaaatacg cggggccttg   3900
agatacattg agtctttcta aggactgtag caagtcatta aaacatttta aacaaagaat   3960
gaaatgactg gattttaaat gtttaaattc actctggtag cagtataagg aatggattga   4020
agagaggtaa tcctggttca ggggggaccag tgaagtagcc cttgcagtaa ctaaggtgag   4080
aaatgacagc ttgaattagc acgttggcag tggagatgga ggggagtgga cagattaaag   4140
tgatttagga ggtagactca aaatgatttt gtgatgtatt ttatctgaag ggacgagtac   4200
```

```
agtgttaatg atgactcttt tatgcctatc tgtaaggatc aggcttgttg gaagaaggct    4260
cagctatgga cactatgagt ttgatattgt tatagggcat acaaatgagg atttgcagga    4320
gggagagggc tgtgtagatc tgatgcctag aaaaatctag actggagata agtatttgac    4380
agttaatggg ctcatgggta gtagttggag tgtgggagtg aacagtcaga aatagagtgg    4440
gcccagcctg aattctatag accattgctt ctcagacttg aatgtgcata ggaatcacct    4500
gacatcttgt taaaatgtag gacactgatg ggatcagaga ttcgactttt gttacaggct    4560
cccaggtgat gccagtgttg ctggtctgta gatcactcag gctgtcaaat acggaaaatg    4620
aaaatttaag gacaggctga ggaaaagaag gttacaaaat aatctaggaa agatcagcta    4680
gagaagagaa aaataaggtg tgtgttgttt tgaaatctaa gagtagtgtt taaaggagag    4740
aagagcgtat caacaagaag taattgatag tggcaagcat gcacaaatga tgtaagagca    4800
gagaatgtct attggattta tcaacaaggt cgttgatgat cttaatggga gtcctttctg    4860
tggcattgtg gaagtaaaag ccagattgcg gtagggtggc aagtgaaaca gagattcaga    4920
agtggaacat tttccagtag ttttgctgtg aagatgagga agaaaaatag tgccgtagct    4980
gataggggta ggggaattca cgagagggtt ttttgttttt aaggtgaaga gatttgacca    5040
tgttcatgcc ctgagggaag cacccagtga agaggaaatc aaagtgggca aatcaaagtg    5100
ggccaaatta tgctgcagta ataaccaacc cccaaatctt aatggtttat aacaagcaag    5160
gtttgattct ctaccacatt actaaaagaa gcaaaccaga atatcggttg actgcctaat    5220
gtctactgga gaggttagaa atttaggaaa gcaaggtaaa tttcagtgaa ggaggtggcc    5280
ctgaggacat gaaaggaact ggactgcaga gctcaggttg aggggttagc ctttaaaatg    5340
cacttctttt ataacaagaa agaaaagaga aaaggataaa ttctgataca ggcgggttta    5400
ggtttggtga taaccaactg aggacctttt cttagggctt ttgttttgtg aaaaactgcg    5460
tgtgaatgct gagggcaaac aaaagggtgg tattggcctg ttacagagaa tggggagaca    5520
gtgtgaagta gttgcagata attagaaagc tgataacata aatttgatgg acatcattta    5580
gggtttcttg ccaggaactg aaaactagaa gcagggtatt tgagaatgtc caagaaagtg    5640
ggaaataatc aaaattctat gataaaagaa aatagtcatg aaaaaaatgt gttttgagat    5700
tctccaggca aggagtgaaa taaagtgaag cgtggtagaa ctagaagaag gttgttgagg    5760
gggagagagg catcctacaa aaaggcaaga tccaagtttg gaattaaggt atgttctctg    5820
ctacctgcag catccagaaa ctcattgtgg ggagaacatc attaaaaata caaatgtttt    5880
tatttagagt gtaaattaca ttttcaaggg ctaatcatac atgctcattg taaaagattc    5940
agctgttcat tccttccatt gacagacttc tctggggcac ataccatgta ccagaattat    6000
atctggcaga gacactgcaa gaagtatagg atatggagag tgaataacct cttttcaaat    6060
taatagtaat aaaaacaaga tcctactaca caactgactt atttaatact ttggtcatct    6120
ttcctgttta tatacttgca gaaagatcta cccactgtta accactgggt gtactacaat    6180
tcaactaatt ccttattgat tagcagatgc ttacttggta catatgcatt gtgtaaggta    6240
tcttaaagtc taccaactga tgttgacttt ttaatgaaaa tgaattttgt tgtgatagtt    6300
tggactggaa gattgtgtag atctgtttat tttcagtaga ctgttatgtt atccagtaat    6360
tcaccttttc cggggcgtg aaatctcata aaattagaat aatctttgt gctgttacgg    6420 gcaggaagtg ggcaatgtat tgtgaaatgt caatctagga aattgtttac taaacaaaat    6480
atagagtaat gagttaacat ggaaaagtga gaactgtagg aatagcagat ataggttata    6540
ttctaactaa acagatacat caaaaaacct taagaggact tttagtagag acattttatg    6600
```

```
tcctgacaac tgaaattagc cactcatttt cacttcaaaa aaggaggtaa catatagttc    6660
atttgctttg cttcttcagg tttgttgttt tatcactgat ttctcatatt tattacatta    6720
ggttatcctc ctaccatgt aaacttattt gagctttcac aaagcatgta atactgatta    6780
gaattagaat gtcttacaaa accctgtctc ttgtcttaaa gatgcttatg tcttgttctc    6840
ctgggacaca tactcctcta cccaccctgg gttttcaaac tttatgttaa actttgttgt    6900
gaccagctat tttggtgttt gtttaattgg gatagaatac agtgaagaga agataagagt    6960
tgcactgtac agagtaaggg aagtattttg tgaaattact tgtatatgtg tgtactgggt    7020
cattagtttt actgtggatt gctataaaaa ataaacaatt gaaatctatt gctctagatt    7080
ttacagtatt ttacacattg ctgtctgctt tcatcagtct ccttacccta gctcctgctt    7140
ccctcttttt tccccaaaaa tcaaaaccaa acctcaaaaa ccaaaatac cttgaagatc    7200
attcccaact gcctagttgt tggatacagt agtaattttt tcagttctct gccttactta    7260
cgtccatttt atacttctga gtcctttttt aacaccttc ttcacttcat aggagtggtt    7320
ttctcactgt gtgctcctag tcttttgttt gttctcttga ttactcctct gacttatttt    7380
cttgccttgg ccccgtgaat gccagacttg gtcatccgtc tgtcctcatc tttggaggtg    7440
gtattatttg taaattaaga gaattcctgt gtctctgtga tttcaacttt gcagaacact    7500
ccaaaatttc tatcataact ctaaaaacaa aacctctcag agatcaattt ccatatattc    7560
atctacctag tcattattac aagtcgggaa atttcatctt tgttcttaat tgcctaaaat    7620
ccaaacttag catcctattg tgacctccat caccaccaca tgtacacaaa aatgtacagt    7680
aacacagagc agcttccttt taatgattca tcttactgct gctctctcag gatccaccct    7740
tgaatttgaa aacagttctt tgattctttc ttcctttttg tctctcccca acttccacca    7800
aatagtcatt aagtcctgtg gtttcttttct ttcgattttt gactgttttc tttccattta    7860
tacttttacc ttcctcctcc tttggttctt taacctaaca cactctaatt ttcaccactc    7920
cgcgtgtgtt tccttttgcc tgtggattta tatgcacgtt agaacctaag gtttgtagtc    7980
ccataaattt tgaagaatct gttttttcaac ttttcaactt actatatcta aatataaaag    8040
tctccaaaga attgggtttt ggcattcatt ctctttttt tttttttcacc ttggacattt    8100
cttagatgcg taaagtttct gcaaagtttc atagttcacc aaggaccttt atatttgtcc    8160
agtctgttgt gttttattct cattctttga agcaactgcg tcatttgcca cattggatca    8220
ccttataagc actgatgaat tttatttact ccttctgagc tcagccttac ttaccaattt    8280
attcttctgt ttagtgtaag aactttcaaa tgttcattac aaccaaacta tttccagttt    8340
tcaacttttt tcgtaaacca tttgagtttt aataactttg aaattttaag ataaggagaa    8400
attcataata attagtatgt gagggtttgg ggtaagagaa ccagagttgt aggaagagac    8460
ataaatgagc tttctttgcc aatcatatta gggctaattt tataaatgct tgttggaaaa    8520
ggtctagaag gatatgtacg aaaatttaaa caattaatta ggtctaggaa ggggggtatt    8580
gggctagagg acacctgtgg ataacttct tttatatgta tttgttgaac atatattact    8640
tagcctttat tttcttcagt atcaaataat ttttgcatat gctttcttat gttgacaagg    8700
atgctttttt ctttgcacaa actagagagc tgtagtacac atggatgaac gacgagaaga    8760
acaaattgta cagttactga attctgttca agcgaagaat gataaagagt cagaagcaca    8820
gatatcctgg tttgctcctg aggatcatgg gtacgacaag aaatattttt ttaaagaata    8880
ggcaaagagt aacactttaa taataaaaat aacatcttta ttttcttcga taagtgaatt    8940
```

```
ttaaccttta cgtactttt ttccttatgt agattaaaca gatttagaaa atgactttta    9000
aaaatttaga tggcatgttt ccataggaaa gctaaatggt atgaataata gtgtatctgg    9060
atatgagatg tattaagttg ttatttattg ttctccctac ctgtcctctt tgtatttatg    9120
aaattattct gtctgggaga tctgcaagaa gtgaaattgc taccgtttta gaaagattac    9180
aagaactgta tcatttagag gaaaaattag tacaagtatt tcaaagactg tgtattgtag    9240
catcctattt gtagctcaga aagggtggca agaaaaaaag atgttgtgac ataaaacaag    9300
ttcgagaaat ccagaaaaag agaaacactg taagtaaccg cagtgaagga atgactattc    9360
tgtggatttt tattttaac tatcacaagg aataacttaa tctggcaata tctatttaaa    9420
gggaagaaaa atttgaattt attataagaa tctaagtata ttttcataat tactgtacta    9480
agagaaaaga aaagctttgg atttggatga ctttgaaata tttcaacagc gtattgtttt    9540
gttttgtttt gttccagtgt ttgagtggct catctgacct ttcttccttt cttatttttgt    9600
caaaacagat acggtactga agtttctact aagaacacac catgctcaga gaacaaactt    9660
gacatccagg aaaagaagtt gataaatcaa gaaaaaaaa tgtttagaat caggaacaga    9720
tcatatattg accgagattc tgagtatctc ttgcaagaaa atgaaccaga tggaacttta    9780
gaccaaaaat tattggaaga tttacaaaag aaaaaaaatg accttcggta tattgaaatg    9840
caggtagtag aaagatgtca aaaaatattt tgtcattttt ttcttacact ttataaaaat    9900
gtatgtatgg ttagaggtag ctgcatggca tagatcagtg agatcctcaa caagacatcc    9960
ctgtgggaat taatttcttt tcgaatggta gagaaaagca gtgggaatgg aagttacaca   10020
taacctacag tatcctatct catccacaga agcttatgtg gtgagaagaa atgtttgaga   10080
aatgctagtg ccaatgaaaa aaaaacttac tcttcagctt ttctaggcca gtttagtgag   10140
gtgccatgtg cagtaaaggc agttaaaatt gtaaagcttg ttccagatta cttaatacat   10200
cttcttttta tagatgataa aattaaatat ttcaaaaatt atgtgatgtg ctttgttcac   10260
taacatttta aatacaggac tatcacaaca cctgagatct cctgaattct gatattttct   10320
ttctatgcta ggcaagatat tttaaggtcc ctttcagtta aaacataaaa ttgtgtgatt   10380
tgtgggtgtt ctagagatgt aataaagtgg tctcatgtat gtatgtatat gtttaagaga   10440
aattactgag gaaactctga gggccatatc tttaatatgt aaatacatac tgctgtcttt   10500
gataaaggaa ggatatagca cctcctatag gaaagaaagg atcccttggc tcactgatga   10560
aagctgaatt tccttaatag gaaagaaagg atccattgac tgttactgat gacagttgga   10620
tttccgtatt agaatagata agctgaggtt gtccagggcc aaattgtgta gctctttgat   10680
gcctgttggg taaaaatgtg atttgaaaat ggaggaaatt tcaggatgaa ttaattgaga   10740
atcttctggt tgagaagagc tgctttaaca gccttaacag gaggaattag tgtctttctc   10800
tttgctgtat atgatggaca gaactcatat actaaagatg ggtgattgat ctagttcaga   10860
gaaagaaaaa tgtgtaaaac atttaaaaag ttggtggtct tcctatttcc catatgttgt   10920
cataaatgct tcatgtgtac tatattattt aagcttctca acaaccttga ataagagact   10980
acatgtctgt tgtagatgag gaaaaagatt taagtgacct acctgaggtt gcatagctca   11040
taacagaatc agatctaaaa ttcagctgtg tttaacaact cagcttttta atcattttta   11100
gcatgtgcaa tattttttct ttatgttctt taataaacat taattttcta cttactggat   11160
gccagttact gtgctatata tgtgtgcgtg tatgtatata tatatattta agacagggtc   11220
tcactctgtc acccaggcta gagtacagtg gtgccatcat ggctcactgc agcctcgacc   11280
tcctgggctc aagtgatcct tccaccttag cctcctgagt agctggcact acaggcatgt   11340
```

```
gccagtacgc ctggttaatt tttgtatttt ttgtagagac agggttttgc tttgttgccc   11400
aggctggtct tgaactcctg ggctcaagca atcctcctac ctccacctcc ccaaattctg   11460
taattatggg agtgagccac accagccagt tatgcttatt actgttttg aagagtaata    11520 agatatttcc tgtcctcaga gagcttatag ttgaattatc tcacatcttc gttatggtca   11580
aaagttaaca aagtagaaac tttggctgcc tgggaaaga atattggact atacctctct    11640
ttccagtggc atttacatgt ataaagcaaa tacgattaat gccagtttga aatgcagtgg   11700
gatagcttgt gtataattat gtgttaagat ggtaacattt gactacctgg ggtgttaata   11760
cttatgtcat taaaaatagt ttttagataa tttaaaaatt attacaagat aagtaagtta   11820
ttacaaggta agataagtgt ggtagctttt gttattttaa atgactagaa ttcatttcag   11880
tcttcacatt gactgttatt tttatggtat tggtaagaat tacctgacca taacaaacat   11940
ggcaataata taatactaga ttaccaaaga cagttcttta tttattttat atatatatat   12000
atatatatat atatatatat atatatatat atatatttta attatttcct ttttttttt    12060 tgagatggag tcttgctctg tcacccaggc tggagtgccg tggcacgatc tcggctcacc   12120
acaacctcca ccaattctcc tgccttaacc tcccaagtag ctgggactac aggcgtgtgc   12180
cactatgccc agctaacttt ttgtattttt agtagagacg ggatttcacc ttgctggcca   12240
ggctggtctc aaactcctga cctcatgatc tgcctgcctc ggcttcccaa agtgctggga   12300
ttacaggcgt gagccaccat acccagccga ttttttccat cttaataaag ggtgtttatt   12360
aaagctgact ttatttttat gccactgaag tttttttttt acattatatg tacctagttg   12420
aatgtaaact acaggactgc ttcttaaatg ttttttatgta atacgggtat agagttccat   12480
aaaagttttc agaattagga agaaattgtc acataaatat aggaaaaata gtcattcctt   12540
ttgtagtatt ctaattgtaa tttaacacat ttgaaattca ttgagtagct tatatgtttc   12600
agaaactggt atttgctttt tatataaagg tttttcattt agatcttgtg gcaaccgtat   12660
gagataaaat ctttgaggca ttcatacttt aagtttgact taactgagat cacagctcta   12720
aaatggcagt accagatttt ctgactgcag atattacttg ttttaagttt tctcttacac   12780
tcaaaggcaa gtatatcctg aaatttttga ttctgctcca gtacttaatg tattagtaaa   12840
tagtgcactg ttgggtggga aaacataat atagaaatca aatctaagat gaatatataa    12900
aacatattga aaaatagtga aagtaattta gcaattatta gaatactgtt agaggacaga   12960
tccgatttca ttttactgcc actgacttaa agcattgtct ctattttgct ggatgtaatg   13020
gagttctggt tttgaatgtt tcagacataa aaggaattgg taaattattc tttataatgt   13080
ttttacacaa gccatgagat aataaaaata ctttcggatt ctagccaatt taccctgtga   13140
tgtatcctaa ataccatgat tataatttga ttacatatct tctgtgaaaa tttaaaactt   13200
tttttaaatt tcagcatttc agagaaaagc tgccttcgta tggaatgcaa aaggtaaagt   13260
gcttttttcc actatttaat ttgatttgca aattaaatac acaattttt ttaaagctct    13320 atatcaagaa aaaatgtaaa ttaatgaact ttcttttaca ggatagtatt ggaagttaat   13380
tttattcttt tgaattaagg acaaaaagaa aaaaaggtt cataaacaat tttcctcatg    13440
tttgctcctg ttttttgtcca taattgaaat ctttgaaatt taaaaagtaa aatttcctcc   13500
tataagttag tttggataaa taccttgcag ttaagtcaag accaaatact tcagttaaaa   13560
ataatataca aattattgta ttaattaaaa tcaatgtaca aaaaaagtac tactaaaaat   13620
acagttaatt ttaatttatt acactatatc ttaacatatg attaccctat gtagaataat   13680
```

```
aggatctctc atccttctct gttttctcaa ccttatttta ttttattttta ctttattttt    13740
tacttttcat agcacttgtt accacctgac atctgtttgt cttccctcc caggccagtg      13800
taagttcttg aggataggat ttgttttgtt cactctgtgt ctcttgactc agaacagtgc     13860
ctggcattct aaagacttcc agtaaataaa cttctgattg gatgaatcac atttcacttc     13920
tgagtattta ccagctataa tttcagtgtt caaacttaaa acttttttctg atatatacac    13980
atctatgtat gtataatgtg ttagaataag tggggaatat atatatatgt atacacatat    14040
atatatatat atatatatat atatatatat atatatatat atttttttttt tttttttttt    14100
tttttttttt tgagagggag tcttgctctg ttgccaggct ggagtgcagt ggcgcaatct     14160
cggcttactg caaactcccg actctcgggt tcaagcgatc ctcctgcctc agcttcccga     14220
gtagctgggg ttacaggcac ccaccacgcc cagctaattt ttgtgttttt agtagagatg     14280
gggtttcacc atgttggcca ggatggtctc aatctcctga cctcatgatc cgcctacctc     14340
agcctcccaa agtgctggga ttataggcat gagccaccat gcccggccta agtgggaat     14400
ttttaaaagg taggttttca agttaaattg ttttatacat gaaaataacc cctaacatcc    14460
ctttgaggta gtaagatgac ttcgtttata cagtgaatat tattattaaa aatattaatg    14520
tatacaattt tgaggaagaa tgaaacccaa atatgaggtt ttctagatag ctttggttta    14580
gatattcaat gactttattt taattatttg aaaggaagta attttaaaat acaatattct    14640
cttccttgct cctaaaatgg catacaaaac ttgttctgca gacaaagcca tatttatgaa    14700
ttatataaat ttgtaatgtc ctcaatagtt gtttaggcca ggagtttgct tctgtactca    14760
gtagccccac atatcaacat tattttaatt cttctccatg gaacttataa gctgtctctt    14820
cttgtttatg tcaatatgtt tttctttaac agtgctttgg ctttgttctt tataaatttgg   14880
tgcacttatc tcttgcaggt tggtagatcc agatatccaa actgccagta ttggatatgg    14940
caaaattttag aaagcattaa tatgtttgtt aaaaatagct atgttcagtt tggtcgaatt   15000
ttgattaata tcttttttca gacttagtca acatgtgata ttctttattt tcccttttga    15060
aataggaatt ggtaaatttta attgataacc atcaggtaac agtaataagt ggtgaaactg    15120
gttgtggcaa aaccactcaa gttactcagt tcattttgga taactacatt gaaagaggaa    15180
aaggatctgc ttgcagaata gtttgtactc agccaagaag aattagtgcc atttcagtaa    15240
gtaatctctt aacttattaa aaattgtctt tttaaaagta atcttgctag aacctactga    15300
ttctgaaggt gtggagtgat tcttaattag gcttaggatt ggtgactatg aaagcaaata    15360
gttgcttaac atgtttaata ataaagccca aaaaattgag taacctctct cttaacagat    15420
aatagatatt tatgaattca agataaaatt gatatccagg caaatttcag tacatgttca    15480
caagaatgaa atagataaaa tatttataga attgattaca agcttcaaat aatctccatc    15540
atttgattct ttaaattta ctacttggtt tatttaactt ttttttttac ttctgtcatt     15600
ttttgagtat gtaaatacac tgaatggtgg tgaaagtggg aaaccttgtt tttttttttta   15660
agctgcattt ctgtagtcag tgatttattt atttattttt tgagacaggg tcttattttg    15720
tcacttaagc tggagcgcag tggtgataac acggctcagt gcagcctcaa cctctagggt    15780
tcaagtgatc ctcctgcctc cgccccccaa gtaggtggta ctataggcat gtgctaccat    15840
acctggctaa tatttgtatt ttttgtagag atggggtttt gccatgttgc ccatgctggt    15900
ctcgaactac tgggctcaag cgatctgccc acttcagcct cccggagtgc tgggattaca    15960
ggcataagtc tctgtgtcca gccatagtca gtcattttg aatgcagcta ctcagtaaga    16020
ggaaatttat gaggaaaaat aaggtattgt ttctggtttg tcaagtccaa aatttggga    16080
```

```
aggcatactt aagtaacagt ttataagtaa cttttagttc aggttgacta tacgaaatcc    16140
agaatgctcc caaatccaga actgtttgag tagcaaaatg gaaatgctca ctagagcatt    16200
tcacattttg aattttcaga tttgggatgt ttaacaaggg caagtataat gcaaatattc    16260
caaaatagaa accggaaaca cttctggtcc tgatcatttt ggctaaggaa tactcagcct    16320
gtacattgat tttgttgtcg tcatcgtttt tagttagatg acctagttaa atatgtgagt    16380
tatatatttt ttaaaggtgt ttgggggtttc ttgtcatatt tcagtgtgca tagtgaattt    16440
atttatgcta tataattctg tgtataaatt ataaagattt gtgtttgtct ttggttttat    16500
ggcagtgctg cttatcacat gtctaagtca tttaatatag aatctgtggt taaaaacatt    16560
accaattatg acagcacttg gcagtaaata cagtatatgt tttaagcttt ggtttctaag    16620
aagtactata aagaaagagc agtagacttc accccttttt aaaaagaagt gtgtaaattt    16680
atgggataca agtgcaattt tgttacatgc ataggttgtg tagtggttaa gtgagagctt    16740
ctaggttgtc catcacccac atcatataca ttgtacccat taagtaattt ctcatcatct    16800
gtcctcctcc tgtcttctct tctgagtctc catcgtttgc cattccacac tctatgtcca    16860
catatacctg gttttttagca cccacttatg tgaaaatatga tattttgtct ttttgtgtct    16920
atttcgacat gatttcactc ttacagctaa atagtattcc attgtggtgt atatatacac    16980
cacattttcc ttatccagtc atccattgat gagcacttag attgattccg tatctttact    17040
gttatgaata gtactgtgat aaacatgcaa gacaagtatt ttttttttt tgacacattg    17100 atttcttttc ctttgggtag aaacccagca gtgggattgc tggatcaaat gatagctcta    17160
tttttagttc tttgagcaat ctccatactg ttttctatag aggctgtgct aatttgcatt    17220
cctaccaaca gtatgtaaga gttctctttt atccatgtcc tggccaagat ctattatttt    17280
ttgactcttt aatagtagcc attttgactg gggtaagatg atatctcatt gtggttttaa    17340
tttgcatttc tctgatgatt agtgatgttg tgcattttttc atatacctgt tagtcatttg    17400
tatatcttct tttgaaaaat gtctgttctt gtcttttgcc ctccttttaa ggggatgatt    17460
tgtcttttat tgttgttgtt tgagtttctt gtatatactg ggtatttgtc cactgctgga    17520
tgaatagttt gcacatattt tcttccgttc tggaaattat ctgttactc tgttgattat    17580 ttcttttgtt gtgtagaaac ttcttagtta attcccatttt gtctattttt attttttgtcg    17640 cctgtgcttt tgaggtctta gtcataaaatt ctttgcctag accaatgtcc aaaggagttt    17700
ttccctaggt tttcttctag tagtttcagt ttcaggtagt cttcacccctt ttatggggac    17760 tatattccag gaaattgcat aaaattacag aatggtgaaa aataaaccac ttttgtcata    17820
acacactttt gtagctagac ttaaatattt tcactaatat atagcagtta ctgtatatgc    17880
tgatagtagg aagaaatgct aagtaggtaa ttttttctctt cttttttcca ccatctgttg    17940
gaatttgagt agacaggtta atgtggtctg tcagtgtata ctagatatac ttattggaaa    18000
gttttacttg taaagtatta tttcttacaa attatgccat tttctatttc taatacctta    18060
ttatcactgt tctgtcacag aataactgtt ggttacttttt agttgtacaa atcagtatta    18120
gattataaca tttcatcttt ccaaatctta ttttttggcag tcataacttt caaaacatga    18180
ccaagaacta gaaattcaac accagtccct accacaaaca aaaacacaag ggaagagtat    18240
caatatgtaa ttacttttcaa attacacata acttctacaa gtttagatct tgatttacaa    18300
ctcttagaaa agaccagaaa agtataaatt aatgagagga tgctatagaa aggcactttg    18360
aaactagtga tgagagaact tggccttaaa agactttata agaggaaatg aaaaataaac    18420
```

```
agctcttaag agaggcacac actgttttag atacctcaga ttttaatatc tattttttta    18480
actcatttag aaatctgaag aacaattttt caacagtcct agattttcat ggacattcag    18540
gatatttgtt ctaaaggaaa ttatattctc tttatgtttt atttgaatta aaggttgcgg    18600
aaagagtagc tgcagaaagg gcagaatctt gtggcagtgg taatagtact ggatatcaaa    18660
ttcgtctcca gaggtaagaa atgttcactt cttatataca ggcagatttt agtgaaactt    18720
tgaagctgga gattcaaaag aaaggatatt ttccccatttt ttatgatggt tattactatt    18780
acaattacca tttaaagtaa ctgcagcgta gatgacttgc tgccacaaat ttatctttta    18840
accccacatc agacttgtat tgcctttttt aaatgatgct tttatatttg aatgattag     18900 aaaaataaac attttttcctg gacatagatt agtagaccat tactctctct gaaaagattg   18960
tgtagacctt tcagtaccac ctccatatac ttccgactga cttttttattg atttttgatat 19020 cttaaccccc tatccaactc cactgtgcag tacatagttg gtccttttct ggagcttagg    19080
actccatttg cctttttatg ttttaattta cttaatgttt tttagagata ggttctcact    19140
ctgttgctct ggctgaagtg cagtggtgca gtcaactcac tgcagccgaa gactcctgtg    19200
ctcaagcagt cctcccacct cagcctctca agtagctggg cctaccggcg acaccacca    19260 caactggcta atttttttac ttttcgagcc tggatctcgc tgtgttgccc aggctggtct    19320
tgagctcctg ggctcaagca accctcccat cttggcctca agtgttggg attacaagcc     19380 tgagccacca tgcctgacac atttgccttt tcaaatgagc tttccaatta cgaaccaaat   19440
atttaggccc cataagtaat tcagttgttg tctgaatgtg aatggtcgta tcttttaaaa    19500
gaaattaaca ttatatcaat gacaacaaag ataatgtata atgaacttga agtatttccc    19560 attacccccat tgtggtaggt gttcttataa gtaaaaaatt aagtgtgaag attttcatta   19620
aaactgaaag catttctaaa attgaagata taaacctttg tggtagttaa ttattagaag    19680
agaaaaccaa ggcttattaa ttcatgtctt tcattcacag tcggttgcca aggaaacagg    19740
gttctatctt atactgtaca acaggaatca tccttcagtg gctccagtca gacccgtgag    19800
tatgtttcaa ttaaggaaat ataagtgtta tcaaaagatg taattattaa attggattt     19860 actagttgtt aaagaaaaat ggttttaaaa ttttgtactt cacacttctg ccttaggtat    19920
ttgtccagtg ttagtcatat cgtacttgat gaaatccatg aaagaaatct gcagtcagat    19980
gttttaatga ctgttgttaa agaccttctc aatttttcgat ctgacttgaa agtaatattg   20040
atgagtgcaa cattgaatgc agaaaagttt tcagaatatt ttggtgagta aaatgtatag    20100
ttattacatt agaaaaggta ctagaaaaac aattaaaaaa attaatatgg tactaggtaa    20160
agagtagtca aaatgaatgt ttagctgtta atttttatttt aatattattc taccctccag   20220
tttcatggat tagacaattg ggtctatttt taaatggtgg catcatctct catagtgagg    20280
acaggtagct tcttgttgct accaccacac aattaagatg gcatcattga agtcaaacca    20340
cagatttgca taatttttata aacttctttc tgttgttttt ctgtggcttt tatcacaggt    20400
tagggtggca gtttgctgct aatactgcta gtgaccactt atggaacacc ttcaatgttc    20460
caggtagtat atttgccact ttgtcttcct tagtctttat aacactttat gaggtagttg    20520
ctattatcat tcacatttt acagatgaga aagcagcctc agagcagtta agtaggtttc      20580
ccaagctgaa gctagattgg accagctgca aaagcacatt cttttaaaat taatcctcac    20640
tgtctttcct gcttatactt gtgaaggaag gagggggaaa gggagggaat tacaatgtaa    20700
tatatttatg tttaataaat gttccttgtca tcagcttttt aaaagtcctt taaaatacat    20760
cccagttaat actgaaaacc atgtaagatt agttggggta ggtgttatta ttgttatttt    20820
```

```
taaatgagac ttctagaact aacattgagt actttgctca aatgtgtgca catcatgggt    20880
agagcagtga tacctactta ggtattttga cctctgatgt gatgtttgct ttttacagtg    20940
tgtactgctt gtttcgcttg ttatgaaatg taaagagcat ttaaataaca gtaccgaagt    21000
gattttttta ttagtaattt tgaaatagta acaatctatt tgtttaggtt ttgttttgat    21060
tacctttctc cgctaattcc gggtgctaca agtagtaatg cttatctaga attcagtaaa    21120
actttgatat tctggatatt ctattatggc accatctggg ttaatgatga agagaaaata    21180
gacttctaac taatggattt tgagttcaac ttaaaactct attctttgat attctgtgtt    21240
attttgtaga actgtgagat gtgtgtacag tttggtagca gtaaaatggt attgagtgaa    21300
gactagactg ctgtttttta ttaaagtagg tgtggaaaag tagggtagaa ttgtaaaagc    21360
tacaggacca ttttctggaa ttaatagtaa gtaatagagt cattgtccta tttacagtat    21420
attaatgttt ttaacatttg agtacaaatt tatgcttata ttttgtctgc cgtaataggt    21480
aactgtccaa tgatacatat acctggtttt accttccgg ttgtggaata tcttttggaa     21540
gatgtaattg aaaaaataag gtaagtaaac attaggaaat aaaaaacatt aaaaagtact    21600
aatatatcac ttttctcatg tcaaaccttta gtctcagaaa cccatcattg actatttcct   21660
tgtaaaacat ttttctggga attagccaca cttggctgca cattaaaatt gcctggagct    21720
ttttaaaatc cagatgcctg atttatactc cctacctaaa ttacattaca gtgtctgagg    21780
tagtagccag gcatccgtgg ttttttttaa ttgagacaga gtctctctct gtcgcctagc    21840
ctagagtgca gtggagctat ctccgctcac ggcaacctcc gccttccagg ttgaagtgat    21900
tctcccacct cagcctccca agtaactagg attacaggtg tgtgccacca tgcccagcta    21960 attttttgtat ttttagtaga aactagtttc accgtgttgg ccaggctggt ctcaaactcc    22020
tgacctcaag tgatttgcct gcctcagcat cccaaagtcc tggtattaca ggtgtgagcc    22080
accacgcctg gctggtgtca gtgttttttg aagattcctg ggcagcaaag tttgggaacc    22140 tttgtctttta gtgtttgaac ccttttgctg gttctcctgc ctgattttca ctttcctttg    22200
ttggcttcca ttgccgaacc tttaaatata atttcccca gtcttctcaa tcatttatgt     22260
tttcactgtg caaacctgtt tatatccta actgtagttc tgtattttca cagcttttcag   22320 tagtgtagct tcagaactga agcttctcct gaccttcgaa ctggctttct gctcaatagt    22380
attctagtac cacagatgcc ttgaacctaa catttctcaa gcctaaatca ttatcttata    22440
ttctcccacc aaaaaaataa aacaatgtgt cttgcccagc atactttata atggttaata    22500
attatcctcc acttagttttt ctgacctata aatcaaaaag ttagtgtgta tcaggcagtt   22560
atgtaccagg gtatggcaac tgttttacac agtgagtaac caagttaatc caagtcattt    22620
tgtactgcct tcaaacacac acaaactctg ggaactttct tcttgaacat gctttctcat    22680
ttttatttct ttgctaaggt ccttactatc tctcctgtgc taatacaata gttcctcttt    22740
tggtactatg ttcttcactc ttagggaagc actctttgtg ctatacatga ggctttatca    22800
cttttttttt tttttttact ttatcacatt tttaaaaatc tcatgccagt actgttacaa    22860
acattaatct ctcaaataag ataactaaag gccagatgtt taatgccttg tctaaggtta    22920
cacagctagt cagtagcaga ggagggatat tctgacttgg gagtccatgc tccagcccct    22980
cccccattcc atctagatgc tgtcctctag ttgagctcag agatgccttg gggttaaagt    23040
gtgggttcat ttttgtcttt tcccacctcg tgcctctcag gactgacaat gataggtaga    23100
attattgtcc agatgcgccc tctatggttt tagcaatcac tacaggatgg tagtagaatc    23160
```

-continued

```
atagtacagc actcaattga catatgagag acttgaatac tgattctgga tctgccatta    23220
actacaactg tgtgactgag cagaattaaa tagttctcta gcgtgggtct gtagatctgg    23280
atacactatc tgaatctcct gcaggcacta attaaaattc ttagattaac agacccaagg    23340
catacctacc aaatccaaat catcagggat gggatttagg agtctgtatt ttacaagctc    23400
tctgagggat tcaattctta cgtgcagtca ggtttggact taacattaat attaactttt    23460
gttctaaagc aaacttaaaa tagaaggtaa aagttactta ctttagtctt tttctaaatt    23520
tttgactaaa aatgatctat aggtttatat acttcaataa agaagaatga tttttatcca    23580
aaatatcagg ttttataagt taatgaacac aaactgatat tttagctagc attcacttga    23640
aagcataatg aaaatgttct ttggaatcct ttttgaaaat cctaaatata aaatgtcaca    23700
gattttagct aaaactagag tttcaaaaaa gtgaagatat tcaagaatgt ttttatttta    23760
ggtatgttcc agaacaaaaa gaacacagat cccagtttaa gaggggtttc atgcaagggc    23820
atgtaaatag acaagaaaaa gaagaaaaag aagcaatata taaagaacgt tggccagatt    23880
atgtaaggga actgcgaaga aggtaagttt attttgtctg aaggtgagaa atcagtggct    23940
aaaataaaca aaaagccaga ggctgggggc atcttcttga atctgtacgt acttaaagga    24000
gagcattgtg agtctcttat tcgagctaaa tattgtgctg atttgacttt taagcagtaa    24060 ttacccagt aattctctcc gatctgtaga ttatgttcct ccatttgcag attgagttaa    24120
```

(partial - unable to continue; verifying remaining rows)

```
ttttaagctt ttgtagcaag ttaacagaaa acttgattaa gtatttcatg actttgtgtt    24180
taactttgat aggtattctg caagtactgt agatgttata gaaatgatgg aggatgataa    24240
agttgatctg aatttgattg ttgccctcat ccgatacatt gttttggaag aagaggttag    24300
ttttattttt ctttcttcag ttaacataat tttaatttta ttaacgtatc aaggccatga    24360
aaaatacagt tttcttaaat gcttatgaaa tagactggaa gaaattactt ttgatactag    24420
aaatcatctc atagtagcaa aagatttagg catttgacct gtttgaagaa aagactaaac    24480
aaatatatgg attataaatc tcattttta aaagtgagct tagctggatg cagtggctca    24540
tgcctgtaat cccagcactc tgggaggcca aggcaggtgg atcacttgag gccaggagtt    24600
cgagaccagc ctggccaatg tggcaaaacc ctgtctctac taaaaataca aaatttgct    24660 gggcgtggtg acacaggcct gtaatcccag ctacttggga ggccgagcat gagaatcact    24720
tgaacccagg aggcagatgc tgcagtgatc cgagatcatg ccattgtact ccatcctggg    24780
tgacagagca agactctctc aaaaacaata attaaaaaaa aaaagcttat atactttaa    24840 ttattaacga aaattatcct gagctagtat aattttaatg gagacttcag tgtgcacaca    24900
attttactgt tactgcattt tgttgatgtg atcctttgta atggttattt ccccttcata    24960
taggatggtg cgatactggt ctttctgcca ggctgggaca atatcagcac tttacatgat    25020
ctcttgatgt cacaagtaat gtttaaatca ggtactatgt aaatgtattt tactgtaatt    25080
caaagagtgg tatttgaatt atatatgatg tgtatttttt tcttttattc aaagaagtgt    25140
tgcttctact aggtcacaga tgaaggtgaa gcttttatt tagtattatg aagagaatat    25200
tttctttctt tttcacaatt tgcctaataa aattggctct taaagcatag gtatgtgagg    25260
tttttcattt tttcacttac tgctgcaaaa aagaaatccc ttggcccagt gtttctgaat    25320
tctgagtata caacagagtc acccatggag cttctttaag attcagatac ctagacccca    25380
tcatcacccc aaatctaaga atgcgacctg aacatctgaa gttgttaaaa attcctcaag    25440
tgattttgat cctgtatgaa cagcatattt tgaaacatat aaactctaga gaatgaatg    25500 agaacctttt tttctataaa atttagagta ttttcagcaa tcattaactt caaatataaa    25560
```

```
aactacaaag aaaattctat ttaatttta cagttctgaa tataattttt ttattttgag    25620
atggagtctc gctctgttgc caggttggag tgcagtgatg ccatctcggc tcactgcaac    25680
ctccgcctcc tttgttcaag cagttctcct gcctcagtct ccagagtagc tgggattaca    25740
ggcatgtgac accatgcccg gctgactttc tgcatttta gtagagatgg ggtttcacta    25800
tgttgaccag gctggtctcg aactccagac ctgaagtgat cctcccatct cagctttcca    25860
aagtgctggg attacaggct tgagccacca cgtgtggcct ctgaatataa tttctaaccc    25920
tactctgttg aagtgctttt gacaaaatta attatttatt tattaattta ttttgaaac    25980 agcatctcac tctcttgccc aggctggagt gcagtggtgc gatctcggct cactgcaacc    26040
tctaccttcc aggttcatga gattctcctg ccctgcctcc tgagtagctg ggactgcagg    26100
cacctgccac cacgcccgcc taattttttg tattttagt agagacaggg ttttactgtg    26160
taagccagga tggtcttgat ctcctgacct tgtgatctgc ctgcctcggc ctcccaagtg    26220
ctgggattac aggcatgagc caccacgccc agccagacaa aatttatagg cactagaaaa    26280
tattttgatc taattgtatt gactaaaata ataaatgtat atatttatta tttgttaaat    26340
cctgttatgc tctgaaagca ttctctgtaa ttaaaattat ttactatcta gcttgcaaag    26400
tattttgatc taattgactt ctctataaag aaatactgct ttctgttttc ttttgtgtg    26460 ataactttat agaaaaattt gtcatgatta gacagctgaa ttttcaaac aactagaatt    26520 ttttttattgg ctaaatctaa ctctggcctt tccttccccc attattataa acattattgt    26580
atagtgtact tataatttta aaaatgtgt gtgcatatat ttaccaatga agataagata    26640
tataccaaaa tataacgtta tcatttagtg tatgtgatgg agagtgggaa aagggtatat    26700
tatagattat tataattgac ttcgttaact ttctagtttg aattaattat tctcaaggaa    26760
agagttgcta atgtatacac ttccactacc agctcaattc cttttaaagg aaatctttcc    26820
agaacttgag tgttttttct caaattatgt tgaaaaaat ttagccttga taatcagttg    26880
tatagttaac cactatcatg gggagaaaat tggcctaact ctgtgctgag aaattgagtt    26940
ttgaaactca gtttattaaa tgcttatcaa tttcttgttt ttttcttttc ataagagtat    27000
agattttgtt ctcattaact ctcttagttg tatggtgtca acaatataaa ttttttttcc    27060
caattatata gtcttcaaca gaattgtttt tactttatt atccctggct aacttttaaa    27120 cttttttataa tgaaacattt taaatataca aaaaaactag agacttttt ttttttttg    27180 aggtggagtc tcgctctgtt tcccaggctg gagtgcagtg gcacgatctc agctcactgc    27240
aacctccgcc tcccaggttc aagcagttcc ctgcctcagc ctcccgagta gctgggatta    27300
taggcaccca tcaccacacc tgggtaattt ttgtatttt agtagagaca gggtttcacc    27360
atcttagcca ggttggtctt gaactcctga ccttgtaatc cacctgcctt ggcctctcaa    27420
agtgctggga ttgcgggcgt gagccactgc acccagccaa aactagagaa tcttaatgaa    27480
tccacgactt cagtgccaac aattattttt tcagtcctag ttttttctta aagtcaattg    27540
cagctgtcac atttcatttc taaatgtata agcaagaatc tctaaaggca attttctata    27600
taaccatcat gtctttatca tacctaatcc ttaataccat ctgataatcc agtctgtaat    27660 cagatttttcc catttttctg aaaagtgtct ttcacaacta gcctgttcaa actatagaaa    27720
gtgtcaacat cttttgatct agctctagaa cattgctccc ctccactccc tgcttttcct    27780
catggtaatg taaagtcatg gaaaagacca ggccatttgt tctctaataa gtccaacttt    27840
ctgaatttgt gtgactcttt atgctatcat ttcatttgat tctctcttac ctttatttcc    27900
```

-continued

```
tgtaactcga aagttatatc tgaaagcttg attcaattca agtattttg gcttgaatat      27960 tatagttgta atatttcata ctgtcacaga gacaagtaat tcagaggatt cttttttagc      28020
aacatcagtt gcttggcagc tgttcactac ttttattt taagattcgt aaaatctctt       28080
cacagtcaga gtccatgggg atcatcatat cctttagata acaacagttc ttttctgggg     28140
aagtatagct gacttgaatc atttgggcat ttaagtcaga ttgtattttt gtaagcatag     28200
ttaaatgtga aattaactct tgctttcttg atactctccc tttcacccat cactgtatta    28260
caccagactt tctgtgttgg ctaataattg tgaatgggct tgagctattt catttggaaa    28320 cttaaaagt aggaatttct tatatttta acaaatatg tgtaaaatgt gggtcacttt       28380
tggaatgtat tattattatt attattatta tttttgagac ggagtctcgc tctgtcacct    28440
aggctggagt gcagtggcgc gatctcggct cactgcaagc tccgcctccc aggttcacgc    28500
cattctcctg cctcagcctc ccaggtagct gggactacag gcgcccgcca acacgcccag    28560
ctaagttttt gtatttttag tatagacggg gtttcaccgt gttagccagg atggtcttga    28620
tctcctgacc tcgtgatccg cccgcctcgg cctcccaaag tgctgggatt acaggcatga    28680
gccaccgcgc ctggcctgga atgtattatt tttaacaagg actatttcat tattttctaa   28740
ctaggacatg ggtatttaat aagtaatttg ctctaaaaat ttagatatta tcggtttgat    28800
taaaatagtg aggattgcca ggtgcagggc tcatgcctgt aatctgtaat cccagtactt    28860
cggaaggctg aggtgggtgg attgcttgag cttgggagtt caagaccagc ctgggcaaca    28920
tggcaaatcc ccatctctac aaaaaataca aaaattagcc aaacatggtt gtgcatgcct    28980
gtggtctcag ctactcggga ggctgaggtg ggaggatcac ttgagcccag ggggcagagg    29040
ttgcagtgag cagagatcac accacagcaa cgggcaacag aatgagaccc tgactgaaca    29100
acaaaaaaat aggatcaccc aaagtgtaca aacgtattca tgttaaacag aattgttgcc    29160
tattcattca gtttttattg gtgtaatttg aaaagattac tcccaacttt tgagcattct    29220
ttaagaattt ggggaaaata cttatcaata tgaaataaac taacagaaca aaatgttagc    29280
ttgaacttgg agcgctcaga aaacaagact ataaagaaat taagttggtc tgtttgtatg    29340
tagaaataaa aataaagaat ttttggttca cttaaacaca tgggcagttt gtcaactcag    29400
atggtttagc tgttttcatt aaataatgtt caatgtctta tcaaaaaaag aattgagtgg    29460
ttcagcttct gaattcattg tctcatatgt gtttgatgga gcttttctgc aactctttat    29520
cttaaaattt aattctcttt aattttcaga taaattttta attataccctt tacattcact   29580 gatgcctaca gttaaccaga cacaggtatg ttaaatggat acatttgtta aatgtatttc    29640
aaactgaggc aagctttaag gactgcttgt tacgtgtttt ccttattt ttttaaggag      29700 tattttcaaa tagtaattca tgtaaaaaaa tacttctttg agaaccttg caaatgagtc     29760 ttcagggat gattgctcaa aaacttgaat atcagcggat aacccacaaa tcagattagt     29820
tttgtctaca ttaggaaaaa gttaaagaa ttggtttcac cagtaacttc gttgagttc      29880 ctgagtaaga gaaaaggtc tgtgagtact actaaaagta accaaaccta gaaattaatg     29940
atctgtgaca tactacagtt tgatgatgat ttgagattta atttcacaaa gctagtatat    30000
tcacaggtat aaaatttctg ttttaataat gtattatgaa tgtttggctc catcagatac    30060
aggcgctttc ctaattagag tgaacactac attctcagag gcaggataat gttatgatct    30120
acagtatttg caggctcttg caaaatgaaa ttgattagaa aacctgctcc tcccccatt     30180 tctagtttat ccttttctct ttttataaga aaatatcaag atactttct ttgagaccct     30240 tttaatattt ttgttgctgg taccttagtc atgaattaga tacagagtac atacctgaga    30300
```

-continued

```
gaagagaggg ggcaagaaag aaaactcttg attccaaaga ctgaaagagt atccagcatg    30360
gaagtattca tcttccacac cataacctag taaattatgt attcctttgc tggagagtat    30420
gtgaatagcc tgggaaacat tttctgtatt gactaccagt tttgtaaatg aagggataag    30480 ttttttgcttt ttgtttgttt gcattatcgc cagtggtact tgattaccta tcttctttct   30540
actttagtga cattgtcggg ttgtggggca gtatttgtag aattctccat ttaaaggaga   30600
tttttttttt tcactccaat ctgatctcaa gctagtagac agtggttggt acagctgcac   30660
agttgacatt tgttctgctg ggttgggcat ctgcctgatt attcagtgtt cttacccatg    30720
gagacttgac ttcattattc ttgtcctaac agaaatatcc ctccctctac tttataacct    30780
ccagcttttg ttaaaaaact gctgtaaatt taaataatga tacctcattg gaaatcttgt    30840
ttgtgataag attgtgacat ctgtgggaga tttaatgtgg tttaccaaaa gataattttg    30900
taatattgaa aatgatctgt acttcataaa tacatcgata aatattagat gtatatgtca    30960
gtgaatgaac atagaatgct aaaaatgaac agtatctgag gtaattcctc taattacaaa    31020
tataatgtat tagaagttag tgtacttttg tgattctgat gtatttattt ttacaggtgt    31080
ttaaaagaac ccctcctggt gttcggaaaa tagtaattgc taccaacatt gcggagacta    31140
ggtaaaaata gttttaaata tcaaatactg atgattacat aagttttaaa caccataacg    31200
tgtttatata ccttaatctt ttttctctac catataccctt gtaatttatt aaaaataaaa   31260 cctttttttat ggcagtgagc atagtttat ttttttgtggg cttttttgag acaaggtctc   31320
attctgtcac ccatgctgca gtgcagtggc acgatcatgg ctcactgcag ccttgatctc    31380
ctcagctcaa gtgagccttc cacctcagcc tcccaagtag cttgtactac aggcttgtgc    31440
caccacacct gtctgatttt ttaaatttct tgtagagatg gagtctcact atgttgccca    31500
ggctgatctc taactcctgg gctcaaaatg atcctattac ctcaacctcc caaagtgctg    31560
ggatgacagg cctaagccac catgcatggc cagttttgtg ggggttttttt aacctatagt   31620 aatgctttag ctcagaaata gcatttttagg tgttggtttt tgtttgtttt gttttcctaa   31680
agaagcatgg gagctgaggt aaattttgtc ctttcgcctg tttctggttg ggggtagtat    31740
ttggtaatta gttatatcca gcctttaaat gttcttgtat tctcttggag gtactaagat    31800
gtagtttagt cactgaaaca gattcttttc tggaagctga tattaaacca tgctgttggg    31860
gctcccatag tgctaggtat gaggcaacct gtgatatttg actgtaggca agtaagaatt    31920
tagtatatga tctgaagaac taatactgtg ctgtcactta cagtgcctga cactgcctac    31980
tgttaggtac tcgatcccta taatattggt aatgtgggtg tgaagagtag tgaaaatcct    32040
gaatggctaa aatcatttga tgtaataaaa aaaaatgct ctgaaatacc tatttattgg     32100
tcttttatag gttaatagtg ctttcgatgt gtgtgtgtgt gtgtgtgtgt gtgtgtgtgt    32160
gttttaacat tttatatatc tgttttccaa acagcattac catagatgat gtcgtttatg    32220
tgatagatgg aggaaaaata aaagagacgc attttgatac tcagaacaat atcagtacaa    32280
tgtccgctga gtgggttagt aaagctaatg ccaaacagag aaaaggtcga gctggaaggt    32340
aaggtgggaa ctctgtccaa agcttttaga acacacaaaa attttgtgta acaaaatgtg    32400
atgttggcat ttaaagatat ttattaaaag agttaccttt cttattattt tgagcttatt    32460
gcaaaacatt tttaaatagg aaagttgttc taatcgtagt ttgtttggaa aagtatctgc    32520
caagttttct attttatgaa tcttttgcct tcaatttcta agtttgatta ataagttatg    32580
ttacttataa tagttggttt tcattttttt aaagcatata ttgtgtgata ataatagcaa    32640
```

```
ctaatacttt tgagtgtca gatcatctcc tgaacacttg atccatatta actttcttaa   32700
tcctcactac agtactatga ggtaggttat tatatccatt ttacagataa ggaaattaag   32760
gtacaaggaa attaaatgac ttgtccaaag tcccatagct ttctaaatta cagagccagg   32820
atttgaatcc aggcattctg actacacagg ctaggctcct aatcactgaa ttttatagca   32880
gtactgattt ttcaccagta gttttcaatg aaagcacaag gaaagtactt ttcctcataa   32940
tgtcataata acttaagaag taaaactatc tctgtcttaa tgataggaaa aatgatctgt   33000
cttgaacttc tacaaagaat tggactttaa tgcatatttc acagtatttc tgcacttatt   33060
catatgagtg ataagagcca tatatggatt ttcagaagag ggttttttctt ttgcctctta   33120 cagatagaat gagagatttc cattaatctt tcgatacaga cttaagaaaa ggagagttga   33180
aagaaaactt tacaggccat ttatcaaccc ctcgttttaa gtttgtacaa tatccataaa   33240
gctctgactg acttgctgta atctttgcac attatcccag tataatttga tttcaagaca   33300
gtttattaga tagttgatgc tattgaacca aaatcgtggt ttagtcaaag aagtatacccc  33360 tcctaataat cagttatcag ggaataactt gataagggac ccagaaagac tgaggttttc   33420
ccatgtagac ccatcacctc taaatattga ttcaaaaagt attcaccata gtgaacaggt   33480
tttggcacac ctttatatgt gaataataaa catactaagc cttagatttg ttccatgaaa   33540
caataataga gctaaatact aatccttcgt cctcactcct gtgcggtagg ttaactgtgg   33600
aattgctgtt ttaatttaaa aggaaaacag tcttttgtag gctccatgga taaaaattcc   33660
ttctgcaaac cttattattt tggagatcag aaaaagctat agtatgtggc tttcaatgga   33720
ggtactcttt tttttttttt ttttttttt ttttgagacg gagtctcgct ctgtcgccca   33780
ggctggagtg cagtggcggg atctcggctc actgcaagct ccgcctcccg ggttcacgcc   33840
attctcctgc ctcagcctcc caagtagctg ggactacagg cgcccgccac tacgcccggc   33900
taattttttt gtattttag tagagacggg gtttcaccgt tttagccggg atggtctcga   33960
tctcctgacc tcgtgatccg cccgcctcgg cctcccaaag tgctgggatt acaggcgtga   34020
gccaccgcgc ccggcctcaa tggaggtact cttatttag ttttctactgg agagatattg   34080 aggtatatta tataatagac agtgggtcta tgtagactca tggaaaaaat aactaagatt   34140
tttagaattc attttttgttc ctatagcagc aagagcctaa agaaatatct cttctacttg   34200
agaatacatg aatatggtca cctcttcaca tctagttttt tttttttttt ttttgagat   34260 gaagtctcgc tgtgtcacca gactggagta catggcacga tcttggctca ctgcaacctc   34320
tgcctcctgg gttcaagtga tcctcctgcc tcagcctccc actgggacta caggagcaca   34380
ccaccacacc cagctaatttt ttgtattat ttttttagtac agatgggtt tcaccatgtt   34440 ggccaggctg gtctcaaact cctgacttta ggtgatacac ccacctcggc gtcccagagt   34500
gctgggatta ctggtgtgag ccatcgcgcc cggcctacat ctagtcttat cattgttcaa   34560
aaaatgatat cattcatggc tctagttaca tacataaaac agaaacttt aatatccctc   34620 tgaaaactca ctaaatatat agtacttaaa atgttttca gtaatataga caggttagca   34680
taatgccagg attcattaca taataagatt gatcacaagg catacttgac gttactattc   34740
ttaaccttaa cctaggtaga ctgctgttac tgagcacagt aatttggaat ctgtcagaaa   34800
tagggaagca aattattggc atggggagga attactgtgt atctttctta aaactgtgat   34860
gagggtagag ggtataacgt ttttctaaac agaagaaata catgattcat aaaaaggaaa   34920
aaataattac gtacattagc tattatgtgg catgtaagaa attgatattg gctacttccc   34980
tgcctagtat tttctctgca gttctaaaaa gtcattgatg actgtccctc tttgtttcat   35040
```

```
tttgttttgt ttttttttta agagttcaac ctggtcattg ctatcatctg tataatggtc   35100
ttagagcaag tcttctagat gactatcaac tgccagaaat tttgagaact cctttggaag   35160
aactttgttt acaaataaag gtaaattagg tgggagaatg aagaaactaa atggaagtga   35220
tctcattttc aacatctttt gtagaacaaa gtactgtatt aatctccaag aaacaattat   35280
taactcacaa tttatttcat gtgtgcatta gtaaattgtg tgtttaaact tccttcaaat   35340
gtatattcaa cacttttaaa ttatatactg ctctagagga ggcaggctgc ctgtgtttga   35400
atcctgcttc tacccggaa  aagctagttc tgttatattg ggcaggttgt ttaaattaac   35460
ctcctaaaat ccttagaaca gtgcctggca cgtggtaagt gtttagtaaa cagtagctac   35520
tgttattaca tgttaacatg ttatccttca ttataaacta cttatttcag tatcttgtgt   35580
cttttgatat agttagactt gttttgaaga tagtgagtaa tcagcttgtt cactgagatt   35640
ttagccagct acttttgaag atagtgggta atcaacttgt tcattgagat tttagccagc   35700 tactttcct  attaatagag ttgatggtag aaagtagtaa tatatatagg actttaaaca   35760 tgttttata  gaaatacaaa tataatttta attcattttg gtaaaataac ttgaaagtca   35820
tgtataaatt tgatgctttg agtcatcagc ccaggtagga ctaagttgta atgctaatat   35880
attaatatta tatgtattta ataatatttg tctcccccac ttagatttta aggctaggtg   35940
gaattgctta ttttctgagt agattaatgg acccaccatc aaatgaggca gtgttactct   36000
ccataagaca cctgatggag ctggtaaatt tgttttcttg tttttttaat tctaacttag   36060
aatactacag catgtaaacc agttaattat aatgtttact ctcattactg caaagtagac   36120
caataatgtc caatgccaaa tttgattggc tatttgacta tcaatttaga actatcaggt   36180
tatgagatag gcattagaaa gttataaagt gatatcttcg taataattct taaaagacta   36240 ggatctttt  gcacattttt tttattgta  ggcttgattt aagattacat aaaatttgaa   36300
atttttaagt tactggtctt taattactgg cgagtaaaac aaatatgcag ctaaatgatt   36360
tatcacaaag gaaggactat gtagtaatta cttacatcaa gaagaacatt cccagtatgc   36420
taaaagcccc cttcctaccc tctcataatc actccactgt cccttaatcc caatcatgat   36480
agataacctc tatcatgact ttaactataa tggcttgatt tttttttttg atggttttta   36540
caagtatgca tcttcataaa gagttcagtt ttgcctattt tgtgaacttt acatgaaccc   36600
atacagaatg tgtgtggttt ttttgttctt tgagggagca gagctctgga ttatttcact   36660
taatattatg agattcaaat gtattgttgc tttagctatg gtttttttc ttttcctct    36720 tttttttttt tttttttttt tgagacagag tctcactttg tcacccaggc tggagtatac   36780
tggcatgatc tcagatcact gcaacctcca cgtcctgggt tataaggtac atgtatgatc   36840
aagttgggta gataacgccc aacagttttc catggttgca aaccacttaa actcctacca   36900
gtggtggatg agagttccca ttgctttgta gcttcaccaa cctttcttat taattggcct   36960
tttattctaa ccatgctggt aggtatgtag tggttttaat ttgcatttct atgactgtca   37020
ttgaagtttt cagcagcttt tatgtttatt atccatttgt gtagtctctc ataaattgct   37080
agtgtcttct gttaggttgc agatcataca gtcctttgt  actcttgatc tgcgcttttt   37140
attggttgta tattgcatat ctgttttcaa cttttccttt tttaatacct tgataaaattc  37200 cttatttat  tttattttat tttatttttg gagagagtct cactctgtca cgcaggttgg   37260
atggagtgca gtggcatgat ctcggctcac tgcagcctgc aacctccacc tcccagattc   37320
aagcgattct cctgcctcag cctcctgctg ggattacagg cacctgccac catgtctggc   37380
```

```
taatttttgt attttttcgta gagatggggt ttcaccatgt tgaccaggct ggtctggaac   37440
tcctgacctc aagtgatccg cacacctcag cctcccaaag tgctgggatc ataggcatga   37500
gccaccactc ccagtctaaa ttcctaattt taatgcagta agatgtatca ttctcaaagg   37560
ttattgcttt ttacactttta ataagtcttt tcctgaggtc ataaagatac atttaaaaaa   37620
aatttactgt tttgtttata atgcatctgc agttgatgtg tgttggggtt gaggtagaaa   37680 taaaagttt tataaataaa tgtagagcat tgactgagca ccatttatag aaaagttcat   37740 ctcttttttgt ccttgttctg cagtctttga taggtcaatg tctgtggatt tgtgtgtctg   37800
tttctaggct tatttctcat ctgttggcct gtatttctct cctgagctgg tatcacattg   37860
ccttaattac tctagcttta tgataaatct tgttttctag tggaacaaat cactcccttt   37920
cattcttctt caaaaacgtc ttgactctag agactgaggt gggaggactg cttgagccca   37980
ggagtttgag ggacacagtg agctgtgctt gcaccactgc actccaaccc agatgacaga   38040
acaagaccct atctcttaaa aaaaaaataa taatagtaaa ttttttttaaa acagagtgtc   38100 ttggtccttc ttggtgattt gttttttccaa atacatttga gaatctttgg agtttgattt   38160
tgattgaatt ccatctataa atcagttgg ggagaactga catctttaca gtattgagtc   38220
ttagcaaaaa gatcatcatc tattcctctg tttatttggg tattcagtct cagtatttta   38280
gagttttctt tggggtttta tatgtcttta tttagatttt ttaaaattta gatttcaaat   38340
atttaaaagc agaatccaaa ataccacta atcttctagg ttagtggtat ttttggattc   38400
tgcttttaaa tatttcatca tctttcgagt ctgataatac agaaataaag ttgctttttg   38460
aatgattgta ttcattaatg ctgtaaagtc cccttattca ataacttca tgtagatttt   38520 tttctgcata tattatcaca tctttaaata attagagtttt tatttattct tttttaagtt   38580
tctgggaccc ttaatacaat gttgagcaga agtgatatga tagtgtgcct tcttgtctta   38640
ttcttcttaa aggagaagct atcagcaaat cattgagagt aaagtgtttg ttggtgtttt   38700
tttttttttt tttttttttt ttggtgtgtg gaagctctta ttacgttaag tttactaaga   38760
catttttatc ttgtatggat aatcagtttt atcaaatatc ttctgcttct gatgagatta   38820
tggtatgact attttagttg gttcatgtat tcagttaaac tgatgtttca aatattaaac   38880 aaattttct ttttagagta aacctaactt gccagcattc aatttgccat tatttttgttt   38940 tgtgattttc atatgtaagt ttatttagtt ttcttcagat gtccttgtaa gatttagata   39000
tcaagctatt ctaggttcag aaaacaagtt gagggtttta catttctttt atttgaaaga   39060
ggtcttttaa aaaaaaaaa attaagtgta ttttctccaa aactgtttag taaaaatctg   39120
tgtctgatgg gatgcttatg ggttctttta ttattatttc ttgtttgcat ctatatgcct   39180
agttatttta attgtgcact ggaaattctg tttacaaaat tctttataga taaaaatttg   39240
aagcttggga tgagggtagc tttttttcag caaggtttta tgttcctttc tgccaggaaa   39300
agaggcccca acctctgcac tcacctcccc tagatgtctc tcattcccta acctcttgat   39360
ttacaattct tgttaactc cttgtatctt caggctactt ttctagctgt ccacagtggg   39420
gtggttggac cagatgacct agggaatcag agcagaagtc actcccattt tctgtggttt   39480
tagatagttc cttttctttt tgcttttctg tctcgcgtca cctaaactac tagaatctag   39540
agagtgtgca ttatgtattc cagatgtata atagtgtatc ttttgttttt gttgtttgtt   39600
tctacaactt ttatacttta ttaggtgact ttatttaaca gaaagtttgt catttctggt   39660
atttctctca acacagaaaa gccaagttgt gtgttaattt tggttatgtt taaataagtt   39720
tgtaaccttt gctgacctca caacttatgt tttggtaggg aaaactaaag ctgaacaata   39780
```

```
tttgggcatt tggacttaga agagagagta gtggcttgtt actcttttta aagcaagcta    39840
aaatcgtttt aaatgtaatg ctttacagga tctattttaa acacacactc ttcctttaca    39900
gaacgctttg gataaacaag aagaattgac acctcttgga gtccacttgg cacgattacc    39960
cgttgagcca catattggaa aaatgattct ttttggagca ctgttctgct gcttagaccc    40020
agtactcact attgctgcta gtctcagttt caaagatcca tttgtcattc cactggtaag    40080
aaaaatggaa ataaaaccga gttattttag atgtgaacag gagttgctta gatatatttt    40140
tcattagcgt tttattagaa tgtcattctc cattatagca tcagagcaat ttaaattggc    40200
tatgtctgct attttttaagg gaaaagaaaa gattgcagat gcaagaagaa aggaattggc    40260
aaaggatact agaagtgatc acttaacagt tgtgaatgcg tttgaggtaa aaaaaaaaa    40320 ttttgtcctg gattatgata gtttattcaa atgaaatgct aataatagaa taaggatcat    40380
atttaacctt ttgaaatctc tgttataagg ccgggcgcgg tggctcatgc ctgtaatcat    40440
agcactttgg gaggctgagg caggtgtatc acctgaagtc aggagtttga gaccaggctg    40500
gccaacatgg cgaaaccctg tctctactac aaatacaaaa attagctgtg tgtggtggtg    40560
ggcatttgta atcccagcta ctcaggaggc tgaggcagga gaattgcttg aactccgggg    40620
cgcggtggtt gcagtgagct gaaatcatgc cactgcactt cagcctgggc gatggagtga    40680
gactcaatct caaaaaaacc aaaaaaccaa aatctatatt atcataggta tcaggagtaa    40740
attactgaga atgttgaaat ttagctgaac atttgaaaaa agttataatt cattttaat     40800 tttgtaatag ttcattacat ttaccgtttt ggggaaataa tagttttgg taagaatgaa     40860 caagtgaata gttatttta aaattttgta tttaataatt tctttgtatc tttggcttat    40920
taacgctaat gacagtctct ttctattcat taataaacta ccctgtattc agatttaaca    40980
tgtaatagag gatcataatc atgtacataa ttcagattaa agagacattt tctgctccca    41040
aaagccacgt gtatctgagg gtaaacattt atcacctatc ttggtaaaat ttaaatgtaa    41100
tttggttttt agaggcagta tcttttttct gtggctctac attctgtttc atgtgacata    41160
ttatgggaaa gttcatgttt ttttgtcttt gagcttattc agcttgtctt tcctttttcc    41220
ccatttccct cctcttaaaa aaaaagcaa actataaaga aaatctgtga atttgaaaat    41280
atataatagc atttaagtca gttaatagt gtgttctttt tgattagtgt attatgtaca    41340
gtttggatgc cattttgtgt aaaatacata attaatatat tactatatac ttaattgtat    41400
aaaggtctgg aacttcagtg gtggttgtct cttaaggact aggatcatgg ggagtgtatg    41460
tgtttttagt tttatcagtt ataaaattct ttgaattttt tacaaagaaa attaaatatt    41520 agtagaaatat taagctttta ctaaagtaaa gagggaaacc agtagtaatc tttgtttgcg    41580
ggagaaatat agatttcttc atttcttgtc cccatagggc tgggaagagg ctaggcgacg    41640
tggtttcaga tacgaaaagg actattgctg ggaatatttc ctgtcttcaa acacactgca    41700
ggtaatggtg aatgttttgc agtaattatc atatatgcta gattagagaa tatatacatc    41760
cattttgtac aattagatct atagcaaaaa agtcaaatat atggaaattg agtatatttg    41820
tatatataca caaagtaatg ggggatcttt ctgaaatcaa ctgcaacaaa acaaggaaaa    41880
gaaacatggt tccagaggat aagagcaagg cacagtaggg ttcgatttct gttcctgtcc    41940
ccacattcta gttgctattt tgatgattca aactgagaat ttttgctaac actactaaaa    42000
tctgttgaaa agtatcaaat aggatagata tctgtaagtt ttctggttta gtatagtgaa    42060
acaccacagg caagcatttg taaaacagaa gaaaacagta aagagggcat atgccatcac    42120
```

```
atttcagact acactgaact gggtattcga agccagtgag aatagaaata tcctcatctt    42180
ctcccagtac acatacactc cagctatgtg acatgaggcc tgatactgga catttaacag    42240
atctacaaat tagtaaacaa aaaaatctaa cataccaaat cagaagtgcc cagtcattag    42300
caaaatggaa aaaaggatc accacaattc ggaaggaaag gaaaagaaaa aaaaaagagt    42360
ggaatgccat gtttcagtag aaaacacctt taaactgttt cataatatgg aatagctaat    42420
aagaatatga attcagcaaa acataggtta gaaaataaac agtagagtga atgaaaagac    42480
acctgagcta agaaaacaaa ttgaagatca aaagaaatca caaggaacag aatggacacc    42540
ccttaaaaac aagttattgc cataggaaaa aagcttgaag taatcacagt ttatggaggt    42600
acctgaaaaa gacaaaaatt aaagcaataa gtaaatcttt aaagacagga agacaggact    42660
catccattat gagaacagta gacattagtg tctgcataca aatcctgtgt aattgaacgt    42720
ttattttgag atgtatgtaa gaacacgttt tgaatggaa ataatgaaat gaacagagaa    42780
gtgaacagaa gcatgaaaac ataactgaat ccaagtgttt gagaatgtca tgtccagtca    42840
ggatatgaat tcaggtgtaa agaaaaacaa caggcattca agaaatactg taccctgag    42900
ctcttcttga aaagcccatt gacggtgaaa tgctgttagt taaagggga atcacagtgg    42960
agatttcagg aatggagagt gcatgcttaa tcagctggtg tatatacatt agaagtattt    43020
aaatatagag ctaataacaa aatggtgtta ggaattacac atgcaaaata gaatgtaaag    43080
attattatcc tgaacagtat aaaataatgg cagtaaaaac caggaggtgt ctaagaaagt    43140
caggtgtcag aaaaattagg tggggaaagt cacacctttc ataaagggga tatatactta    43200
aatataacca actttatgtt tcataatctc taaaaggaat tccttaggaa atatttctgt    43260
tatgaaaata caagattcat ctggtcattc actttccttt ctatttaact tttctttaaa    43320
ttgtactaaa gttaattgtt ttataaagaa tttctatact atgattctgt tattaggatg    43380
catttcttct atcagtatat atacttaatg ggtgtctgca atcttattta tttagaagac    43440
tgagtattga ggcaagggaa gtacttttct atgttacttg aatgctttgt aataagccat    43500
gtatcattat ttaaaaaaaa aacaaaacct taagcttacc tgccatttt aaccatattt    43560
aattctcagt aatagaaata tggatgtgga ttattttctt tatgcttttc tatatttttt    43620
aaaaaatggg ggtggaaagt aattttaaaa attctattag tctttcacaa aatagagtaa    43680
tccttaaaca tcagtggcta ttccttacaa catgcaaact ttttctgtga aagtcgggt    43740
aatatttag gcttacaggc cataagatct cagttacaag cattgacctc tgccattgta    43800
gtgcaaaaac aaccaaatgt agatgaatgg gtgtggctgt gttccaataa aatgttattg    43860
acaaaaacag cttttgtagt ttgccaaccc ttgctttaaa acatgtttgc taaagtgttt    43920
tcataaagca gggatagctt acaactcaat ttatctatta gtgtatggtt tatagcctca    43980
atgtgtgaaa ggtattctag ttctatttgt taccattgct ccctagatgc tgcataacat    44040
gaaaggacag tttgctgagc atcttcttgg agctggattt gtaagcagta gaaatcctaa    44100
agatccagaa tctaatataa attcaggtac agcaggaaac acagtgtaaa taagtatctt    44160
ttgtctattg tatcagtatt ttactttct tttcccctct accttctcac cccccataga    44220
taatgagaag ataattaaag ctgtcatctg tgctggttta tcccaaag ttgctaaaat    44280
tcgactaaat ttgggtaaaa aaagaaaaat gtaagcattg aagattatta ttaattactc    44340
gtaattctct tcttaaactt ttgaaatctg ctcatgtaac aaggcttata ttataaattt    44400
gttcttattc atatgtgggt tatattcttg ttctttaat catttcagag aaggtgaact    44460
gtttagccat tggtatcact ttccctcaca acacatcctg gaatcacctc tttgataacc    44520
```

```
cattattcac aaagaatgct accacatgat accagtgtaa atattagaag agccagcctg   44580
ctagtaaata ccagtggctg gataaaaatt gcttagagta gattttattt cagaaacttt   44640
tttcctcttg ccttataaat ggataactta gctctttgaa taacattgtg atttcactat   44700
tttgagaaat aaagtgtaat aatatattta caggtagcct cagtagtaat tggagacaac   44760
agtgaagcat gagctagaat gagctcattc tagctaaagg atacagagaa actaagagtc   44820
acaaatggcc agtagtgtgg ttgctgctat tttggaagac actctgtatt agaattatga   44880
ttgaatcatt aaaatagtca gtgacccagt gcatgagttt ttaatttgat agatgtgtct   44940
taaggaagta atttcaaatg ttttctaaca gctatattgt aaataatata gatttctagt   45000
agccatggga aaattgtggt tttataatac tgtaatgcat ctccataggt gggcattaaa   45060
acagtcattg tgtagtaaca tgtaaagtat ttaaactgat gttaaatgaa agttggatat   45120
tctagaatta taaacatgaa aaaataaaga ctttaaagat aggccaaagt gcagacattg   45180
ttcttgggca gtggttctca actggcatga ttttgccccc aaaggggaca ttggaaagtg   45240
tctggagata cttgtggttg tcataacagt gtgtcagtag tactaaagtc aagaaaccct   45300
attccaaggt ataaagtaat gggtagctga tgaattttaa tcattgtggt tggattattc   45360
acattttaag tgacctaagt acttttttcaa aataatactt ggccagaaat ttttttgtat   45420
gtgtgtacct aactttacag gtagcttaac agtgagtcac tttgaaattc attttatttt   45480
cctctctgcc atcctgggag ggcttttctga aaaaatgtag ttttctttgg actggtgcat   45540
tgttttggtc cagactaggg gtcagcaaat tttgacctat aggccaaaaa cttgtttttg   45600
tccttttttt gttggaacac aaacatgttg ttttcatgtt gtctattctg ctttccttct   45660
acactagcag agttggacag aaattataga gccccaaata tagaccctaa aatatttact   45720
ctctggtcct gtatagaaat ttgctgggcc aggcacagtg gctcacacct gtaatcctag   45780
cactttggtt ggctgaggct gttagattac ttgagcccag gaggtggagg ttgcagtgag   45840
tcaagatcac accactgcac gttgagagat catgctactg cagtccagcc tgggtgacag   45900
aacgagaccc tgtctcaaaa aaaagaaaaa agaaatttgt gaagttctac tgctctagtt   45960
atgcagggtg gcaggatggc attggtaaat tgacttgaag tgagaaaaaa taatttctgg   46020
ttttattcta agtattttaaa actgtaaatt cataaccatg attcatgatt ttgattacaa   46080
gtcttatgaa ttcttagaac ttcagaagtg gccgggtgtg gtggctcaca cctgtaatcc   46140
tggcactttg ggaggccaag gtaggcggac cacctgaggt cagaagtttg agaccagcct   46200
ggccatcgtg gtgaaacccc atctctacta agaatacaaa aactaattgg gtatggtggt   46260
ggcacatgcc tgtaatccca gctacccagg aggctgaggc aggagaatcg ccggaacccg   46320
ggaggcggag gctgcagtga gctgagattg gccactgca ctccagtctg ggtgacagag   46380
caagactccg tctcaaaaaa aaaaaaaaa acttcgaaag agacactcgt aaaacaaat    46440 aggaaagatt agtggattat tagctttat gctgttagtt aatacaggta attaacatta   46500
actatttaaa aataaattat taaacatctc cctgttgaat aatactaaag acttttacaa   46560
attgagataa aatgtgtatg actatcaaaa aaaaaatgac ctaggaattg agagattgaa   46620
ttagaactgt caacatgaat ttaaacagaa ttcttaactt ttcatttttt attcatctgg   46680
gtcatactct gtaaaatttt taagttgata attttacagt tattttgtaa atcaagggct   46740
gtttatcagt attatgattg tcatagtaaa atgtataaac tcttggtatg aatcacttaa   46800
ttattttagg tacttttttg ttatttattc ttcagtggta tagtgtgcat taacattaag   46860
```

```
gaaaagaata ttctgccatt tttctaaaat gttgagtaat tatacctgca agaagaagat    46920
tagttacatg atttaaatta ttcatactga tagcattttt tcatatattt ttaaggaaat    46980
tatgctctgt cctcaaatat aaatatattt ttttgcaaaa ataaactgaa ttattctctg    47040 gaatttttt agattccggg atttgtttgg tttttaccaa gctcttctat cagttttca    47100 agtagtgtaa aaaagaaaa tcctctagaa gacttctttt taacaaactg cattttaact    47160 tttttaaag ggtaaaagtt tacacaaaaa ccgatggcct ggttgctgtt catcctaaat    47220
ctgttaatgt ggagcaaaca gactttcact acaactggct tatctatcac ctaaagatga    47280
gaacaagcag tgtaagtgaa catttaaaat aattaaggat ctgattatca gtctcattgt    47340
atttttatga ttgtgtagtt ttaacaatta tatacaaaat ttttttttg ttgtgtctta    47400 ttcctgtgac gtgagtaact ttttccctct aacaaataac ctattctttt aattttcagg    47460
tctgtaatga tggatctttg tattttaatt agttaggaca gttatttgat tgcataattt    47520
tctttcagaa cttgctttca agaaatattg gcatatttta tggtgtacag gagtttacat    47580
tgtatagaaa gttttgttag catgtcagta taccttataa gtattgttca gcatgttgag    47640
attctgttta tttatatttt tctctttaga acagtaattt gagatgattt ataaaaaact    47700
ggataaaaat aacttcggca acattagtgt tttgcttttg tcactcagaa aatattttgt    47760
tcagagtagt gcttagttta aactaaaaaa tattaaaata cctatgttct ctgaataatg    47820
aagatggctc atttaaaatg gtatttctta caaatctctg taattacaat agaaggttaa    47880
tattttagaa ggaagatact cattaattaa tactggtaat attgttgaat ttatatagta    47940
atcttttcag actcctgaat gtattaattc actttaattt tcattacaga tatacttgta    48000
tgactgcaca gaggtttccc catactgtct cttgttttt ggaggtgaca tttccatcca    48060
gaaggataac gatcaggaaa ctattgctgt agatgagtgg attgtatttc agtctccagc    48120
aagaattgcc catcttgtta aggtgactga ctttatgtga ttatcttaaa tctacatgta    48180
agtcagcatg tggtcatgtg gttttgttct aactgttaaa tagattaaca tttcttgctc    48240
tatttcagca gagcaaataa ttttgaaaaa atgattcctg gttttctga attgtgtttt    48300 gaggtggtaa cagaccagcc attctaaatg gctcagtgtg attgcagtgt gaattttaac    48360
tgcactttag ttattcactc ataaccacac tttagttgat tgctcactaa atgttttagc    48420
ttttgagcca tcgcttgtga aactccttgt atcaggtaaa ttagtttcat ttattatgtt    48480
atttggtaat atatctgcct tgttgaaca tgtataattt ttccaacctt aggaattaag    48540
aaaggaacta gatattcttc tgcaagagaa gattgaaagt cctcatcctg tagactggaa    48600
tgacactaaa tccagagact gtgcagtact gtcagctatt atagacttga tcaaaacaca    48660
ggaaaaggca actcccagga actttccgcc acgattccag gatggatatt acagctgaca    48720
gcttttcagg ggtggtctga aaagccagtt tgacagccat tcttcatcat tgtttaaatt    48780
ttggctggat gccaaaccct gggacatgaa caattttcat gtgtaaggta gaagccttca    48840
gtaggtagta aagacttaat gtgcatgact tgatgttata tgtagagata tatatatata    48900
tatatatata ccataaaagc aatatgttct ctgatcatat actctgctgt ggtcatgccc    48960
actctttggg agtatattcc ctttatatat attgagtatt gtaccacttg agaaattcct    49020
ttgttctgtt atacaaaatt aatctttctg ctcataatga ttgatgatac caccagtaaa    49080
aataggatgt ttaccccaaa acaagtgtca attaagaatt tgaacacaac cacatttttt    49140
aaaatgaaac ttctatcgga agtaaattaa tttgttgtaa taaagtccag tatttaataa    49200
aatgtacaat gttaaatctc agccaacctc ttggattggt ttctacattt tcacctatgg    49260
```

```
cttggttcat ttgatatttt tactattttt aaaacacgtg cccttttat atcaccctgt    49320 gcctcataat acagcaattg agagcacggt ctggagcctg attacctcag ttccagtctc    49380
agctctgtca gttagtcagt gtcttggctt ctctccttt tccttatctt gtaagataca    49440
gttggccctt catatccatg cattccacat ctgtggattc aaacaactgt ggatagaaga    49500
tatttgggga aaaaaggat ggttgtgtct atactgaaca tgtgcagact ttttccttg    49560 tcattccta aacaatacag tttaacagct atttatatag tatttacatt gtattaggta    49620
```

<210> SEQ ID NO 234
<211> LENGTH: 1376
<212> TYPE: DNA
<213> ORGANISM: H. sapiens

<400> SEQUENCE: 234

```
ttgatgatac caccagtaaa aataggatgt ttaccccaaa acaagtgtca attaagaatt      60
tgaacacaac cacattttt aaaatgaaac ttctatcgga agtaaattaa tttgttgtaa     120
taaagtccag tatttaataa aatgtacaat gttaaatctc agccaacctc ttggattggt     180
ttctacattt tcacctatgg cttggttcat ttgatatttt tactattttt aaaacacgtg     240 cccttttat atcaccctgt gcctcataat acagcaattg agagcacggt ctggagcctg     300
attacctcag ttccagtctc agctctgtca gttagtcagt gtcttggctt ctctctcttt     360
ttccttatct tgtaagatac agctggccct tcatatccat gcattccaca tctgtggatt     420
caaaccactg tggatagaag atatttgggg aaaaaagga tggctgcgtc tatactgaac     480
atgtgcagac ttttttcctt gtcattccct aaacaataca gtttaacagc tatttatata     540
gtattcacat tggattacgt attataaata atccacagat gacttaaaga acatgggagg     600
ttgcgcctac gtaacattgc caaaaaccac gcccattta ttataaaaga cctcgagcca     660
tccatggcac cctggacatt ctgcggtgcc ccgctccact gtaaaccaca ccccataccc     720 cccaccccg accaccccga ttcccctcc tatgttcctc cctctccac cgtcttacta     780 cccgccgtaa tgatccgccc gaattaccca ccacaaatac cccctcctcg caccctagcg     840 tctacccct taaccaaaag tcccacacac atcctctttc catacacgcc tcacaacccc     900
ccgctaatac taccccacc ccccacatca ccctcgtctt actacatcag cgccttcccc     960 tcaccccct atcccccccc cacccctct ccagccccc accctccct tgttccccac     1020 tttctccccc aaattccacc tccccccaaa aagtatcacc ttactcatca attatactat    1080
ccctcggtct tccacctccc ccaagttaca cccccttttc tcccttacc ccacaaccat    1140 acctttcatc tttatttatc caaaaattct caaatctcat cccccatttt tcatccccc    1200 cctcgtttat atgtcgacac acaccccctc ataaacatat cacacgccct cccccccccc    1260
ctacgatatg ccacatcgtc ccataaataa cccgacacac ccttcgtata attcctgctg    1320
ctccaccccc ccgcacctcc cccccatttt ctatccccct ccccgcaacc actaat         1376
```

<210> SEQ ID NO 235
<211> LENGTH: 3502
<212> TYPE: DNA
<213> ORGANISM: H. sapiens

<400> SEQUENCE: 235

```
attccagcgg ttgctggttc tgacgggttg tagtctgcca ggacaatgag ttatgactac      60
catcagaact ggggccgtga tggggtccc cgcagctccg gtggggggcta tggaggggg    120
```

```
ccagcagggg gtcatggagg taaccgaggc tccggaggag gcggcggcgg cggagggggt    180
ggtcgaggcg gcaggggccg gcatcccggg cacctgaaag gccgcgaaat cggcatgtgg    240
tacgcgaaaa aacaggggca gaagaacaag gaagcggaga ggcaagagag agctgtagta    300
cacatggatg aacgacgaga agaacaaatt gtacagttac tgaattctgt tcaagcgaag    360
aatgataaag agtcagaagc acagatatcc tggtttgctc ctgaggatca tggatacggt    420
actgaagttt ctactaagaa cacaccatgc tcagagaaca aacttgacat ccaggaaaag    480
aagttgataa atcaagaaaa aaaaatgttt agaatcagga acagatcata tattgaccga    540
gattctgagt atctcttgca agaaaatgaa ccagatggaa ctttagacca aaaattattg    600
gaagatttac aaaagaaaaa aaatgacctt cggtatattg aaatgcagca tttcagagaa    660
aagctgcctt cgtatggaat gcaaaaggaa ttggtaaatt taattgataa ccatcaggta    720
acagtaataa gtggtgaaac tggttgtggc aaaaccactc aagttactca gttcattttg    780
gataactaca ttgaaagagg aaaaggatct gcttgcagaa tagtttgtac tcagccaaga    840
agaattagtg ccatttcagt tgcggaaaga gtagctgcag aaagggcaga atcttgtggc    900
agtggtaata gtactggata tcaaattcgt ctccagagtc ggttgccaag gaaacagggt    960
tctatcttat actgtacaac aggaatcatc cttcagtggc tccagtcaga cccgtatttg   1020
tccagtgtta gtcatatcgt acttgatgaa atccatgaaa gaaatctgca gtcagatgtt   1080
ttaatgactg ttgttaaaga ccttctcaat tttcgatctg acttgaaagt aatattgatg   1140
agtgcaacat gaatgcaga aaagttttca gaatattttg gtaactgtcc aatgatacat   1200
atacctggtt ttacctttcc ggttgtggaa tatcttttgg aagatgtaat tgaaaaaata   1260
aggtatgttc cagaacaaaa agaacacaga tgccagttta gaggggttt catgcaaggg   1320 catgtaaata gacaagaaaa agaagaaaaa gaagcaatat ataaagaacg ttggccagat   1380
tatgtaaggg aactgcgaag aaggtattct gcaagtactg tagatgttat agaaatgatg   1440
gaggatgata aagttgatct gaatttgatt gttgccctca tccgatacat tgttttggaa   1500
gaagaggatg tgcgatact ggtctttctg ccaggctggg acaatatcag cactttacat   1560
gatctcttga tgtcacaagt aatgtttaaa tcagataaat ttttaattat acctttacat   1620
tcactgatgc ctacagttaa ccagacacag gtgtttaaaa gaaccctcc tggtgttcgg   1680 aaaatagtaa ttgctaccaa cattgcggag actagcatta ccatagatga tgtcgtttat   1740
gtgatagatg gaggaaaaat aaaagagacg cattttgata ctcagaacaa taacagtaca   1800
atgtccgctg agtgggttag taaagctaat gccaaacaga gaaaaggtcg agctggaaga   1860
gttcaacctg gtcattgcta tcatctgtat aatggtctta gagcaagtct tctagatgac   1920
tatcaactgc cagaaatttt gagaactcct ttggaagaac tttgtttaca aataaagatt   1980
ttaaggctag gtggaattgc ttattttctg agtagattaa tggacccacc atcaaatgag   2040
gcagtgttac tctccataag acacctgatg gagctgaacg ctttggataa acaagaagaa   2100
ttgacacctc ttggagtcca cttggcacga ttacccgttg agccacatat tggaaaaatg   2160
attctttttg gagcactgtt ctgctgctta gacccagtac tcactattgc tgctagtctc   2220
agtttcaaag atccatttgt cattccactg gctgggaag aggctaggcg acgtggtttc   2280
agatacgaaa aggactattg ctgggaatat tttctgtctt caaacacact gcagatgctg   2340
cataacatga aaggacagtt tgctgagcat cttcttggag ctggatttgt aagcagtaga   2400
aatcctaaag atccagaatc taatataaat tcagataatg agaagataat taagctgtc   2460 atctgtgctg gtttatatcc caaagttgct aaaattcgac taaatttggg taaaaaaga   2520
```

-continued

```
aaaatggtaa aagtttacac aaaaaccgat ggcctggttg ctgttcatcc taaatctgtt    2580
aatgtggagc aaacagactt tcactacaac tggcttatct atcacctaaa gatgagaaca    2640
agcagtatat acttgtatga ctgcacagag gtttccccat actgtctctt gttttttgga    2700
ggtgacattt ccatccagaa ggataacgat caggaaacta ttgctgtaga tgagtggatt    2760
gtatttcagt ctccagcaag aattgcccat cttgttaagg aattaagaaa ggaactagat    2820
attcttctgc aagagaagat tgaaagtcct catcctgtag actggaatga cactaaatcc    2880
agagactgtg cagtactgtc agctattata gacttgatca aaacacagga aaaggcaact    2940
cccaggaact ttccgccacg attccaggat ggatattaca gctgacagct tttcaggggt    3000
ggtctgaaaa gccagtttga cagccattct tcatcattgt ttaaattttg gctggatgcc    3060
aaaccctggg acatgaacaa ttttcatgtg taaggtagaa gccttcagta ggtagtaaag    3120
acttaatgtg catgacttga tgttatatgt agagatatat atatatatat atatatacca    3180
taaaagcaat atgttctctg atcatatact ctgctgtggt catgcccact ctttgggagt    3240
atattccctt tatatatatt gagtattgta ccacttgaga aattcctttg ttctgttata    3300
caaaattaat ctttctgctc ataatgattg atgataccac cagtaaaaat aggatgttta    3360
ccccaaaaca gtgtcaatt aagaatttga acacaaccac attttttaaa atgaaacttc    3420
tatcggaagt aaattaattt gttgtaataa agtccagtat ttaataaaat gtacaatgtt    3480
aaatctcaaa aaaaaaaaaa aa                                            3502
```

<210> SEQ ID NO 236
<211> LENGTH: 20
<212> TYPE: DNA
<213> ORGANISM: Artificial Sequence
<220> FEATURE:
<223> OTHER INFORMATION: PCR Primer

<400> SEQUENCE: 236
gatggagctg aacgctttgg                                               20

<210> SEQ ID NO 237
<211> LENGTH: 22
<212> TYPE: DNA
<213> ORGANISM: Artificial Sequence
<220> FEATURE:
<223> OTHER INFORMATION: PCR Primer

<400> SEQUENCE: 237
caatatgtgg ctcaacgggt aa                                            22

<210> SEQ ID NO 238
<211> LENGTH: 29
<212> TYPE: DNA
<213> ORGANISM: Artificial Sequence
<220> FEATURE:
<223> OTHER INFORMATION: PCR Probe

<400> SEQUENCE: 238
aattgacacc tcttggagtc cacttggca                                     29

<210> SEQ ID NO 239
<211> LENGTH: 20
<212> TYPE: DNA
<213> ORGANISM: Artificial Sequence
<220> FEATURE:
<223> OTHER INFORMATION: Antisense Compound

```
<400> SEQUENCE: 239
atacagtaac tgctatatat                                                    20

<210> SEQ ID NO 240
<211> LENGTH: 20
<212> TYPE: DNA
<213> ORGANISM: Artificial Sequence
<220> FEATURE:
<223> OTHER INFORMATION: Antisense Compound

<400> SEQUENCE: 240
ttcttaattc ctaaggttgg                                                    20

<210> SEQ ID NO 241
<211> LENGTH: 20
<212> TYPE: DNA
<213> ORGANISM: Artificial Sequence
<220> FEATURE:
<223> OTHER INFORMATION: Antisense Compound

<400> SEQUENCE: 241
actacaaccc gtcagaacca                                                    20

<210> SEQ ID NO 242
<211> LENGTH: 20
<212> TYPE: DNA
<213> ORGANISM: Artificial Sequence
<220> FEATURE:
<223> OTHER INFORMATION: Antisense Compound

<400> SEQUENCE: 242
tcataactca ttgtcctggc                                                    20

<210> SEQ ID NO 243
<211> LENGTH: 20
<212> TYPE: DNA
<213> ORGANISM: Artificial Sequence
<220> FEATURE:
<223> OTHER INFORMATION: Antisense Compound

<400> SEQUENCE: 243
ggagcaaacc aggatatctg                                                    20

<210> SEQ ID NO 244
<211> LENGTH: 20
<212> TYPE: DNA
<213> ORGANISM: Artificial Sequence
<220> FEATURE:
<223> OTHER INFORMATION: Antisense Compound

<400> SEQUENCE: 244
cctcaggagc aaaccaggat                                                    20

<210> SEQ ID NO 245
<211> LENGTH: 20
<212> TYPE: DNA
<213> ORGANISM: Artificial Sequence
<220> FEATURE:
<223> OTHER INFORMATION: Antisense Compound

<400> SEQUENCE: 245
atgatcctca ggagcaaacc                                                    20

<210> SEQ ID NO 246
<211> LENGTH: 20
```

```
<212> TYPE: DNA
<213> ORGANISM: Artificial Sequence
<220> FEATURE:
<223> OTHER INFORMATION: Antisense Compound

<400> SEQUENCE: 246
aatctcggtc aatatatgat                                                 20

<210> SEQ ID NO 247
<211> LENGTH: 20
<212> TYPE: DNA
<213> ORGANISM: Artificial Sequence
<220> FEATURE:
<223> OTHER INFORMATION: Antisense Compound

<400> SEQUENCE: 247
ctcagaatct cggtcaatat                                                 20

<210> SEQ ID NO 248
<211> LENGTH: 20
<212> TYPE: DNA
<213> ORGANISM: Artificial Sequence
<220> FEATURE:
<223> OTHER INFORMATION: Antisense Compound

<400> SEQUENCE: 248
agtttcacca cttattactg                                                 20

<210> SEQ ID NO 249
<211> LENGTH: 20
<212> TYPE: DNA
<213> ORGANISM: Artificial Sequence
<220> FEATURE:
<223> OTHER INFORMATION: Antisense Compound

<400> SEQUENCE: 249
ggttttgcca caaccagttt                                                 20

<210> SEQ ID NO 250
<211> LENGTH: 20
<212> TYPE: DNA
<213> ORGANISM: Artificial Sequence
<220> FEATURE:
<223> OTHER INFORMATION: Antisense Compound

<400> SEQUENCE: 250
attcttcttg gctgagtaca                                                 20

<210> SEQ ID NO 251
<211> LENGTH: 20
<212> TYPE: DNA
<213> ORGANISM: Artificial Sequence
<220> FEATURE:
<223> OTHER INFORMATION: Antisense Compound

<400> SEQUENCE: 251
tggcactaat tcttcttggc                                                 20

<210> SEQ ID NO 252
<211> LENGTH: 20
<212> TYPE: DNA
<213> ORGANISM: Artificial Sequence
<220> FEATURE:
<223> OTHER INFORMATION: Antisense Compound

<400> SEQUENCE: 252
```
tgaaatggca ctaattcttc                                          20

<210> SEQ ID NO 253
<211> LENGTH: 20
<212> TYPE: DNA
<213> ORGANISM: Artificial Sequence
<220> FEATURE:
<223> OTHER INFORMATION: Antisense Compound

<400> SEQUENCE: 253
gcaactgaaa tggcactaat                                          20

<210> SEQ ID NO 254
<211> LENGTH: 20
<212> TYPE: DNA
<213> ORGANISM: Artificial Sequence
<220> FEATURE:
<223> OTHER INFORMATION: Antisense Compound

<400> SEQUENCE: 254
tgtttccttg gcaaccgact                                          20

<210> SEQ ID NO 255
<211> LENGTH: 20
<212> TYPE: DNA
<213> ORGANISM: Artificial Sequence
<220> FEATURE:
<223> OTHER INFORMATION: Antisense Compound

<400> SEQUENCE: 255
ggacaaatac gggtctgact                                          20

<210> SEQ ID NO 256
<211> LENGTH: 20
<212> TYPE: DNA
<213> ORGANISM: Artificial Sequence
<220> FEATURE:
<223> OTHER INFORMATION: Antisense Compound

<400> SEQUENCE: 256
tatgactaac actggacaaa                                          20

<210> SEQ ID NO 257
<211> LENGTH: 20
<212> TYPE: DNA
<213> ORGANISM: Artificial Sequence
<220> FEATURE:
<223> OTHER INFORMATION: Antisense Compound

<400> SEQUENCE: 257
gcactcatca atattacttt                                          20

<210> SEQ ID NO 258
<211> LENGTH: 20
<212> TYPE: DNA
<213> ORGANISM: Artificial Sequence
<220> FEATURE:
<223> OTHER INFORMATION: Antisense Compound

<400> SEQUENCE: 258
ttaccaaaat attctgaaaa                                          20

<210> SEQ ID NO 259
<211> LENGTH: 20
<212> TYPE: DNA
<213> ORGANISM: Artificial Sequence

```
<220> FEATURE:
<223> OTHER INFORMATION: Antisense Compound

<400> SEQUENCE: 259
gacagttacc aaaatattct                                              20

<210> SEQ ID NO 260
<211> LENGTH: 20
<212> TYPE: DNA
<213> ORGANISM: Artificial Sequence
<220> FEATURE:
<223> OTHER INFORMATION: Antisense Compound

<400> SEQUENCE: 260
cattggacag ttaccaaaat                                              20

<210> SEQ ID NO 261
<211> LENGTH: 20
<212> TYPE: DNA
<213> ORGANISM: Artificial Sequence
<220> FEATURE:
<223> OTHER INFORMATION: Antisense Compound

<400> SEQUENCE: 261
tgtatcattg gacagttacc                                              20

<210> SEQ ID NO 262
<211> LENGTH: 20
<212> TYPE: DNA
<213> ORGANISM: Artificial Sequence
<220> FEATURE:
<223> OTHER INFORMATION: Antisense Compound

<400> SEQUENCE: 262
gtatatgtat cattggacag                                              20

<210> SEQ ID NO 263
<211> LENGTH: 20
<212> TYPE: DNA
<213> ORGANISM: Artificial Sequence
<220> FEATURE:
<223> OTHER INFORMATION: Antisense Compound

<400> SEQUENCE: 263
tccaaaagat attccacaac                                              20

<210> SEQ ID NO 264
<211> LENGTH: 20
<212> TYPE: DNA
<213> ORGANISM: Artificial Sequence
<220> FEATURE:
<223> OTHER INFORMATION: Antisense Compound

<400> SEQUENCE: 264
ttcagatcaa ctttatcatc                                              20

<210> SEQ ID NO 265
<211> LENGTH: 20
<212> TYPE: DNA
<213> ORGANISM: Artificial Sequence
<220> FEATURE:
<223> OTHER INFORMATION: Antisense Compound

<400> SEQUENCE: 265
tcaaattcag atcaacttta                                              20
```

```
<210> SEQ ID NO 266
<211> LENGTH: 20
<212> TYPE: DNA
<213> ORGANISM: Artificial Sequence
<220> FEATURE:
<223> OTHER INFORMATION: Antisense Compound

<400> SEQUENCE: 266
tcttccaaaa caatgtatcg                                               20

<210> SEQ ID NO 267
<211> LENGTH: 20
<212> TYPE: DNA
<213> ORGANISM: Artificial Sequence
<220> FEATURE:
<223> OTHER INFORMATION: Antisense Compound

<400> SEQUENCE: 267
ctgatattgt cccagcctgg                                               20

<210> SEQ ID NO 268
<211> LENGTH: 20
<212> TYPE: DNA
<213> ORGANISM: Artificial Sequence
<220> FEATURE:
<223> OTHER INFORMATION: Antisense Compound

<400> SEQUENCE: 268
tgtgacatca agagatcatg                                               20

<210> SEQ ID NO 269
<211> LENGTH: 20
<212> TYPE: DNA
<213> ORGANISM: Artificial Sequence
<220> FEATURE:
<223> OTHER INFORMATION: Antisense Compound

<400> SEQUENCE: 269
cagtgaatgt aaaggtataa                                               20

<210> SEQ ID NO 270
<211> LENGTH: 20
<212> TYPE: DNA
<213> ORGANISM: Artificial Sequence
<220> FEATURE:
<223> OTHER INFORMATION: Antisense Compound

<400> SEQUENCE: 270
ggcatcagtg aatgtaaagg                                               20

<210> SEQ ID NO 271
<211> LENGTH: 20
<212> TYPE: DNA
<213> ORGANISM: Artificial Sequence
<220> FEATURE:
<223> OTHER INFORMATION: Antisense Compound

<400> SEQUENCE: 271
attttccgaa caccaggagg                                               20

<210> SEQ ID NO 272
<211> LENGTH: 20
<212> TYPE: DNA
<213> ORGANISM: Artificial Sequence
<220> FEATURE:
<223> OTHER INFORMATION: Antisense Compound
```

```
<400> SEQUENCE: 272
attactattt tccgaacacc                                                   20

<210> SEQ ID NO 273
<211> LENGTH: 20
<212> TYPE: DNA
<213> ORGANISM: Artificial Sequence
<220> FEATURE:
<223> OTHER INFORMATION: Antisense Compound

<400> SEQUENCE: 273
tagcaattac tattttccga                                                   20

<210> SEQ ID NO 274
<211> LENGTH: 20
<212> TYPE: DNA
<213> ORGANISM: Artificial Sequence
<220> FEATURE:
<223> OTHER INFORMATION: Antisense Compound

<400> SEQUENCE: 274
gttggtagca attactattt                                                   20

<210> SEQ ID NO 275
<211> LENGTH: 20
<212> TYPE: DNA
<213> ORGANISM: Artificial Sequence
<220> FEATURE:
<223> OTHER INFORMATION: Antisense Compound

<400> SEQUENCE: 275
gctttactaa cccactcagc                                                   20

<210> SEQ ID NO 276
<211> LENGTH: 20
<212> TYPE: DNA
<213> ORGANISM: Artificial Sequence
<220> FEATURE:
<223> OTHER INFORMATION: Antisense Compound

<400> SEQUENCE: 276
cattagcttt actaacccac                                                   20

<210> SEQ ID NO 277
<211> LENGTH: 20
<212> TYPE: DNA
<213> ORGANISM: Artificial Sequence
<220> FEATURE:
<223> OTHER INFORMATION: Antisense Compound

<400> SEQUENCE: 277
tttggcatta gctttactaa                                                   20

<210> SEQ ID NO 278
<211> LENGTH: 20
<212> TYPE: DNA
<213> ORGANISM: Artificial Sequence
<220> FEATURE:
<223> OTHER INFORMATION: Antisense Compound

<400> SEQUENCE: 278
agaccattat acagatgata                                                   20

<210> SEQ ID NO 279
```

```
<211> LENGTH: 20
<212> TYPE: DNA
<213> ORGANISM: Artificial Sequence
<220> FEATURE:
<223> OTHER INFORMATION: Antisense Compound

<400> SEQUENCE: 279
ctctaagacc attatacaga                                                  20

<210> SEQ ID NO 280
<211> LENGTH: 20
<212> TYPE: DNA
<213> ORGANISM: Artificial Sequence
<220> FEATURE:
<223> OTHER INFORMATION: Antisense Compound

<400> SEQUENCE: 280
acttgctcta agaccattat                                                  20

<210> SEQ ID NO 281
<211> LENGTH: 20
<212> TYPE: DNA
<213> ORGANISM: Artificial Sequence
<220> FEATURE:
<223> OTHER INFORMATION: Antisense Compound

<400> SEQUENCE: 281
agaagacttg ctctaagacc                                                  20

<210> SEQ ID NO 282
<211> LENGTH: 20
<212> TYPE: DNA
<213> ORGANISM: Artificial Sequence
<220> FEATURE:
<223> OTHER INFORMATION: Antisense Compound

<400> SEQUENCE: 282
catctagaag acttgctcta                                                  20

<210> SEQ ID NO 283
<211> LENGTH: 20
<212> TYPE: DNA
<213> ORGANISM: Artificial Sequence
<220> FEATURE:
<223> OTHER INFORMATION: Antisense Compound

<400> SEQUENCE: 283
ggagttctca aaatttctgg                                                  20

<210> SEQ ID NO 284
<211> LENGTH: 20
<212> TYPE: DNA
<213> ORGANISM: Artificial Sequence
<220> FEATURE:
<223> OTHER INFORMATION: Antisense Compound

<400> SEQUENCE: 284
ccaaaggagt tctcaaaatt                                                  20

<210> SEQ ID NO 285
<211> LENGTH: 20
<212> TYPE: DNA
<213> ORGANISM: Artificial Sequence
<220> FEATURE:
<223> OTHER INFORMATION: Antisense Compound

<400> SEQUENCE: 285
```

-continued ttcttccaaa ggagttctca                                              20

<210> SEQ ID NO 286
<211> LENGTH: 20
<212> TYPE: DNA
<213> ORGANISM: Artificial Sequence
<220> FEATURE:
<223> OTHER INFORMATION: Antisense Compound

<400> SEQUENCE: 286
caaagttctt ccaaaggagt                                              20

<210> SEQ ID NO 287
<211> LENGTH: 20
<212> TYPE: DNA
<213> ORGANISM: Artificial Sequence
<220> FEATURE:
<223> OTHER INFORMATION: Antisense Compound

<400> SEQUENCE: 287
agaaaataag caattccacc                                              20

<210> SEQ ID NO 288
<211> LENGTH: 20
<212> TYPE: DNA
<213> ORGANISM: Artificial Sequence
<220> FEATURE:
<223> OTHER INFORMATION: Antisense Compound

<400> SEQUENCE: 288
tactcagaaa ataagcaatt                                              20

<210> SEQ ID NO 289
<211> LENGTH: 20
<212> TYPE: DNA
<213> ORGANISM: Artificial Sequence
<220> FEATURE:
<223> OTHER INFORMATION: Antisense Compound

<400> SEQUENCE: 289
tccattaatc tactcagaaa                                              20

<210> SEQ ID NO 290
<211> LENGTH: 20
<212> TYPE: DNA
<213> ORGANISM: Artificial Sequence
<220> FEATURE:
<223> OTHER INFORMATION: Antisense Compound

<400> SEQUENCE: 290
actgcctcat ttgatggtgg                                              20

<210> SEQ ID NO 291
<211> LENGTH: 20
<212> TYPE: DNA
<213> ORGANISM: Artificial Sequence
<220> FEATURE:
<223> OTHER INFORMATION: Antisense Compound

<400> SEQUENCE: 291
tttccaatat gtggctcaac                                              20

<210> SEQ ID NO 292
<211> LENGTH: 20
<212> TYPE: DNA

```
<213> ORGANISM: Artificial Sequence
<220> FEATURE:
<223> OTHER INFORMATION: Antisense Compound

<400> SEQUENCE: 292
tcatttttcc aatatgtggc                                               20

<210> SEQ ID NO 293
<211> LENGTH: 20
<212> TYPE: DNA
<213> ORGANISM: Artificial Sequence
<220> FEATURE:
<223> OTHER INFORMATION: Antisense Compound

<400> SEQUENCE: 293
cagccctcaa acgcattcac                                               20

<210> SEQ ID NO 294
<211> LENGTH: 20
<212> TYPE: DNA
<213> ORGANISM: Artificial Sequence
<220> FEATURE:
<223> OTHER INFORMATION: Antisense Compound

<400> SEQUENCE: 294
gacagaaaat attcccagca                                               20

<210> SEQ ID NO 295
<211> LENGTH: 20
<212> TYPE: DNA
<213> ORGANISM: Artificial Sequence
<220> FEATURE:
<223> OTHER INFORMATION: Antisense Compound

<400> SEQUENCE: 295
ttcatgttat gcagcatctg                                               20

<210> SEQ ID NO 296
<211> LENGTH: 20
<212> TYPE: DNA
<213> ORGANISM: Artificial Sequence
<220> FEATURE:
<223> OTHER INFORMATION: Antisense Compound

<400> SEQUENCE: 296
agaagatgct cagcaaactg                                               20

<210> SEQ ID NO 297
<211> LENGTH: 20
<212> TYPE: DNA
<213> ORGANISM: Artificial Sequence
<220> FEATURE:
<223> OTHER INFORMATION: Antisense Compound

<400> SEQUENCE: 297
actgcttaca aatccagctc                                               20

<210> SEQ ID NO 298
<211> LENGTH: 20
<212> TYPE: DNA
<213> ORGANISM: Artificial Sequence
<220> FEATURE:
<223> OTHER INFORMATION: Antisense Compound

<400> SEQUENCE: 298
attatctgaa tttatattag                                               20
```

```
<210> SEQ ID NO 299
<211> LENGTH: 20
<212> TYPE: DNA
<213> ORGANISM: Artificial Sequence
<220> FEATURE:
<223> OTHER INFORMATION: Antisense Compound

<400> SEQUENCE: 299
ttctcattat ctgaatttat                                               20

<210> SEQ ID NO 300
<211> LENGTH: 20
<212> TYPE: DNA
<213> ORGANISM: Artificial Sequence
<220> FEATURE:
<223> OTHER INFORMATION: Antisense Compound

<400> SEQUENCE: 300
ttatcttctc attatctgaa                                               20

<210> SEQ ID NO 301
<211> LENGTH: 20
<212> TYPE: DNA
<213> ORGANISM: Artificial Sequence
<220> FEATURE:
<223> OTHER INFORMATION: Antisense Compound

<400> SEQUENCE: 301
gcacagatga cagctttaat                                               20

<210> SEQ ID NO 302
<211> LENGTH: 20
<212> TYPE: DNA
<213> ORGANISM: Artificial Sequence
<220> FEATURE:
<223> OTHER INFORMATION: Antisense Compound

<400> SEQUENCE: 302
aaccagcaca gatgacagct                                               20

<210> SEQ ID NO 303
<211> LENGTH: 20
<212> TYPE: DNA
<213> ORGANISM: Artificial Sequence
<220> FEATURE:
<223> OTHER INFORMATION: Antisense Compound

<400> SEQUENCE: 303
atataaacca gcacagatga                                               20

<210> SEQ ID NO 304
<211> LENGTH: 20
<212> TYPE: DNA
<213> ORGANISM: Artificial Sequence
<220> FEATURE:
<223> OTHER INFORMATION: Antisense Compound

<400> SEQUENCE: 304
tttgggatat aaaccagcac                                               20

<210> SEQ ID NO 305
<211> LENGTH: 20
<212> TYPE: DNA
<213> ORGANISM: Artificial Sequence
<220> FEATURE:
```

<223> OTHER INFORMATION: Antisense Compound

<400> SEQUENCE: 305
gcaactttgg gatataaacc                                               20

<210> SEQ ID NO 306
<211> LENGTH: 20
<212> TYPE: DNA
<213> ORGANISM: Artificial Sequence
<220> FEATURE:
<223> OTHER INFORMATION: Antisense Compound

<400> SEQUENCE: 306
ttttagcaac tttgggatat                                               20

<210> SEQ ID NO 307
<211> LENGTH: 20
<212> TYPE: DNA
<213> ORGANISM: Artificial Sequence
<220> FEATURE:
<223> OTHER INFORMATION: Antisense Compound

<400> SEQUENCE: 307
tagataagcc agttgtagtg                                               20

<210> SEQ ID NO 308
<211> LENGTH: 20
<212> TYPE: DNA
<213> ORGANISM: Artificial Sequence
<220> FEATURE:
<223> OTHER INFORMATION: Antisense Compound

<400> SEQUENCE: 308
ggtgatagat aagccagttg                                               20

<210> SEQ ID NO 309
<211> LENGTH: 20
<212> TYPE: DNA
<213> ORGANISM: Artificial Sequence
<220> FEATURE:
<223> OTHER INFORMATION: Antisense Compound

<400> SEQUENCE: 309
atactgcttg ttctcatctt                                               20

<210> SEQ ID NO 310
<211> LENGTH: 20
<212> TYPE: DNA
<213> ORGANISM: Artificial Sequence
<220> FEATURE:
<223> OTHER INFORMATION: Antisense Compound

<400> SEQUENCE: 310
agtatatact gcttgttctc                                               20

<210> SEQ ID NO 311
<211> LENGTH: 20
<212> TYPE: DNA
<213> ORGANISM: Artificial Sequence
<220> FEATURE:
<223> OTHER INFORMATION: Antisense Compound

<400> SEQUENCE: 311
gacagtactg cacagtctct                                               20

```
<210> SEQ ID NO 312
<211> LENGTH: 20
<212> TYPE: DNA
<213> ORGANISM: Artificial Sequence
<220> FEATURE:
<223> OTHER INFORMATION: Antisense Compound

<400> SEQUENCE: 312
tagctgacag tactgcacag                                              20

<210> SEQ ID NO 313
<211> LENGTH: 20
<212> TYPE: DNA
<213> ORGANISM: Artificial Sequence
<220> FEATURE:
<223> OTHER INFORMATION: Antisense Compound

<400> SEQUENCE: 313
tgtacatttt attaaatact                                              20

<210> SEQ ID NO 314
<211> LENGTH: 20
<212> TYPE: DNA
<213> ORGANISM: Artificial Sequence
<220> FEATURE:
<223> OTHER INFORMATION: Antisense Compound

<400> SEQUENCE: 314
gagatttaac attgtacatt                                              20

<210> SEQ ID NO 315
<211> LENGTH: 20
<212> TYPE: DNA
<213> ORGANISM: Artificial Sequence
<220> FEATURE:
<223> OTHER INFORMATION: Antisense Compound

<400> SEQUENCE: 315
tgatataaaa agggcacgtg                                              20

<210> SEQ ID NO 316
<211> LENGTH: 20
<212> TYPE: DNA
<213> ORGANISM: Artificial Sequence
<220> FEATURE:
<223> OTHER INFORMATION: Antisense Compound

<400> SEQUENCE: 316
cttcccagcc cagtggaatg                                              20

<210> SEQ ID NO 317
<211> LENGTH: 20
<212> TYPE: DNA
<213> ORGANISM: H. sapiens

<400> SEQUENCE: 317
atatatagca gttactgtat                                              20

<210> SEQ ID NO 318
<211> LENGTH: 20
<212> TYPE: DNA
<213> ORGANISM: H. sapiens

<400> SEQUENCE: 318
ccaaccttag gaattaagaa                                              20
```

```
<210> SEQ ID NO 319
<211> LENGTH: 20
<212> TYPE: DNA
<213> ORGANISM: H. sapiens

<400> SEQUENCE: 319
gccaggacaa tgagttatga                                               20

<210> SEQ ID NO 320
<211> LENGTH: 20
<212> TYPE: DNA
<213> ORGANISM: H. sapiens

<400> SEQUENCE: 320
cagatatcct ggtttgctcc                                               20

<210> SEQ ID NO 321
<211> LENGTH: 20
<212> TYPE: DNA
<213> ORGANISM: H. sapiens

<400> SEQUENCE: 321
atcctggttt gctcctgagg                                               20

<210> SEQ ID NO 322
<211> LENGTH: 20
<212> TYPE: DNA
<213> ORGANISM: H. sapiens

<400> SEQUENCE: 322
ggtttgctcc tgaggatcat                                               20

<210> SEQ ID NO 323
<211> LENGTH: 20
<212> TYPE: DNA
<213> ORGANISM: H. sapiens

<400> SEQUENCE: 323
atcatatatt gaccgagatt                                               20

<210> SEQ ID NO 324
<211> LENGTH: 20
<212> TYPE: DNA
<213> ORGANISM: H. sapiens

<400> SEQUENCE: 324
atattgaccg agattctgag                                               20

<210> SEQ ID NO 325
<211> LENGTH: 20
<212> TYPE: DNA
<213> ORGANISM: H. sapiens

<400> SEQUENCE: 325
cagtaataag tggtgaaact                                               20

<210> SEQ ID NO 326
<211> LENGTH: 20
<212> TYPE: DNA
<213> ORGANISM: H. sapiens

<400> SEQUENCE: 326
aaactggttg tggcaaaacc                                               20
```

```
<210> SEQ ID NO 327
<211> LENGTH: 20
<212> TYPE: DNA
<213> ORGANISM: H. sapiens

<400> SEQUENCE: 327
tgtactcagc caagaagaat                                               20

<210> SEQ ID NO 328
<211> LENGTH: 20
<212> TYPE: DNA
<213> ORGANISM: H. sapiens

<400> SEQUENCE: 328
gccaagaaga attagtgcca                                               20

<210> SEQ ID NO 329
<211> LENGTH: 20
<212> TYPE: DNA
<213> ORGANISM: H. sapiens

<400> SEQUENCE: 329
gaagaattag tgccatttca                                               20

<210> SEQ ID NO 330
<211> LENGTH: 20
<212> TYPE: DNA
<213> ORGANISM: H. sapiens

<400> SEQUENCE: 330
attagtgcca tttcagttgc                                               20

<210> SEQ ID NO 331
<211> LENGTH: 20
<212> TYPE: DNA
<213> ORGANISM: H. sapiens

<400> SEQUENCE: 331
agtcggttgc caaggaaaca                                               20

<210> SEQ ID NO 332
<211> LENGTH: 20
<212> TYPE: DNA
<213> ORGANISM: H. sapiens

<400> SEQUENCE: 332
agtcagaccc gtatttgtcc                                               20

<210> SEQ ID NO 333
<211> LENGTH: 20
<212> TYPE: DNA
<213> ORGANISM: H. sapiens

<400> SEQUENCE: 333
tttgtccagt gttagtcata                                               20

<210> SEQ ID NO 334
<211> LENGTH: 20
<212> TYPE: DNA
<213> ORGANISM: H. sapiens

<400> SEQUENCE: 334
```
aaagtaatat tgatgagtgc                                      20

<210> SEQ ID NO 335
<211> LENGTH: 20
<212> TYPE: DNA
<213> ORGANISM: H. sapiens

<400> SEQUENCE: 335
agaatatttt ggtaactgtc                                      20

<210> SEQ ID NO 336
<211> LENGTH: 20
<212> TYPE: DNA
<213> ORGANISM: H. sapiens

<400> SEQUENCE: 336
attttggtaa ctgtccaatg                                      20

<210> SEQ ID NO 337
<211> LENGTH: 20
<212> TYPE: DNA
<213> ORGANISM: H. sapiens

<400> SEQUENCE: 337
ggtaactgtc caatgataca                                      20

<210> SEQ ID NO 338
<211> LENGTH: 20
<212> TYPE: DNA
<213> ORGANISM: H. sapiens

<400> SEQUENCE: 338
ctgtccaatg atacatatac                                      20

<210> SEQ ID NO 339
<211> LENGTH: 20
<212> TYPE: DNA
<213> ORGANISM: H. sapiens

<400> SEQUENCE: 339
gatgataaag ttgatctgaa                                      20

<210> SEQ ID NO 340
<211> LENGTH: 20
<212> TYPE: DNA
<213> ORGANISM: H. sapiens

<400> SEQUENCE: 340
taaagttgat ctgaatttga                                      20

<210> SEQ ID NO 341
<211> LENGTH: 20
<212> TYPE: DNA
<213> ORGANISM: H. sapiens

<400> SEQUENCE: 341
cgatacattg ttttggaaga                                      20

<210> SEQ ID NO 342
<211> LENGTH: 20
<212> TYPE: DNA
<213> ORGANISM: H. sapiens

<400> SEQUENCE: 342
ccaggctggg acaatatcag                                               20

<210> SEQ ID NO 343
<211> LENGTH: 20
<212> TYPE: DNA
<213> ORGANISM: H. sapiens

<400> SEQUENCE: 343
catgatctct tgatgtcaca                                               20

<210> SEQ ID NO 344
<211> LENGTH: 20
<212> TYPE: DNA
<213> ORGANISM: H. sapiens

<400> SEQUENCE: 344
ttataccttt acattcactg                                               20

<210> SEQ ID NO 345
<211> LENGTH: 20
<212> TYPE: DNA
<213> ORGANISM: H. sapiens

<400> SEQUENCE: 345
cctttacatt cactgatgcc                                               20

<210> SEQ ID NO 346
<211> LENGTH: 20
<212> TYPE: DNA
<213> ORGANISM: H. sapiens

<400> SEQUENCE: 346
cctcctggtg ttcggaaaat                                               20

<210> SEQ ID NO 347
<211> LENGTH: 20
<212> TYPE: DNA
<213> ORGANISM: H. sapiens

<400> SEQUENCE: 347
ggtgttcgga aaatagtaat                                               20

<210> SEQ ID NO 348
<211> LENGTH: 20
<212> TYPE: DNA
<213> ORGANISM: H. sapiens

<400> SEQUENCE: 348
tcggaaaata gtaattgcta                                               20

<210> SEQ ID NO 349
<211> LENGTH: 20
<212> TYPE: DNA
<213> ORGANISM: H. sapiens

<400> SEQUENCE: 349
aaatagtaat tgctaccaac                                               20

<210> SEQ ID NO 350
<211> LENGTH: 20
<212> TYPE: DNA
<213> ORGANISM: H. sapiens

-continued

<210> SEQ ID NO 351
<211> LENGTH: 20
<212> TYPE: DNA
<213> ORGANISM: H. sapiens

<400> SEQUENCE: 350
gctgagtggg ttagtaaagc                                               20

<210> SEQ ID NO 351
<211> LENGTH: 20
<212> TYPE: DNA
<213> ORGANISM: H. sapiens

<400> SEQUENCE: 351
gtgggttagt aaagctaatg                                               20

<210> SEQ ID NO 352
<211> LENGTH: 20
<212> TYPE: DNA
<213> ORGANISM: H. sapiens

<400> SEQUENCE: 352
ttagtaaagc taatgccaaa                                               20

<210> SEQ ID NO 353
<211> LENGTH: 20
<212> TYPE: DNA
<213> ORGANISM: H. sapiens

<400> SEQUENCE: 353
tatcatctgt ataatggtct                                               20

<210> SEQ ID NO 354
<211> LENGTH: 20
<212> TYPE: DNA
<213> ORGANISM: H. sapiens

<400> SEQUENCE: 354
tctgtataat ggtcttagag                                               20

<210> SEQ ID NO 355
<211> LENGTH: 20
<212> TYPE: DNA
<213> ORGANISM: H. sapiens

<400> SEQUENCE: 355
ataatggtct tagagcaagt                                               20

<210> SEQ ID NO 356
<211> LENGTH: 20
<212> TYPE: DNA
<213> ORGANISM: H. sapiens

<400> SEQUENCE: 356
ggtcttagag caagtcttct                                               20

<210> SEQ ID NO 357
<211> LENGTH: 20
<212> TYPE: DNA
<213> ORGANISM: H. sapiens

<400> SEQUENCE: 357
tagagcaagt cttctagatg                                               20

<210> SEQ ID NO 358
<211> LENGTH: 20
<212> TYPE: DNA
<213> ORGANISM: H. sapiens

<400> SEQUENCE: 358
ccagaaattt tgagaactcc                                               20

<210> SEQ ID NO 359
<211> LENGTH: 20
<212> TYPE: DNA
<213> ORGANISM: H. sapiens

<400> SEQUENCE: 359
aattttgaga actcctttgg                                               20

<210> SEQ ID NO 360
<211> LENGTH: 20
<212> TYPE: DNA
<213> ORGANISM: H. sapiens

<400> SEQUENCE: 360
tgagaactcc tttggaagaa                                               20

<210> SEQ ID NO 361
<211> LENGTH: 20
<212> TYPE: DNA
<213> ORGANISM: H. sapiens

<400> SEQUENCE: 361
actcctttgg aagaactttg                                               20

<210> SEQ ID NO 362
<211> LENGTH: 20
<212> TYPE: DNA
<213> ORGANISM: H. sapiens

<400> SEQUENCE: 362
tttctgagta gattaatgga                                               20

<210> SEQ ID NO 363
<211> LENGTH: 20
<212> TYPE: DNA
<213> ORGANISM: H. sapiens

<400> SEQUENCE: 363
ccaccatcaa atgaggcagt                                               20

<210> SEQ ID NO 364
<211> LENGTH: 20
<212> TYPE: DNA
<213> ORGANISM: H. sapiens

<400> SEQUENCE: 364
gttgagccac atattggaaa                                               20

<210> SEQ ID NO 365
<211> LENGTH: 20
<212> TYPE: DNA
<213> ORGANISM: H. sapiens

<400> SEQUENCE: 365
gccacatatt ggaaaaatga                                               20

<210> SEQ ID NO 366
<211> LENGTH: 20
<212> TYPE: DNA

```
<213> ORGANISM: H. sapiens

<400> SEQUENCE: 366
gtgaatgcgt ttgagggctg                                           20

<210> SEQ ID NO 367
<211> LENGTH: 20
<212> TYPE: DNA
<213> ORGANISM: H. sapiens

<400> SEQUENCE: 367
tgctgggaat attttctgtc                                           20

<210> SEQ ID NO 368
<211> LENGTH: 20
<212> TYPE: DNA
<213> ORGANISM: H. sapiens

<400> SEQUENCE: 368
cagatgctgc ataacatgaa                                           20

<210> SEQ ID NO 369
<211> LENGTH: 20
<212> TYPE: DNA
<213> ORGANISM: H. sapiens

<400> SEQUENCE: 369
cagtttgctg agcatcttct                                           20

<210> SEQ ID NO 370
<211> LENGTH: 20
<212> TYPE: DNA
<213> ORGANISM: H. sapiens

<400> SEQUENCE: 370
gagctggatt tgtaagcagt                                           20

<210> SEQ ID NO 371
<211> LENGTH: 20
<212> TYPE: DNA
<213> ORGANISM: H. sapiens

<400> SEQUENCE: 371
ttcagataat gagaagataa                                           20

<210> SEQ ID NO 372
<211> LENGTH: 20
<212> TYPE: DNA
<213> ORGANISM: H. sapiens

<400> SEQUENCE: 372
attaaagctg tcatctgtgc                                           20

<210> SEQ ID NO 373
<211> LENGTH: 20
<212> TYPE: DNA
<213> ORGANISM: H. sapiens

<400> SEQUENCE: 373
agctgtcatc tgtgctggtt                                           20

<210> SEQ ID NO 374
<211> LENGTH: 20
```

-continued

```
<212> TYPE: DNA
<213> ORGANISM: H. sapiens

<400> SEQUENCE: 374
tcatctgtgc tggtttatat                                        20

<210> SEQ ID NO 375
<211> LENGTH: 20
<212> TYPE: DNA
<213> ORGANISM: H. sapiens

<400> SEQUENCE: 375
gtgctggttt atatcccaaa                                        20

<210> SEQ ID NO 376
<211> LENGTH: 20
<212> TYPE: DNA
<213> ORGANISM: H. sapiens

<400> SEQUENCE: 376
ggtttatatc ccaaagttgc                                        20

<210> SEQ ID NO 377
<211> LENGTH: 20
<212> TYPE: DNA
<213> ORGANISM: H. sapiens

<400> SEQUENCE: 377
atatcccaaa gttgctaaaa                                        20

<210> SEQ ID NO 378
<211> LENGTH: 20
<212> TYPE: DNA
<213> ORGANISM: H. sapiens

<400> SEQUENCE: 378
cactacaact ggcttatcta                                        20

<210> SEQ ID NO 379
<211> LENGTH: 20
<212> TYPE: DNA
<213> ORGANISM: H. sapiens

<400> SEQUENCE: 379
caactggctt atctatcacc                                        20

<210> SEQ ID NO 380
<211> LENGTH: 20
<212> TYPE: DNA
<213> ORGANISM: H. sapiens

<400> SEQUENCE: 380
aagatgagaa caagcagtat                                        20

<210> SEQ ID NO 381
<211> LENGTH: 20
<212> TYPE: DNA
<213> ORGANISM: H. sapiens

<400> SEQUENCE: 381
gagaacaagc agtatatact                                        20

<210> SEQ ID NO 382
```

```
<210> SEQ ID NO 382
<211> LENGTH: 20
<212> TYPE: DNA
<213> ORGANISM: H. sapiens

<400> SEQUENCE: 382
agagactgtg cagtactgtc                                              20

<210> SEQ ID NO 383
<211> LENGTH: 20
<212> TYPE: DNA
<213> ORGANISM: H. sapiens

<400> SEQUENCE: 383
ctgtgcagta ctgtcagcta                                              20

<210> SEQ ID NO 384
<211> LENGTH: 20
<212> TYPE: DNA
<213> ORGANISM: H. sapiens

<400> SEQUENCE: 384
agtatttaat aaaatgtaca                                              20

<210> SEQ ID NO 385
<211> LENGTH: 20
<212> TYPE: DNA
<213> ORGANISM: H. sapiens

<400> SEQUENCE: 385
aatgtacaat gttaaatctc                                              20

<210> SEQ ID NO 386
<211> LENGTH: 20
<212> TYPE: DNA
<213> ORGANISM: H. sapiens

<400> SEQUENCE: 386
cacgtgccct ttttatatca                                              20

<210> SEQ ID NO 387
<211> LENGTH: 3534
<212> TYPE: DNA
<213> ORGANISM: M. musculus

<400> SEQUENCE: 387
gccattttca gcggttgagt tttggcagag ctgctagtcg gctccgacaa tgagctacga    60
ctatcatcag agctggagcc gcgatggggg cccacggggc tccggccagg gctccagcgg   120
cggcggcggc ggagggagcc ggggctcggg cggcggcgga gggggccgcg gcggccgggg   180
ccggcatccc gcacacctta agggtcgcga gatcggcctg tggtacgcca agaagcagac   240
gcagaagaac aaggaggctg agaggcagga gagagctgta gtgcacatgg atgaacgtcg   300
agaagagcaa attgtgcagc tgctgaattc agtccaagct aagactgaca agattcaga   360 agcgcagata tcctggtttg ctcctgagga tcatgggtat ggtactgaag tttcttcaga   420
gaaaaaaata aactcagaga agaaacttga caaccaggaa aagaaattgc taaaccaaga   480
aaaaaagaca tttaggatca cagacaaatc atatattgac cgagattctg agtatttatt   540
gcaagaaaat gagccaaacc taagcttaga tcaacattta ctggaagatt tacaaggaa   600 aaaaactgac cctcgatata tagagatgca gcgtttcaga aaaagctgc cttcatatgg   660 aatgcagaag gagctggtaa atctaatcaa taaccatcag gtgacagtaa taagtggtga   720
```

```
aactggttgt ggcaaaacca ctcaggttac gcagttcatc ttggataact acatcgaaag    780
aggaaaaggg tctgcctgca gaatagtgtg tactcagccg agaagaatta gtgccatttc    840
agtcgctgag agagtggcca cagaaagggc agagtcttgt ggcaatggta atagtactgg    900
ataccagatt cgtcttcaaa gtcggttgcc aaggaaacaa ggttctatct tatactgcac    960
aacaggaatc attcttcagt ggctccagtc cgactcacgt ttgtccagtg ttagtcatat   1020
tgtacttgat gaaattcatg aaaggaatct acagtcggat gttttaatga ctgttattaa   1080
agatcttctc cattttcgat ctgatctcaa agtaatattg atgagtgcaa ctttgaatgc   1140
tgagaaattt tcagaatatt ttggtaactg tccaatgata catatacccg ggtttacttt   1200
tccagttgtg gaatatcttt tggaagatat cattgaaaaa ataagatatg ttccagacca   1260
aaaagaacat agatcccagt tcaagagggg tttcatgcag ggtcatgtaa atagacaaga   1320
aaaagaagaa aaagaggcca tctataagga acgctggcca gcgtatataa aggaactgcg   1380
gacaagatac tctgcaagta ccgtagatgt tttgcaaatg atggatgatg ataaagttga   1440
tctgaatttg attgctgccc ttattcgata cattgttttg gaagaagagg atggtgcaat   1500
attggtcttt ctaccaggct gggacaatat cagtactttg catgatctct tgatgtcaca   1560
agtgatgttt aaatcagata agtttctcat tatacctta cattcactga tgcctaccgt   1620
caaccagaca caggtattta aaaaaactcc tcccggtgtt cggaaaatag taattgctac   1680
caacattgca gagactagca tcaccataga tgatgtggtt tatgtaatag atggaggaaa   1740
aattaaagaa acacactttg acacacagaa caacatcagt accatgtctg ctgagtgggt   1800
tagtaaagct aatgccaaac agaggaaagg gagagctgga agagttcagc ctggtcattg   1860
ttatcatctg tataatggtc ttagagcaag tcttctagat gactaccaac taccagaaat   1920
tttgagaact cctttggaag aactctgttt gcaaataaag atcttgaggc tgggtggaat   1980
tgcttatttt ctgagtagat taatggatcc accatcaaat gaggcagtgg tgctctccat   2040
aaaacaccta atggaactga gtgctttgga taagcaagaa gaattaacac ctcttggtgt   2100
ccatttagcc cgactgcctg ttgagccaca tattggaaaa atgattctct ttggagcttt   2160
gttctgctgc ttagatccag ttctcaccat tgctgccagt ctcagcttta aagatccctt   2220
tgtcattcca ttgggaaaag aaaagattgc agatgcaaga agaaaagaac tggcaaagga   2280
aactagaagt gatcacctga cagttgtgaa tgcatttgag ggctgggaag aagccaaacg   2340
acgtggtttc aggtatgaaa aggactactg ctgggaatat tttctgtctt cgaacacact   2400
acagatgctg cataacatga agggacagtt tgctgagcat cttcttggag ctggatttgt   2460
aagcagtaga agtcccaaag atccaaaagc taatataaat tcagataatg agaagataat   2520
taaagctgtc atctgtgctg gtttatatcc caaagttgct aaaatccgac taaatttggg   2580
taaaaagagg aaaatggtaa aagttcacac gaagtctgac ggcctggttt ctattcatcc   2640
taagtctgtc aacgtggagc agacagactt ccactacaac tggcttatct atcacctgaa   2700
gatgagaaca agcagtatat acttgtacga ctgtacagaa gtgtcaccat actgcctcct   2760
gttctttgga ggagatattt ccatccagaa agataaggat caggaaatta ttgctgtaga   2820
tgagtggatt gtgtttcagt ctccagaaag aattgcccat cttgttaagg gactaagaaa   2880
ggaactggat agccttctac aagagaagat tgaaagccct catcctgtag actgggacga   2940
cactaagtca agagactgtg cagtactgtc agcattcta gacttgatca aaactcaaaa   3000
aaaggctact ccaaggaact tgccaccacg gtcacaggac ggatattata gctgacagct   3060
```

```
ttctgtgatg gcctaaaacc tatcctggtg tccataattt ccaatttttt tcttttttt    3120 agttttggc  aaaatgccaa gccctgggtt atgacttgct tttgtgtgta agttagaaac    3180
tttcattggg tagtaaagag ttaatgtgca tgactaaaca gtgccatcta gctactataa    3240
agacattgga aaaagtaata tgctttctga ccttatcctc tgttgtagat atgtccacac    3300
tttgggagaa ttcccaaagt tgtaacattg agaaattcct ttatgctatt atgcaaaatt    3360
aattttctgt tcataatgac tgtccagaga caataaaaat agaaagttgg gccaaaaagc    3420
agtatgaagt aagaatttga atacaaccac attttttaaa aatgaaattc tattattagt    3480
aaatttgttg taataaagtc cgatatttaa taaaatgtac aatgtataaa tccc         3534

<210> SEQ ID NO 388
<211> LENGTH: 3072
<212> TYPE: DNA
<213> ORGANISM: R. norvegicus

<400> SEQUENCE: 388
gcccgcttcc ggtcctgggc gccatttca  gcggttgagt tttggtggta cctgtagtcg      60
tctcggacaa tgagctacga ctatcatcag agctggagcc gcgacggggg cccacggggc     120
tccggccagg gctctggcgg cggcggtgga gggagccggg gctccggcgg cggcggaggg     180
ggccgcggcg gccggggccg gcatccggcc caccttaagg gtcgcgagat aggcctatgg     240
tacgcaaaaa agcaaacgca gaagaacaag gaggctgaga gacaagagag agctgtagtg     300
cacatggatg aacggcgaga agagcaaatt gtgcagctgc taaattcagt ccaagcaaag     360
aatgataaag attcagaagc acagatatcc tggtttgctc ctgaggatca tgggtatggt     420
actgaagttt cttcagagaa aaaaataaac tcagagaaga aacttgacaa ccaggaaaag     480
aaattgctga ccaagaaaaa aagacatat  aggatcacag acaaatcata tattgaccga     540
gattctgagt atttattgca acaaaatgaa ccaaacctag cttagacca  acaattattg     600 gaagatttac aaaagaaaaa aactgacccct cggtatatag agatgcagcg tttcagaaaa     660
aagctgcctt catatggaat gcagaaggag ctggtaaatt taatcaataa ccatcaggtg     720
acagtgataa gtggtgagac tggttgtggc aaaaccactc aggttactca gttcatcttg     780
gataactaca tcgaaagagg aatagggtct gcctgcagaa tagtgtgtac tcagccaaga     840
agaattagtg ccatttcagt tgctgagagg gtggctgcag aaagggcaga gtcttgtggc     900
aatggtaata gtactggata ccagattcgt ctccaaagtc ggttgccaag gaaacaaggc     960
tctatcctat actgcacaac aggaatcatt cttcagtggc tccagtcaga ctcacgtttg    1020
tccagtgtta gtcatattgt acttgatgaa attcatgaaa ggaatctaca gtcagatgtt    1080
ttaatgactg ttattaaaga tctcctccat tttcgatcgg atctcaaagt aatattgatg    1140
agtgcaacct tgaatgctga gaaattttca gaatattttg gtaactgtcc aatgatacat    1200
atacctgggt ttacttttcc agttgtggaa tatcttttgg aagatatcat tgaaaaaata    1260
agatattttc cagaacaaaa agaacataga tcccagttca aaggggtttt catgcagggt    1320
catgtaaata gacaagaaaa agaagaaaaa gaggcgatct ataagaacg  ctggccagct    1380 tatataaagg aactacagac aagatactct gcaagtacca tagatgtttt ggaaatgatg    1440
gatgatgata aagttgatct gaatttgatt gctgccctta ttcgatacat tgttttggaa    1500
gaagaggacg gtgcaatatt ggtctttcta ccaggctggg acaatatcag tactttgcat    1560
gatctcttga tgtcacaagt gatgtttaaa tcagataggt tcttattat  acctttacat    1620 tcactgatgc ccactgtaaa ccagacacag gtatttaaaa aaactcctcc tggtgttcgg    1680
```

-continued

```
aaaatagtaa ttgctaccaa cattgcagag actagcatca ccatagatga tgtggtctat    1740
gtaatagatg gagggaaaat taaagaaaca cactttgaca cacagaacaa catcagtacc    1800
atgtctgctg agtgggttag taaagctaat gccaaacaga ggaaagggag agctggaaga    1860
gttcagcctg gtcattgtta tcatctgtat aatggtctta gagcaagtct tctagatgac    1920
taccaactac cagaaatttt gagaactcct tggaagaac tttgtttgca aataaagatc     1980
ttgaggctgg gtggaattgc ttattttctg agtaggttaa tggatccacc atcagatgag    2040
gcagtagtgc tctccataaa acatctaatg gaactgagtg ctttggataa gcaagaagaa    2100
ttgacacctc ttggagtcca tttagcccga ctgcctgttg agccacatat tggaaaaatg    2160
attctctttg gagctttgtt ctgttgctta gatccagtcc tcaccattgc tgccagtctc    2220
agctttaaag atccctttgt cattccattg ggaaaagaaa agattgcaga tgcaagaaga    2280
aaggaactgg caaaggaaac tagaagtgat catctgacag ttgtgaatgc gtttgagggc    2340
tgggaagaag ctaaacggcg tggtttcaga tatgaaaaag actactgctg ggaatatttt    2400
ctctcttcaa acacactaca gatgctgcat aacatgaagg gacagtttgc tgagcatctt    2460
cttggagctg gatttgtaag cagtagaagt cccaaagatc caaaagctaa tataaattca    2520
gataatgaga agatcattaa agctgtcatc tgtgctggtt tatatcccaa agttgctaaa    2580
atccgactaa atttgggtaa aaaaaggaaa atggtgaaag ttcacacaaa gtctgatggt    2640
ctggtttcta ttcatcctaa gtctgtcaat gtggagcaga cagacttcca ctacaactgg    2700
cttatctatc acctgaagat gagaacaagc agtatatact tgtacgactg cacagaagtc    2760
tcaccatact gcctcttgtt ctttggagga gatatttcca tccagaaaga taaggatcag    2820
gaaattattg ctgtagacga atggattgtg tttcagtctc cagaaagaat tgctcatctt    2880
gttaagggac taagaaagga actggatatc cttctacaag agaagattga gtgccctcat    2940
cctgtagatt ggaacgacac caaatccaga gactgtgcag tactgtcagc gattctagac    3000
ttgatcaaaa cacaagaaaa ggctattcca aggaacttgc caccacgatc acaggatgga    3060
tattacagct ga                                                        3072
```

<210> SEQ ID NO 389
<211> LENGTH: 19
<212> TYPE: DNA
<213> ORGANISM: Artificial Sequence
<220> FEATURE:
<223> OTHER INFORMATION: Antisense Compound

<400> SEQUENCE: 389
cgagaggcgg acgggaccg                                                    19

<210> SEQ ID NO 390
<211> LENGTH: 21
<212> TYPE: DNA
<213> ORGANISM: Artificial Sequence
<220> FEATURE:
<223> OTHER INFORMATION: Antisense Compound

<400> SEQUENCE: 390
cgagaggcgg acgggaccgt t                                                 21

<210> SEQ ID NO 391
<211> LENGTH: 21
<212> TYPE: DNA
<213> ORGANISM: Artificial Sequence
<220> FEATURE:

```
-continued
<223> OTHER INFORMATION: Antisense Compound

<400> SEQUENCE: 391
ttgctctccg cctgccctgg c                                              21

<210> SEQ ID NO 392
<211> LENGTH: 19
<212> TYPE: DNA
<213> ORGANISM: Artificial Sequence
<220> FEATURE:
<223> OTHER INFORMATION: Antisense Compound

<400> SEQUENCE: 392
gctctccgcc tgccctggc                                                 19
```

MODULATION OF THE RNA INTERFERENCE PATHWAY

CROSS REFERENCE TO RELATED APPLICATIONS

The current application claims priority benefit of U.S. Ser. No. 60/472,723, filed May 22, 2003, and U.S. Provisional Application Ser. No. 60/562,693, filed Apr. 14, 2004, each of which is hereby incorporated by reference in its entirety.

FIELD OF THE INVENTION

The present invention provides compositions and methods for modulating the RNAi pathway and for RNAi pathway component identification. In some embodiments, the present invention relates to compounds, particularly oligonucleotide compounds that hybridize with nucleic acid molecules encoding EIF2C2. Such compounds are shown herein to modulate the expression of EIF2C2.

The present invention also relates to compounds, particularly oligonucleotide compounds, that hybridize with nucleic acid molecules encoding DDX36. Such compounds are shown herein to modulate the expression of DDX36.

BACKGROUND OF THE INVENTION

Most eukaryotes possess a cellular defense system for protecting their genomes against invading foreign genetic elements. Insertion of foreign elements is believed to be generally accompanied by formation of double-stranded RNA (dsRNA) that is interpreted by the cell as a signal for unwanted gene activity. dsRNA induces potent and specific gene silencing through a mechanism referred to as RNA interference (RNAi) in animals or posttranscriptional gene silencing (PTGS) in plants. The currently accepted mechanism commences with processing of the long dsRNA by Dicer RNase III into small interfering RNAs (siRNAs) that are double-stranded and are predominantly 21 or 22 nucleotides in length. Thereafter, siRNA duplexes are assembled into a multi-component complex, called the RISC complex (RNA-induced silencing complex), which guides the sequence-specific recognition, hybridization, and cleavage of endogenous mRNA.

One of the components of RISC is EIF2C2, a member of the large family of Argonaute proteins that are characterized by the presence of a PAZ domain and a C-terminal Piwi domain (Hammond et al., Science, 2001, 293, 1146-1150). Although these domains have an unknown function, it has been suggested that the PAZ domain may act as a protein-protein interaction motif. Dicer also contains a PAZ domain and this may provide a mechanism for interaction between Dicer and EIF2C2 to facilitate siRNA incorporation into RISC (Martinez et al., Cell, 2002, 110, 563-574). Other members of the Argonaute family have been implicated in translational control, microRNA processing, and development in diverse species (Carmell et al., Genes Dev., 2002, 16, 2733-2742).

The gene encoding human EIF2C2 was first cloned in 1999 during the course of cloning EIF2C1 (Koesters et al., Genomics, 1999, 61, 210-218). EIF2C1 is a eukaryotic protein translation initiation factor that forms part of the GTP-binding complex and assists with methionyl-tRNA(i) binding to the 40S ribosomal subunit. EIF2C2 (also called Ago2, Argonaute 2, and eukaryotic translation initiation factor 2C,2) was accidentally isolated as a crosshybridizing cDNA clone and found to be 85% identical to EIF2C1 which is frequently lost in human cancers such as Wilms tumors, neuroblastoma, and carcinomas of the breast, liver, and colon. The gene encoding EIF2C2 was again cloned in 2001 when the protein was sequenced and it was identified as a member of the Argonaute family and as a homolog of rde-1, a protein essential for RNAi in C. elegans (Hammond et al., Science, 2001, 293, 1146-1150).

EIF2C2 has been identified as a component of RISC and may facilitate siRNA incorporation into RISC, however EIF2C2 may also have other biochemical functions. For example, a common form of inherited mental retardation called fragile X syndrome is caused by the loss of FMR1 expression, a gene which encodes an RNA-binding protein. The FMR1 complex in Drosophila contains two ribosomal proteins, 5S RNA, and EIF2C2. Since the Drosophila FMR1 complex can also associate with Dicer, a model has been suggested for translation control in Drosophila whereby the RNAi and FMR1 pathways intersect and raise the possibility that defects in the RNAi-related machinery may cause human disease (Caudy et al., Genes Dev., 2002, 16, 2491-2496; Ishizuka et al., Genes Dev., 2002, 16, 2497-2508).

EIF2C2 has also been found in a large 15 subunit ribonucleoprotein (RNP) that contains Gemin3, Gemin4, and numerous microRNAs. RNPs are assembled and restructured by the Survival of Motor Neurons (SMN) complex, a complex which results in the neurodegenerative disease spinal muscular atrophy when its levels are reduced (Mourelatos et al., Genes Dev., 2002, 16, 720-728).

EIF2C2 and Dicer have also been found to be mislocalized to perinuclear regions of germline cells in mutant ovaries of Drosophila with a null allele of maelstrom. As maelstrom is a component of Drosophila nuage, the perinuclear granules that are a hallmark of germline cells across the animal kingdom, the mislocalization of EIF2C2 and Dicer in maelstrom mutants suggests a potential connection between nuage and the microRNA or RNAi pathways (Findley et al., Development, 2003, 130, 859-871).

Currently, there are no known therapeutic agents which effectively inhibit the synthesis of EIF2C2. Suppression of EIF2C2 expression in Drosophila S2 cells with two different double-stranded RNA approximately 1000 nucleotides in length was used to demonstrate that EIF2C2 is essential for RNAi in these cells (Hammond et al., Science, 2001, 293, 1146-1150).

Consequently, there remains a long felt need for agents capable of effectively inhibiting EIF2C2 function. These agents would serve to mediate RNAi pathways and could potentially serve to ameliorate disease conditions associated with aberrant RNA processing or metabolism.

The present invention provides compositions and methods for modulating EIF2C2 expression and consequently the RNAi pathway.

SUMMARY OF THE INVENTION

The present invention is directed to compounds, especially nucleic acid and nucleic acid-like oligomeric compounds, which are targeted to a nucleic acid encoding EIF2C2, and which modulate the expression of EIF2C2. Pharmaceutical and other compositions comprising the compounds of the invention are also provided. Further provided are methods of screening for modulators of EIF2C2 and methods of modulating the expression of EIF2C2 in cells, tissues or animals, the methods comprising contacting said cells, tissues or animals with one or more of the compounds or compositions of the invention. Methods of treating an animal, particularly a human, suspected of having or being prone to a disease or condition associated with expression of EIF2C2 are also set forth herein. Such methods comprise administering a therapeutically or prophylactically effective amount of one or more of the compounds or compositions of the invention to the person in need of treatment. The present invention also provides methods of identifying a gene or protein involved in a pathway comprising the steps of detecting a difference between a first expression profile of a candidate gene in a sample and a second expression profile of the candidate gene in the sample contacted with a first oligomeric compound targeted to the candidate gene; and comparing a first control expression profile of a control gene in a sample contacted with the first oligomeric compound targeted to a candidate gene, to a second control expression profile of the control gene in a sample contacted with the first oligonucleotide and a second oligomeric compound targeted to the control gene, wherein a difference between the first control expression profile and the second control expression profile indicates that the candidate gene is not involved in the pathway. Also provided are methods of identifying a gene or protein involved in a pathway comprising comparing an expression profile of a candidate gene to the expression profile of a control gene in a sample contacted with a first oligomeric compound targeted to the candidate gene followed by a second oligomeric compound targeted to a control gene, wherein a difference between the expression profile of the candidate gene and the expression profile of the control gene indicates that the candidate gene targeted by said first oligomeric compound is involved in the pathway.

DETAILED DESCRIPTION OF THE INVENTION

A. Overview of the Invention

The present invention employs compounds, preferably oligomeric compounds including oligonucleotides and similar species for use in modulating the function or effect of nucleic acid molecules encoding EIF2C2. This is accomplished by providing oligomeric compounds that specifically hybridize with one or more nucleic acid molecules encoding EIF2C2. As used herein, the terms "target nucleic acid" and "nucleic acid molecule encoding EIF2C2" have been used for convenience to encompass DNA encoding EIF2C2, RNA (including pre-mRNA and mRNA or portions thereof) transcribed from such DNA, and also cDNA derived from such RNA. The hybridization of a compound of this invention with its target nucleic acid is generally referred to as "antisense". Consequently, a mechanism believed to be included in the practice of some of the embodiments of the invention is referred to herein as "antisense inhibition"; i.e., through the hybridization of an oligomeric compound of the present invention to a target nucleic acid. Such inhibition is typically based upon hydrogen bonding-based hybridization of oligonucleotide strands or segments such that at least one strand or segment is cleaved, degraded, or otherwise rendered inoperable. In this regard, in some embodiments it is preferred to target specific nucleic acid molecules and their functions for such inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One result of such interference with target nucleic acid function is modulation of the expression of EIF2C2. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" refers to the pairing of complementary strands of oligomeric compounds. In some embodiments, a preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound is specifically hybridizable when binding of the compound to the target nucleic acid interferes with the normal function of the target nucleic acid to cause a loss of activity, and there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays. In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated. Examples of stringent hybridization conditions are known to those skilled in the art and are set forth, for example, in Maniatis et al, Molecular Cloning: A Laboratory Manual. Cold Spring Harbor Laboratory Press, NY, Vol. 1, 2, 3 (1989).

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). In some embodiments it is preferred that the oligomeric compounds of the present invention comprise at least 70%, at least 80%, at least 85%, at least 90%, at least 95, at least 97, at least 98%, at least 99%, and 100% sequence complementarity to a target region within the target nucleic acid to which they are targeted. For example, an oligomeric compound in which 18 of 20 nucleobases are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656), using default parameters.

B. Compounds of the Invention

According to the present invention, compounds include oligomeric compounds, including oligonucleotides, siRNAs, external guide sequence (EGS) oligonucleotides, alternate splicers, and other oligomeric compounds which hybridize to at least a portion of the target nucleic acid. As such, oligomeric compounds may be introduced in the form of single-stranded, double-stranded, circular or hairpin oligomeric compounds and may contain structural elements such as internal or terminal bulges or loops. Once introduced to a system, the oligomeric compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While in some embodiments a single-stranded oligonucleotide may be the preferred form of compound, in some embodiments double-stranded structures, such as double-stranded RNA (dsRNA) molecules, are preferred. In some instances dsRNAs have been shown to induce potent and specific modulation, especially inhibition, of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell*, 1995, 81, 611-620). Montgomery et al. have shown that the primary interference effects of dsRNA are posttranscriptional (Montgomery et al., *Proc. Natl. Acad. Sci. USA*, 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean hybridization-mediated gene silencing involving the introduction of dsRNA leading to the sequence-specific reduction of endogenous targeted mRNA levels (Fire et al., *Nature*, 1998, 391, 806-811). Recently, it has been shown that it is, in fact, the single-stranded RNA oligomers of antisense polarity of the dsRNAs which are the potent inducers of RNAi (Tijsterman et al., *Science*, 2002, 295, 694-697).

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties including, without limitation, enhanced cellular uptake, enhanced affinity for a target nucleic acid and increased stability in the presence of nucleases. Oligomeric compounds may be single or double stranded.

While in some embodiments oligonucleotides are a preferred form of the compounds of the present invention, the present invention also comprehends other families of compounds as well, including, but not limited to, oligonucleotide analogs and mimetics such as those described herein.

The compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In embodiments wherein at least one portion of the oligomeric compounds are double stranded, the sense and/or antisense strand of the oligomeric compound is from about 8 to about 80 nucleobases in length.

In some embodiments, the oligomeric compounds of the invention are 12 to 50 nucleobases in length. One having ordinary skill in the art will appreciate that this embodies oligomeric compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In some embodiments, the oligomeric compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

In some embodiments preferred compounds are oligonucleotides from about 12 to about 50 nucleobases, even more preferably those comprising from about 15 to about 30 nucleobases.

For example, in the context of a double stranded oligomeric compound, the sense and/or antisense strand may comprise from about 8 to about 80 nucleobases, from about 12 to 50 nucleobases in length, and from about 15 to 30 nucleobases in length.

Compounds 8-80 nucleobases in length comprising a stretch of at least eight (8) consecutive nucleobases selected from within the illustrative compounds are considered to be suitable compounds as well.

Exemplary compounds include oligonucleotide sequences that comprise at least the 8 consecutive nucleobases from the 5'-terminus of one of the illustrative preferred compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly, compounds are represented by oligonucleotide sequences that comprise at least the 8 consecutive nucleobases from the 3'-terminus of one of the illustrative compounds (the remaining nucleobases being a consecutive stretch of the same oligonucleotide beginning immediately downstream of the 3'-terminus of the compound which is specifically hybridizable to the target nucleic acid and continuing until the oligonucleotide contains about 8 to about 80 nucleobases). One of skill in the art armed with the compounds described herein will be able, without undue experimentation, to identify further oligomeric compounds.

C. Targets of the Invention

"Targeting" a compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes EIF2C2.

The targeting process usually also generally includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites", as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding EIF2C2, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such a mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such a mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of a mRNA comprises an N7-methylated guanosine residue joined to the 5'-most residue of the mRNA via a 5'-5' triphosphate linkage. The 5' cap region of a mRNA is considered to include the 5' cap structure itself as well as the first 50 nucleotides adjacent to the cap site. In some embodiments it is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence, resulting in exon-exon junctions at the sites where exons are joined. Targeting exon-exon junctions can be useful in situations where the overproduction of a normal splice product is implicated in disease, or where the overproduction of an aberrant splice product is implicated in disease. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources known as "fusion transcripts" are also suitable target sites. It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids. The locations on the target nucleic acid to which the preferred oligomeric compounds of the present invention hybridize are hereinbelow referred to as "preferred target segments." As used herein the term "preferred target segment" is defined as at least an 8-nucleobase portion of a target region to which a oligomeric compound of the present invention is targeted. While not wishing to be bound by theory, it is presently believed that these target segments represent portions of the target nucleic acid which are accessible for hybridization.

While the specific sequences of certain target segments are set forth herein, one of skill in the art will recognize that these serve to illustrate and describe particular embodiments within the scope of the present invention. Additional target segments may be identified by one having ordinary skill.

Target segments 8-80 nucleobases in length comprising a stretch of at least eight (8) consecutive nucleobases selected from within the illustrative target segments are considered to be suitable for targeting.

Target segments can include DNA or RNA sequences that comprise at least the 8 consecutive nucleobases from the 5'-terminus of one of the illustrative target segments (the remaining nucleobases being a consecutive stretch of the same DNA or RNA beginning immediately upstream of the 5'-terminus of the target segment and continuing until the DNA or RNA contains about 8 to about 80 nucleobases). Similarly target segments are represented by DNA or RNA sequences that comprise at least the 8 consecutive nucleobases from the 3'-terminus of one of the illustrative target segments (the remaining nucleobases being a consecutive stretch of the same DNA or RNA beginning immediately downstream of the 3'-terminus of the target segment and continuing until the DNA or RNA contains about 8 to about 80 nucleobases). One having skill in the art armed with the target segments illustrated herein will be able, without undue experimentation, to identify further target segments.

Once one or more target regions, segments or sites have been identified, compounds are chosen which are sufficiently complementary to the target, i.e., hybridize sufficiently well and with sufficient specificity, to give the desired effect.

Let $R(n, n+m-1)$ be a region from a target nucleobase sequence, where "n" is the 5'-most nucleobase position of the region, where "n+m−1" is the 3'-most nucleobase position of the region and where "m" is the length of the region. A set "S(m)", of regions of length "m" is defined as the regions where n ranges from 1 to L−m+1, where L is the length of the target nucleobase sequence and L>m. A set, "A", of all regions can be constructed as a union of the sets of regions for each length from where m is greater than or equal to 8 and is less than or equal to 80.

This set of regions can be represented using the following mathematical notation:

$$A = \bigcup_m S(m) \text{ where } m \in N | 8 \le m \le 80$$

and $$S(m) = \{R_{n,n+m-1} | n \in \{1, 2, 3, \ldots, L-m+1\}\}$$

where the mathematical operator | indicates "such that", where the mathematical operator $\epsilon$ indicates "a member of a set" (e.g. y$\in$Z indicates that element y is a member of set Z), where x is a variable, where N indicates all natural numbers, defined as positive integers, and where the mathematical operator $\cup$ indicates "the union of sets".

For example, the set of regions for m equal to 8, 9 and 80 can be constructed in the following manner. The set of regions, each 8 nucleobases in length, S(m=8), in a target nucleobase sequence 100 nucleobases in length (L=100), beginning at position 1 (n=1) of the target nucleobase sequence, can be created using the following expression:

$$S(8) = \{R_{1,8} | n \in \{1, 2, 3, \ldots, 93\}\}$$

and describes the set of regions comprising nucleobases 1-8, 2-9, 3-10, 4-11, 5-12, 6-13, 7-14, 8-15, 9-16, 10-17, 11-18, 12-19, 13-20, 14-21, 15-22, 16-23, 17-24, 18-25, 19-26, 20-27, 21-28, 22-29, 23-30, 24-31, 25-32, 26-33, 27-34, 28-35, 29-36, 30-37, 31-38, 32-39, 33-40, 34-41, 35-42, 36-43, 37-44, 38-45, 39-46, 40-47, 41-48, 42-49, 43-50, 44-51, 45-52, 46-53, 47-54, 48-55, 49-56, 50-57, 51-58, 52-59, 53-60, 54-61, 55-62, 56-63, 57-64, 58-65, 59-66, 60-67, 61-68, 62-69, 63-70, 64-71, 65-72, 66-73, 67-74, 68-75, 69-76, 70-77, 71-78, 72-79, 73-80, 74-81, 75-82, 76-83, 77-84, 78-85, 79-86, 80-87, 81-88, 82-89, 83-90, 84-91, 85-92, 86-93, 87-94, 88-95, 89-96, 90-97, 91-98, 92-99, 93-100.

An additional set for regions 20 nucleobases in length, in a target sequence 100 nucleobases in length, beginning at position 1 of the target nucleobase sequence, can be described using the following expression:

$$S(20) = \{R_{1,20} | n \in \{1, 2, 3, \ldots, 81\}\}$$

and describes the set of regions comprising nucleobases 1-20, 2-21, 3-22, 4-23, 5-24, 6-25, 7-26, 8-27, 9-28, 10-29, 11-30, 12-31, 13-32, 14-33, 15-34, 16-35, 17-36, 18-37, 19-38, 20-39, 21-40, 22-41, 23-42, 24-43, 25-44, 26-45, 27-46, 28-47, 29-48, 30-49, 31-50, 32-51, 33-52, 34-53, 35-54, 36-55, 37-56, 38-57, 39-58, 40-59, 41-60, 42-61, 43-62, 44-63, 45-64, 46-65, 47-66, 48-67, 49-68, 50-69, 51-70, 52-71, 53-72, 54-73, 55-74, 56-75, 57-76, 58-77, 59-78, 60-79, 61-80, 62-81, 63-82, 64-83, 65-84, 66-85, 67-86, 68-87, 69-88, 70-89, 71-90, 72-91, 73-92, 74-93, 75-94, 76-95, 77-96, 78-97, 79-98, 80-99, 81-100.

An additional set for regions 80 nucleobases in length, in a target sequence 100 nucleobases in length, beginning at position 1 of the target nucleobase sequence, can be described using the following expression:

$$S(80) = \{R_{1,80} | n \in \{1, 2, 3, \ldots, 21\}\}$$

and describes the set of regions comprising nucleobases 1-80, 2-81, 3-82, 4-83, 5-84, 6-85, 7-86, 8-87, 9-88, 10-89, 11-90, 12-91, 13-92, 14-93, 15-94, 16-95, 17-96, 18-97, 19-98, 20-99, 21-100.

Thus, in this example, A would include regions 1-8, 2-9, 3-10 . . . 93-100, 1-20, 2-21, 3-22 . . . 81-100, 1-80, 2-81, 3-82 . . . 21-100.

The union of these aforementioned example sets and other sets for lengths from 10 to 19 and 21 to 79 can be described using the mathematical expression $$A = \bigcup_m S(m)$$

where $\cup$ represents the union of the sets obtained by combining all members of all sets.

The mathematical expressions described herein defines all possible target regions in a target nucleobase sequence of any length L, where the region is of length m, and where m is greater than or equal to 8 and less than or equal to 80 nucleobases and, and where m is less than L, and where n is less than L−m+1.

D. Screening and Target Validation

In some embodiments, the "preferred target segments" identified herein may be employed in a screen for additional compounds that modulate the expression of EIF2C2. "Modulators" are those compounds that decrease or increase the expression of a nucleic acid molecule encoding EIF2C2 and which comprise at least an 8-nucleobase portion which is complementary to a preferred target segment. The screening method comprises the steps of contacting a preferred target segment of a nucleic acid molecule encoding EIF2C2 with one or more candidate modulators, and selecting for one or more candidate modulators which decrease or increase the expression of a nucleic acid molecule encoding EIF2C2. Once it is shown that the candidate modulator or modulators modulate (e.g. either decrease or increase) the expression of a nucleic acid molecule encoding EIF2C2, the modulator may then be employed in further investigative studies of the function of EIF2C2, or for use as a research, diagnostic, or therapeutic agent in accordance with the present invention. The preferred target segments of the present invention may be also be combined with their respective complementary antisense compounds of the present invention to form stabilized double-stranded (duplexed) oligonucleotides. Such double stranded oligonucleotide moieties have been shown in the art to modulate target expression and regulate translation as well as RNA processing via a hybridization mechanism. Moreover, the double stranded moieties may be subject to chemical modifications (Fire et al., *Nature*, 1998, 391, 806-811; Timmons and Fire, *Nature* 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.* 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The compounds of the present invention can also be applied in the areas of drug discovery and target validation. The present invention comprehends the use of the compounds and preferred target segments identified herein in drug discovery efforts to elucidate relationships that exist between EIF2C2 and a disease state, phenotype, or condition. These methods include detecting or modulating EIF2C2 comprising contacting a sample, tissue, cell, or organism with the compounds of the present invention, measuring the nucleic acid or protein level of EIF2C2 and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The compounds of the present invention can be utilized for diagnostics, therapeutics, prophylaxis and as research reagents and kits. Furthermore, oligonucleotides, which are able to inhibit gene expression with exquisite specificity, are often used by those of ordinary skill to elucidate the function of particular genes or to distinguish between functions of various members of a biological pathway. For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As used herein, the phrase, "expression profile" refers to a biochemical profile of a cell and is generally measured by detecting evidence of gene expression (i.e. gene expression profile). The gene expression profile is often measured by the amount of mRNA present in the cell. However, an expression profile can also include the level of the protein or other biological markers linked to a specific gene. Methods of measuring the levels of such biological markers present in a system are well-known to those of skill in the art and include, without limitation, nucleic acid subtraction techniques including representational difference analysis and differential display analysis, microchip analysis, SAGE, and the like. In some embodiments of the present invention, the gene expression profile of a cell that is treated with an agent (experimental expression profile) is compared to the gene expression profile of the same type of cell that has not been treated with the agent (control expression profile). For example, to analyze gene expression at the RNA or mRNA level, RNA and/or mRNA is isolated from the cells. The levels of specific genes can be analyzed using techniques well known to those of ordinary skill in the art, including, without limitation, microchip analysis, serial analysis of gene expression (SAGE), differential display, and the like. The technique that is used is not essential to identify genes involved in the RNAi pathway. The experimental expression profile is compared to the control expression profile. The control expression profile may be determined prior to, contemporaneously with, or after determination of the experimental expression profile.

Further, the control expression profile may be determined by reference to publicly available data concerning expression profiles. Genes or gene products determined to be present in increased levels in the control expression profile compared to the experimental expression profile are "down-regulated", while genes or gene products determined to be present in decreased levels in the control expression profile compared to the experimental expression profile are "up-regulated".

In some embodiments, expression profiles are determined by measuring protein levels. It is well known to one of ordinary skill in the art to determine and compare protein expression levels between two groups of cells. The cells are treated as above, but instead of isolating RNA or mRNA, the proteins are isolated and analyzed to determine the proteins that have been modulated during bone metastasis. Expression profiles may be determined in the absence or presence of other compositions, including, without limitation, putative modulators, known modulators, growth factors, and combinations and subcombinations thereof.

As used herein, the term "detecting" means to establish, discover, or ascertain evidence of an activity (for example, gene expression) or biomolecule (for example, a polypeptide). Methods of detection are well known to those of skill in the art. For example, methods of detecting polynucleotides include, but are not limited to PCR, Northern blotting, Southern blotting, RNA protection, and DNA hybridization (including in situ hybridization). Methods of detecting polypeptides include, but are not limited to, Western blotting, ELISA, enzyme activity assays, slot blotting, peptide mass fingerprinting, electrophoresis, and immunochemistry, and immunohistochemistry. Other examples of detection methods include, but are not limited to, radioimmunoassay (RIA), chemiluminescence immunoassay, fluoroimmunoassay, time-resolved fluoroimmunoassay (TR-FIA), two color fluorescent microscopy, or immunochromatographic assay (ICA), all well known by those of skill in the art. In some embodiments of the present invention, polynucleotide expression is detected using PCR methodologies and polypeptide production is detected using ELISA technology. As used herein, the term "evidence of gene expression" refers to any measurable indicia that a gene is expressed. Evidence of gene expression may be gained from methods including, but not limited to, PCR, FISH, ELISA, or Western blots. Evidence of gene expression may also be gained through the use of phenotypic characteristics or pathological changes characteristic of gene expression. For example, in the mouse model of spinal muscular atrophy by Hsieh-Li et al (Nature Genetics 24, 66-70), several measurable indicia of gene expression (or levels of gene expression) are set forth, including the development of furry hair, survival time, length of tails, and chronic necrosis from the tip of the tail toward the root.

As one nonlimiting example, expression patterns within cells or tissues treated with one or more oligomeric compounds are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

The compounds of the invention are useful for research and diagnostics, because these compounds hybridize to nucleic acids encoding EIF2C2. Primers and probes are useful in methods requiring the specific detection of nucleic acid molecules encoding EIF2C2 and in the amplification of said nucleic acid molecules for detection or for use in further studies of EIF2C2. Hybridization of the primers and probes disclosed herein with a nucleic acid encoding EIF2C2 can be detected by means known in the art. Such means may include conjugation of an enzyme to the primers and/or probes, radiolabelling of the primers and/or probes or any other suitable detection means. Kits using such detection means for detecting the level of EIF2C2 in a sample may also be prepared.

The specificity and sensitivity of hybridization based oligonucleotides is also harnessed by those of skill in the art for therapeutic uses. Such compounds have been employed as therapeutic moieties in the treatment of disease states in animals, including humans. Oligonucleotide drugs, including ribozymes, have been safely and effectively administered to humans and numerous clinical trials are presently underway. It is thus established that oligomeric compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of EIF2C2 is treated by administering oligomeric compounds in accordance with this invention. For example, in one non-limiting embodiment, the methods comprise the step of administering to the animal in need of treatment, a therapeutically effective amount of an EIF2C2 inhibitor. The EIF2C2 inhibitors of the present invention effectively inhibit the activity of the EIF2C2 protein or inhibit the expression of the EIF2C2 protein. In some embodiments, the activity or expression of EIF2C2 in an animal is inhibited by about 10%, about 30%, about 50%, about 60%, about 70%, about 75%, about 80%, about 90%, about 95%, or more.

For example, the reduction of the expression of EIF2C2 may be measured in serum, adipose tissue, liver or any other body fluid, tissue or organ of the animal. In some embodiments, the cells contained within said fluids, tissues or organs being analyzed contain a nucleic acid molecule encoding EIF2C2 protein and/or the EIF2C2 protein itself.

The oligomeric compounds of the invention can be utilized in pharmaceutical compositions by adding an effective amount of a compound to a suitable pharmaceutically acceptable diluent or carrier. Use of the compounds and methods of the invention may also be useful prophylactically.

F. Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of oligomeric compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Modified oligonucleotide backbones containing a phosphorus atom therein include, but are not limited to, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugar and Internucleoside Linkages-Mimetics

In some oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539, 082; 5,714,331; and 5,719,262, each of which is herein incorporated by reference. Further teaching of PNA compounds can be found in Nielsen et al., *Science,* 1991, 254, 1497-1500.

Some embodiments of the invention include oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. In some embodiments the invention provides oligonucleotides having morpholino backbone structures of the above-referenced U.S. Pat. No. 5,034,506.

Modified Sugars

Modified oligonucleotides may also contain one or more substituted sugar moieties. Some oligonucleotides of the present invention comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Some oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-O-methoxyethyl (2'-O—$CH_2CH_2OCH_3$, also known as 2'-O-(2-methoxyethyl) or 2'-methoxyethoxy or 2'-MOE) (Martin et al., *Helv. Chim. Acta*, 1995, 78, 486-504) i.e., an alkoxyalkoxy group. In some embodiments a further modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$, also described in examples hereinbelow.

Other modifications include 2'-methoxy(2'-O—$CH_3$), 2'-aminopropoxy(2'-$OCH_2CH_2CH_2NH_2$), 2'-allyl(2'-$CH_2$—CH=$CH_2$), 2'-O-allyl(2'-O—$CH_2$—CH=$CH_2$) and 2'-fluoro (2'-F). The 2'-modification may be in the arabino (up) position or ribo (down) position. In some embodiments a 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

In some embodiments a modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—$CH_2$—)$_n$ group bridging the 2' oxygen atom and the 4' carbon atom wherein n is 1 or 2. LNAs and preparation thereof are described in WO 98/39352 and WO 99/14226.

Natural and Modified Nucleobases

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl(—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750, 692, which is commonly owned with the instant application and also herein incorporated by reference.

Conjugates

Another modification of the oligonucleotides of the invention involves chemically linking to the oligonucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethyl-ammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270, incorporated by reference herein). These terminal modifications protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or can be present on both termini. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl riucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270, incorporated by reference herein).

Particularly preferred 3'-cap structures of the present invention include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925; incorporated by reference herein).

Further 3' and 5'-stabilizing groups that can be used to cap one or both ends of an oligomeric compound to impart nuclease stability include those disclosed in WO 03/004602 published on Jan. 16, 2003.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes oligomeric compounds which are chimeric compounds. "Chimeric" oligomeric compounds or "chimeras," in the context of this invention, are oligomeric compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric compounds of the invention may be formed as composite structures of two or more oligonucleotides, modified oligonucleotides, oligonucleosides and/or oligonucleotide mimetics as described above. Chimeric antisense compounds can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers". Such compounds have also been referred to in the art as hybrids. In a gapmer that is 20 nucleotides in length, a gap or wing can be 1, 2, 3, 4, 5, 6, 7, 8, 9, 10, 11, 12, 13, 14, 15, 16, 17 or 18 nucleotides in length. In one embodiment, a 20-nucleotide gapmer is comprised of a gap 8 nucleotides in length, flanked on both the 5' and 3' sides by wings 6 nucleotides in length. In another embodiment, a 20-nucleotide gapmer is comprised of a gap 10 nucleotides in length, flanked on both the 5' and 3' sides by wings 5 nucleotides in length. In another embodiment, a 20-nucleotide gapmer is comprised of a gap 12 nucleotides in length flanked on both the 5' and 3' sides by wings 4 nucleotides in length. In a further embodiment, a 20-nucleotide gapmer is comprised of a gap 14 nucleotides in length flanked on both the 5' and 3' sides by wings 3 nucleotides in length. In another embodiment, a 20-nucleotide gapmer is comprised of a gap 16 nucleotides in length flanked on both the 5' and 3' sides by wings 2 nucleotides in length. In a further embodiment, a 20-nucleotide gapmer is comprised of a gap 18 nucleotides in length flanked on both the 5' and 3' ends by wings 1 nucleotide in length. Alternatively, the wings are of different lengths, for example, a 20-nucleotide gapmer may be comprised of a gap 10 nucleotides in length, flanked by a 6-nucleotide wing on one side (5' or 3') and a 4-nucleotide wing on the other side (5' or 3').

In a hemimer, an "open end" chimeric antisense compound, 20 nucleotides in length, a gap segment, located at either the 5' or 3' terminus of the oligomeric compound, can be 1, 2, 3, 4, 5, 6, 7, 8, 9, 10, 11, 12, 13, 14, 15, 16, 17, 18 or 19 nucleotides in length. For example, a 20-nucleotide hemimer can have a gap segment of 10 nucleotides at the 5' end and a second segment of 10 nucleotides at the 3' end. Alternatively, a 20-nucleotide hemimer can have a gap segment of 10 nucleotides at the 3' end and a second segment of 10 nucleotides at the 5' end.

Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

G. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The oligomeric compounds of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, examples of pharmaceutically acceptable salts and their uses are further described in U.S. Pat. No. 6,287,860, which is incorporated herein in its entirety.

The present invention also includes pharmaceutical compositions and formulations which include the oligomeric compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In some embodiments, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Formulations for topical administration include those in which the oligomeric compounds of the invention are admixed with a topical delivery agent such as lipids, liposomes, fatty acids, fatty acid esters, steroids, chelating agents and surfactants. Lipids and liposomes of the present invention include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligomeric compounds of the invention may be encapsulated within liposomes or may form complexes thereto, in particular to cationic liposomes. Alternatively, oligomeric compounds may be complexed to lipids, in particular to cationic lipids. Fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315, 298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Oral formulations are those in which oligonucleotides of the invention are administered in conjunction with one or more penetration enhancers surfactants and chelators. Surfactants include fatty acids and/or esters or salts thereof, bile acids and/or salts thereof. Bile acids/salts and fatty acids and their uses are further described in U.S. Pat. No. 6,287,860, which is incorporated herein in its entirety. The present invention further provides combinations of penetration enhancers, for example, fatty acids/salts in combination with bile acids/salts. In some embodiments the present invention provides a combination of the sodium salt of lauric acid, capric acid and UDCA. Further penetration enhancers include polyoxyethylene-9-lauryl ether, polyoxyethylene-20-cetyl ether.

Oligomeric compounds of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligomeric compounds and their preparation are described in detail in U.S. application Ser. Nos. 09/108,673 (filed Jul. 1, 1998), 09/315,298 (filed May 20, 1999) and 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Oligonucleotides may be formulated for delivery in vivo in an acceptable dosage form, e.g. as parenteral or non-parenteral formulations. Parenteral formulations include intravenous (IV), subcutaneous (SC), intraperitoneal (IP), intravitreal and intramuscular (IM) formulations, as well as formulations for delivery via pulmonary inhalation, intranasal administration, topical administration, etc. Non-parenteral formulations include formulations for delivery via the alimentary canal, e.g. oral administration, rectal administration, intrajejunal instillation, etc. Rectal administration includes administration as an enema or a suppository. Oral administration includes administration as a capsule, a gel capsule, a pill, an elixir, etc.

In some embodiments, an oligonucleotide may be administered to a subject via an oral route of administration. The subject may be an animal or a human (man). An animal subject may be a mammal, such as a mouse, a rat, a dog, a guinea pig, a monkey, a non-human primate, a cat or a pig. Non-human primates include monkeys and chimpanzees. A suitable animal subject may be an experimental animal, such as a mouse, rat, mouse, a rat, a dog, a monkey, a non-human primate, a cat or a pig.

In some embodiments, the subject may be a human. In certain embodiments, the subject may be a human patient in need of therapeutic treatment as discussed in more detail herein. In certain embodiments, the subject may be in need of modulation of expression of one or more genes as discussed in more detail herein. In some particular embodiments, the subject may be in need of inhibition of expression of one or more genes as discussed in more detail herein. In particular embodiments, the subject may be in need of modulation, i.e. inhibition or enhancement, of EIF2C2 in order to obtain therapeutic indications discussed in more detail herein.

In some embodiments, non-parenteral (e.g. oral) oligonucleotide formulations according to the present invention result in enhanced bioavailability of the oligonucleotide. In this context, the term "bioavailability" refers to a measurement of that portion of an administered drug which reaches the circulatory system (e.g. blood, especially blood plasma) when a particular mode of administration is used to deliver the drug. Enhanced bioavailability refers to a particular mode of administration's ability to deliver oligonucleotide to the peripheral blood plasma of a subject relative to another mode of administration. For example, when a non-parenteral mode of administration (e.g. an oral mode) is used to introduce the drug into a subject, the bioavailability for that mode of administration may be compared to a different mode of administration, e.g. an IV mode of administration. In some embodiments, the area under a compound's blood plasma concentration curve ($AUC_o$) after non-parenteral (e.g. oral, rectal, intrajejunal) administration may be divided by the area under the drug's plasma concentration curve after intravenous (i.v.) administration ($AUC_{iv}$) to provide a dimensionless quotient (relative bioavailability, RB) that represents fraction of compound absorbed via the non-parenteral route as compared to the IV route. A composition's bioavailability is said to be enhanced in comparison to another composition's bioavailability when the first composition's relative bioavailability ($RB_1$) is greater than the second composition's relative bioavailability ($RB_2$).

In general, bioavailability correlates with therapeutic efficacy when a compound's therapeutic efficacy is related to the blood concentration achieved, even if the drug's ultimate site of action is intracellular (van Berge-Henegouwen et al., *Gastroenterol.*, 1977, 73, 300). Bioavailability studies have been used to determine the degree of intestinal absorption of a drug by measuring the change in peripheral blood levels of the drug after an oral dose (DiSanto, Chapter 76 *In: Remington's Pharmaceutical Sciences*, 18th Ed., Gennaro, ed., Mack Publishing Co., Easton, Pa., 1990, pages 1451-1458).

In general, an oral composition's bioavailability is said to be "enhanced" when its relative bioavailability is greater than the bioavailability of a composition substantially consisting of pure oligonucleotide, i.e. oligonucleotide in the absence of a penetration enhancer.

Organ bioavailability refers to the concentration of compound in an organ. Organ bioavailability may be measured in test subjects by a number of means, such as by whole-body radiography. Organ bioavailability may be modified, e.g. enhanced, by one or more modifications to the oligonucleotide, by use of one or more carrier compounds or excipients, etc. as discussed in more detail herein. In general, an increase in bioavailability will result in an increase in organ bioavailability.

Oral oligonucleotide compositions according to the present invention may comprise one or more "mucosal penetration enhancers," also known as "absorption enhancers" or simply as "penetration enhancers." Accordingly, some embodiments of the invention comprise at least one oligonucleotide in combination with at least one penetration enhancer. In general, a penetration enhancer is a substance that facilitates the transport of a drug across mucous membrane(s) associated with the desired mode of administration, e.g. intestinal epithelial membranes. Accordingly it is desirable to select one or more penetration enhancers that facilitate the uptake of an oligonucleotide, without interfering with the activity of the oligonucleotide, and in a such a manner the oligonucleotide can be introduced into the body of an animal without unacceptable side-effects such as toxicity, irritation or allergic response.

Embodiments of the present invention provide compositions comprising one or more pharmaceutically acceptable penetration enhancers, and methods of using such compositions, which result in the improved bioavailability of oligonucleotides administered via non-parenteral modes of administration. Heretofore, certain penetration enhancers have been used to improve the bioavailability of certain drugs. See Muranishi, *Crit. Rev. Ther. Drug Carrier Systems*, 1990, 7, 1 and Lee et al., *Crit. Rev. Ther. Drug Carrier Systems*, 1991, 8, 91. It has been found that the uptake and delivery of oligonucleotides, relatively complex molecules which are known to be difficult to administer to animals and man, can be greatly improved even when administered by non-parenteral means through the use of a number of different classes of penetration enhancers.

In some embodiments, compositions for non-parenteral administration include one or more modifications from naturally-occurring oligonucleotides (i.e. full-phosphodiester deoxyribosyl or full-phosphodiester ribosyl oligonucleotides). Such modifications may increase binding affinity, nuclease stability, cell or tissue permeability, tissue distribution, or other biological or pharmacokinetic property. Modifications may be made to the base, the linker, or the sugar, in general, as discussed in more detail herein with regards to oligonucleotide chemistry. In some embodiments of the invention, compositions for administration to a subject, and in particular oral compositions for administration to an animal or human subject, will comprise modified oligonucleotides having one or more modifications for enhancing affinity, stability, tissue distribution, or other biological property.

Suitable modified linkers include phosphorothioate linkers. In some embodiments according to the invention, the oligonucleotide has at least one phosphorothioate linker. Phosphorothioate linkers provide nuclease stability as well as plasma protein binding characteristics to the oligonucleotide. Nuclease stability is useful for increasing the in vivo lifetime of oligonucleotides, while plasma protein binding decreases the rate of first pass clearance of oligonucleotide via renal excretion. In some embodiments according to the present invention, the oligonucleotide has at least two phosphorothioate linkers. In some embodiments, wherein the oligonucleotide has exactly n nucleosides, the oligonucleotide has from one to n−1 phosphorothioate linkages. In some embodiments, wherein the oligonucleotide has exactly n nucleosides, the oligonucleotide has n−1 phosphorothioate linkages. In other embodiments wherein the oligonucleotide has exactly n nucleoside, and n is even, the oligonucleotide has from 1 to n/2 phosphorothioate linkages, or, when n is odd, from 1 to (n−1)/2 phosphorothioate linkages. In some embodiments, the oligonucleotide has alternating phosphodiester (PO) and phosphorothioate (PS) linkages. In other embodiments, the oligonucleotide has at least one stretch of two or more consecutive PO linkages and at least one stretch of two or more PS linkages. In other embodiments, the oligonucleotide has at least two stretches of PO linkages interrupted by at least on PS linkage.

In some embodiments, at least one of the nucleosides is modified on the ribosyl sugar unit by a modification that imparts nuclease stability, binding affinity or some other beneficial biological property to the sugar. In some cases, the sugar modification includes a 2'-modification, e.g. the 2'-OH of the ribosyl sugar is replaced or substituted. Suitable replacements for 2'-OH include 2'-F and 2'-arabino-F. Suitable substitutions for OH include 2'-O-alkyl, e.g. 2-O-methyl, and 2'-O-substituted alkyl, e.g. 2'-O-methoxyethyl, 2'-O-aminopropyl, etc. In some embodiments, the oligonucleotide contains at least one 2'-modification. In some embodiments, the oligonucleotide contains at least 2 2'-modifications. In some embodiments, the oligonucleotide has at least one 2'-modification at each of the termini (i.e. the 3'- and 5'-terminal nucleosides each have the same or different 2'-modifications). In some embodiments, the oligonucleotide has at least two sequential 2'-modifications at each end of the oligonucleotide. In some embodiments, oligonucleotides further comprise at least one deoxynucleoside. In particular embodiments, oligonucleotides comprise a stretch of deoxynucleosides such that the stretch is capable of activating RNase (e.g. RNase H) cleavage of an RNA to which the oligonucleotide is capable of hybridizing. In some embodiments, a stretch of deoxynucleosides capable of activating RNase-mediated cleavage of RNA comprises about 6 to about 16, e.g. about 8 to about 16 consecutive deoxynucleosides. In further embodiments, oligonucleotides are capable of eliciting cleaveage by dsRNAse enzymes.

Oral compositions for administration of non-parenteral oligonucleotide compositions of the present invention may be formulated in various dosage forms such as, but not limited to, tablets, capsules, liquid syrups, soft gels, suppositories, and enemas. The term "alimentary delivery" encompasses e.g. oral, rectal, endoscopic and sublingual/buccal administration. A common requirement for these modes of administration is absorption over some portion or all of the alimentary tract and a need for efficient mucosal penetration of the nucleic acid(s) so administered.

Delivery of a drug via the oral mucosa, as in the case of buccal and sublingual administration, has several desirable features, including, in many instances, a more rapid rise in plasma concentration of the drug than via oral delivery (Harvey, Chapter 35 In: Remington's Pharmaceutical Sciences, 18th Ed., Gennaro, ed., Mack Publishing Co., Easton, Pa., 1990, page 711).

Endoscopy may be used for drug delivery directly to an interior portion of the alimentary tract. For example, endoscopic retrograde cystopancreatography (ERCP) takes advantage of extended gastroscopy and permits selective access to the biliary tract and the pancreatic duct (Hirahata et al., Gan To Kagaku Ryoho, 1992, 19(10 Suppl.), 1591). Pharmaceutical compositions, including liposomal formulations, can be delivered directly into portions of the alimentary canal, such as, e.g., the duodenum (Somogyi et al., Pharm. Res., 1995, 12, 149) or the gastric submucosa (Akamo et al., Japanese J. Cancer Res., 1994, 85, 652) via endoscopic means. Gastric lavage devices (Inoue et al., Artif. Organs, 1997, 21, 28) and percutaneous endoscopic feeding devices (Pennington et al., Ailment Pharmacol. Ther., 1995, 9, 471) can also be used for direct alimentary delivery of pharmaceutical compositions.

In some embodiments, oligonucleotide formulations may be administered through the anus into the rectum or lower intestine. Rectal suppositories, retention enemas or rectal catheters can be used for this purpose and may be preferred when patient compliance might otherwise be difficult to achieve (e.g., in pediatric and geriatric applications, or when the patient is vomiting or unconscious). Rectal administration can result in more prompt and higher blood levels than the oral route. (Harvey, Chapter 35 In: Remington's Pharmaceutical Sciences, 18th Ed., Gennaro, ed., Mack Publishing Co., Easton, Pa., 1990, page 711). Because about 50% of the drug that is absorbed from the rectum will bypass the liver, administration by this route significantly reduces the potential for first-pass metabolism (Benet et al., Chapter 1 In: Goodman & Gilman's The Pharmacological Basis of Therapeutics, 9th Ed., Hardman et al., eds., McGraw-Hill, New York, N.Y., 1996).

One advantageous method of non-parenteral administration oligonucleotide compositions is oral delivery. Some embodiments employ various penetration enhancers in order to effect transport of oligonucleotides and other nucleic acids across mucosal and epithelial membranes. Penetration enhancers may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Accordingly, some embodiments comprise oral oligonucleotide compositions comprising at least one member of the group consisting of surfactants, fatty acids, bile salts, chelating agents, and non-chelating surfactants. Further embodiments comprise oral oligonucleotide comprising at least one fatty acid, e.g. capric or lauric acid, or combinations or salts thereof. Other embodiments comprise methods of enhancing the oral bioavailability of an oligonucleotide, the method comprising co-administering the oligonucleotide and at least one penetration enhancer.

Other excipients that may be added to oral oligonucleotide compositions include surfactants (or "surface-active agents"), which are chemical entities which, when dissolved in an aqueous solution, reduce the surface tension of the solution or the interfacial tension between the aqueous solution and another liquid, with the result that absorption of oligonucleotides through the alimentary mucosa and other epithelial membranes is enhanced. In addition to bile salts and fatty acids, surfactants include, for example, sodium lauryl sulfate, polyoxyethylene-9-lauryl ether and polyoxyethylene-20-cetyl ether (Lee et al., Critical Reviews in Therapeutic Drug Carrier Systems, 1991, page 92); and perfluorohemical emulsions, such as FC-43 (Takahashi et al., J. Pharm. Phamacol., 1988, 40, 252).

Fatty acids and their derivatives which act as penetration enhancers and may be used in compositions of the present invention include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glyceryl 1-monocaprate, 1-dodecylazacycloheptan-2-one, acylcarnitines, acylcholines and mono- and di-glycerides thereof and/or physiologically acceptable salts thereof (i.e., oleate, laurate, caprate, myristate, palmitate, stearate, linoleate, etc.) (Lee et al., *Critical Reviews in Therapeutic Drug Carrier Systems,* 1991, page 92; Muranishi, *Critical Reviews in Therapeutic Drug Carrier Systems,* 1990, 7, 1; El-Hariri et al., *J. Pharm. Pharmacol.,* 1992, 44, 651).

In some embodiments, oligonucleotide compositions for oral delivery comprise at least two discrete phases, which phases may comprise particles, capsules, gel-capsules, microspheres, etc. Each phase may contain one or more oligonucleotides, penetration enhancers, surfactants, bioadhesives, effervescent agents, or other adjuvant, excipient or diluent. In some embodiments, one phase comprises at least one oligonucleotide and at lease one penetration enhancer. In some embodiments, a first phase comprises at least one oligonucleotide and at least one penetration enhancer, while a second phase comprises at least one penetration enhancer. In some embodiments, a first phase comprises at least one oligonucleotide and at least one penetration enhancer, while a second phase comprises at least one penetration enhancer and substantially no oligonucleotide. In some embodiments, at least one phase is compounded with at least one degradation retardant, such as a coating or a matrix, which delays release of the contents of that phase. In some embodiments, a first phase comprises at least one oligonucleotide, at least one penetration enhancer, while a second phase comprises at least one penetration enhancer and a release-retardant. In particular embodiments, an oral oligonucleotide comprises a first phase comprising particles containing an oligonucleotide and a penetration enhancer, and a second phase comprising particles coated with a release-retarding agent and containing penetration enhancer.

A variety of bile salts also function as penetration enhancers to facilitate the uptake and bioavailability of drugs. The physiological roles of bile include the facilitation of dispersion and absorption of lipids and fat-soluble vitamins (Brunton, Chapter 38 *In: Goodman & Gilman's The Pharmacological Basis of Therapeutics,* 9th Ed., Hardman et al., eds., McGraw-Hill, New York, N.Y., 1996, pages 934-935). Various natural bile salts, and their synthetic derivatives, act as penetration enhancers. Thus, the term "bile salt" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (CDCA, sodium chenodeoxycholate), ursodeoxycholic acid (UDCA), sodium tauro-24,25-dihydrofusidate (STDHF), sodium glycodihydrofusidate and polyoxyethylene-9-lauryl ether (POE) (Lee et al., *Critical Reviews in Therapeutic Drug Carrier Systems,* 1991, page 92; Swinyard, Chapter 39 *In: Remington's Pharmaceutical Sciences,* 18th Ed., Gennaro, ed., Mack Publishing Co., Easton, Pa., 1990, pages 782-783; Muranishi, *Critical Reviews in Therapeutic Drug Carrier Systems,* 1990, 7, 1; Yamamoto et al., *J. Pharm. Exp. Ther.,* 1992, 263, 25; Yamashita et al., *J. Pharm. Sci.,* 1990, 79, 579).

In some embodiments, penetration enhancers useful in some embodiments of present invention are mixtures of penetration enhancing compounds. One such penetration enhancer is a mixture of UDCA (and/or CDCA) with capric and/or lauric acids or salts thereof e.g. sodium. Such mixtures are useful for enhancing the delivery of biologically active substances across mucosal membranes, in particular intestinal mucosa. Other penetration enhancer mixtures comprise about 5-95% of bile acid or salt(s) UDCA and/or CDCA with 5-95% capric and/or lauric acid. Particular penetration enhancers are mixtures of the sodium salts of UDCA, capric acid and lauric acid in a ratio of about 1:2:2 respectively. Anther such penetration enhancer is a mixture of capric and lauric acid (or salts thereof) in a 0.01:1 to 1:0.01 ratio (mole basis). In particular embodiments capric acid and lauric acid are present in molar ratios of e.g. about 0.1:1 to about 1:0.1, in particular about 0.5:1 to about 1:0.5.

Other excipients include chelating agents, i.e. compounds that remove metallic ions from solution by forming complexes therewith, with the result that absorption of oligonucleotides through the alimentary and other mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315). Chelating agents of the invention include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Therapeutic Drug Carrier Systems,* 1991, page 92; Muranishi, *Critical Reviews in Therapeutic Drug Carrier Systems,* 1990, 7, 1; Buur et al., *J. Control Rel.,* 1990, 14, 43).

As used herein, non-chelating non-surfactant penetration enhancers may be defined as compounds that demonstrate insignificant activity as chelating agents or as surfactants but that nonetheless enhance absorption of oligonucleotides through the alimentary and other mucosal membranes (Muranishi, *Critical Reviews in Therapeutic Drug Carrier Systems,* 1990, 7, 1). This class of penetration enhancers includes, but is not limited to, unsaturated cyclic ureas, 1-alkyl- and 1-alkenylazacyclo-alkanone derivatives (Lee et al., *Critical Reviews in Therapeutic Drug Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39, 621).

Agents that enhance uptake of oligonucleotides at the cellular level may also be added to the pharmaceutical and other compositions of the present invention. For example, cationic lipids, such as lipofectin (Junichi et al, U.S. Pat. No. 5,705, 188), cationic glycerol derivatives, and polycationic molecules, such as polylysine (Lollo et al., PCT Application WO 97/30731), can be used.

Some oral oligonucleotide compositions also incorporate carrier compounds in the formulation. As used herein, "carrier compound" or "carrier" can refer to a nucleic acid, or analog thereof, which may be inert (i.e., does not possess biological activity per se) or may be necessary for transport, recognition or pathway activation or mediation, or is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.,* 1995, 5, 115; Takakura et al., *Antisense & Nucl. Acid Drug Dev.,* 1996, 6, 177).

A "pharmaceutical carrier" or "excipient" may be a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, EXPLOTAB); and wetting agents (e.g., sodium lauryl sulphate, etc.).

Oral oligonucleotide compositions may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the present invention.

Some embodiments of the invention provide pharmaceutical compositions containing one or more oligomeric compounds and one or more other chemotherapeutic agents which function by a non-hybridization mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VIP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of oligomeric compounds and other non-oligomeric compound-type drugs are also within the scope of this invention. Two or more combined compounds may be used together or sequentially.

In some embodiments, compositions of the invention may contain one or more oligomeric compounds, particularly oligonucleotides, targeted to a first nucleic acid and one or more additional oligomeric compounds targeted to a second nucleic acid target. Alternatively, compositions of the invention may contain two or more oligomeric compounds targeted to different regions of the same nucleic acid target. Numerous examples of oligomeric compounds are known in the art. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 μg to 100 g per kg of body weight, from 0.1 μg to 10 g per kg of body weight, from 1.0 μg to 1 g per kg of body weight, from 10.0 μg to 100 mg per kg of body weight, from 100 μg to 10 mg per kg of body weight, or from 1 mg to 5 mg per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligomeric compound is administered in maintenance doses, ranging from 0.01 μg to 100 g per kg of body weight, once or more daily, to once every 20 years.

The effects of treatments with therapeutic compositions can be assessed following collection of tissues or fluids from a patient or subject receiving said treatments. It is known in the art that a biopsy sample can be procured from certain tissues without resulting in detrimental effects to a patient or subject. In certain embodiments, a tissue and its constituent cells comprise, but are not limited to, blood (e.g., hematopoietic cells, such as human hematopoietic progenitor cells, human hematopoietic stem cells, $CD34^+$ cells $CD4^+$ cells), lymphocytes and other blood lineage cells, bone marrow, breast, cervix, colon, esophagus, lymph node, muscle, peripheral blood, oral mucosa and skin. In other embodiments, a fluid and its constituent cells comprise, but are not limited to, blood, urine, semen, synovial fluid, lymphatic fluid and cerebro-spinal fluid. Tissues or fluids procured from patients can be evaluated for expression levels of the target mRNA or protein. Additionally, the mRNA or protein expression levels of other genes known or suspected to be associated with the specific disease state, condition or phenotype can be assessed. mRNA levels can be measured or evaluated by real-time PCR, Northern blot, in situ hybridization or DNA array analysis. Protein levels can be measured or evaluated by ELISA, immunoblotting, quantitative protein assays, protein activity assays (for example, caspase activity assays) immunohistochemistry or immunocytochemistry. Furthermore, the effects of treatment can be assessed by measuring biomarkers associated with the disease or condition in the aforementioned tissues and fluids, collected from a patient or subject receiving treatment, by routine clinical methods known in the art. These biomarkers include but are not limited to: glucose, cholesterol, lipoproteins, triglycerides, free fatty acids and other markers of glucose and lipid metabolism; liver transaminases, bilirubin, albumin, blood urea nitrogen, creatine and other markers of kidney and liver function; interleukins, tumor necrosis factors, intracellular adhesion molecules, C-reactive protein and other markers of inflammation; testosterone, estrogen and other hormones; tumor markers; vitamins, minerals and electrolytes.

Each of the patents, patent applications, and publications described herein is hereby incorporated by reference in its entirety.

While the present invention has been described with specificity in accordance with certain of its preferred embodiments, the following examples serve only to illustrate the invention and are not intended to limit the same.

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N-4-benzoyl-5-methylcytidine penultimate intermediate for 5-methyl dC amidite, [5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, [5'-O-(4,4'-Dimethoxytriphenylmethyl)-2'-O-(2-methoxyethyl)-$N^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-$N^4$-isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylamino-oxyethyl) nucleoside amidites, 2'-(Dimethylaminooxyethoxy) nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O—[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 2

Oligonucleotide and Oligonucleoside Synthesis

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M NH$_4$OAc solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625, 050, herein incorporated by reference.

Phosphoramidite oligonucleotides are prepared as described in U.S. Pat. No. 5,256,775 or U.S. Pat. No. 5,366, 878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides may be synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.,* 1998, 120, 11820-11821; Matteucci, M. D. and Caruthers, M. H. *J. Am. Chem. Soc.,* 1981, 103, 3185-3191; Beaucage, S. L. and Caruthers, M. H. *Tetrahedron Lett.,* 1981, 22, 1859-1862; Dahl, B. J., et al., *Acta Chem. Scand.* 1990, 44, 639-641; Reddy, M. P., et al., *Tetrahedrom Lett.,* 1994, 25, 4311-4314; Wincott, F. et al., *Nucleic Acids Res.,* 1995, 23, 2677-2684; Griffin, B. E., et al., *Tetrahedron,* 1967, 23, 2301-2313; Griffin, B. E., et al., *Tetrahedron,* 1967, 23, 2315-2331).

RNA oligomeric compounds of the present invention can be synthesized by the methods herein or purchased from Dharmacon Research, Inc (Lafayette, Colo.). Once synthesized, complementary RNA oligomeric compounds can then be annealed by methods known in the art to form double stranded (duplexed) RNA oligomeric compounds. For example, duplexes can be formed by combining 30 µl of each of the complementary strands of RNA oligomeric compound (50 µM RNA solution) and 15 µl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed oligomeric compounds can be used in kits, assays, screens, or other methods to investigate the role of a target nucleic acid.

Example 4

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me]Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia (NH₄OH) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl)phosphodiester] chimeric oligonucleotides are prepared as per the above procedure for the 2'-O-methyl chimeric oligonucleotide with the substitution of 2'-O-(methoxyethyl)amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Oligomeric Compounds Targeting EIF2C2

In accordance with the present invention, a series of nucleic acid duplexes comprising the oligomeric compounds of the present invention and their complements can be designed to target EIF2C2. The nucleobase sequence of the antisense strand of the duplex comprises at least a portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini. The antisense and sense strands of the duplex comprise from about 17 to 25 nucleotides, or from about 19 to 23 nucleotides. Alternatively, the antisense and sense strands comprise 20, 21 or 22 nucleotides.

For example, a duplex comprising an antisense strand having the sequence CGAGAGGCGGACGGGACCG (SEQ ID NO: 389) and having a two-nucleobase overhang of deoxythymidine(dT) would have the following structure:

```
cgagaggcggacgggaccgTT    (SEQ ID NO: 390)
|||||||||||||||||||      Antisense Strand
TTgctctccgcctgccctggc    (SEQ ID NO: 391)
                         Complement
```

Overhangs can range from 2 to 6 nucleobases and these nucleobases may or may not be complementary to the target nucleic acid. In another embodiment, the duplexes may have an overhang on only one terminus.

In another embodiment, a duplex comprising an antisense strand having the same sequence CGAGAGGCGGACGG-GACCG (SEQ ID NO: 389) may be prepared with blunt ends (no single stranded overhang) as shown:

```
cgagaggcggacgggaccg      (SEQ ID NO: 389)
|||||||||||||||||||      Antisense Strand
gctctccgcctgccctggc      (SEQ ID NO: 392)
                         Complement
```

These sequence are shown to contain thymine (T) but one of skill in the art will appreciate that thymine (T) is generally replaced by uracil (U) in RNA sequences.

The RNA duplex can be unimolecular or bimolecular; i.e, the two strands can be part of a single molecule or may be separate molecules.

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 μM. Once diluted, 30 μL of each strand is combined with 15 μL of a 5× solution of annealing buffer. The final concentration of said buffer is 100 mM potassium acetate, 30 mM HEPES-KOH pH 7.4, and 2 mM magnesium acetate. The final volume is 75 μL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 μM. This solution can be stored frozen (−20° C.) and freeze-thawed up to 5 times.

Once prepared, the duplexed oligomeric compounds are evaluated for their ability to modulate EIF2C2 expression.

When cells reached 80% confluency, they are treated with duplexed oligomeric compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex oligomeric compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M $NH_4OAc$ with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+/−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 7

Oligonucleotide Synthesis

96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per methods known in the art. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis

96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of oligomeric compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached approximately 90% confluence. Cells were seeded into 96-well plates (Falcon-Primaria #353872) at a density of approximately 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached approximately 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

HeLa Cells:

The human epitheloid carcinoma cell line HeLa was obtained from the American Tissue Type Culture Collection (Manassas, Va.). HeLa cells were routinely cultured in DMEM, high glucose (Invitrogen Corporation, Carlsbad, Calif.) supplemented with 10% fetal bovine serum (Invitrogen Corporation, Carlsbad, Calif.). Cells were routinely passaged by trypsinization and dilution when they reached 90% confluence. Cells were seeded into 24-well plates (Falcon-Primaria #353846) at a density of approximately 50,000 cells/well or in 96-well (Falcon-Primaria #353872) plates at a density of approximately 5,000 cells/well for use in RT-PCR analysis. For Northern blotting or other analyses, cells were harvested when they reached 90% confluence.

Treatment with Oligomeric Compounds:

When cells reached 65-75% confluency, they were treated with oligomeric compounds. For cells grown in 96-well plates, wells were washed once with 100 μL OPTI-MEM™-1 reduced-serum medium (Invitrogen Corporation, Carlsbad, Calif.) and then treated with 130 μL of OPTI-MEM™-1 containing 3.75 μg/mL LIPOFECTIN™ (Invitrogen Corporation, Carlsbad, Calif.) and the desired concentration of oligomeric compounds. Cells were treated and data were obtained in triplicate. After 4-7 hours of treatment at 37° C., the medium was replaced with fresh medium. Cells were harvested 16-24 hours after oligonucleotide treatment.

The concentration of oligomeric compounds used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGT-CATCGCTCCTCAGGG, SEQ ID NO: 1) which is targeted to human H-ras, or ISIS 18078, (GTGCGCGCGAGC-CCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCAT-TCTGCCCCCAAGGA, SEQ ID NO: 3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of oligomeric compounds oligonucleotides used herein are from 50 nM to 300 nM.

Example 10

Analysis of Oligomeric Compound Inhibition of EIF2C2 Expression

Modulation of EIF2C2 expression can be assayed in a variety of ways known in the art. For example, EIF2C2 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of EIF2C2 can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to EIF2C2 can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Phenotypic Assays for the Use of EIF2C2 Inhibitors

Once EIF2C2 inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of EIF2C2 in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with EIF2C2 inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the EIF2C2 inhibitors. Hallmark genes, or those genes suspected to be associated with a specific disease state, condition, or phenotype, are measured in both treated and untreated cells.

Example 12

RNA Isolation

Poly(A)+ mRNA Isolation

Poly(A)+ mRNA was isolated according to Miura et al., (*Clin. Chem.,* 1996, 42, 1758-1764). Other methods for poly (A)+ mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of EIF2C2 mRNA Levels

Quantitation of EIF2C2 mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

Isolated RNA is subjected to a reverse transcriptase (RT) reaction to produce complementary DNA (cDNA). The cDNA is the substrate for the real-time PCR. RT and real-time PCR reagents were obtained from Invitrogen Corporation, (Carlsbad, Calif.). RT, real-time PCR reactions were carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension). The RT, real-time PCR procedure used to measure gene target quantities is herein below referred to as real-time PCR, or quantitative real-time PCR.

Gene target quantities obtained by real time PCR are normalized using either the expression level of GAPDH, a gene whose expression is constant, or by quantifying total RNA using RiboGreen™ (Molecular Probes, Inc. Eugene, Oreg.). GAPDH expression is quantified by real-time PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 µL of RiboGreen™ working reagent (RiboGreen™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Probes and primers to human EIF2C2 were designed to hybridize to a human EIF2C2 sequence, using published sequence information (a consensus sequence derived from GenBank accession numbers AI468419, BE258335, BE252037, BE261873, and AF121255, incorporated herein as SEQ ID NO: 4). For human EIF2C2 the PCR primers were: forward primer: CCAGCTACACTCAGACCAACAGA (SEQ ID NO: 5) reverse primer: GAAAACGGAGAATCTAATAAAATCAATGAC (SEQ ID NO: 6) and the PCR probe was: FAM-CGTGACAGCCAGCATCGAACATGAGA-TAMRA (SEQ ID NO: 7) where FAM is the fluorescent dye and TAMRA is the quencher dye. For human GAPDH the PCR primers were:

forward primer: GAAGGTGAAGGTCGGAGTC (SEQ ID NO: 8)

reverse primer: GAAGATGGTGATGGGATTTC (SEQ ID NO: 9) and the

PCR probe was: 5' JOE-CAAGCTTCCCGTTCTCAGCC-TAMRA 3' (SEQ ID NO: 10) where JOE is the fluorescent reporter dye and TAMRA is the quencher dye.

Example 14

Northern Blot Analysis of EIF2C2 mRNA Levels

Eighteen hours after treatment with oligomeric compounds, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human EIF2C2, a human EIF2C2 specific probe was prepared by PCR using the forward primer CCAGCTA-CACTCAGACCAACAGA (SEQ ID NO: 5) and the reverse primer GAAAACGGAGAATCTAATAAAATCAATGAC (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Inhibition of Human EIF2C2 Expression by Chimeric Phosphorothioate Oligonucleotides Having 2'-MOE Wings and a Deoxy Gap In accordance with the present invention, a series of oligomeric compounds were designed to target different regions of the human EIF2C2 RNA, using published sequences (a consensus sequence derived from GenBank accession numbers AI468419, BE258335, BE252037, BE261873, and AF121255, incorporated herein as SEQ ID NO: 4). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on human EIF2C2 mRNA levels by quantitative real-time PCR as described in other examples herein. Data are averages from three experiments in which T24 cells were treated with the antisense oligonucleotides of the present invention. The positive control for each datapoint is identified in the table by sequence ID number. If present, "N.D." indicates "no data".

TABLE 1

Inhibition of human EIF2C2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 136742 | Coding | 4 | 1557 | gcatacgtgttcttcaggtg | 77 | 11 | 1 |
| 136743 | Coding | 4 | 1562 | ggcccgcatacgtgttcttc | 77 | 12 | 1 |

TABLE 1-continued

Inhibition of human EIF2C2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 136744 | Coding | 4 | 1568 | gctgcaggcccgcatacgtg | 76 | 13 | 1 |
| 136745 | Coding | 4 | 1631 | tgtctcccacgcgcttgacc | 68 | 14 | 1 |
| 136746 | Coding | 4 | 1653 | tgcgtggccatccccagcac | 69 | 15 | 1 |
| 136747 | Coding | 4 | 1680 | ctctgcacgttcttcatctg | 68 | 16 | 1 |
| 136748 | Coding | 4 | 1686 | gtggtcctctgcacgttctt | 51 | 17 | 1 |
| 136749 | Coding | 4 | 1692 | tgtggcgtggtcctctgcac | 79 | 18 | 1 |
| 136750 | Coding | 4 | 1698 | agggtctgtggcgtggtcct | 80 | 19 | 1 |
| 136751 | Coding | 4 | 1750 | gatgttgttcacgcctccca | 54 | 20 | 1 |
| 136752 | Coding | 4 | 1755 | agcaggatgttgttcacgcc | 71 | 21 | 1 |
| 136753 | Coding | 4 | 1782 | tggaacaccggcggccttcc | 87 | 22 | 1 |
| 136754 | Coding | 4 | 1938 | tgtatgatctcctgccggtg | 82 | 23 | 1 |
| 136755 | Coding | 4 | 2042 | ggccttcagagacaccgtcg | 92 | 24 | 1 |
| 136756 | Coding | 4 | 2050 | ctggaactggccttcagaga | 75 | 25 | 1 |
| 136757 | Coding | 4 | 2053 | ctgctggaactggccttcag | 87 | 26 | 1 |
| 136758 | Coding | 4 | 2058 | agaacctgctggaactggcc | 84 | 27 | 1 |
| 136759 | Coding | 4 | 2061 | tggagaacctgctggaactg | 76 | 28 | 1 |
| 136760 | Coding | 4 | 2071 | caactcgtggtggagaacct | 67 | 29 | 1 |
| 136761 | Coding | 4 | 2163 | agccgggtgtggtgcctctt | 88 | 30 | 1 |
| 136762 | Coding | 4 | 2166 | aagagccgggtgtggtgcct | 81 | 31 | 1 |
| 136763 | Coding | 4 | 2200 | acttttcccaacccgctcgt | 35 | 32 | 1 |
| 136764 | Coding | 4 | 2216 | ctgctggaatgtttccactt | 90 | 33 | 1 |
| 136765 | Coding | 4 | 2223 | gtcgtgcctgctggaatgtt | 80 | 34 | 1 |
| 136766 | Coding | 4 | 2265 | tagaagtcgaactcggtggg | 20 | 35 | 1 |
| 136767 | Coding | 4 | 2284 | gccagcgtgactacacaggt | 85 | 36 | 1 |
| 136768 | Coding | 4 | 2300 | tgcttgtcccctggatgcca | 61 | 37 | 1 |
| 136769 | Coding | 4 | 2326 | ccagaggacgtgatagtgcg | 87 | 38 | 1 |
| 136770 | Coding | 4 | 2352 | tcatcagaggagaaacgatt | 66 | 39 | 1 |
| 136771 | Coding | 4 | 2443 | caggtgagcgtagtatgctg | 79 | 40 | 1 |
| 136772 | Coding | 4 | 2461 | cctggcccggaaggccacca | 58 | 41 | 1 |
| 136773 | Coding | 4 | 2511 | gaggtatggcttccttcagc | 77 | 42 | 1 |
| 136774 | Coding | 4 | 2517 | tgcccagaggtatggcttcc | 84 | 43 | 1 |
| 136775 | Coding | 4 | 2538 | tggtggtctcgcccgttact | 86 | 44 | 1 |
| 136776 | Coding | 4 | 2549 | tggccagtgcttggtggtct | 90 | 45 | 1 |
| 136777 | Coding | 4 | 2553 | gccttggccagtgcttggtg | 21 | 46 | 1 |
| 136778 | Stop Codon | 4 | 2603 | catgtcaagcaaagtacatg | 85 | 47 | 1 |

TABLE 1-continued

Inhibition of human EIF2C2 mRNA levels by chimeric
phosphorothioate oligonucleotides having 2'-MOE wings
and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 136779 | Stop Codon | 4 | 2604 | acatgtcaagcaaagtacat | 81 | 48 | 1 |
| 136780 | 3'UTR | 4 | 2629 | cggtacacaatcgctaaaca | 81 | 49 | 1 |
| 136781 | 3'UTR | 4 | 2636 | tcccactcggtacacaatcg | 83 | 50 | 1 |
| 136782 | 3'UTR | 4 | 2652 | tagctggtctcgtgaatccc | 90 | 51 | 1 |
| 136783 | 3'UTR | 4 | 2657 | gagtgtagctggtctcgtga | 69 | 52 | 1 |
| 136784 | 3'UTR | 4 | 2668 | tctgttggtctgagtgtagc | 92 | 53 | 1 |
| 136785 | 3'UTR | 4 | 2676 | gctggccatctgttggtctg | 98 | 54 | 1 |
| 136786 | 3'UTR | 4 | 2707 | tctcatgttcgatgctggct | 99 | 55 | 1 |
| 136787 | 3'UTR | 4 | 2726 | tctaataaaatcaatgacgt | 62 | 56 | 1 |
| 136788 | 3'UTR | 4 | 2757 | tgggacggaaggcattctgg | 89 | 57 | 1 |
| 136789 | 3'UTR | 4 | 2793 | ctcatacagtctgcagtcaa | 66 | 58 | 1 |
| 136790 | 3'UTR | 4 | 2800 | ttgggttctcatacagtctg | 68 | 59 | 1 |
| 136791 | 3'UTR | 4 | 2805 | tgacattgggttctcataca | 76 | 60 | 1 |
| 136792 | 3'UTR | 4 | 2821 | caaaccatatttcctatgac | 54 | 61 | 1 |
| 136793 | 3'UTR | 4 | 2831 | tagattttagcaaaccatat | 70 | 62 | 1 |
| 136794 | 3'UTR | 4 | 2840 | agcagcttatagattttagc | 80 | 63 | 1 |
| 136795 | 3'UTR | 4 | 2843 | ataagcagcttatagatttt | 81 | 64 | 1 |
| 136796 | 3'UTR | 4 | 2854 | actctgttttaataagcagc | 81 | 65 | 1 |
| 136797 | 3'UTR | 4 | 2860 | cacgggactctgttttaata | 79 | 66 | 1 |
| 136798 | 3'UTR | 4 | 2876 | ggagattttaggacacacg | 71 | 67 | 1 |
| 136799 | 3'UTR | 4 | 2897 | tgagttcatagactggtttt | 64 | 68 | 1 |
| 136800 | 3'UTR | 4 | 2903 | aagccctgagttcatagact | 75 | 69 | 1 |
| 136801 | 3'UTR | 4 | 2910 | tgttttaaagccctgagttc | 26 | 70 | 1 |
| 136802 | 3'UTR | 4 | 2914 | aaaatgttttaaagccctga | 65 | 71 | 1 |
| 136803 | 3'UTR | 4 | 2980 | tgagcccatcaatttcatag | 82 | 72 | 1 |
| 136804 | 3'UTR | 4 | 2989 | cagctagtttgagcccatca | 83 | 73 | 1 |
| 136805 | 3'UTR | 4 | 3000 | cagaagattcacagctagtt | 83 | 74 | 1 |
| 136806 | 3'UTR | 4 | 3048 | tgttcaaggcttaaaacca | 69 | 75 | 1 |
| 136807 | 3'UTR | 4 | 3057 | acatcagaatgttcaaggct | 74 | 76 | 1 |
| 136808 | 3'UTR | 4 | 3073 | atcaactttagtgacaacat | 70 | 77 | 1 |
| 136809 | 3'UTR | 4 | 3075 | aaatcaactttagtgacaac | 53 | 78 | 1 |
| 136810 | 3'UTR | 4 | 3090 | acgagcatcgcctggaaatc | 62 | 79 | 1 |
| 136811 | 3'UTR | 4 | 3117 | aacttgggtgagccacgcca | 69 | 80 | 1 |
| 136812 | 3'UTR | 4 | 3137 | ccaccggccctcagtcgagg | 70 | 81 | 1 |
| 136813 | 3'UTR | 4 | 3181 | ggcggtgctggcagaacacg | 81 | 82 | 1 |

TABLE 1-continued

Inhibition of human EIF2C2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 136814 | 3'UTR | 4 | 3207 | tgctccttagttcaggccgg | 76 | 83 | 1 |
| 136815 | 3'UTR | 4 | 3220 | caccttctggcactgctcct | 43 | 84 | 1 |
| 136816 | 3'UTR | 4 | 3257 | ctctctggacctggaaatgc | 80 | 85 | 1 |
| 136817 | 3'UTR | 4 | 3260 | aacctctctggacctggaaa | 80 | 86 | 1 |
| 136818 | 3'UTR | 4 | 3278 | aaatggcacttgtctgccaa | 54 | 87 | 1 |
| 136819 | 3'UTR | 4 | 3284 | ttattaaaatggcacttgtc | 68 | 88 | 1 |

As shown in Table 1, SEQ ID NOs 11, 12, 13, 14, 15, 16, 17, 18, 19, 20, 21, 22, 23, 24, 25, 26, 27, 28, 29, 30, 31, 33, 34, 36, 37, 38, 39, 40, 41, 42, 43, 44, 45, 47, 48, 49, 50, 51, 52, 53, 54, 55, 56, 57, 58, 59, 60, 61, 62, 63, 64, 65, 66, 67, 68, 69, 71, 72, 73, 74, 75, 76, 77, 78, 79, 80, 81, 82, 83, 85, 86, 87 and 88 demonstrated at least 50% inhibition of human EIF2C2 expression in this assay. More preferred are SEQ ID NOs 24, 33 and 45. The target regions to which these preferred sequences are complementary are herein referred to as "preferred target segments" and are therefore, preferred in some embodiments for targeting by compounds of the present invention. These preferred target segments are shown in Table 2. These sequences are shown to contain thymine (T) but one of skill in the art will appreciate that thymine (T) is generally replaced by uracil (U) in RNA sequences. The sequences represent the reverse complement of the preferred antisense compounds shown in Table 1. "Target site" indicates the first (5'-most) nucleotide number on the particular target nucleic acid to which the oligonucleotide binds. Also shown in Table 2 is the species in which each of the preferred target segments was found.

TABLE 2

Sequence and position of preferred target segments identified in EIF2C2.

| SITE ID | TARGET SEQ ID NO | TARGET SITE | SEQUENCE | REV COMP OF SEQ ID | ACTIVE IN | SEQ ID NO |
|---|---|---|---|---|---|---|
| 49882 | 4 | 73 | cacctgaagaacacgtatgc | 11 | H. sapiens | 89 |
| 49883 | 4 | 78 | gaagaacacgtatgcgggcc | 12 | H. sapiens | 90 |
| 49884 | 4 | 84 | cacgtatgcgggcctgcagc | 13 | H. sapiens | 91 |
| 49885 | 4 | 147 | ggtcaagcgcgtgggagaca | 14 | H. sapiens | 92 |
| 49886 | 4 | 169 | gtgctggggatggccacgca | 15 | H. sapiens | 93 |
| 49887 | 4 | 196 | cagatgaagaacgtgcagag | 16 | H. sapiens | 94 |
| 49888 | 4 | 202 | aagaacgtgcagaggaccac | 17 | H. sapiens | 95 |
| 49889 | 4 | 208 | gtgcagaggaccacgccaca | 18 | H. sapiens | 96 |
| 49890 | 4 | 214 | aggaccacgccacagaccct | 19 | H. sapiens | 97 |
| 49891 | 4 | 266 | tgggaggcgtgaacaacatc | 20 | H. sapiens | 98 |
| 49892 | 4 | 271 | ggcgtgaacaacatcctgct | 21 | H. sapiens | 99 |
| 49893 | 4 | 298 | ggaaggccgccggtgttcca | 22 | H. sapiens | 100 |
| 49894 | 4 | 454 | caccggcaggagatcataca | 23 | H. sapiens | 101 |
| 49895 | 4 | 558 | cgacggtgtctctgaaggcc | 24 | H. sapiens | 102 |
| 49896 | 4 | 566 | tctctgaaggccagttccag | 25 | H. sapiens | 103 |
| 49897 | 4 | 569 | ctgaaggccagttccagcag | 26 | H. sapiens | 104 |

TABLE 2-continued

Sequence and position of preferred target segments identified in EIF2C2.

| SITE ID | TARGET SEQ ID NO | TARGET SITE | SEQUENCE | REV COMP OF SEQ ID | ACTIVE IN | SEQ ID NO |
|---|---|---|---|---|---|---|
| 49898 | 4 | 574 | ggccagttccagcaggttct | 27 | H. sapiens | 105 |
| 49899 | 4 | 577 | cagttccagcaggttctcca | 28 | H. sapiens | 106 |
| 49900 | 4 | 587 | aggttctccaccacgagttg | 29 | H. sapiens | 107 |
| 49901 | 4 | 679 | aagaggcaccacacccggct | 30 | H. sapiens | 108 |
| 49902 | 4 | 682 | aggcaccacacccggctctt | 31 | H. sapiens | 109 |
| 49904 | 4 | 732 | aagtggaaacattccagcag | 33 | H. sapiens | 110 |
| 49905 | 4 | 739 | aacattccagcaggcacgac | 34 | H. sapiens | 111 |
| 49907 | 4 | 800 | acctgtgtagtcacgctggc | 36 | H. sapiens | 112 |
| 49908 | 4 | 816 | tggcatccaggggacaagca | 37 | H. sapiens | 113 |
| 49909 | 4 | 842 | cgcactatcacgtcctctgg | 38 | H. sapiens | 114 |
| 49910 | 4 | 868 | aatcgtttctcctctgatga | 39 | H. sapiens | 115 |
| 49911 | 4 | 959 | cagcatactacgctcacctg | 40 | H. sapiens | 116 |
| 49912 | 4 | 977 | tggtggccttccgggccagg | 41 | H. sapiens | 117 |
| 49913 | 4 | 1027 | gctgaaggaagccatacctc | 42 | H. sapiens | 118 |
| 49914 | 4 | 1033 | ggaagccatacctctgggca | 43 | H. sapiens | 119 |
| 49915 | 4 | 1054 | agtaacgggcgagaccacca | 44 | H. sapiens | 120 |
| 49916 | 4 | 1065 | agaccaccaagcactggcca | 45 | H. sapiens | 121 |
| 49918 | 4 | 1119 | catgtactttgcttgacatg | 47 | H. sapiens | 122 |
| 49919 | 4 | 1120 | atgtactttgcttgacatgt | 48 | H. sapiens | 123 |
| 49920 | 4 | 1145 | tgtttagcgattgtgtaccg | 49 | H. sapiens | 124 |
| 49921 | 4 | 1152 | cgattgtgtaccgagtggga | 50 | H. sapiens | 125 |
| 49922 | 4 | 1168 | gggattcacgagaccagcta | 51 | H. sapiens | 126 |
| 49923 | 4 | 1173 | tcacgagaccagctacactc | 52 | H. sapiens | 127 |
| 49924 | 4 | 1184 | gctacactcagaccaacaga | 53 | H. sapiens | 128 |
| 49925 | 4 | 1192 | cagaccaacagatggccagc | 54 | H. sapiens | 129 |
| 49926 | 4 | 1223 | agccagcatcgaacatgaga | 55 | H. sapiens | 130 |
| 49927 | 4 | 1242 | acgtcattgattttattaga | 56 | H. sapiens | 131 |
| 49928 | 4 | 1273 | ccagaatgccttccgtccca | 57 | H. sapiens | 132 |
| 49929 | 4 | 1309 | ttgactgcagactgtatgag | 58 | H. sapiens | 133 |
| 49930 | 4 | 1316 | cagactgtatgagaacccaa | 59 | H. sapiens | 134 |
| 49931 | 4 | 1321 | tgtatgagaacccaatgtca | 60 | H. sapiens | 135 |
| 49932 | 4 | 1337 | gtcataggaaatatggtttg | 61 | H. sapiens | 136 |
| 49933 | 4 | 1347 | atatggtttgctaaaatcta | 62 | H. sapiens | 137 |
| 49934 | 4 | 1356 | gctaaaatctataagctgct | 63 | H. sapiens | 138 |
| 49935 | 4 | 1359 | aaaatctataagctgcttat | 64 | H. sapiens | 139 |
| 49936 | 4 | 1370 | gctgcttattaaaacagagt | 65 | H. sapiens | 140 |

TABLE 2-continued

Sequence and position of preferred target segments identified in EIF2C2.

| SITE ID | TARGET SEQ ID NO | TARGET SITE | SEQUENCE | REV COMP OF SEQ ID | ACTIVE IN | SEQ ID NO |
|---|---|---|---|---|---|---|
| 49937 | 4 | 1376 | tattaaaacagagtcccgtg | 66 | H. sapiens | 141 |
| 49938 | 4 | 1392 | cgtgtgtcctaaaaatctcc | 67 | H. sapiens | 142 |
| 49939 | 4 | 1413 | aaaaccagtctatgaactca | 68 | H. sapiens | 143 |
| 49940 | 4 | 1419 | agtctatgaactcagggctt | 69 | H. sapiens | 144 |
| 49942 | 4 | 1430 | tcagggctttaaaacatttt | 71 | H. sapiens | 145 |
| 49943 | 4 | 1496 | ctatgaaattgatgggctca | 72 | H. sapiens | 146 |
| 49944 | 4 | 1505 | tgatgggctcaaactagctg | 73 | H. sapiens | 147 |
| 49945 | 4 | 1516 | aactagctgtgaatcttctg | 74 | H. sapiens | 148 |
| 49946 | 4 | 1564 | tggttttaaagccttgaaca | 75 | H. sapiens | 149 |
| 49947 | 4 | 1573 | agccttgaacattctgatgt | 76 | H. sapiens | 150 |
| 49948 | 4 | 1589 | atgttgtcactaaagttgat | 77 | H. sapiens | 151 |
| 49949 | 4 | 1591 | gttgtcactaaagttgattt | 78 | H. sapiens | 152 |
| 49950 | 4 | 1606 | gatttccaggcgatgctcgt | 79 | H. sapiens | 153 |
| 49951 | 4 | 1633 | tggcgtggctcacccaagtt | 80 | H. sapiens | 154 |
| 49952 | 4 | 1653 | cctcgactgagggccggtgg | 81 | H. sapiens | 155 |
| 49953 | 4 | 1697 | cgtgttctgccagcaccgcc | 82 | H. sapiens | 156 |
| 49954 | 4 | 1723 | ccggcctgaactaaggagca | 83 | H. sapiens | 157 |
| 49956 | 4 | 1773 | gcatttccaggtccagagag | 85 | H. sapiens | 158 |
| 49957 | 4 | 1776 | tttccaggtccagagaggtt | 86 | H. sapiens | 159 |
| 49958 | 4 | 1794 | ttggcagacaagtgccattt | 87 | H. sapiens | 160 |
| 49959 | 4 | 1800 | gacaagtgccattttaataa | 88 | H. sapiens | 161 |

As these "preferred target segments" have been found by experimentation to be open to, and accessible for, hybridization with the oligomeric compounds of the present invention, one of skill in the art will recognize or be able to ascertain, using no more than routine experimentation, further embodiments of the invention that encompass other compounds that specifically hybridize to these preferred target segments and consequently inhibit the expression of EIF2C2.

According to the present invention, oligomeric compounds include, oligonucleotides, siRNAs, external guide sequence (EGS) oligonucleotides, alternate splicers, and other short oligomeric compounds which hybridize to at least a portion of the target nucleic acid.

Example 16

Western Blot Analysis of EIF2C2 Protein Levels

Western blot analysis (immunoblot analysis) is carried out using standard methods. Cells are harvested 16-20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to EIF2C2 is used, with a radiolabeled or fluorescently labeled secondary antibody directed against the primary antibody species. Bands are visualized using a PHOSPHORIMAGER™ (Molecular Dynamics, Sunnyvale Calif.).

Example 17

Phenotypic Assay and Identification of EIF2C2 as a Component in the RNAi Mechanism In accordance with the present invention, oligomeric compounds targeted to EIF2C2 were tested for their ability to modulate the RNAi pathway. Although not wishing to be bound by theory, it is thought that if EIF2C2 is involved in the RNAi pathway or critical to the process of target reduction as an endpoint to this pathway, then a reduction of EIF2C2 levels should result in compromise of the pathway and a failure of oligomeric oligonucleotide constructs such as siRNAs, known to operate within the pathway, to reduce mRNA levels of their target nucleic acid molecules.

EIF2C2 expression was inhibited using RNAse H-dependent antisense oligonucleotides, herein referred to as RNAse H oligonucleotides. On day one, T-24 cells were treated with one of the following RNAse H oligonucleotides at 200 nM: ISIS 136755 (SEQ ID NO: 24), an oligonucleotide targeted to EIF2C2; ISIS 144230 (SEQ ID NO: 163), an oligonucleotide targeted to EIF2C1 which has also been implicated in the control of the RNAi pathway; ISIS 116848 (SEQ ID NO: 162), a control mismatch oligonucleotide targeted to human PTEN; or a combination of ISIS 136755 and ISIS 144230. All of these compounds are RNAse H oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl(2'-MOE) nucleotides. The internucleoside (backbone) linkages are phosphorothioate (P=S) throughout the oligonucleotide. All cytidine residues are 5-methylcytidines. A control group of cells received no oligonucleotide treatment and mRNA levels were normalized to this group.

After 24 hours, on day 2, all cells were treated with a double-stranded compound (siRNA) directed to human PTEN at a dose of 100 nM. Reduction of PTEN mRNA levels were measured as an endpoint and confirmed that the RNAi pathway was affected by treatment with RNAse H compounds that inhibit EIF2C2.

The double stranded compound, herein referred to as the PTEN siRNA, was a 20-mer RNA duplex comprising ISIS 29591 (SEQ ID NO: 164) having a two-nucleobase overhang of deoxythymidine (dT) on the 3' end annealed to the complement of ISIS 29591 (SEQ ID NO: 165) which also had a two-nucleobase overhang of deoxythymidine (dT) on the 3' end making the duplex complementary over the central 18 nucleobases. The cells were then harvested on day 3 and the levels of PTEN and EIF2C2 mRNA were measured relative to the control group.

Cells in the control group receiving no oligonucleotide treatment as well as those treated with the PTEN mismatch (ISIS 116848) or the EIF2C1 oligonucleotide (ISIS 144230) followed by treatment with the PTEN siRNA compound all showed a considerable decrease in the amount of PTEN mRNA confirming that the PTEN siRNA was utilized in the RNAi pathway to reduce PTEN mRNA levels. There was no change in the levels of EIF2C2 mRNA after the PTEN siRNA treatment. Quantitatively, compared to untreated control group, the PTEN mRNA levels were lowered by at least 85% in all groups while EIF2C2 mRNA levels remained at 100% of control.

However, in cells treated with the EIF2C2 oligonucleotide (ISIS 136755) or the combination of ISIS 136755 and ISIS 144230, the mRNA levels of EIF2C2 were dramatically decreased by 90% while the levels of PTEN mRNA in these cells were only slightly decreased to 82% (treatment with ISIS 136755) and 62% (treatment with ISIS 136755 and ISIS 144230) of control.

These results demonstrate that oligomeric compounds targeted to EIF2C2 can alter the capacity of the RNAi machinery to process siRNAs, reducing the levels of EIF2C2 and further support a role for EIF2C2 in this pathway. In the case where EIF2C2 was not targeted (mRNA levels of EIF2C2 were not reduced), the double stranded RNA (PTEN siRNA) targeting PTEN was able to reduce PTEN mRNA levels. However, when EIF2C2 was targeted for reduction, (treatment with ISIS 136755 and concomitant reduction of EIF2C2 mRNA levels), the RNAi pathway was shut down as evidenced by the inability of the PTEN siRNA to effectively reduce levels of PTEN mRNA.

Example 18

Modulation of the RNAi Pathway by Chimeric Phosphorothioate Oligonucleotides Targeted to EIF2C2: Hela Cells In a further embodiment, oligomeric compounds targeted to EIF2C2 were tested for their ability to modulate the RNAi pathway in Hela cells. If EIF2C2 is involved in the RNAi pathway in Hela cells, then a reduction of EIF2C2 should result in a compromised RNAi pathway and a failure of siRNAs to reduce mRNA molecules of their target nucleic acid molecules.

The phenotypic assay was conducted as described in Example 17. On day one, Hela cells were treated with one of the following RNAseH oligonucleotides at a dose of 200 nM: ISIS 136755 (SEQ ID NO: 24), ISIS 136764 (SEQ ID NO: 33), or ISIS 136776 (SEQ ID NO: 45), all 3 of which are targeted to EIF2C2; or ISIS 144230 (SEQ ID NO: 163), an RNAse H oligonucleotide targeted to EIF2C1, which has also been implicated in the control of the RNAi pathway. A control group of cells received no oligonucleotide treatment and mRNA levels were normalized to this group.

After 24 hours, all cells were treated with the PTEN siRNA at a dose of 100 nM. The cells were harvested on day 3 and the levels of PTEN mRNA were measured relative to the control group.

Cells in the control group receiving no antisense oligonucleotide treatment as well as those treated with the EIF2C1 oligonucleotide (ISIS 144230) followed by treatment with the PTEN siRNA compound all showed a considerable decrease in the amount of PTEN mRNA, demonstrating that the PTEN siRNA was utilized in the RNAi pathway in Hela cells to reduced PTEN mRNA levels. Quantitatively, PTEN mRNA levels were lowered by 80% and 82% in cells receiving no antisense oligonucleotide treatment and cells treated with ISIS 144230, respectively.

Conversely, Hela cells treated with antisense oligonucleotides targeted to EIF2C2 did not exhibit a considerable reduction in PTEN mRNA. PTEN levels were reduced by 50%, 54% and 61% in cells treated with ISIS 136755, ISIS 136764 and ISIS 136776, respectively. Thus, when EIF2C2 was targeted for reduction, the RNAi pathway was disrupted as evidenced by the inability of the PTEN siRNA to markedly reduce levels of PTEN mRNA. These results demonstrate that EIF2C2 is a critical component of the RNAi pathway in Hela cells.

Example 19

Modulation of the RNAi Pathway by Double-Stranded Compounds (siRNAs) Targeted to EIF2C2

In a further embodiment siRNAs which are targeted to EIF2C2 were tested for their ability to modulate the RNAi pathway. The resultant reduction in EIF2C2 levels is expected to result in the same phenotype that was observed in cells treated with RNAse H oligonucleotides targeted to EIF2C2, i.e. a disruption in the RNAi pathway.

The EIF2C2 siRNA1 designed to target EIF2C2 was a 21-mer RNA duplex comprising an antisense strand (SEQ ID NO: 166) having a two-nucleobase overhang of deoxythymidine (dT) on the 3' end annealed to the complement of the antisense strand (i.e., the sense strand; SEQ ID NO: 167) also having a two-nucleobase overhang of deoxythymidine (dT) on the 3' end make the duplex complementary over the central 19 nucleobases. Nucleobases 1 through 19 of SEQ ID NOs 166 and 167 are oligoribonucleotides and nucleobases 20 and 21 are deoxythymidines. Internucleoside (backbone) linkages are phosphodiester throughout the compounds. EIF2C2 siRNA2 and EIF2C2 siRNA3 are duplexes comprising an antisense strand having a blunt end annealed to the complement of the antisense strand (i.e., the sense strand) making the duplex complementary over its entire length. SEQ ID NOs 168, 169, 170 and 171 are oligoribonucleotides with phosphodiester internucleoside linkages throughout. The compounds are shown in Table 3. "Target site" indicates the first (5'-most) nucleotide number on the particular target sequence to which the compound binds. All compounds in Table 3 are oligoribonucleotides. The internucleoside (backbone) linkages are phosphodiester (P=O) through the compound.

TABLE 3 siRNAs targeted to EIF2C2

| Name | TARGET SEQ ID NO | TARGET SITE | Region | SEQUENCE | Strand | SEQ ID NO |
|---|---|---|---|---|---|---|
| EIF2C2 siRNA1 | 4 | 2045 | Coding | CTGGCCTTCAGAGACACCGTT | Antisense | 166 |
|  |  |  |  | CGGTGTCTCTGAAGGCCAGTT | Sense | 167 |
| EIF2C2 siRNA2 | 4 | 2706 | 3' UTR | TCTCATGTTCGATGCTGGCTG | Antisense | 168 |
|  |  |  |  | GCCAGCATCGAACATGAGACG | Sense | 169 |
| EIF2C2 siRNA3 | 4 | 2756 | 3' UTR | TGGGACGGAAGGCATTCTGGA | Antisense | 170 |
|  |  |  |  | CAGAATGCCTTCCGTCCCAGA | Sense | 171 |

On day one, T-24 cells were treated with 100 nM of the siRNAs described in Table 3. As a positive control for the disruption of the RNAi pathway, a group of cells was treated with the RNAse H oligonucleotide ISIS 136764 (SEQ ID NO: 33) at 200 nM. A control group of cells received no siRNA treatment and mRNA levels were normalized to this group.

After 24 hours, all cells were treated with double-stranded compound directed to human PTEN. This double-stranded compound, herein referred to as the PTEN siRNA2, was a 21-mer RNA duplex comprising ISIS 271790 (SEQ ID NO: 172) having a two-nucleobase overhang of deoxythymidine (dT) on the 3' end annealed to the complement of ISIS 271766 (SEQ ID NO: 173) also having a two-nucleobase overhang of deoxythymidine (dT) on the 3' end, making the duplex complementary over the central 19 nucleobases. ISIS 271790 and ISIS 271766 are composed of oligoribonucleotides at nucleotide positions 1-19 and 2'-deoxynucleotides at positions 20 and 21. Internucleoside linkages are phosphodiester throughout the compounds. The cells were harvested the following day and the levels of PTEN mRNA were measured and normalized to the control group.

Cells in the control group receiving no EIF2C2 siRNA treatment, thus experiencing no reduction in EIF2C2 expression, followed by treatment with PTEN siRNA2 showed a considerable decrease in the amount of PTEN mRNA, suggesting that the PTEN siRNA2 was utilized in the RNAi pathway to reduce PTEN mRNA levels and that the presence of EIF2C2 is a prerequisite for the function of the RNAi pathway. However, PTEN mRNA levels were reduced only 30% in the cells treated with ISIS 136764 (the RNAse H oligonucleotide targeted to EIF2C2), and were lowered by 42% in the cells treated with the dsRNA equivalent of ISIS 136755. To further confirm this result, the experiment was repeated and in this case the siRNAs used for the first treatment were the siRNA equivalents of ISIS 136786 and ISIS 136788, treatment with which resulted in a 37% and 40% reduction in PTEN mRNA when the PTEN siRNA2 was introduced to the cells, respectively. These data demonstrate that when EIF2C2 is reduced by either an RNAse H oligonucleotide or an siRNA, the RNAi pathway is disrupted.

Example 20

Processing of Antisense Compounds Following Modulation of the RNAi Pathway siRNAs vs. RNAse H Oligonucleotides Although a variety of oligomeric compounds inhibit gene expression through a antisense mechanisms, oligomeric compounds of varying chemistries and structures act through different branches of the antisense pathway. The phenotypic assay described herein can be used to distinguish the antisense pathways through which different oligomeric compounds elicit target reduction. In accordance with the present invention, following disruption of the RNAi pathway, cells were treated with either siRNAs or RNAse H oligonucleotides to determine whether the levels of their target nucleic acid molecules were reduced.

On day one, T-24 cells were treated with 200 nM of one of the following RNASE H oligonucleotides at 200 nM: ISIS 136755 (SEQ ID NO: 24), an RNAse H oligonucleotide targeted to EIF2C2; or ISIS 144230 (SEQ ID NO: 163), an RNAse H oligonucleotide targeted to EIF2C1. A control group of cells received no oligonucleotide treatment and mRNA levels were normalized to this group. Each treatment was performed in triplicate.

After 24 hours, one of the replicate groups was treated with an siRNA and a second was treated with an RNAse H oligonucleotide, both of which are directed to human PTEN, at a dose of 100 nM. The siRNA was PTEN siRNA2 and the RNAse H oligonucleotide was ISIS 116847 (CTGCTAGC-CTCTGGATTTG, SEQ ID NO: 174). The third replicate was untreated. The cells were harvested on the third day and the levels of PTEN were measured relative to the control group.

The data are presented in Table 4 as percent reduction in mRNA expression. The RNAse H oligonucleotides used to inhibit the expression of EIF2C2 and EIF2C1 are indicated in the "first treatment" column. The oligomeric compounds used to test the activity of the RNAi pathway are indicated in the "second treatment" columns, where "UTC" indicates untreated control cells, "PTEN (116847)" indicates treatment with the RNAse H oligonucleotide, and "PTEN (siRNA2)" indicates treatment with the siRNA targeted to PTEN.

TABLE 4

Processing of siRNAs and RNAse H oligonucleotides in cells with compromised RNAi

| First treatment | Target mRNA measured | % reduction in mRNA Second treatment | | |
|---|---|---|---|---|
| | | UTC | PTEN (116847) | PTEN (siRNA2) |
| UTC | PTEN | 0 | 86 | 22 |
| | EIF2C1 | 0 | 17 | 0 |
| | EIF2C2 | 0 | 0 | 0 |
| EIF2C1 (144230) | PTEN | 0 | 86 | 81 |
| | EIF2C1 | 88 | 90 | 86 |
| | EIF2C2 | 0 | 0 | 4 |
| EIF2C2 (135755) | PTEN | 0 | 80 | 23 |
| | EIF2C1 | 5 | 15 | 10 |
| | EIF2C2 | 83 | 85 | 85 |

As predicted for cells in which the RNAi pathway has been disrupted by EIF2C2 reduction, treatment with PTEN siRNA2 did not result in a considerable decrease in PTEN mRNA expression (only a 23% reduction). Conversely, treatment of the cells with ISIS 116847 did result in a marked decrease in PTEN mRNA expression (an 80% reduction) in cells in which the RNAi pathway was compromised. These data demonstrate that, although both RNAse H oligonucleotides and siRNAs elicit target reduction through antisense mechanisms, the RNAse H oligonucleotides do so through a different branch of the antisense pathway than do siRNAs.

The effects of EIF2C2 disruption on processing of oligomeric compounds directed to an additional target, H-ras, were investigated. EIF2C2 was disrupted as described, using 100 nM of ISIS 136755. After 24 hours, cells were treated with 200 nM of: ISIS 13920 (TCCGTCATCGCTCCTCAGGG, SEQ ID NO: 175), an RNAse H oligonucleotide targeted to H-ras; a double-stranded compound targeted to H-ras, herein referred to as H-ras siRNA; ISIS 2566 (GCCCACAC-CGACGGCGCCCAC, SEQ ID NO: 176), an RNAse H oligonucleotide targeted to H-ras; or ISIS 2570 (CCACAC-CGACGGCGCCC, SEQ ID NO: 177), an RNAse H oligonucleotide targeted to H-ras. ISIS 13920 is a chimeric oligonucleotide having a 9-nucleotide "gap" segment composed of 2'-deoxynucleotides which is flanked by a 3-nucleotide "wing" segment on the 5' terminus and an 8-nucleotide "wing" segment on the 3' terminus. The wing segments are composed of 2'-O-methoxyethyl(2'-MOE)nucleotides. Internucleoside (backbone) linkages are phosphorothioate throughout the oligonucleotide. All cytidine residues are 5-methylcytidines. H-ras siRNA is a 21-mer duplex comprising SEQ ID NO: 178 (GCCCACACCGACGGCGCCCTT) having a two-nucleobase overhang of deoxythymidine (dT) on the 3' end annealed to the complement of SEQ ID NO: 178 (GGGCGCCGTCGGTGTGGGCTT; SEQ ID NO: 179), also having a two-nucleobase overhang of deoxythymidine (dT) on the 3' end making the duplex complementary over the central 19 nucleobases. The central 19 nucleobases of both the antisense and sense strands are oligoribonucleotides. Internucleoside linkages are phosphodiester throughout both strands. ISIS 2566 and ISIS 2570 are oligonucleotides 21 and 17 nucleotides in length, respectively, and are uniformly composed of 2'-deoxynucleotides. Internucleoside linkages are phosphorodiester throughout the compounds. A control group of cells received no oligonucleotide treatment and mRNA levels were normalized to this group.

On day 3, cells were harvested and H-ras mRNA levels were measured. ISIS 13920 reduced H-ras mRNA levels by 70% and 52% in cells receiving no treatment or cells in which EIF2C2 had been reduced by treatment with ISIS 136755, respectively. However, whereas the RNAse H oligonucleotide was able to markedly reduce H-ras levels, the H-ras siRNA reduced target mRNA levels by only 26%. In cells in which EIF2C2 was not disrupted, the H-ras siRNA reduced targeted levels by 71%. H-ras levels in cells treated with ISIS 2566 or ISIS 2570 were reduced to similar levels in cells receiving no oligonucleotide treatment or cells in which EIF2C2 was disrupted with ISIS 136755, indicating that the reduction in EIF2C2 did not affect the activity of these two compounds.

These data confirm that while both RNAse H oligonucleotides and siRNAs elicit target reduction through an antisense mechanism, they do so through different branches of the antisense pathway. Furthermore, these results illustrate that although the RNAi pathway is disrupted, antisense mechanisms are still operating within the cells and the observed phenotypes are not due to a non-specific disruption of cellular mechanisms.

The divergent pathways utilized by RNAse H oligonucleotides and siRNAs were further tested following disruption of the RNAi pathway with siRNAs targeted to EIF2C2. The assay was conducted as described in Example 19, using ISIS 116847 as an additional treatment after the initial treatments with EIF2C2 siRNA1, EIF2C2 siRNA2, EIF2C2 siRNA2 and ISIS 136764 (RNAse H oligonucleotide) to disrupt EIF2C2 expression. A control group received no oligonucleotide treatment as mRNA levels were normalized to this group.

As cited in Example 19, the PTEN siRNA reduced target mRNA was reduced by 37%, 37% and 40% in cells treated with ISIS 136764, si136786 and si136788, respectively. In cells receiving no treatment to reduce EIF2C2, the PTEN siRNA reduced target expression by 75%. However, the RNAse H oligonucleotide targeted to PTEN reduced target expression in all cells, regardless of whether the cells received no treatment or a compound targeted to EIF2C2. Quantitatively, the RNAse H oligonucleotide reduced PTEN mRNA expression at least 80% in cells, regardless of the oligomeric compound used to disrupt EIF2C2. A similar result was observed in cells treated with in which EIF2C2 expression was inhibited with an RNAse H oligonucleotide (ISIS 136764) or an siRNA (si135755) to reduce EIF2C2, i.e., the target reduction activity of the RNAse H oligonucleotide was not affected by the disruption of the RNAi pathway (93% and 74% reductions, respectively), whereas the siRNA was not as effective at reducing PTEN expression (30% and 64% reductions, respectively). These data further confirm that siRNAs and RNAse H oligonucleotides affect target reduction through different branches of the antisense pathway.

Example 21

Processing of Antisense Compounds Following Modulation of the RNAi Pathway siRNAs vs. Single-Strand RNAs In a further embodiment, the effects of modulation of the RNAi pathway on the activity of single-strand RNAs were tested and compared to the activity of siRNAs in the phenotypic assay. This assay was used to determine whether siR- NAs and single-strand RNAs modulate target expression through the same branch of the antisense pathway.

On day one, T-24 cells were treated with 200 nM of: ISIS 136755 (SEQ ID NO: 24), an RNAse H oligonucleotide targeted to EIF2C2; or ISIS 144320 (SEQ ID NO: 163), an RNAse H oligonucleotide targeted to EIF2C1. A control group of cells received no oligonucleotide treatment and mRNA levels were normalized to this group.

After 24 hours, cells were treated with ISIS 303912 (TTTGTCTCTGGTCCTTACTT, SEQ ID NO: 180), a single-strand RNA (asRNA) compound targeted to PTEN, at a dose of 100 nM. ISIS 303912 is an oligoribonucleotide 20 nucleotides in length. Internucleoside (backbone) linkages are phosphodiester throughout the compound.

On day 3, cells were harvested and levels of PTEN and EIF2C2 mRNA were measured and normalized to the control group. Cells in the control group receiving no oligonucleotide treatment as well as those treated with the EIF2C1 oligonucleotide (ISIS 144230) followed by treatment with the PTEN single-strand RNA compound showed a considerable decrease in PTEN mRNA (72% and 70%, respectively), suggesting that the PTEN single-strand RNA (asRNA) was utilized in the RNAi pathway to reduce PTEN levels. There was no reduction in the level of EIF2C2 in cells receiving no treatment or in cells receiving ISIS 144230 (EIF2C1) treatment. However, in cells in which EIF2C2 was disrupted by treatment with ISIS 136755, the single-strand RNA (asRNA) ISIS 303912 was unable to reduce PTEN mRNA levels, which were equal to PTEN mRNA levels in untreated control cells. Furthermore, EIF2C2 was reduced by 42% in these cells. These data demonstrate that, in addition to siRNAs, single-strand RNA compounds are utilized in the RNAi pathway.

Additional RNAse H oligonucleotides targeted to EIF2C2 were tested for their ability to disrupt the RNAi pathway utilized by single-strand RNA compounds. Cells receiving a first treatment with ISIS 136764 (SEQ ID NO: 33) or ISIS 136776 (SEQ ID NO: 45) exhibited 66% and 64% reductions in EIF2C2, respectively. The single-strand RNA compound (ISIS 303912) elicited 50% and 30% reductions in PTEN mRNA levels in these cells, respectively. When EIF2C2 was not reduced, in cells receiving no oligonucleotide treatment or in cells receiving ISIS 144230 (targeted to EIF2C1) treatment, ISIS 303912 reduced PTEN mRNA levels by 70% and 66%, respectively. These data confirm that when EIF2C2 is reduced, i.e. when the RNAi pathway is disrupted, the ability of single-strand RNA compounds to inhibit target mRNA expression is compromised. An additional experiment using the phenotypic assay demonstrated that the siRNA of ISIS 303912 and its complement was unable to reduce target expression in cells in which the RNAi pathway was compromised.

Together, these data demonstrate that single-strand (asRNA) and double-strand (siRNA) RNA compounds modulate the expression of their targets through the RNAi pathway, whereas RNAse H oligonucleotides operate through a different branch of the antisense pathway.

The assay described herein, wherein the RNAi pathway is modulated by single-strand oligonucleotides targeted to EIF2C2, is useful for evaluating chemical modifications to oligomeric compounds, including but not limited to, conjugates, terminal caps, sugar modifications, nucleoside modifications and linkage modifications.

Example 22

Modulation of the RNAi Pathway Using Oligomeric Compounds Target to EIF2C2

RNA Enzyme-Dependent Activities

In a further embodiment, the participation of RNA-cleaving enzymes in the RNAi pathway was investigated utilizing the same method whereby reduction of EIF2C2 compromised the RNAi pathway.

On day one, T-24 cells were treated with a 200 nM dose of either ISIS 136755 (SEQ ID NO: 24), an RNAse H oligonucleotide targeted to EIF2C2, or ISIS 25690 (ATC-CCTTTCTTCCGCATGTG, SEQ ID NO: 181), an RNAse H oligonucleotide targeted to RNAse III. ISIS 25690 is a chimeric oligonucleotide 20 nucleotides in length, composed of a 10-nucleotide "gap" segment comprised of 2'-deoxynucleotides which is flanked by 5-nucleotide "wing" segments on both sides (5' and 3'). The wing segments are comprised of 2'-O-methoxyethyl (2'-MOE) nucleotides. Internucleoside (backbone) linkages are phosphorothioate throughout the compound. All cytidine residues are 5-methylcytidines. A control group of cells received no oligonucleotide treatment and served as the group to which data were normalized.

After 24 hours, cells were treated with a 100 nM dose of either ISIS 116847 (SEQ ID NO: 174), an RNAse H oligonucleotide targeted to PTEN; or PTEN siRNA2 (SEQ ID NO: 172 annealed to SEQ ID NO: 173). On day 3, cells were harvested and PTEN mRNA levels were measured and normalized to untreated control cells. In cells treated with ISIS 136755, which compromises the RNAi pathway, the PTEN siRNA2 reduced target levels by only 37%. However, in cells receiving no oligonucleotide treatment or RNAse III oligonucleotide treatment, PTEN mRNA levels were considerably reduced suggesting that RNAse III is not involved in the processing event that results in siRNA-reduced PTEN levels.

In summary, the inhibition of RNAse III expression did not affect the reduction of target by siRNAs or RNAse H oligonucleotides. The PTEN siRNA2 reduced target levels by 82% and 83% in untreated cells and RNAse III oligonucleotide-treated cells, respectively. A second RNAse H oligonucleotide, ISIS 29592, was tested in an additional dose-response experiment and showed that the inhibition of RNAse III did not affect the ability of the RNAse H oligonucleotide ISIS 29592, at either a 50 or 150 nM dose, to reduce PTEN mRNA levels.

These data demonstrate that inhibiting the expression of RNAse III does not affect the ability of siRNAs or RNAse H oligonucleotides to elicit reduction of their target, illustrating that RNAse III does not participate in the same pathway as EIF2C2, nor does it participate in the same pathway utilized by RNAse H oligonucleotides.

In a similar assay, the dependence of siRNA activity upon RNAse H1 activity was tested. It is known in the art that RNAse H oligonucleotides utilize the activity of the RNA cleaving enzyme RNAse H1. To further test whether EIF2C2 and RNAse H1 participate in the same pathway, RNAse H1 expression was inhibited using an RNAse H oligonucleotide. Cells were treated with 100 nM of the following RNAse H oligonucleotides: ISIS 136755, targeted to EIF2C2; or ISIS 194178 (TGTGCCTGATTCCGTGTGAA, SEQ ID NO: 182), targeted to RNAse H1. An untreated group served as the control group to which data were normalized. After 24 hours, cells were treated with 50 or 150 nM of ISIS 29592, an RNASE H oligonucleotide targeted to PTEN. On day 3, cells were harvested and PTEN mRNA was measured and normalized to untreated control groups. In cells treated with ISIS 194178 (directed to RNAse H1), target levels were reduced by 67% and 65% following the 50 and 150 nM treatments with ISIS 29592, respectively. Cells in which EIF2C2 or RNAse III was disrupted exhibited a greater reduction in PTEN mRNA levels (at least 82%). As the RNAse H oligonucleotide ISIS 29592 was able to reduce target mRNA to a greater extent in EIF2C2-disrupted cells as compared to RNAse H1-disrupted cells, these data further demonstrate that EIF2C2 and RNAse H1 do not act in the same pathway.

In similar assays, treatment of cells with RNAse H oligonucleotide targeted to RNAse III or RNAse H1, followed by either a 50 or 150 nM dose of PTEN siRNA2 in T-24 cells or a 50, 100 or 150 nM dose of PTEN siRNA in Hela cells, similarly did not affect the ability of the siRNAs to be utilized in the RNAi pathway. Reduction of EIF2C2 did compromise the RNAi pathway, however, this disruption in the pathway was partially rescued at the higher doses of PTEN siRNA or PTEN siRNA2.

Example 23

Modulation of the RNAi Pathway by Chimeric Phosphorothioate Oligonucleotides Having 2'-MOE Wings and a Deoxy Gap Targeted to RNAi Pathway Components In a further embodiment, the RNAi phenotypic assay described herein was used to test putative RNAi pathway components. The assay was performed as described for EIF2C2 disruption using RNAse H oligonucleotides targeted to putative RNAi pathway components. By way of example, on day one, T-24 cells were treated with 200 nM of ISIS 110074 (SEQ ID NO: 206), an RNAse H oligonucleotide targeted to nucleolin. A control group of cells received no treatment and all data were normalized to this group. After 24 hours, all cells were treated with 100 nM of PTEN siRNA. On day 3, the cells were harvested and levels of PTEN mRNA were measured and normalized to the control group.

The phenotypic assay was repeated for each of the genes described in Table 5 (described by gene name), using the RNAse H oligonucleotides indicated in Table 5 (described by ISIS #). The GenBank accession number used to design the compounds is indicated. "Target site" indicates the first (5'-most) nucleotide nucleotide number on the particular target sequence to which the compound binds. All compounds in Table 5 are chimeric oligonucleotides 20 nucleotides in length, composed of a central "gap" region comprised of ten 2'-deoxyoligonucleotides, which is flanked on both sides (5' and 3' directions) by five-nucleotide "wing" segments. The wings are composed of 2'-O-methoxyethyl(2'-MOE)nucleotides. Internucleoside (backbone) linkages are phosphorothioate throughout the compounds. All cytidines are 5-methylcytidines.

In Table 5, "+" indicates that a first treatment with a single-strand oligonucleotide targeted to the gene resulted in a compromised RNAi pathway, as judged by the inability of the PTEN siRNA to reduce target mRNA levels. A "−" indicates that disruption of the gene of interest did not significantly affect the RNAi pathway.

TABLE 5

Effects of antisense inhibition of candidate RNAi pathway components in the phenotypic assay

| Gene Name | Isis # | Accession # | Target Site | Sequence | SEQ ID NO | RNAi inhib |
|---|---|---|---|---|---|---|
| WRN | 137484 | AF091214.1 | 2511 | ttggaccttcaaattcccag | 183 | − |
| RECQL | 136948 | NM_002907.1 | 454 | agctgctaataaacaggctt | 184 | − |
| RECQL2 | 137557 | U39817.1 | 2169 | acacaggcagggagctggta | 185 | − |
| RECQL4 | 137129 | NM_004260.1 | 1655 | ggtcatgcccgagtgtatgc | 186 | − |
| RECQL5 | 137193 | AF135183.1 | 179 | aagaccttcttcagcgtact | 187 | − |
| RNASE L | 139346 | L10381.1 | 2372 | tgtgatttgccaaggactct | 188 | − |
| PKR | 139421 | NM_002759.1 | 1269 | ttgctttgaaaacttggcca | 189 | − |
| DCR1 | 138648 | AB028449.1 | 4225 | gctgaccttttgcttctca | 190 | − |
| EIF2C1 | 144230 | NM_012199.1 | 1785 | tcacctcagcatacaccggc | 163 | − |
| EIF2C2 | 136755 | AF121255.2 | 558 | ggccttcagagacaccgtcg | 24 | + |
| EIF2C2 | 136764 | AF121255.2 | 732 | ctgctggaatgtttccactt | 33 | + |
| eIF2C3 | 241286 | NM_024852.1 | 196 | cttgaaaacagttagccagc | 191 | − |
| eIF2C4 | 309475 | AB046787.1 | 3581 | cagcataaaatgggcacttt | 192 | − |
| FMR1 | 305998 | NM_002024.1 | 3582 | ttgtgaaatcatgtgcagtt | 193 | − |
| FMR2 | 308010 | NM_002025.1 | 5979 | cagaatttgataacccagca | 194 | − |
| FXR1 | 308138 | NM_005087.1 | 1026 | caatgctttctttagtgcca | 195 | − |

TABLE 5-continued

Effects of antisense inhibition of candidate RNAi pathway components in the phenotypic assay

| Gene Name | Isis # | Accession # | Target Site | Sequence | SEQ ID NO | RNAi inhib |
|---|---|---|---|---|---|---|
| FXR2 | 308192 | NM_004860.2 | 263 | gcacctcgacgggcagtccc | 196 | - |
| Gemin 1 | 178907 | NM_000344.1 | 1056 | aagaagagttacccattcca | 197 | - |
| Gemin 2 | 297263 | NM_003616.1 | 762 | agtgaatgagcctcaggtaa | 198 | - |
| Gemin 2 | 297285 | NM_003616.1 | 1164 | aatttctatgcaagctgctt | 199 | - |
| Gemin 3 | 297338 | NM_007204.3 | 1170 | tgctgagtcttttcctcaaa | 200 | - |
| Gemin 3 | 297343 | NM_007204.3 | 1338 | agtttagccatagcatcaag | 201 | - |
| Gemin 4 | 297445 | NM_015721.1 | 3348 | ccatgacttttgtggacag | 202 | - |
| Gemin 5 | 297573 | AL117665.1 | 2073 | aagcagccttgacatactga | 203 | - |
| Gemin 6 | 297687 | NM_024775.8 | 499 | cgcgacagaataatctcatt | 204 | - |
| Gemin 7 | 297725 | NM_024707.1 | 527 | tctgcagctgtgacacgtag | 205 | + |
| nucleolin | 110074 | NM_005381.1 | 692 | gtcatcgtcatcctcatcat | 206 | + |
| p100 | 162016 | NM_014390.1 | 1515 | ttcctccaatggtgacagtg | 207 | - |
| p100 | 162022 | NM_014390.1 | 661 | atccctttcttggctgcctt | 208 | - |
| RNAse H1 | 194178 | AF048994.1 | 1006 | tgtgcctgattccgtgtgaa | 182 | - |
| RNAse H2 | 194186 | AY363912.1 | 1003 | cctacgtgtggttctcctta | 211 | - |
| RNAse III | 25690 | AF189011.1 | 3051 | atcccttcttccgcatgtg | 181 | - |
| RNAse III | 25691 | AF189011.1 | 3085 | gccaaggcgtgacatgatat | 212 | - |
| NUFIP1 | 234277 | NM_012345.1 | 2813 | gaattcatttattaacccat | 213 | - |

Example 24

Cell-Free RNAi Cleavage Assay

In vitro assays are useful tools for dissecting cellular pathways and characterizing pathway components. Moreover, in vitro assays are composed of known components and are easily manipulated. In a further embodiment, a cell-free RNase cleavage assay was developed. In this assay, an S-100 lysate isolated from HeLa cells provided the cellular components necessary for the RNAse cleavage. Added to this lysate were a target sequence, the cleavage of which is evaluated, and an siRNA, to trigger the RNAi-dependent cleavage of the target. The target sequence was 50 nucleotides in length (GATTTCTATGGGGAAGTAAGGACCAGAGACAAAAAGGGAGTAACTATTCC; SEQ ID NO: 225) and was derived from the human PTEN mRNA with GenBank accession number NM_000314.2. The target sequence was radiolabeled at the 5' end with $^{33}$P or at the 3' end with $^{32}$P. The siRNA used was a duplex comprised of ISIS 271784 (AGTAAGGACCAGAGACAAATT, SEQ ID NO: 226) having a two-nucleobase overhang of deoxythymidine on the 3' end annealed to its complement, ISIS 297803 (TTTGTCTCTGGTCCTTACTTT, SEQ ID NO: 227), also having a two-nucleobase overhang of deoxythymidine (dT) on the 3' end, making the duplex complementary over the central 18 nucleobases. The target site of this siRNA is nucleotide 14 of SEQ ID NO: 225. The following components were mixed: 2 µl of a 5× buffer (5× buffer contains 100 mM potassium acetate, 30 mM HEPES at pH 7.4, 2 mM magnesium acetate, 5 mM dithiothreitol, 10 mM creatine phosphatase, 10 µg/µl creatine kinase, 100 µM nucleotide triphosphate, 500 µM adenosine triphosphate and 0.1 units/µl Rnasin), 1 µl of the siRNA, and 2 µl of water. After this reaction incubated for 15 minutes at room temperature, 75,000 counts per minute (CPM) of radiolabeled target was added, and this reaction was incubated for an additional hour at room temperature. The reaction was terminated by adding 200 µL of stop buffer (10 µg transfer RNA at 50 ng/µl, 300 µM sodium acetate, 0.1% sodium dodecyl sulfate). To isolate the substrate, a phenol/chloroform extraction was followed by an ethanol precipitation, both of which are performed by routine protocols known in the art.

The isolated DNA was then separated by polyacrylamide electrophoresis. The gel was dried and subsequently exposed to film, to visualize the cleavage products. This assay revealed that active cleavage sites within the target sequence (SEQ ID NO: 225) are between nucleotides 23 and 24, nucleotides 17 and 18 and nucleotides 30 and 31.

One use of this assay includes the reconstitution of nuclease activity, wherein known or candidate RNAi components are added to the system. Furthermore, the cleavage assay is utilized to investigate and define the molecular mechanisms of the RNAi pathway. As the system is amenable to manipulation, known or candidate RNAi components are overexpressed, reduced or removed, and the consequences on the RNAi pathway are assessed. Additionally, relationships between siRNA or single-strand RNA structure and activity are analyzed to determine the competency of the RNAi pathway to accept chemically modified siRNAs or single-strand RNAs. Moreover, candidate RNAi components, identified through the methods, or through additional methods, are further characterized to understand the manner in which they participate in the RNAi pathway.

Example 25

Biochemical Capture Assay

Identification of Cellular Components Involved in RISC Activity siRNAs are incorporated into the RNA-induced silencing complex (RISC), a multi-component complex which guides the sequence-specific recognition, hybridization and degradation of the target mRNA. EIF2C2 is one of the components of RISC. In accordance with the present invention, a biochemical capture assay was developed to identify RISC components. This assay employs a biotin-conjugated RNA substrate, to which RISC binds. Subsequently, using its affinity to avidin-conjugated beads, the biotin-conjugated RNA substrate is isolated, and RISC and its components are simultaneously isolated.

In this assay, HeLa cell S-100 cytoplasmic lysate (4C, Ghent, Belgium) is first precleared by incubation with neutravidin beads (a deglycosylated form of avidin, available from Pierce Biotechnology, Inc., Rockford, Ill.) for 1 hour, at 4 C, with rotation, for the purpose of removing lysate components that will nonspecifically bind to the neutravidin beads. After preclearing of the Hela lysate, a volume containing 5.5 mg of total protein was mixed with biotin-conjugated siRNA to achieve a final concentration of 200 nM siRNA. Also added to this reaction were ATP regeneration system; Rnase out to inhibit RNAse activity; and protease inhibitors and 1 mM dithiothreitol in Buffer B (30 mM HEPES, pH 7.4, 100 mM KCL, 2 mM $MgCl_2$ and 10% glycerol). This reaction, which is a total volume of 2 mL, is incubated for 60 minutes at 30 C., with rotation. A 75 µl volume of NeutrAvidin beads in Buffer B is added and followed by a 2 hour incubation at 30 C., with rotation. The reaction is next spun for 10 minutes at 14,000×g, and the supernatant is removed. The beads are resuspended in Buffer B, and the reaction is again spun for 10 minutes at 14,000×g. The bead-washing step is repeated twice using Buffer BH (Buffer B with 3% glycerol and 300 mM KCl) and once more with Buffer B. Following the final wash step, 50 µl of a 2% sodium dodecyl sulfate solution is added, and the mixture is heated for 10 minutes at 95 C. After heating, 25 µl of a 4× concentration of protein sample buffer, 10 µl of reducing buffer and 15 µl of water are added. From this mixture, a volume of 10 µl is loaded onto a polyacrylamide gel and the proteins are separated by one-dimensional gel electrophoresis.

Different chemical modifications are incorporated into the siRNA substrates to test whether RISC binds preferentially to one or more chemical modifications. One siRNA substrate used was a duplex of the antisense strand with the sequence TTTGTCTCTGGTCCTTACTT (SEQ ID NO: 228) and the complementary sense strand with the sequence AAGTAAG-GACCAGAGACAAA (SEQ ID NO: 229). This siRNA is directed to human PTEN. ISIS 326908 has the nucleotide sequence of SEQ ID NO: 228 and is an oligoribonucleotide with phosphorothioate internucleoside linkages, and a biotin conjugated to the 3'-terminus. ISIS 308746 has the nucleotide sequence of SEQ ID NO: 229 and is an oligoribonucleotide with phosphodiester linkages. ISIS 331693 has the nucleotide sequence of SEQ ID NO: 228 and is an oligoribonucleotide with phosphodiester internucleoside linkages, and biotin conjugated to the 3'-terminus. An additional siRNA substrate used is targeted to human Raf kinase C. For this siRNA, the antisense strand is ISIS 271056 (TCCCGCCTGTGACATG-CATTT, SEQ ID NO: 230) and the sense strand is ISIS 330079 (ATGCATGTCACAGGCGGGATT, SEQ ID NO: 231). Both ISIS 271056 and ISIS 330079 have a biotin conjugated to the 5' terminus through an 18S hexaethylene glycol spacer. The spacer serves to increase the distance between the label and the active substrate thereby reducing the steric hindrance of the bulky biotin group on the reaction. The siRNAs used as RISC substrates were: ISIS 326908 annealed to ISIS 308746; ISIS 331693 annealed to ISIS 308746; and ISIS 271056 annealed to ISIS 330079: A control reaction lacked biotin and siRNA. The siRNAs were added to the lysate, and the assay was performed as described. Samples were loaded onto replicate polyacrylamide gels. Following separation of proteins by gel electrophoresis, one gel was prepared for immunoblot analysis, which was used to confirm that a known RISC component, EIF2C2, was present in the isolate. The second gel was used to identify additional proteins present in the isolate.

The protein bands that were identified as candidate RISC components were excised from the gel and diced into <1 $mm^3$ pieces. The proteins within the gel pieces were reduced and alkylated and then digested with trypsin in situ. Peptides resulting from trypsin proteolysis were extracted from the gel matrix and analyzed by high-pressure liquid chromatography (HPLC) and mass spectrometry (MS). HPLC/MS and MS/MS were performed using a ThermoFinnigan LCQ Classic ion trap mass spectrometer (Ontario, Canada) with upgraded ion optics. For each gel band, 75% of the sample was loaded onto in house-fabricated microcapillary HPLC column assemblies, which feature a preconcentration column for rapid loading and de-salting, a resolving column packed with 5 µm C18-coated silica spheres, and an electrospray emitter with a 5 µm tip (New Objective, Inc., Woburn, Mass.). Peptides were gradient eluted at an initial flow rate of 68 nL/min using solvents composed of 0.1M acetic acid in water (solvent A) and 0.1M acetic acid, 70% acetonitrile in water (solvent B). As peptides eluted from the HPLC column, they were ionized by electrospray ionization and directed into the heated inlet of the mass spectrometer, where they were desolvated and transported to the ion trap. For MS experiments, ions of mass-to-charge (m/z) 300 to 2000 are stored in the trap simultaneously and scanned out of the trap in order of increasing m/z, where they are detected. From each mass spectrum, the 5 most abundant ions were then automatically identified by the instrument control software and selected for subsequent MS/MS analysis. Each MS/MS analysis involves isolation of the ion of interest by ejection of the higher- and lower-mass ions from the trap, excitation of the isolated ion (which induces collision-activated dissociation (CAD) of the peptide ion) and detection of the fragment ions. When peptide ions are collisionally activated in this way, the vibrational energy imparted to the ion generally results in fragmentation at various positions along the peptide backbone. The fragment ions generated by backbone cleavages yield a MS/MS spectrum in which the observed ions differ in mass by one amino acid. Therefore, the MS/MS spectrum can be used for either manual interpretation to arrive at the amino acid peptide sequence, or can be used for automated interpretation by comparison with databases of protein sequences.

The MS/MS spectra resulting from the HPLC/MS/MS analyses of the one-dimensional gel bands were searched against a database of human proteins retrieved from the National Center for Biotechnology Information (NCBI) on May 16, 2003. Database searching was performed using the SEQUEST software from ThermoFinnigan. This software takes the uninterpreted MS/MS spectrum and compares it to peptide sequences in the database by generating a theoretical spectrum for each database peptide sequence of the correct mass and protease specificity. The theoretical and experimental spectra are then aligned with each other and a correlation score is calculated. When the spectra align well, the correlation score is high and confidence increases that the experimentally observed spectrum comes from the identified database peptide. In the mass spectrometry analysis of the peptides from these gel bands, a single protein species was usually identifiable as the major component in the gel band, yielding multiple unique, high-confidence peptides identified from this dominant protein by database searching. The duplex of ISIS 326908 (SEQ ID NO: 228; P=S backbone, biotin-conjugated) and ISIS 308746 (SEQ ID NO: 229; P=O backbone, biotin-conjugated) attracted the following proteins in the HeLa S-100 lysate: leucine-rich PPR motif-containing protein (GenBank accession #NP_573566.1), heterogeneous nuclear ribonucleoprotein U isoform a (GenBank accession #NP_114032.1), nucleolin (GenBank accession #NP_005372.1), NS1-associated protein 1 (GenBank accession #NP_006363.3), and polypyrimidine tract binding protein 1 (GenBank accession #AAP35465.1). The duplex of ISIS 271056 (SEQ ID NO: 230; P=O, 18S- and biotin-conjugated) and ISIS 330079 (SEQ ID NO: 231; P=O, 18S- and biotin-conjugated) attracted the following proteins in the HeLa S-100 lysate: SWI/SNF-related matrix-associated actin-dependent regulator of chromatin a3 (GenBank accession #NP_620636.1) and DEAD/H (Asp-Glu-Ala-Asp/His) box polypeptide 36 (GenBank accession #NP_065916.1). These proteins are thus putative RISC components.

Example 26

EIF2C2 Variants

It is advantageous to selectively inhibit the expression of one or more mutants of EIF2C2. Consequently, in some embodiments of the present invention are oligomeric compounds that target, hybridize to, and specifically inhibit the expression of mutants of EIF2C2.

Example 27

In Vivo Studies

In order to determine the potency of oligomeric compositions in treating EIF2C2-related diseases and disorders, various in vivo studies are performed.

Because the body's blood-brain barrier serves as an effective means of preventing important and useful drugs from reaching the brain tissue, consideration is given to the means of delivering oligomeric compounds. Recently, catheter and infusion pump systems have been developed that overcome this obstacle by directly delivering the medications directly to the spinal space and/or ventricular spaces. See, e.g., The Blood-Brain Barrier and Drug Delivery to the CNS. (2000) Eds. D. J. Begley, M. W. Bradbury and J. Kreuter, Marcel Dekker, New York. Also, oligomeric compounds can be conjugated via a biodegradable disulfide bond to a polymer carrier such as polyethylene glycol (PEG) to effect delivery across the blood-brain barrier.

Compounds are formulated as pharmaceutical compositions appropriate for the selected subject.

Fragile X Syndrome

Fragile X Syndrome is thought to be caused by the expansion and hypermethylation of the CGG triplet in the fragile X mental retardation gene 1 (FMR1), leading to a loss of production of the fragile X mental retardation protein (FMRP), an RNA-binding protein.

In vivo models for Fragile X Syndrome are established to identify modulators of Fragile X Syndrome, in such models levels of FMRP protein and or mRNA are detected subsequent to treatment with an oligomeric composition of the present invention, increasing doses of oligomeric compounds targeting EIF2C2 nucleic acid are administered to subjects either known to have Fragile X Syndrome (humans who have provided informed consent) or which provide an art-accepted model of Fragile X Syndrome (for example, see Kooy et al., (1999) Neuroanatomy of the fragile X knockout mouse brain. Eur. J. Hum. Gen. 7: 526-532; Kooy et al., (2001), Brain studies of mouse models for neurogenetic disorders using in vivo magnetic resonance imaging (MRI). Eur. J. Hum. Genet., 9:153-159 (2001). Levels of FMRP protein and/or FMRP mRNA in subject animals to whom the oligomeric compounds of the present invention are administered are compared to placebo and to controls. Compounds that change expression of FMRP are identified as modulators of Fragile X Syndrome.

Spinal Muscular Atrophy

Homozygous mutation of the telomeric SMN (SMN1) gene in humans is associated with proximal spinal muscular atrophy (SMA), a severe motor neuron disease leading to muscle weakness with an onset predominantly in infancy and childhood. In vivo models for Spinal muscular atrophy are established to identify modulators of Spinal muscular atrophy. In such models levels of SMN1 protein and or mRNA are detected subsequent to treatment with an oligomeric compound of the present invention. Increasing doses of oligomeric compounds targeting SMN1 nucleic acid are administered to subjects either known to have Spinal muscular atrophy (humans who have provided informed consent) or which provide an art-accepted model of Spinal muscular atrophy (for example, mouse lines carrying a knockout mutation of the mouse Smn1 or 2 gene; see, e.g. Hsieh-Li et al., (2000) A mouse model for spinal muscular atrophy. Nature Genetics 24, 66-70). Transgenic mice harboring the human SMN2 with the Smn gene knockout show pathological changes in spinal cord and skeletal muscle similar to SMA patients. Levels of FMRP protein and/or mRNA in subject animals to whom the oligomeric compounds of the present invention are administered are compared to placebo and to controls. Also, pathological changes in spinal cord and skeletal muscle are examined. Controls may include regulators of SMN mRNA processing, including Htra2-beta1, a splicing factor that promotes the inclusion of SMN exon 7 and stimulates full-length SMN2 expression to almost 90%.

Compounds that increase expression of SMN are identified as inhibitors of Spinal muscular atrophy.

Example 28

Antisense Compounds Directed to DDX36 Identified Through the Biochemical Capture Assay Eukaryotic gene expression is governed by the rate of transcription of genes, mRNA stability, assembly of ribonucleoprotein complexes, and the rate at which transcripts are degraded. Members of a large superfamily of proteins characterized by the presence of seven to eight conserved peptide motifs, including the conserved amino acid motif Asp-Glu-Ala-Asp/His (DEAD/H), are called the DEAD/H box proteins and are RNA-dependent ATPases required for the major transactions of RNA. DEAD/H box proteins are implicated in a number of biophysical processes involving alteration of RNA secondary structure such as transcription initiation, editing, splicing, ribosome biogenesis, RNA export, translation, RNA turnover and organelle gene expression. The activity of the DEAD/H box proteins in these processes must be highly specific to ensure that only short stretches of dsRNA are rearranged (Tanner and Linder, *Mol. Cell,* 2001, 8, 251-262).

DEAD/H box proteins contain additional conserved motifs necessary for binding a nucleotide triphosphate (usually ATP), substrate recognition and substrate binding. The DEAD/H box proteins are divided into two subfamilies, the DEAD box family and the DEAH box family, and are often assigned the designation DDX or DHX to indicate the presence of the DEAD or DEAH amino acid sequence, respectively. Related family members included proteins with the DExD or DExH motifs, where x can be any amino acid (Tanner and Linder, *Mol. Cell,* 2001, 8, 251-262).

Several members of the DEAD/H box family of proteins function as RNA helicases that unwind double-stranded RNA (dsRNA) in an energy dependent manner through the hydrolysis of a nucleotide triphosphate, usually ATP. RNA helicases unwind dsRNA in either a 5' to 3' or 3' to 5' direction when tested in vitro. 5' or 3' overhangs enable the helicases to load onto the substrate. The putative substrates for the well-characterized helicases contain duplex regions that are generally below 10 bp. Thus, it is unnecessary for RNA-dependent enzymes to possess a processive unwinding activity (Tanner and Linder, *Mol. Cell,* 2001, 8, 251-262).

Many of the putative targets of DEAD/H box proteins contain only short basepaired regions. In these cases, the proteins may act to ensure that correct interactions are formed or to drive a multistep reaction to completion. Still other members of the family may harness the energy of ATP hydrolysis to remodel the interactions of RNA and proteins, rather than to unwind dsRNA. The members of the DEAD/H box family that are not demonstrated to function as helicases are often still referred to as DEAD/H RNA helicases by virtue of the DEAD/H box motif present in the protein sequence (Schwer, *Nat. Struct. Biol.,* 2001, 8, 113-116; Tanner and Linder, *Mol. Cell,* 2001, 8, 251-262).

An evolutionarily conserved mechanism regulating gene expression is double-stranded RNA-induced gene silencing known as RNA interference (RNAi). When dsRNA corresponding to the sense and antisense sequence of an endogenous mRNA is introduced into a cell, it mediates sequence-specific genetic interference, and the cognate mRNA is degraded into small interfering RNAs (siRNAs) and the gene silenced. The mRNA degradation reaction is catalyzed by a group of RNase III-related enzymes known as the Dicer family. The siRNAs or small endogenously encoded dsRNAs called microRNAs are incorporated into a multicomponent RNP complex, the RNA-induced silencing complex (RISC), which uses dsRNAs as a guide to select complementary mRNA substrates. At least one DEAD/H box RNA helicase is part of the RISC complex (Denli and Hannon, *Trends Biochem. Sci.,* 2003, 28, 196-201).

DEAD/H proteins have also been implicated in fertility, spermatogenesis, and embryogenesis. The protein encoded by the *Drosophila* maleless (m/e) gene belongs to the DEAD/H box protein family. The m/e gene is involved in the regulation of X chromosome dosage compensation in *Drosophila* and is required for male fertility, although a loss of function mutation in females has no effect on viability.

RNA helicase A has been proposed as the human homologue of maleless based on sequence similarity (Lee and Hurwitz, *J. Biol. Chem.,* 1993, 268, 16822-16830). However, mechanisms involved in fertility involve numerous genes (Hackstein et al., *Trends Genet.,* 2000, 16, 565-572). A search of human EST database for sequences homologous to *Drosophila* m/e identified an entry with significant sequence identity in both nucleic acid and amino acid sequences. Human DDX36 (DEAH (Asp-Glu-Ala-His) box polypeptide 36, also known as KIAA1488 protein, and MLEL1) was subsequently cloned from human testis cDNA and a human fetal brain cDNA library, and the resulting gene was 3.6 kb, with an open reading frame coding for a protein of 1008 amino acids. DDX36 was mapped to chromosome 3q25.1-3q25.2 (Fu et al., *Sheng Wu Hua Xue Yu Sheng Wu Wu Li Xue Bao (Shanghai),* 2002, 34, 655-661).

Northern blot analysis of DDX36 expression in multiple human tissues revealed a strong signal in testis, but no signal or weak signal in other tissues tested (pancreas, thymus, prostate, ovary, small intestine, colon, peripheral blood leukocytes, heart, brain, placenta, lung, liver, skeletal muscle, kidney, and spleen. Considering its potential role in post-transcriptional gene regulation in the *Drosophila* germline, it was suggested that DDX36 may have a latent function in sex development, spermatogenesis, and post-transcriptional regulation in human testis (Fu et al., *Sheng Wu Hua Xue Yu Sheng Wu Wu Li Xue Bao (Shanghai),* 2002, 34, 655-661).

The role of DDX36 in post-transcriptional regulation makes it an attractive target for therapeutic and investigative strategies aimed at RNAi technology. Accordingly, a series of antisense compounds was designed to target different regions of the human DDX36 RNA, using published sequences (GenBank accession number NM_020865.1, incorporated herein as SEQ ID NO: 232, the complement of nucleotides 60488216 to 60537835 of GenBank accession number NT_005612.14, incorporated herein as SEQ ID NO: 233, GenBank accession number BM456781.1, incorporated herein as SEQ ID NO: 234, and GenBank accession number BC036035.1, incorporated herein as SEQ ID NO: 235). The compounds are shown in Table 6. "Target site" indicates the first (5'-most) nucleotide number on the particular target sequence to which the compound binds. All compounds in Table 6 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-(2-methoxyethyl) nucleotides, also known as 2'-MOE nucleotides. The internucleoside (backbone) linkages are phosphorothioate (P=S) throughout the oligonucleotide. All cytidine residues are 5-methylcytidines.

The compounds were analyzed for their effect on human DDX36 mRNA levels by quantitative real-time PCR as described in other examples herein. Probes and primers to human DDX36 were designed to hybridize to a human DDX36 sequence, using published sequence information (GenBank accession number NM_020865.1, incorporated herein as SEQ ID NO: 232). For human DDX36 the PCR primers were:

forward primer: GATGGAGCTGAACGCTTTGG (SEQ ID NO: 236)

reverse primer: CAATATGTGGCTCAACGGGTAA (SEQ ID NO: 237) and the PCR probe was: FAM-AATTGACACCTCTTGGAGTC-CACTTGGCA-TAMRA (SEQ ID NO: 238) where FAM is the fluorescent dye and TAMRA is the quencher dye.

Data, shown in Table 6, are averages from two experiments in which A549 cells were treated with 65 nM of antisense oligonucleotides of the present invention. The control oligonucleotide for this assay was ISIS 18078 (SEQ ID NO: 2). If present, "N.D." indicates "no data".

TABLE 6

Inhibition of human DDX36 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 357773 | Intron | 11 | 17857 | atacagtaactgctatatat | 48 | 239 |
| 357774 | Intron24: Exon25 junction | 11 | 48523 | ttcttaattcctaaggttgg | 38 | 240 |
| 357775 | 5'UTR | 4 | 43 | actacaacccgtcagaacca | 15 | 241 |
| 357776 | Start Codon | 4 | 65 | tcataactcattgtcctggc | 89 | 242 |
| 357777 | Coding | 4 | 410 | ggagcaaaccaggatatctg | 52 | 243 |
| 357778 | Coding | 4 | 415 | cctcaggagcaaaccaggat | 54 | 244 |
| 357779 | Coding | 4 | 420 | atgatcctcaggagcaaacc | 47 | 245 |
| 357780 | Coding | 4 | 553 | aatctcggtcaatatatgat | 53 | 246 |
| 357781 | Coding | 4 | 558 | ctcagaatctcggtcaatat | 63 | 247 |
| 357782 | Coding | 4 | 750 | agtttcaccacttattactg | 60 | 248 |
| 357783 | Coding | 4 | 765 | ggttttgccacaaccagttt | 78 | 249 |
| 357784 | Coding | 4 | 854 | attcttcttggctgagtaca | 53 | 250 |
| 357785 | Coding | 4 | 862 | tggcactaattcttcttggc | 76 | 251 |
| 357786 | Coding | 4 | 867 | tgaaatggcactaattcttc | 44 | 252 |
| 357787 | Coding | 4 | 872 | gcaactgaaatggcactaat | 76 | 253 |
| 357788 | Coding | 4 | 965 | tgtttccttggcaaccgact | 72 | 254 |
| 357789 | Coding | 4 | 1032 | ggacaaatacgggtctgact | 72 | 255 |
| 357790 | Coding | 4 | 1045 | tatgactaacactggacaaa | 47 | 256 |
| 357791 | Coding | 4 | 1154 | gcactcatcaatattacttt | 74 | 257 |
| 357792 | Coding | 4 | 1193 | ttaccaaaatattctgaaaa | 17 | 258 |
| 357793 | Coding | 4 | 1198 | gacagttaccaaaatattct | 57 | 259 |
| 357794 | Coding | 4 | 1203 | cattggacagttaccaaaat | 59 | 260 |
| 357795 | Coding | 4 | 1208 | tgtatcattggacagttacc | 71 | 261 |
| 357796 | Coding | 4 | 1213 | gtatatgtatcattggacag | 82 | 262 |
| 357797 | Coding | 4 | 1250 | tccaaaagatattccacaac | 23 | 263 |
| 357798 | Coding | 4 | 1472 | ttcagatcaactttatcatc | 47 | 264 |
| 357799 | Coding | 4 | 1477 | tcaaattcagatcaacttta | 27 | 265 |
| 357800 | Coding | 4 | 1511 | tcttccaaaacaatgtatcg | 28 | 266 |
| 357801 | Coding | 4 | 1559 | ctgatattgtcccagcctgg | 83 | 267 |

TABLE 6-continued

Inhibition of human DDX36 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 357802 | Coding | 4 | 1586 | tgtgacatcaagagatcatg | 60 | 268 |
| 357803 | Coding | 4 | 1635 | cagtgaatgtaaaggtataa | 55 | 269 |
| 357804 | Coding | 4 | 1640 | ggcatcagtgaatgtaaagg | 71 | 270 |
| 357805 | Coding | 4 | 1694 | attttccgaacaccaggagg | 84 | 271 |
| 357806 | Coding | 4 | 1700 | attactattttccgaacacc | 35 | 272 |
| 357807 | Coding | 4 | 1705 | tagcaattactattttccga | 55 | 273 |
| 357808 | Coding | 4 | 1710 | gttggtagcaattactattt | 37 | 274 |
| 357809 | Coding | 4 | 1835 | gctttactaacccactcagc | 81 | 275 |
| 357810 | Coding | 4 | 1840 | cattagctttactaacccac | 65 | 276 |
| 357811 | Coding | 4 | 1845 | tttggcattagctttactaa | 59 | 277 |
| 357812 | Coding | 4 | 1907 | agaccattatacagatgata | 59 | 278 |
| 357813 | Coding | 4 | 1912 | ctctaagaccattatacaga | 57 | 279 |
| 357814 | Coding | 4 | 1917 | acttgctctaagaccattat | 57 | 280 |
| 357815 | Coding | 4 | 1922 | agaagacttgctctaagacc | 60 | 281 |
| 357816 | Coding | 4 | 1927 | catctagaagacttgctcta | 54 | 282 |
| 357817 | Coding | 4 | 1958 | ggagttctcaaaatttctgg | 77 | 283 |
| 357818 | Coding | 4 | 1963 | ccaaaggagttctcaaaatt | 35 | 284 |
| 357819 | Coding | 4 | 1968 | ttcttccaaaggagttctca | 31 | 285 |
| 357820 | Coding | 4 | 1973 | caaagttcttccaaaggagt | 29 | 286 |
| 357821 | Coding | 4 | 2018 | agaaaataagcaattccacc | 20 | 287 |
| 357822 | Coding | 4 | 2023 | tactcagaaaataagcaatt | 11 | 288 |
| 357823 | Coding | 4 | 2033 | tccattaatctactcagaaa | 41 | 289 |
| 357824 | Coding | 4 | 2054 | actgcctcatttgatggtgg | 84 | 290 |
| 357825 | Coding | 4 | 2165 | tttccaatatgtggctcaac | 55 | 291 |
| 357826 | Coding | 4 | 2170 | tcatttttccaatatgtggc | 78 | 292 |
| 357827 | Coding | 4 | 2351 | cagccctcaaacgcattcac | 47 | 293 |
| 357828 | Coding | 4 | 2414 | gacagaaaatattcccagca | 49 | 294 |
| 357829 | Coding | 4 | 2447 | ttcatgttatgcagcatctg | 79 | 295 |
| 357830 | Coding | 4 | 2471 | agaagatgctcagcaaactg | 54 | 296 |
| 357831 | Coding | 4 | 2493 | actgcttacaaatccagctc | 68 | 297 |
| 357832 | Coding | 4 | 2535 | attatctgaatttatattag | 17 | 298 |
| 357833 | Coding | 4 | 2540 | ttctcattatctgaatttat | 7 | 299 |
| 357834 | Coding | 4 | 2545 | ttatcttctcattatctgaa | 40 | 300 |
| 357835 | Coding | 4 | 2564 | gcacagatgacagctttaat | 84 | 301 |
| 357836 | Coding | 4 | 2569 | aaccagcacagatgacagct | 77 | 302 |
| 357837 | Coding | 4 | 2574 | atataaaccagcacagatga | 39 | 303 |

TABLE 6-continued

Inhibition of human DDX36 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 357838 | Coding | 4 | 2580 | tttgggatataaaccagcac | 79 | 304 |
| 357839 | Coding | 4 | 2585 | gcaactttgggatataaacc | 83 | 305 |
| 357840 | Coding | 4 | 2590 | ttttagcaactttgggatat | 66 | 306 |
| 357841 | Coding | 4 | 2717 | tagataagccagttgtagtg | 58 | 307 |
| 357842 | Coding | 4 | 2722 | ggtgatagataagccagttg | 66 | 308 |
| 357843 | Coding | 4 | 2744 | atactgcttgttctcatctt | 57 | 309 |
| 357844 | Coding | 4 | 2749 | agtatatactgcttgttctc | 68 | 310 |
| 357845 | Coding | 4 | 2996 | gacagtactgcacagtctct | 80 | 311 |
| 357846 | Coding | 4 | 3001 | tagctgacagtactgcacag | 74 | 312 |
| 357847 | 3'UTR | 4 | 3569 | tgtacattttattaaatact | 33 | 313 |
| 357848 | 3'UTR | 4 | 3581 | gagatttaacattgtacatt | 38 | 314 |
| 357849 | 3'UTR | 12 | 235 | tgatataaaaagggcacgtg | 56 | 315 |
| 357850 | Exon18: Exon20 junction | 13 | 2241 | cttcccagcccagtggaatg | 22 | 316 |

As shown in Table 1, SEQ ID NOs 239, 240, 242, 243, 244, 245, 246, 247, 248, 249, 250, 251, 252, 253, 254, 255, 256, 257, 259, 260, 261, 262, 264, 265, 266, 267, 268, 269, 270, 271, 252, 273, 274, 275, 276, 277, 278, 279, 280, 281, 282, 283, 284, 285, 286, 289, 290, 291, 292, 293, 294, 295, 296, 297, 300, 301, 302, 303, 304, 305, 306, 307, 308, 309, 310, 311, 312, 313, 314 and 315 demonstrated at least 27% inhibition of human DDX36 expression in this assay and are therefore are preferred in some embodiments. More preferred are SEQ ID NOs 242, 290, 271 and 301. The target regions to which these preferred sequences are complementary are herein referred to as "preferred target segments" and are therefore preferred for targeting by compounds of the present invention. These preferred target segments are shown in Table 7. These sequences are shown to contain thymine (T) but one of skill in the art will appreciate that thymine (T) is generally replaced by uracil (U) in RNA sequences. The sequences represent the reverse complement of the preferred antisense compounds shown in Table 6. "Target site" indicates the first (5'-most) nucleotide number on the particular target nucleic acid to which the oligonucleotide binds also shown in Table 7 is the species in which each of the preferred target segments was found.

TABLE 7

Sequence and position of target segments identified in DDX36.

| SITE ID | TARGET SEQ ID NO | TARGET SITE | SEQUENCE | REV COMP OF SEQ ID | ACTIVE IN | SEQ ID NO |
|---|---|---|---|---|---|---|
| 269776 | 11 | 17857 | atatatagcagttactgtat | 239 | H. sapiens | 317 |
| 269777 | 11 | 48523 | ccaaccttaggaattaagaa | 240 | H. sapiens | 318 |
| 269779 | 4 | 65 | gccaggacaatgagttatga | 242 | H. sapiens | 319 |
| 269780 | 4 | 410 | cagatatcctggtttgctcc | 243 | H. sapiens | 320 |
| 269781 | 4 | 415 | atcctggtttgctcctgagg | 244 | H. sapiens | 321 |
| 269782 | 4 | 420 | ggtttgctcctgaggatcat | 245 | H. sapiens | 322 |
| 269783 | 4 | 553 | atcatatattgaccgagatt | 246 | H. sapiens | 323 |
| 269784 | 4 | 558 | atattgaccgagattctgag | 247 | H. sapiens | 324 |

TABLE 7-continued

Sequence and position of target segments identified in DDX36.

| SITE ID | TARGET SEQ ID NO | TARGET SITE | SEQUENCE | REV COMP OF SEQ ID | ACTIVE IN | SEQ ID NO |
|---|---|---|---|---|---|---|
| 269785 | 4 | 750 | cagtaataagtggtgaaact | 248 | H. sapiens | 325 |
| 269786 | 4 | 765 | aaactggttgtggcaaaacc | 249 | H. sapiens | 326 |
| 269787 | 4 | 854 | tgtactcagccaagaagaat | 250 | H. sapiens | 327 |
| 269788 | 4 | 862 | gccaagaagaattagtgcca | 251 | H. sapiens | 328 |
| 269789 | 4 | 867 | gaagaattagtgccatttca | 252 | H. sapiens | 329 |
| 269790 | 4 | 872 | attagtgccatttcagttgc | 253 | H. sapiens | 330 |
| 269791 | 4 | 965 | agtcggttgccaaggaaaca | 254 | H. sapiens | 331 |
| 269792 | 4 | 1032 | agtcagacccgtatttgtcc | 255 | H. sapiens | 332 |
| 269793 | 4 | 1045 | tttgtccagtgttagtcata | 256 | H. sapiens | 333 |
| 269794 | 4 | 1154 | aaagtaatattgatgagtgc | 257 | H. sapiens | 334 |
| 269796 | 4 | 1198 | agaatattttggtaactgtc | 259 | H. sapiens | 335 |
| 269797 | 4 | 1203 | attttggtaactgtccaatg | 260 | H. sapiens | 336 |
| 269798 | 4 | 1208 | ggtaactgtccaatgataca | 261 | H. sapiens | 337 |
| 269799 | 4 | 1213 | ctgtccaatgatacatatac | 262 | H. sapiens | 338 |
| 269801 | 4 | 1472 | gatgataaagttgatctgaa | 264 | H. sapiens | 339 |
| 269802 | 4 | 1477 | taaagttgatctgaatttga | 265 | H. sapiens | 340 |
| 269803 | 4 | 1511 | cgatacattgttttggaaga | 266 | H. sapiens | 341 |
| 269804 | 4 | 1559 | ccaggctgggacaatatcag | 267 | H. sapiens | 342 |
| 269805 | 4 | 1586 | catgatctcttgatgtcaca | 268 | H. sapiens | 343 |
| 269806 | 4 | 1635 | ttatacctttacattcactg | 269 | H. sapiens | 344 |
| 269807 | 4 | 1640 | cctttacattcactgatgcc | 270 | H. sapiens | 345 |
| 269808 | 4 | 1694 | cctcctggtgttcggaaaat | 271 | H. sapiens | 346 |
| 269809 | 4 | 1700 | ggtgttcggaaaatagtaat | 272 | H. sapiens | 347 |
| 269810 | 4 | 1705 | tcggaaaatagtaattgcta | 273 | H. sapiens | 348 |
| 269811 | 4 | 1710 | aaatagtaattgctaccaac | 274 | H. sapiens | 349 |
| 269812 | 4 | 1835 | gctgagtgggttagtaaagc | 275 | H. sapiens | 350 |
| 269813 | 4 | 1840 | gtgggttagtaaagctaatg | 276 | H. sapiens | 351 |
| 269814 | 4 | 1845 | ttagtaaagctaatgccaaa | 277 | H. sapiens | 352 |
| 269815 | 4 | 1907 | tatcatctgtataatggtct | 278 | H. sapiens | 353 |
| 269816 | 4 | 1912 | tctgtataatggtcttagag | 279 | H. sapiens | 354 |
| 269817 | 4 | 1917 | ataatggtcttagagcaagt | 280 | H. sapiens | 355 |
| 269818 | 4 | 1922 | ggtcttagagcaagtcttct | 281 | H. sapiens | 356 |
| 269819 | 4 | 1927 | tagagcaagtcttctagatg | 282 | H. sapiens | 357 |
| 269820 | 4 | 1958 | ccagaaattttgagaactcc | 283 | H. sapiens | 358 |
| 269821 | 4 | 1963 | aattttgagaactcctttgg | 284 | H. sapiens | 359 |
| 269822 | 4 | 1968 | tgagaactcctttggaagaa | 285 | H. sapiens | 360 |

TABLE 7-continued

Sequence and position of target segments identified in DDX36.

| SITE ID | TARGET SEQ ID NO | TARGET SITE | SEQUENCE | REV COMP OF SEQ ID | ACTIVE IN | SEQ ID NO |
|---|---|---|---|---|---|---|
| 269823 | 4 | 1973 | actcctttggaagaactttg | 286 | H. sapiens | 361 |
| 269826 | 4 | 2033 | tttctgagtagattaatgga | 289 | H. sapiens | 362 |
| 269827 | 4 | 2054 | ccaccatcaaatgaggcagt | 290 | H. sapiens | 363 |
| 269828 | 4 | 2165 | gttgagccacatattggaaa | 291 | H. sapiens | 364 |
| 269829 | 4 | 2170 | gccacatattggaaaaatga | 292 | H. sapiens | 365 |
| 269830 | 4 | 2351 | gtgaatgcgtttgagggctg | 293 | H. sapiens | 366 |
| 269831 | 4 | 2414 | tgctgggaatattttctgtc | 294 | H. sapiens | 367 |
| 269832 | 4 | 2447 | cagatgctgcataacatgaa | 295 | H. sapiens | 368 |
| 269833 | 4 | 2471 | cagtttgctgagcatcttct | 296 | H. sapiens | 369 |
| 269834 | 4 | 2493 | gagctggatttgtaagcagt | 297 | H. sapiens | 370 |
| 269837 | 4 | 2545 | ttcagataatgagaagataa | 300 | H. sapiens | 371 |
| 269838 | 4 | 2564 | attaaagctgtcatctgtgc | 301 | H. sapiens | 372 |
| 269839 | 4 | 2569 | agctgtcatctgtgctggtt | 302 | H. sapiens | 373 |
| 269840 | 4 | 2574 | tcatctgtgctggtttatat | 303 | H. sapiens | 374 |
| 269841 | 4 | 2580 | gtgctggtttatatcccaaa | 304 | H. sapiens | 375 |
| 269842 | 4 | 2585 | ggtttatatcccaaagttgc | 305 | H. sapiens | 376 |
| 269843 | 4 | 2590 | atatcccaaagttgctaaaa | 306 | H. sapiens | 377 |
| 269844 | 4 | 2717 | cactacaactggcttatcta | 307 | H. sapiens | 378 |
| 269845 | 4 | 2722 | caactggcttatctatcacc | 308 | H. sapiens | 379 |
| 269846 | 4 | 2744 | aagatgagaacaagcagtat | 309 | H. sapiens | 380 |
| 269847 | 4 | 2749 | gagaacaagcagtatatact | 310 | H. sapiens | 381 |
| 269848 | 4 | 2996 | agagactgtgcagtactgtc | 311 | H. sapiens | 382 |
| 269849 | 4 | 3001 | ctgtgcagtactgtcagcta | 312 | H. sapiens | 383 |
| 269850 | 4 | 3569 | agtatttaataaaatgtaca | 313 | H. sapiens | 384 |
| 269851 | 4 | 3581 | aatgtacaatgttaaatctc | 314 | H. sapiens | 385 |
| 269852 | 12 | 235 | cacgtgccctttttatatca | 315 | H. sapiens | 386 |

As these "preferred target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of DDX36.

The mouse DDX36 RNA is known (GenBank accession number NM_028136.1, incorporated herein as SEQ ID NO: 387), as is the rat DDX36 RNA (GenBank accession number XM_227203.2, incorporated herein as SEQ ID NO: 388).

According to the present invention, antisense compounds include antisense oligomeric compounds, antisense oligonucleotides, siRNAs, external guide sequence (EGS) oligonucleotides, alternate splicers, and other short oligomeric compounds which hybridize to at least a portion of the target nucleic acid.

Example 30

Western Blot Analysis of DDX36 Protein Levels

Western blot analysis (immunoblot analysis) is carried out using standard methods. Cells are harvested 16-20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to DDX36 is used, with a radiolabeled or fluorescently labeled secondary anti-

Example 31

Targeting of Individual Oligonucleotides to Specific Variants of DDX36

A search of the National Center for Biotechnology Information database revealed alternative mRNA variants of DDX36 which are the result of alternative splicing. The sequence with the Genbank accession number NM_020865.1 represents a variant of DDX36 designated herein as DDX36-1 and is incorporated herein as SEQ ID NO: 232. The sequence with the Genbank accession number BC036035.1 represents a variant of DDX36 designated herein as DDX36-2 and is incorporated herein as SEQ ID NO: 235.

It is advantageous to selectively inhibit the expression of one or more variants of DDX36. Consequently, in one embodiment of the present invention are oligonucleotides that selectively target, hybridize to, and specifically inhibit one or more, but fewer than all the variants of DDX36. A summary of the target sites of the variants is shown in Table 8. The oligonucleotides of the present invention that selectively target only one human DDX36 variant are presented in Table 8. The absence of an oligonucleotide of the present invention from Table 8 indicates that the oligonucleotide can target more than one variant of DDX36.

TABLE 8

Targeting of individual oligonucleotides to specific variants of DDX36

| ISIS # | SEQ ID NO | Target Site | Target Variant | Target SEQ ID NO |
|---|---|---|---|---|
| 357827 | 293 | 2351 | DDX36-1 | 232 |
| 357850 | 316 | 2241 | DDX36-2 | 235 |

Example 32

Analysis of DDX36 mRNA Levels

DDX36 mRNA levels were measured by quantitative real-time PCR as described in other examples herein. Primers to human DDX36 were designed to hybridize to a human DDX36 sequence, using published sequence information (GenBank accession number NM_020865.1, incorporated herein as SEQ ID NO: 232). The forward primer was GATGGAGCTGAACGCTTTGG (SEQ ID NO: 236) and the reverse primer was CAATATGTGGCTCAACGGGTAA (SEQ ID NO: 237). The human gene glyceraldehyde-3-phosphate dehydrogenase (GAPDH) RNA (Clontech, Palo Alto, Calif.) was used as a control.

What is claimed is:

1. A method of reducing the expression of EIF2C2 in a cell by at least 50% comprising contacting the cell with an antisense compound consisting of 15 to 30 linked nucleosides in which the entire nucleobase sequence of the antisense compound is at least 90% complementary to a nucleobase sequence within nucleotides 1938 to 2572 of SEQ ID NO: 4; and thereby reducing the expression of EIF2C2 in the cell by at least 50%.

2. The method of claim 1 wherein said antisense compound is single-stranded.

3. The method of claim 2 wherein said single-stranded compound is single-stranded RNA.

4. The method of claim 2 wherein said single-stranded compound is a RNase H oligonucleotide.

5. The method of claim 4 wherein said RNase H oligonucleotide is a chimeric oligonucleotide.

6. The method of claim 5 wherein the chimeric oligonucleotide comprises at least one modification selected from the group consisting of a modified internucleoside linkage, a modified sugar residue and a modified nucleobase.

7. The method of claim 6 wherein the modified internucleoside linkage is a phosphorothioate.

8. The method of claim 6 wherein the modified sugar residue is a 2'-O-methoxyethyl.

9. The method of claim 6 wherein the modified nucleobase is 5-methylcytosine.

10. The method of claim 5 wherein the chimeric oligonucleotide comprises a first region having 2'-deoxyribonucleotides and a second and a third region each having 2'-O-methoxyethyl nucleotides, wherein said second and said third regions flank said first region.

11. The method of claim 10 wherein said first region consists of ten 2'-deoxyribonucleotides and said second and said third regions each consist of five 2'-O-methoxyethyl nucleotides.

12. The method of claim 11 wherein said chimeric oligonucleotide further comprises phosphorothioate internucleoside linkages at each position.

13. The method of claim 12 wherein each cytosine residue of said chimeric oligonucleotide is replaced with 5-methylcytosine.

14. The method of claim 1 wherein said antisense compound is double-stranded.

15. The method of claim 14 wherein the double-stranded compound comprises a sense strand and an antisense strand.

16. The method of claim 15 wherein each strand is 21 nucleobases in length.

17. The method of claim 15 wherein the sense strand and antisense strand are complementary over their entire length.

18. The method of claim 15 wherein at least one of said sense strand and said antisense strand has a two nucleobase overhang on the 3' end.

19. The method of claim 18 wherein the overhang consists of two deoxythymidine residues.

20. The method of claim 15 wherein the internucleoside linkages of said sense strand and said antisense strand are phosphodiester.

21. The method of claim 1 wherein the entire nucleobase sequence of the antisense compound is at least 95% complementary to a nucleobase sequence within nucleotides 1938 to 2572 of SEQ ID NO: 4.

22. The method of claim 1 wherein the entire nucleobase sequence of the antisense compound is 100% complementary to a nucleobase sequence within nucleotides 1938 to 2572 of SEQ ID NO: 4.

23. The method of claim 1, wherein the antisense compound has a nucleobase sequence selected from the nucleobase sequences designated as SEQ ID NOs 23, 24, 25, 26, 27, 28, 29, 30, 31, 32, 33, 34, 35, 36, 37, 38, 39, 40, 41, 42, 43, 44, 45, and 46.

24. The method of claim 1 wherein the antisense compound is an oligonucleotide, wherein the oligonucleotide consists of
a gap segment consisting of linked 2'-deoxynucleosides,
a 5' wing segment consisting of linked nucleosides, and
a 3' wing segment consisting of linked nucleosides;
wherein the sugar of each nucleoside of the 5' wing segment is a modified sugar, the sugar of each nucleoside of the 3' wing segment is a modified sugar, and each internucleoside linkage is a phosphorothioate internucleoside linkage.

25. The method of claim 24 wherein the modified sugar is a 2'-O-methoxyethyl sugar.

26. The method of claim 1 wherein the antisense compound is an oligonucleotide, wherein the oligonucleotide consists of
a gap segment consisting often linked 2'-deoxynucleosides,
a 5' wing segment consisting of five linked nucleosides, and
a 3' wing segment consisting of five linked nucleosides;
wherein the sugar of each nucleoside of the 5' wing segment is a 2'-O-methoxyethyl sugar, the sugar of each nucleoside of the 3' wing segment is a 2'-O-methoxyethyl sugar, and each internucleoside linkage is a phosphorothioate internucleoside linkage.

27. The method of claim 26 wherein at least one cytosine is a 5-methylcytosine.

28. The method of claim 27, wherein each cytosine is a 5-methylcytosine.

29. The method of claim 28, wherein the antisense compound has a nucleobase sequence comprising at least 8 contiguous nucleobases of a nucleobase sequence selected from the nucleobase sequences designated as SEQ ID NOs 23, 24, 25, 26, 27, 28, 29, 30, 31, 32, 33, 34, 35, 36, 37, 38, 39, 40, 41, 42, 43, 44, 45, and 46.

30. A method of reducing the expression of EIF2C2 in a cell by at least 50% comprising contacting the cell with an oligonucleotide consisting of 15 to 30 linked nucleosides, wherein the entire nucleobase sequence of the oligonucleotide is at least 90% complementary to a nucleobase sequence within nucleotides 1938 to 2572 of SEQ ID NO: 4; and thereby reducing the expression of EIF2C2 in the cell by at least 50%.

31. The method of claim 30, wherein at least one internucleoside linkage is a modified internucleoside linkage.

32. The method of claim 31, wherein each internucleoside linkage is a phosphorothioate internucleoside linkage.

33. The method of claim 30, wherein at least one nucleoside comprises a modified sugar.

34. The method of claim 33, wherein the modified sugar is a bicyclic sugar.

35. The method of claim 33, wherein the modified sugar is a 2'-O-methoxyethyl sugar.

36. The method of claim 30, wherein at least one nucleoside comprises a modified nucleobase.

37. The method of claim 36, wherein the modified nucleobase is a 5-methylcytosine.

38. The method of claim 30, wherein the oligonucleotide has a nucleobase sequence comprising at least 8 contiguous nucleobases of a nucleobase sequence selected from the nucleobase sequences designated as SEQ ID NOs 23, 24, 25, 26, 27, 28, 29, 30, 31, 32, 33, 34, 35, 36, 37, 38, 39, 40, 41, 42, 43, 44, 45, and 46.

39. The method of claim 30, wherein the oligonucleotide has a nucleobase sequence selected from the nucleobase sequences designated as SEQ ID NOs 23, 24, 25, 26, 27, 28, 29, 30, 31, 32, 33, 34, 35, 36, 37, 38, 39, 40, 41, 42, 43, 44, 45, and 46.

40. The method of claim 30 wherein the oligonucleotide consists of
a gap segment consisting of linked 2'-deoxynucleosides,
a 5' wing segment consisting of linked nucleosides, and
a 3' wing segment consisting of linked nucleosides;
wherein the sugar of each nucleoside of the 5' wing segment is a modified sugar, the sugar of each nucleoside of the 3' wing segment is a modified sugar, and each internucleoside linkage is a phosphorothioate internucleoside linkage.

41. The method of claim 40 wherein the modified sugar is a 2'-O-methoxyethyl sugar.

42. The method of claim 30 wherein the oligonucleotide consists of
a gap segment consisting often linked 2'-deoxynucleosides,
a 5' wing segment consisting of five linked nucleosides, and
a 3' wing segment consisting of five linked nucleosides;
wherein the sugar of each nucleoside of the 5' wing segment is a 2'-O-methoxyethyl sugar, the sugar of each nucleoside of the 3' wing segment is a 2'-O-methoxyethyl sugar, and each internucleoside linkage is a phosphorothioate internucleoside linkage.

43. The method of claim 42 wherein at least one cytosine is a 5-methylcytosine.

44. The method of claim 43, wherein each cytosine is a 5-methylcytosine.

45. The method of claim 44, wherein the oligonucleotide has a nucleobase sequence comprising at least 8 consecutive nucleobases of a nucleobase sequence selected from the nucleobase sequences designated as SEQ ID NOs 23, 24, 25, 26, 27, 28, 29, 30, 31, 32, 33, 34, 35, 36, 37, 38, 39, 40, 41, 42, 43, 44, 45, and 46.

46. The method of claim 44, wherein the oligonucleotide has a nucleobase sequence selected from the nucleobase sequences designated as SEQ ID NOs 23, 24, 25, 26, 27, 28, 29, 30, 31, 32, 33, 34, 35, 36, 37, 38, 39, 40, 41, 42, 43, 44, 45, and 46.

47. The method of claim 30 wherein the entire nucleobase sequence of the oligonucleotide is at least 95% complementary to a nucleobase sequence within nucleotides 1938 to 2572 of SEQ ID NO: 4.

48. The method of claim 30 wherein the entire nucleobase sequence of the oligonucleotide is 100% complementary to a nucleobase sequence within nucleotides 1938 to 2572 of SEQ ID NO: 4.

49. The method of claim 30 wherein the antisense compound is complementary to a nucleobase sequence within nucleotides 1938 to 2572 of SEQ ID NO: 4.

50. The method of claim 1, wherein the oligonucleotide has a nucleobase sequence selected from the nucleobase sequences designated as SEQ ID NOs 24, 33, and 45.

51. The method of claim 30, wherein the oligonucleotide has a nucleobase sequence selected from the nucleobase sequences designated as SEQ ID NOs 24, 33, and 45.

* * * * *